US008148371B2

(12) United States Patent
Isobe et al.

(10) Patent No.: US 8,148,371 B2
(45) Date of Patent: Apr. 3, 2012

(54) ADENINE COMPOUND AND USE THEREOF

(75) Inventors: Yoshiaki Isobe, Osaka (JP); Haruo Takaku, Osaka (JP); Haruhisa Ogita, Saitama (JP); Masanori Tobe, Osaka (JP); Ayumu Kurimoto, Osaka (JP); Tetsuhiro Ogino, Osaka (JP); Hitoshi Fujita, Osaka (JP)

(73) Assignee: Dainippon Sumitomo Pharma Co., Ltd., Osaka-Shi (JP)

( * ) Notice: Subject to any disclaimer, the term of this patent is extended or adjusted under 35 U.S.C. 154(b) by 0 days.

(21) Appl. No.: 12/793,649

(22) Filed: Jun. 3, 2010

(65) Prior Publication Data

US 2010/0256118 A1 Oct. 7, 2010

Related U.S. Application Data

(63) Continuation of application No. 10/528,343, filed as application No. PCT/JP03/12320 on Sep. 26, 2003, now Pat. No. 7,754,728.

(30) Foreign Application Priority Data

Sep. 27, 2002 (JP) ................................ 2002-283428
Oct. 16, 2002 (JP) ................................ 2002-301213

(51) Int. Cl.

| | |
|---|---|
| *C07D 473/18* | (2006.01) |
| *A61K 31/522* | (2006.01) |
| *A61P 37/08* | (2006.01) |
| *A61P 11/06* | (2006.01) |
| *C07D 473/40* | (2006.01) |
| *C07D 473/16* | (2006.01) |

(52) U.S. Cl. ..................... 514/234.2; 544/118; 544/276; 544/277; 514/263.37

(58) Field of Classification Search .................. 544/118, 544/276; 514/234.2, 263.37

See application file for complete search history.

(56) References Cited

U.S. PATENT DOCUMENTS

| | | | | |
|---|---|---|---|---|
| 4,689,338 | A | 8/1987 | Gerster | |
| 4,698,348 | A | 10/1987 | Gerster | |
| 4,714,701 | A | 12/1987 | Beauchamp | |
| 5,792,793 | A | 8/1998 | Oda et al. | |
| 6,028,076 | A | 2/2000 | Hirota et al. | |
| 6,329,381 | B1 | 12/2001 | Kurimoto et al. | |
| 6,376,501 | B1 | 4/2002 | Isobe et al. | |
| 7,157,465 | B2 | 1/2007 | Isobe et al. | |
| 7,642,350 | B2 | 1/2010 | Pryde | |
| 2003/0191086 | A1 | 10/2003 | Hanus et al. | |
| 2004/0132748 | A1 | 7/2004 | Isobe et al. | |
| 2006/0264448 | A1 | 11/2006 | Pryde | |
| 2007/0225303 | A1 | 9/2007 | Ogita et al. | |
| 2009/0192153 | A1 | 7/2009 | Hashimoto et al. | |
| 2009/0324551 | A1 | 12/2009 | Carson et al. | |
| 2011/0046369 | A1* | 2/2011 | Hashimoto et al. | 544/118 |
| 2011/0054168 | A1* | 3/2011 | Kurimoto et al. | 544/118 |
| 2011/0144136 | A1* | 6/2011 | Bazin-Lee et al. | 514/263.22 |

FOREIGN PATENT DOCUMENTS

| | | | |
|---|---|---|---|
| EP | 882727 | A1 | 12/1998 |
| EP | 1035123 | A1 | 9/2000 |
| EP | 1043021 | A1 | 10/2000 |
| JP | 08-165292 | A | 6/1996 |
| JP | 9-347422 | | 11/1997 |
| JP | 347422/1997 | | 11/1997 |
| JP | 9-367449 | | 12/1997 |
| JP | 9-367451 | | 12/1997 |
| JP | 367449/1997 | | 12/1997 |
| JP | 367451/1997 | | 12/1997 |
| JP | 11-193282 | A | 7/1999 |
| WO | WO-02/085905 | A1 | 10/2002 |
| WO | WO-2005/025583 | A2 | 3/2005 |

OTHER PUBLICATIONS

R.F. Krueger et al., Science, vol. 169, Sep. 18, 1970, pp. 1213-1215.
F.R. Nichol et al., Antimicrobial Agents and Chemotherapy, vol. 9, No. 3, Mar. 1976, pp. 433-439.
D.A. Stringfellow et al., Antimicrobial Agents and Chemotherapy, vol. 15, No. 1, Jan. 1979, pp. 111-118.
M.J. Reiter et al., Journal of Leukocyte Biology, vol. 55, Feb. 1994, pp. 234-240.

(Continued)

*Primary Examiner* — Mark Berch
(74) *Attorney, Agent, or Firm* — Birch, Stewart, Kolasch & Birch, LLP

(57) ABSTRACT

A drug for topically administration which is effective as an antiallergic agent. The drug for topically administration contains as an active ingredient an adenine compound represented by the general formula (1):

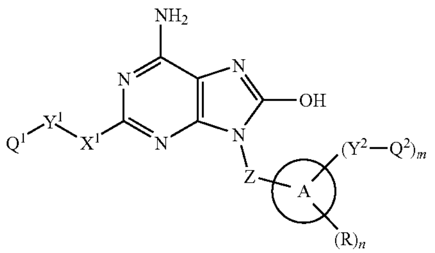

[wherein ring A represents a 6 to 10 membered, mono or bicyclic, aromatic hydrocarbon or a 5 to 10 membered, mono or bicyclic, aromatic heterocycle containing one to three heteroatoms selected among 0 to 2 nitrogen atoms, 0 or 1 oxygen atom, and 0 or 1 sulfur atom; n is an integer of 0 to 2; m is an integer of 0 to 2; R represents halogeno, (un)substituted alkyl, etc.; $X^1$ represents oxygen, sulfur, $NR^1$ ($R^1$ represents hydrogen or alkyl), or a single bond; $Y^1$ represents a single bond, alkylene, etc.; $Y^2$ represents a single bond, alkylene, etc.; Z represents alkylene; and at least one of $Q^1$ and $Q^2$ represents —$COOR^{10}$ (wherein $R^{10}$ represents (un)substituted alkyl, etc.), etc.] or a pharmaceutically acceptable salt of the compound.

12 Claims, 1 Drawing Sheet

OTHER PUBLICATIONS

Hirota et al. Org, Biomol. Chem., vol. 1, pp. 1354-1365, (2003) XP-002416225.

Isobe, Y., et al., "Synthesis and Structure—Activity Relationships of 2-Substituted-8-hydroxyadenine Derivatives as Orally Available Interferon Inducers without Emetic Side Effects," Bioorganic & Medicinal Chemistry, vol. 11, Issue 17, p. 3641-3647 (2003).

Kurimoto, A., et al., "Synthesis and Structure—Activity Relationships of 2-Amino-8-hydroxyadenines as Orally Active Interferon Inducing Agents," Bioorganic & Medicinal Chemistry, vol. 11, Issue 24, p. 5501-5508 (2003).

Kurimoto, A., et al., "Synthesis and evaluation of 2-substitued 8-hydroxyadenines as potent interferon inducers with improved oral bioavailabilities," Bioorganic & Medicinal Chemistry, vol. 12, Issue 5, p. 1091-1099 (2004).

Kurimoto, A., et al., "Prodrugs of 9-Benzyl-8-hydroxy-2-(2-hydroxyethylthio)adenine: Potent Interferon Inducing Agents in Monkeys," Chemical & Pharmaceutical Bulletin, vol. 52, No. 4, p. 466-469 (2004).

Isobe, Y., et al., "Synthesis and Biological Evaluation of Novel 9-Substituted-8-Hydroxyadenine Derivatives as Potent Interferon Inducers," Journal of Medicinal Chemistry, vol. 49, No. 6, p. 2088-2095 (2006).

Kurimoto, A., et al., "Synthesis and Biological Evaluation of 8-Oxoadenine Derivatives as Toll-like Receptor 7 Agonists Introducing the Antedrug Concept," Journal of Medicinal Chemistry, vol. 53, No. 7, p. 2964-2972 (2010).

Isobe, Y., et al., "Synthesis and Structure—Activity Relationships of 2-Substituted-8-hydroxyadenine Derivatives as Orally Available Interferon Inducers without Emetic Side Effects," Bioorganic & Medicinal Chemistry, vol. 11, Issue 17, p. 3641-3647 (2003).

Kurimoto, A., et al., "Synthesis and Structure—Activity Relationships of 2-Amino-8-hydroxyadenines as Orally Active Interferon Inducing Agents," Bioorganic & Medicinal Chemistry, vol. 11, Issue 24, p. 5501-5508 (2003).

Kurimoto, A., et al., "Synthesis and evaluation of 2-substitued 8-hydroxyadenines as potent interferon inducers with improved oral bioavailabilities," Bioorganic & Medicinal Chemistry, vol. 12, Issue 5, p. 1091-1099 (2004).

Kurimoto, A., et al., "Prodrugs of 9-Benzyl-8-hydroxy-2-(2-hydroxyethylthio)adenine: Potent Interferon Inducing Agents in Monkeys," Chemical & Pharmaceutical Bulletin, vol. 52, No. 4, p. 466-469 (2004).

Isobe, Y., et al., "Synthesis and Biological Evaluation of Novel 9-Substituted-8-Hydroxyadenine Derivatives as Potent Interferon Inducers," Journal of Medicinal Chemistry, vol. 49, No. 6, p. 2088-2095 (2006).

Kurimoto, A., et al., "Synthesis and Biological Evaluation of 8-Oxoadenine Derivatives as Toll-like Receptor 7 Agonists Introducing the Antedrug Concept," Journal of Medicinal Chemistry, vol. 53, No. 7, p. 2964-2972 (2010).

* cited by examiner

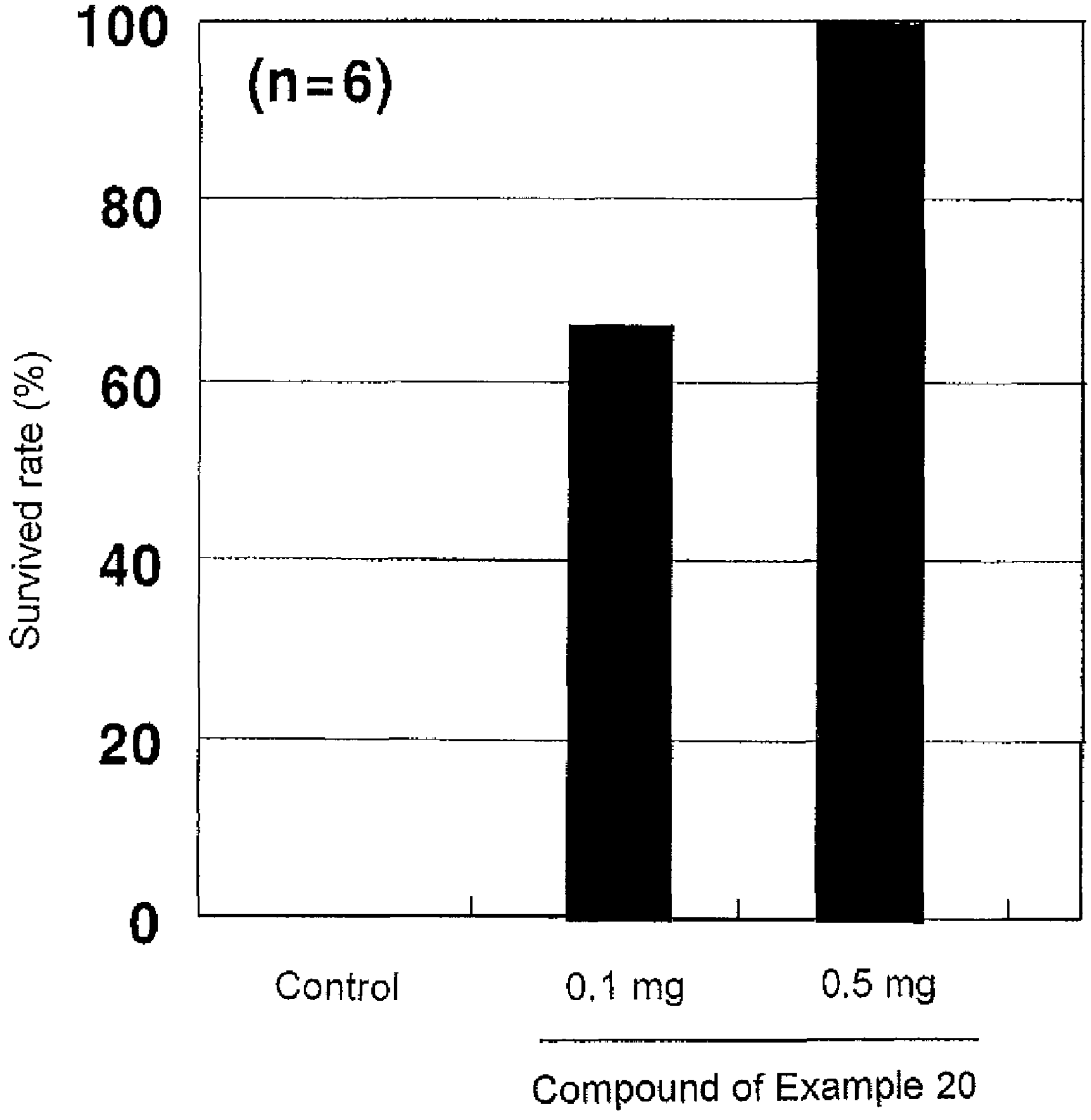
100
80
60
40
20
0
(n=6)
Survived rate (%)
Control
0.1 mg
0.5 mg
Compound of Example 20

ADENINE COMPOUND AND USE THEREOF

This application is a Continuation of the U.S. application Ser. No. 10/528,343 filed Mar. 18, 2005, which is the national stage of International Application PCT/JP2003/012320, filed Sep. 26, 2003, which claims priority under 35 USC §119(a)-(d) of Japanese Application No. 2002-283428, filed Sep. 27, 2002 and of Japanese Application No. 2002-301213, filed Oct. 16, 2002.

TECHNICAL FIELD

The present invention relates to a novel adenine compound which is useful as a prophylactic or therapeutic agent for viral diseases, allergic diseases, etc.

BACKGROUND ART

Interferon is an endogenous protein which plays an important role in mammalian immune system, takes a part of non-specific defensive mechanism in vivo and greatly participates also to specific defensive mechanism in vivo. In fact, interferon has been used in the clinical field as a therapeutic agent for viral diseases, such as hepatitis B and C, etc. Low molecular weight organic compounds which induce biosynthesis of said interferon (interferon inducers) have been developed as an interferon preparation in next generation. Imidazoquinoline derivatives (see European Patent Publication A 145340), adenine derivatives (see WO 98/01448 and WO 99/28321), etc. are illustrated. For example, Imiquimod, an imidazoline derivative is used in the clinical field as an external antiviral agent for genital verruca.

By the way, T cells which play the key role of the immunological response in vivo are classified into two kinds, Th1 cells and Th2 cells. In the body of patients suffering from allergic disease, cytokines such as interleukin 4 (IL-4), interleukin 5 (IL-5), etc. are excessively secreted from TH2 cells and therefore, it is expected that the compound which suppresses immune response of Th2 cells becomes a therapeutic agent for allergic diseases.

It is known that the above imidazoquinoline derivatives and adenine derivatives have not only the interferon inducing activity, but also have the activity suppressing the production of interleukin 4 (IL-4) and interleukin 5 (IL-5). In fact it is known that these derivatives are effective for allergic diseases on animal model.

However, there is anxiety for systemic adverse-effects due to the interferon inducing activity such as fever, interferon-like diseases when these derivatives are administered as an antiallergic agent.

DISCLOSURE OF INVENTION

The problem to be solved by the present invention is to provide a topically administrable medicament which is characterized in suppressing the systemic adverse effect caused by interferon inducing activity.

That is, the present invention provides a novel adenine compound which is characterized in being quickly metabolized to change a less active compound when it is topically administered, and a topically administrable medicament containing this compound as an active ingredient, which is used as the therapy for viral diseases, cancer or allergic diseases, whose systemic pharmacological activity is lessened.

The present inventors have been extensively studied in order to obtain a therapeutic and prophylactic agent for immune deficiency such as allergic diseases which shows excellent effect in the applied area and does not show the systemic adverse effect, when it is externally used in the form of liniments or aerosols useful for diseases such as asthma, etc. and as a result have found that the adenine compounds of the present invention show surprisingly excellent effect on pathologically modeled animals and is characterized in being quickly metabolized in the applied area or the body to change into a less active compound. Namely, the compounds of the present invention are reduced in the systemically pharmacological activity and are useful as a therapeutic or prophylactic agent for viral diseases, cancer, allergic diseases, etc. The present invention was completed based on the above findings.

BRIEF DESCRIPTION OF FIGURES

FIG. 1 shows anti-HSV activity on a compound of Example 20 against a pathologic modeled-animal infected with HSV-2 in its vagina.

Compound A was spread to a vagina of a female mouse (BALB/c) to which previously Depo-Provera was administered, and on next day, HSV-2 was infected to the vagina. Nine days later, the rate of survival or death of mice was observed and compared.

BEST MODE FOR CARRYING OUT THE INVENTION

The present invention relates to

[1] A topically administrable medicament containing an adenine compound represented by a general formula (1):

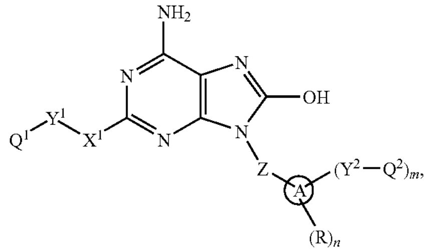

wherein

Ring A is a 6 to 10 membered mono or bicyclic aromatic hydrocarbon ring or a 5 to 10 membered mono or bicyclic heteroaromatic ring containing 1 to 3 hetero atoms selected from the group of 0 to 2 nitrogen atoms, 0 or 1 oxygen atom and 0 or 1 sulfur atom, n is an integer selected from 0 to 2, m is an integer selected from 0 to 2, R is halogen atom, substituted or unsubstituted alkyl group, substituted or unsubstituted cycloalkyl group, substituted or unsubstituted alkoxy group, or substituted or unsubstituted amino group, and when n is 2, R(s) may be the same or different, $X^1$ is oxygen atom, sulfur atom, $NR^1$ (wherein $R^1$ is hydrogen atom or alkyl group) or a single bond, $Y^1$ is a single bond, alkylene which may be substituted by oxo group, or divalent group of the formula below:

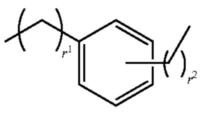

(wherein $r^1$ and $r^2$ are independently an integer selected from 1 to 3), $Y^2$ is a single bond, alkylene optionally substituted by hydroxy group or oxo group, oxyalkylene, cycloalkylene, oxycycloalkylene, divalent group of a monocyclic hetero ring containing 1 or 2 hetero atoms selected from the group consisting of 1 or 2 nitrogen atoms wherein said nitrogen atom may be substituted, oxygen atoms and sulfur atoms wherein said sulfur atom(s) may be oxidized by 1 to 2 oxygen atoms, or divalent group of the formula below:

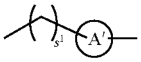

(wherein A is cycloalkylene, $s^1$ is an integer selected from 1 to 3),

Z is alkylene, $Q^1$ is hydrogen atom, halogen atom, hydroxy group, alkoxy group, or a group selected from the group consisting of Substituents illustrated below, $Q^2$ is a group selected from the group consisting of Substituents illustrated below, $R^{10}$ or $R^{11}$ in $Q^2$ may be taken with R to form a 9 to 14 membered fused bi or tricyclic ring together with the adjacent Ring A, when m is 0, $Q^1$ is a group selected from the group consisting of Substituents illustrated below, Substituents: —$COOR^{10}$; —$COSR^{10}$; —$OCOOR^{10}$; —$OCOR^{10}$; —$CONR^{11}R^{12}$; —$OCONR^{11}R^{12}$ (wherein $R^{10}$ is substituted or unsubstituted alkyl group, substituted or unsubstituted cycloalkyl group, substituted or unsubstituted alkeny group, substituted or unsubstituted cycloalkeny group, or substituted or unsubstituted alkynyl group, $R^{11}$ and $R^{12}$ are independently hydrogen atom, substituted or unsubstituted alkyl group, substituted or unsubstituted cycloalkyl group, substituted or unsubstituted alkeny group, substituted or unsubstituted cycloalkeny group, or substituted or unsubstituted alkynyl group, or $R^{11}$ and $R^{12}$ may be taken together to form with the adjacent nitrogen atom a 5 to 7 membered heterocycle containing a nitrogen atom(s));

and any group selected from the following formulas (3)~(6):

(3)

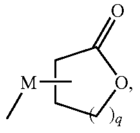

(4)

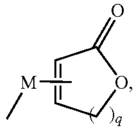

-continued (5)

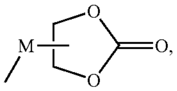

(6)

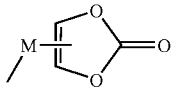

(wherein M is a single bond, oxygen atom or sulfur atom, and q is an integer selected from 1 to 3), and when m is 2, $(Y^2\text{-}Q^2)$(s) may be the same or different, or a pharmaceutically acceptable salt thereof as an active ingredient;

[2] The topically administrable medicament containing an adenine compound described in the above [1], wherein in the general formula (1), at least one of $Q^1$ and $Q^2$ is —$COOR^{10}$, —$COSR^{10}$, —$OCOR^{10}$, —$OCOOR^{10}$ or —$CONR^{11}R^{12}$;

[3] The topically administrable medicament containing an adenine compound described in the above [1] or [2]: wherein in the general formula (1), the substituent(s), by which alkyl group, alkeny group or alkynyl group in $R^{10}$, $R^{11}$ and $R^{12}$ is substituted, are the same or different and at least one substituent selected from the group consisting of halogen atom, hydroxy group, substituted or unsubstituted alkoxy group, substituted or unsubstituted amino group, substituted or unsubstituted aryl group, and substituted or unsubstituted heterocyclic group;

[4] The topically administrable medicament containing an adenine compound described in any one of the above [1] to [3]: wherein in the general formula (1), Z is methylene and Ring A is benzene;

[5] The topically administrable medicament containing an adenine compound described in the above [4]: wherein in the general formula (1), $Y^1$ is $C_{1-5}$ alkylene, $Q^1$ is hydrogen atom, hydroxy group or alkoxy group, $Y^2$ is a single bond, and $Q^2$ is —$COOR^{10}$;

[6] The topically administrable medicament containing an adenine compound described in the above [5]: wherein in the general formula (1), Z is methylene, Ring A is benzene, $R^{10}$ is alkyl group substituted by hydroxy group, amino group, alkylamino group or dialkylamino group, and m is 1;

[7] The topically administrable medicament containing an adenine compound described in the above [4]: wherein in the general formula (1), $Y^1$ is $C_{1-5}$ alkylene, $Q^1$ is hydrogen atom, hydroxy group or alkoxy group, $Y^2$ is $C_{1-3}$ alkylene, $Q^2$ is —$COOR^{10}$, and m is 1;

[8] The topically administrable medicament containing an adenine compound described in the above [4]: wherein in the general formula (1), m is 0, $Y^1$ is $C_{1-6}$ alkylene which may be substituted with oxo group, and $Q^1$ is —$COOR^{10}$, —$COSR^{10}$, —$OCOR^{10}$, —$OCOOR^{10}$, —$CONR^{11}R^{12}$ or —$OCONR^{11}R^{12}$;

[9] The topically administrable medicament containing an adenine compound described in any one of the above [1] to [8]: wherein in the general formula (1), and $X^1$ is oxygen atom, sulfur atom or $NR^1$ (wherein $R^1$ is hydrogen atom or alkyl group);

[10] The topically administrable medicament containing an adenine compound described in any one of the above [1] to [4]: wherein in the general formula (1), m is 0, $X^1$ is a single bond, $Y^1$ is $C_{1-4}$ alkylene which may be substituted by oxo group, and $Q^1$ is —$COOR^{10}$;

[11] The topically administrable medicament containing an adenine compound described in any one of the above [1] to [10]: wherein in the general formula (1), the limitation is either 1) or 2) below:

1) n is 0;

2) n is 1 or 2, and R is alkyl group, alkoxy group or halogen atom;

[12] The adenine compound or its pharmaceutically acceptable salt described in the above [1]: wherein in the general formula (1), at least one of $Q^1$ and $Q^2$ is a substituent selected from the following formulae (3)~(6):

(3)

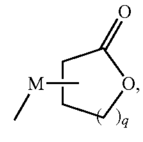

(4)

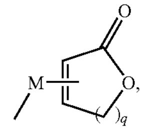

(5)

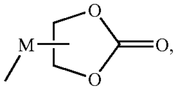

(6)

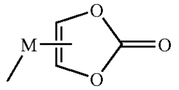

(M is a single bond, oxygen atom or sulfur atom, and q is an integer selected from 1 to 3);

[13] The adenine compound or its pharmaceutically acceptable salt described in the above [1]: wherein in the general formula (1), at least one of $Q^1$ and $Q^2$ is —$COSR^{10}$, —$OCOOR^{10}$, —$OCOR^{10}$ or —$OCONR^{11}R^{12}$ (wherein, $R^{10}$, $R^{11}$ and $R^{12}$ are the same as defined in [1]);

[14] The adenine compound or its pharmaceutically acceptable salt described in the above [1]: wherein in the general formula (1), Q is —$COOR^{20}$ ($R^{20}$ is substituted or unsubstituted alkeny group or substituted or unsubstituted alkynyl group);

[15] The adenine compound or its pharmaceutically acceptable salt described in the above [1]: wherein in the general formula (1), $Q^1$ is —$CONR^{21}R^{22}$ ($R^{21}$ and $R^{22}$ are independently, substituted or unsubstituted alkeny group or substituted or unsubstituted alkynyl group, or $R^{21}$ and $R^{22}$ are taken together to form with the adjacent nitrogen atom a 5 to 7 membered heterocyclic ring containing a nitrogen atom represented by the formula (2):

(2)

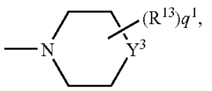

wherein $Y^3$ is a single bond, methylene, oxygen atom, sulfur atom, SO, $SO_2$, $NR^{14}$ (wherein $R^{14}$ is hydrogen atom, $C_{1-4}$ alkyl group, $C_{2-4}$ alkylcarbonyl group, $C_{2-4}$ alkoxycarbonyl group or $C_{1-4}$ alkylsulfonyl group), $q^1$ is an integer selected from 0 to 4, and $R^{13}$ is hydroxy group, carboxy group, $C_{1-4}$ alkyl group, $C_{1-4}$ alkoxy group or $C_{2-4}$ alkoxycarbonyl group;

[16] The adenine compound or its pharmaceutically acceptable salt described in the above [1]: wherein in the general formula (1), Z is methylene, and Ring A is naphthalene;

[17] The adenine compound or its pharmaceutically acceptable salt described in the above [1]: wherein in the general formula (1), Z is methylene, Ring A is a 5 to 10 membered mono or bicyclic hetero ring containing 1 to 3 heteroatoms selected from the group consisting of 0 to 2 nitrogen atoms, 0 or 1 oxygen atom, and 0 or 1 sulfur atom;

[18] The adenine compound or its pharmaceutically acceptable salt described in the above [17]: wherein in the general formula (1) in the above [1], the heteroaromatic ring in Ring A is furan, thiophene, or pyridine;

[19] The adenine compound or its pharmaceutically acceptable salt described in any one of the above described [16] to [18]: wherein in the general formula (1) in the above [1], $Q^1$ is hydrogen atom, hydroxy group or alkoxy group, $Y^1$ is $C_{1-5}$ alkylene, $Q^2$ is —$COOR^{10}$ (wherein $R^{10}$ is the same as defined in claim 1), and m is 1;

[20] The adenine compound or its pharmaceutically acceptable salt described in the above [19]: wherein in the general formula (1) in the above [1], $Y^2$ is a single bond;

[21] The adenine compound, its tautomer or its pharmaceutically acceptable salt described in any one of the above described [16] to [18]: wherein in the general formula (1) in the above [1], m is 0, $Y^1$ is $C_{1-6}$ alkylene which may be substituted by oxo group, and $Q^1$ is —$COOR^{10}$, —$COSR^{10}$, —$OCOR^{10}$, —$OCOOR^{10}$, —$CONR^{11}R^{12}$ or —$OCONR^{11}R^{12}$ (wherein $R^{10}$, $R^{11}$ and $R^{12}$ are the same as defined in [1]);

[22] The adenine compound or its pharmaceutically acceptable salt described in the above [1]: wherein in the general formula (1), $Y^2$ is alkylene or oxyalkylene, and $Q^2$ is —$COSR^{10}$ or —$CONR^{11}R^{12}$ ($R^{10}$, $R^{11}$, and $R^{12}$ is the same as defined in [1]);

[23] The adenine compound or its pharmaceutically acceptable salt described in the above [1]: wherein in the general formula (1), $Y^2$ is divalent group of a saturated monocyclic heteroring containing 1~2 hetero atoms selected from substituted or unsubstituted 1~2 nitrogen atoms, oxygen atoms and sulfur atoms (said sulfur atom may be oxidized by 1 or 2 oxygen atoms);

[24] The adenine compound or its pharmaceutically acceptable salt described in the above [23]: wherein divalent group of the saturated monocyclic heteroring is piperazin-1,4-diyl;

[25] The adenine compound or its pharmaceutically acceptable salt described in the above [23] or [24]: wherein in the general formula (1), $Q^2$ is —$COOR^{10}$ (wherein $R^{10}$ is the same as defined in [1]);

[26] The adenine compound or its pharmaceutically acceptable salt described in any one of the above [12] to [25], wherein in the general formula (1), the substituent(s) by which alkyl group, alkeny group or alkynyl group in $R^{10}$, $R^{11}$, $R^{12}$, $R^{20}$, $R^{21}$ and $R^{22}$ is substituted, are at least one substituent selected from the group consisting of halogen atom, hydroxy group, substituted or unsubstituted alkoxy group, substituted or unsubstituted amino group, substituted or unsubstituted aryl group, and substituted or unsubstituted heterocyclic group;

[27] The adenine compound or its pharmaceutically acceptable salt described in any one of the above [12] to [25], wherein R is hydrogen atom, alkyl group, alkoxy group, or halogen atom;

[28] The adenine compound or its pharmaceutically acceptable salt described in the above [1], wherein in the general formula (1), Z is methylene, Ring A is benzene, $Q^1$ is hydrogen atom, hydroxy group or alkoxy group, $Y^1$ is $C_{1-5}$ alkylene, $Y^2$ is a single bond, $Q^2$ is —$COOR^{23}$ (wherein $R^{23}$ is alkyl group substituted by amino group, alkylamino group or dialkylamino group), and m is 1;

[29] The adenine compound or its pharmaceutically acceptable salt described in the above [1], wherein in the general formula (1), Z is methylene, Ring A is benzene, $Q^1$ is hydrogen atom, hydroxy group or alkoxy group, $Y^1$ is $C_{1-5}$ alkylene, $Y^2$ is a single bond, and $Q^2$ is —$COSR^{24}$ (wherein $R^{24}$ is hydroxy group or alkyl group which is substituted by substituted or unsubstituted amino group);

[30] The adenine compound or its pharmaceutically acceptable salt described in the above [1], wherein in the general formula (1), Z is methylene, Ring A is benzene, $Q^1$ is hydrogen atom, hydroxy group or alkoxy group, $Y^1$ is $C_{1-5}$ alkylene, $Y^2$ is a single bond, and $Q^2$ is —$CONR^{25}R^{26}$ (wherein $R^{25}$ is hydrogen atom, alkyl group, alkeny group, or alkynyl group, and $R^{26}$ is hydroxy group, or alkyl group which is substituted by substituted or unsubstituted amino group);

[31] The adenine compound or its pharmaceutically acceptable salt described in any one of the above [12] to [30], wherein in the general formula (1), $X^1$ is oxygen atom, sulfur atom or $NR^1$ ($R^1$ is hydrogen atom or alkyl group);

[32] A medicament containing the adenine compound or its pharmaceutically acceptable salt described in any one of the above [12] to [30] as an active ingredient;

[33] A pharmaceutical composition containing the adenine compound or its pharmaceutically acceptable salt described in any one of the above [12] to [31] as an active ingredient;

[34] An immunoregulating agent containing the adenine compound or its pharmaceutically acceptable salt described in any one of the above [12] to [31] as an active ingredient;

[35] A prophylactic or therapeutic agent for viral diseases containing the adenine compound or its pharmaceutically acceptable salt described in any one of the above [12] to [31] as an active ingredient;

[36] A prophylactic or therapeutic agent for allergic diseases containing the adenine compound or its pharmaceutically acceptable salt described in any one of the above [12] to [31] as an active ingredient;

[37] A prophylactic or therapeutic agent for allergic diseases described in [36] wherein the disease is asthma or atopic dermatosis;

[38] A prophylactic or therapeutic agent for cancer diseases containing the adenine compound or its pharmaceutically acceptable salt described in any one of the above [12] to [31] as an active ingredient;

[39] A topically administrable preparation containing the adenine compound or its pharmaceutically acceptable salt described in any one of the above [12] to [31] as an active ingredient;

[40] The topically administrable preparation described in any one of the above [1] to [11], wherein the preparation is a prophylactic and therapeutic agent for viral diseases, dermal diseases or allergic diseases;

[41] The topically administrable preparation described in the above [40] wherein the allergic disease is asthma;

[42] The topically administrable preparation described in the above [40] wherein the allergic disease is atopic dermatosis;

[43] The topically administrable preparation described in any one of the above [1] to [11], and [39] to [42] wherein the half-life in serum on the compound of the general formula (1) is less than 1 hour;

[44] The topically administrable preparation described in any one of the above [1] to [11], and [39] to [42] wherein the half-life in liver S9 on the compound of the general formula (1) is less than 1 hour;

[45] The topically administrable preparation described in any one of the above [1] to [11], and [39] to [42] wherein the interferon concentration in serum is less than 10 IU/ml after said compound is topically administered;

and

[46] The topically administrable preparation described in any one of the above [1] to [11], and [39] to [42] wherein the preparation is an inhalation formulation.

The mode of the present invention is described in detail below.

"Halogen" includes fluorine atom, chlorine atom, bromine atom and iodine atom, especially preferably fluorine atom and chlorine atom.

"Alkyl group" includes $C_{1-10}$ straight or branched alkyl group, such as methyl group, ethyl group, propyl group, 1-methylethyl group, butyl group, 2-methylpropyl group, 1-methylpropyl group, 1,1-dimethylethyl group, pentyl group, 3-methylbutyl group, 2-methylbutyl group, 2,2-dimethylpropyl group, 1-ethylpropyl group, 1,1-dimethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, heptyl group, 1-methylhexyl group, 1-ethylpentyl group, octyl group, 1-methylheptyl group, 2-ethylhexyl group, nonyl group, decyl group, etc., preferably $C_{1-6}$ alkyl group, more preferably $C_{1-4}$ alkyl group.

Alkyl moiety in "alkylcarbonyl group", "alkylsulfonyl group", "alkylamino group" and "dialkylamino group" includes the same as the above alkyl group. Two alkyl moieties in the above dialkylamino group may be the same or different.

"Cycloalkyl group" includes a 3 to 8 membered mono cycloalkyl group, such as cyclopropyl group, cyclobutyl group, cyclopentyl group, cycloheptyl group, cyclooctyl group, etc.

"Alkoxy group" includes $C_{1-10}$ straight or branched alkoxy group, such as methoxy group, ethoxy group, propoxy group, 1-methylethoxy group, butoxy group, 2-methylpropoxy group, 1-methylpropoxy group, 1,1-dimethylethoxy group, pentoxy group, 3-methylbutoxy group, 2-methylbutoxy group, 2,2-dimethylpropoxy group, 1-ethylpropoxy group, 1,1-dimethylpropoxy group, hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, heptyloxy group, 1-methylhexyloxy group, 1-ethylpentyloxy group, octyloxy group, 1-methylheptyloxy group, 2-ethylhexyloxy group, nonyloxy group, decyloxy group, etc., preferably $C_{1-6}$ alkoxy group, more preferably $C_{1-4}$ alkoxy group.

Alkoxy moiety in "alkoxycarbonyl group" is the same as in the above alkoxy group.

"Alkenyl group" includes, $C_{2-8}$ straight or branched alkenyl group having 1 to 3 double bonds, such as ethenyl group, 1-propenyl group, 2-propenyl group, 1-methylethenyl group, 1-butenyl group, 2-butenyl group, 3-butenyl group, 2-methyl-2-propenyl group, 1-pentenyl group, 2-pentenyl group, 4-pentenyl group, 3-methyl-2-butenyl group, 1-hexenyl group, 2-hexenyl group, 1-octenyl group, etc., preferably $C_{2-4}$ alkeny group.

"Cycloalkeny group" includes a 3 to 8 membered monocycloalkeny group having 1 or 2 double bonds, such as cyclobutenyl group, cyclopentenyl group, cyclopentadienyl group, cyclohexenyl group, cyclohexadienyl group, cycloheptenyl group, cycloheptadienyl group, cyclooctenyl group, etc.

"Alkynyl group" includes $C_{2-8}$ straight or branched alkynyl group having 1 or 2 triple bonds, such as ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 5-pentynyl group, 1-methyl-3-butynyl group, 1-hexynyl group, 2-hexynyl group, etc., preferably $C_{2-4}$ alkynyl group.

"Aryl group" includes phenyl group, 1-naphthyl group or 2-naphthyl group.

"Heterocyclic group" includes a heteroaromatic group or an aliphatic heterocyclic group.

"The heteroaromatic group" includes a 5 to 10 membered mono or bicyclic heteraromatic group containing 1 to 3 hetero atoms selected from 0 to 3 nitrogen atoms, 0 or 1 oxygen atom, and 0 or 1 sulfur atom, such as furyl group, thienyl group, pyrrolyl group, pyridyl group, indolyl group, isoindolyl group, quinolyl group, isoquinolyl group, pyrazolyl group, imidazolyl group, pyrimidinyl group, pyrazinyl group, pyridazinyl group, thiazolyl group, oxazolyl group, etc. The binding position on said heteroaromatic group is not limited and said heteroaromatic group may be bound via an optional carbon atom or nitrogen atom thereof.

"The aliphatic heterocyclic group" includes a 5 to 8 membered monocyclic aliphatic heterocyclic group containing 1 to 3 hetero atoms selected from 0 to 3 nitrogen atoms, 0 or 1 oxygen atom, and 0 or 1 sulfur atom, such as pyrrolidinyl group, piperazinyl group, piperidinyl group, morpholinyl group, thiomorpholinyl group, 1-oxothiomorpholinyl group, 1,1-dioxothiomorpholinyl group, etc. The binding position on said aliphatic heterocyclic group is not limited and said aliphatic heterocyclic group may be bound via an optional carbon atom or nitrogen atom thereof.

"Alkylene" includes $C_{1-6}$ straight or branched alkylene, such as, methylene, ethylene, trimethylene, tetramethylene, pentamethylene, hexamethylene, 1-methylmethylene, 1-ethylmethylene, 1-propylmethylene, 1-methylethylene, 2-methylethylene, 1-methyltrimethylene, 2-methyltrimethylene, 2-methyltetramethylene, 3-methylpentamethylene, etc.

"Oxyalkylene" includes $C_{1-6}$ straight or branched oxyalkylene, such as a divalent group shown as $—OCH_2—$, $—O(CH_2)_2—$, $—O(CH_2)_3—$, $—O(CH_2)_4—$, $—O(CH_2)_5—$, $—O(CH_2)_6—$, $—OCH(CH_3)—$, $—OCH(CH_2CH_3)—$, $—O—CH(CH_2CH_2CH_3)—$, $—OCH(CH_3)CH_2—$, $—OCH_2CH(CH_3)—$, $—OCH(CH_3)CH_2CH_2—$, $—OCH_2CH(CH_3)CH_2—$, $—OCH_2CH(CH_3)CH_2CH_2—$, or $—OCH_2CH_2CH(CH_3)CH_2CH_2—$.

"Cycloalkylene" includes a 4 to 7 membered monocyclic cycloalkylene, such as 1,3-cyclobutandiyl, 1,3-cyclopentandiyl, 1,3-cyclohexandiyl, 1,4-cyclohexandiyl, 1,3-cycloheptandiyl, 1,5-cycloheptandiyl, etc.

"Oxycycloalkylene" includes oxy a 4 to 7 membered monocyclic alkylene, such as a divalent group selected from the following formulas (7)~(9):

(7)

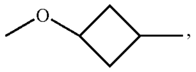

(8)

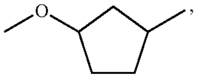

(9)

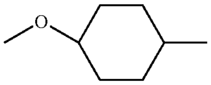

"A 6 to 10 membered mono or bicyclic aromatic hydrocarbon ring" in Ring A includes benzene ring or naphthalene ring.

"A 5 to 10 membered monocyclic or bicyclic heteroaromatic ring containing 1 to 3 hetero atoms selected from 0 to 2 nitrogen atoms, 0 or 1 oxygen atom and 0 or 1 sulfur atom" in Ring A includes pyrrole ring, pyridine ring, furan ring, thiophene ring, pyrimidine ring, pyridazine ring, pyrazine ring, triazine ring, indole ring, benzofuran ring, benzothiophene ring, benzimidazole ring, benzothiazole ring, quinoline ring, quinazoline ring, purine ring, etc., preferably pyridine ring, furan ring and thiophene ring.

"The divalent group of a monocyclic 5 to 7 membered saturated heterocycle containing 1 or 2 hetero atoms selected from 1 or 2 nitrogen atoms, oxygen atom, and sulfur atom (said sulfur atom may be oxidized by 1 or 2 oxygen atoms)" in $Y^2$ includes pyrrolidindiyl group, piperidindiyl group, piperazindiyl group, morpholindiyl group, thiomorpholindiyl group, 1-oxothiomorpholindiyl group, 1,1-dioxothiomorpholindiyl group, etc. and the ring may bind via an optional carbon atom or nitrogen atom with the adjacent Ring A and $Q^2$. Preferable divalent groups of said saturated heterocycle containing a nitrogen atom(s) are 1,3-pyrrolidindiyl group, 1,4-piperazindiyl group, 1,3-piperazindiyl group, 1,4-piperidindiyl group, 1,3-piperidindiyl group, 2,4-morpholindiyl group, 2,4-thiomorpholindiyl group, 1-oxo-2,4-thiomorpholindiyl group, 1,1-dioxo-2,4-thiomorpholindiyl group, etc.

The substituent by which alkyl group, cycloalkyl group, or alkoxy group is substituted in R includes halogen atom, hydroxy group, alkoxy group, amino group, alkylamino group, dialkylamino group, etc. The substituent(s) are the same or different and the number of the substituent(s) are 1 or plural, preferably 1 to 5. The substituent(s) include chlorine atom, fluorine atom, methoxy group, ethoxy group, propoxy group, dimethylamino group, ethylamino group, etc.

Alkyl group in R includes preferably $C_{1-3}$ alkyl group, such as methyl group, ethyl group, propyl group, 1-methylethyl group, etc. Substituted alkyl group in R includes preferably, trifluoromethyl group, 2,2,2-trifluoroethyl group, 2-methoxyethyl group, 2-hydroxyethyl group, 2-dimethylaminoethyl group, etc. Alkoxy group in R includes preferably $C_{1-3}$ alkoxy group, such as methoxy group, ethoxy group, propoxy group, 1-methylethoxy group. Substituted alkoxy group in R includes preferably trifluoromethoxy group, 2,2,2-trifluoroethoxy group, 2-methoxyethoxy group, 2-hydroxyethoxy group, 2-dimethylaminoethoxy group, etc.

The substituents of the substituted amino group in R include alkyl group, alkyl group substituted by hydroxy group, or alkyl group substituted by alkoxy group. The substituent(s) are the same or different, and the number of the substituent(s) is 1 or 2. The substituent(s) include methyl group, ethyl group, propyl group, 1-methylethyl group, 2-ethoxyethyl group, 2-hydroxyethyl group, 2-ethoxyethyl group, etc. Two substituents of the substituted amino group in R may be taken together to form with the adjacent carbon atom a 5 to 7 membered heterocycle containing a nitrogen atom(s), and said heterocycle containing a nitrogen atom(s) includes the same rings as in the heterocycle containing a nitrogen atom(s) which $R^{11}$ and $R^{12}$ are taken to form, as mentioned below. Examples thereof are pyrrolidine, N-methylpiperazine, piperidine, morpholine, etc.

Alkylene in $Y^1$ includes preferably $C_{1-3}$ alkylene, such as methylene, methylmethylene, ethylene, 1-methylethylene, 2-methylethylene, trimethylene, etc.

Alkylene substituted by oxo group in $Y^1$ means divalent group in which an optional methylene constituting of the alkylene is substituted by carbonyl group, and includes preferably $—COCH_2—$, $—CH_2COCH_2—$, and $—CH_2CO—$.

Alkylene in $Y^2$ includes, preferably $C_{1-3}$ alkylene, such as methylene, ethylene, trimethylene, etc.

Alkylene substituted by hydroxy group or oxo group in $Y^2$ means a divalent group in which an optional methylene constituting of the alkylene is substituted by hydroxy group or carbonyl group, and includes preferably, $—CHOHCH_2—$, $—CH_2CHOHCH_2—$, $—CH_2CHOH—$, $—COCH_2—$, $—CH_2COCH_2—$, and $—CH_2CO—$.

Oxyalkylene in $Y^2$ includes a divalent group, preferably, such as $—OCH_2—$, $—O(CH_2)_2—$, or $—O(CH_2)_3—$ and the oxygen atom in said divalent group is bound to Ring A.

When $Y^2$ is divalent group of the following formula:

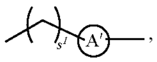

it may bind in the optional direction.

Alkylene in Z includes preferably $C_{1-3}$ alkylene, such as methylene, methylmethylene, etc.

Alkoxy group in $Q^1$ includes preferably, straight or branched $C_{1-4}$ alkoxy group, such as methoxy group, ethoxy group, propoxy group, etc.

When $Q^1$ or $Q^2$ is a substituent group selected from the group consisting of the following groups:

$—COOR^{10}$; $—COSR^{10}$; $—OCOOR^{10}$; $—OCOR^{10}$; $—CONR^{11}R^{12}$; $—OCONR^{11}R^{12}$ (wherein, $R^{10}$, $R^{11}$ and $R^{12}$ are the same as defined above); and a group selecting from the group of the following formulas (3)~(6):

(3)

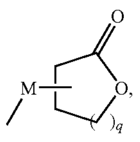

(4)

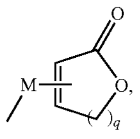

(5)

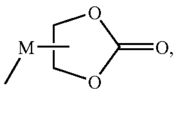

-continued (6)

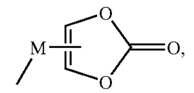

wherein M and q are the same as defined above, the substituent group by which alkyl group, alkeny group, alkynyl group, cycloalkyl group or cycloalkeny group in $R^{10}$, $R^{11}$ and $R^{12}$ is substituted includes halogen atom, hydroxy group, substituted or unsubstituted alkoxy group, substituted or unsubstituted amino group, substituted or unsubstituted aryl group, or substituted or unsubstituted heteroaromatic group, etc. The substituents are the same or different and the number of the substituent(s) is 1 or plural, preferably 1 to 5.

The substituent group of the above mentioned substituted amino group includes alkyl group, alkyl group substituted by hydroxy group, or alkyl group substituted by alkoxy group. The substituent(s) are the same or different and the number of the substituent(s) is 1 or 2. Said two substituents may be taken to form with the adjacent nitrogen atom a 5 to 7 membered heterocycle containing a nitrogen atom(s). Said heterocycle containing a nitrogen atom(s) includes the same rings as in the heterocycle containing a nitrogen atom(s) which $R^{11}$ and $R^{12}$ are taken to form, as mentioned below.

The aryl group mentioned above includes phenyl group, 1-naphthyl group, and 2-naphthyl group. The heteroaromatic group mentioned above includes 2-pyridyl group, 3-pyridyl group, 4-pyridyl group, 2-furyl group, 3-furyl group, etc.

The substituent group on the above substituted aryl group or the above substituted heteroaromatic group includes halogen atom such as chlorine atom, fluorine atom, etc.; hydroxy group; alkyl group such as methyl group, ethyl group, etc.; alkoxy group, such as methoxy group, ethoxy group, etc.; amino group; alkylamino group; dialkylamino group; alkyl group substituted by 1 to 3 halogen atoms such as trifluoromethyl group, etc.

The substituent group of the above substituted alkoxy group includes halogen atom, such as chlorine atom, fluorine atom, etc.; hydroxy group; alkoxy group, such as methoxy group, ethoxy group, propoxy group. etc.; substituted or unsubstituted aryl group; substituted or unsubstituted heteroaromatic group, etc. The substituent group of said aryl group or said heteroaromatic group is the same as the substituent of alkyl group, etc. in the above $R^{10}$, $R^{11}$, and $R^{12}$.

The 5 to 7 membered heterocycle containing a nitrogen atom(s) which $R^{11}$ and $R^{12}$ are taken to form with the adjacent nitrogen atom includes a 5 to 7 membered saturated heterocycle containing a nitrogen atom(s) containing 1 to 3 hetero atoms selected from 1 or 2 nitrogen atoms, 0 or 1 oxygen atom, and 0 or 1 sulfur atom and said sulfur atom may be oxidized by 1 or 2 oxygen atoms. Examples thereof are pyrrolidine, piperazine, piperidine, morpholine, thiomorpholine, 1-oxothiomorpholine, 1,1-dioxothiomorpholine, etc. and each of them may be substituted by hydroxy group, carboxy group, alkyl group, alkylcarbonyl group, alkylsulfonyl group, alkoxy group or alkoxycarbonyl group. Said heterocycle containing a nitrogen atom(s) includes preferably a saturated heterocycle containing a nitrogen atom(s) of the formula (2):

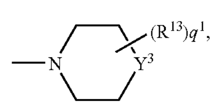

(2)

wherein $Y^3$ is a single bond, methylene, oxygen atom, sulfur atom, SO, $SO_2$, $NR^{14}$ (wherein $R^{14}$ is hydrogen atom, $C_{1-4}$ alkyl group, $C_{2-4}$ alkylcarbonyl group, $C_{2-4}$ alkoxycarbonyl group, or $C_{1-4}$ alkylsulfonyl group), $q^1$ is an integer selected from 0~4, and $R^{13}$ is hydroxy group, carboxy group, $C_{1-4}$ alkyl group, $C_{1-4}$ alkoxy group, or $C_{2-4}$ alkoxycarbonyl group.

$R^{10}$ is preferably substituted or unsubstituted straight or branched $C_{1-6}$ alkyl group. Said substituent includes halogen atom, hydroxy group, alkoxy group, substituted or unsubstituted aryl group, and substituted or unsubstituted amino group. Examples of $R^{10}$ are methyl group, ethyl group, propyl group, 1-methylethyl group, butyl group, 2-methylpropyl group, 1-methylpropyl group, 1,1-dimethylethyl group, 2,2-difluoroethyl group, 2,2,2-trifluoroethyl group, 2-hydroxyethyl group, 3-hydroxypropyl group, 2-methoxyethyl group, 2-ethoxyethyl group, 2-benzyloxyethyl group, 2-dimethylaminoethyl group, 2-morpholinoethyl group, etc.

$R^{11}$ and $R^{12}$ are preferably, substituted or unsubstituted straight or branched $C_{1-6}$ alkyl group. Said substituent group includes hydroxy group, alkoxy group, etc. Examples of $R^{11}$ and $R^{12}$ are methyl group, ethyl group, propyl group, 1-methylethyl group, butyl group, 2-methylpropyl group, 1-methylpropyl group, 1,1-dimethylethyl group, 2-hydroxyethyl group, 3-hydroxypropyl group, 2-methoxyethyl group, 2-ethoxyethyl group, etc. Furthermore, a 5 to 7 heterocycle containing a nitrogen atom(s) which $R^{11}$ and $R^{12}$ are taken to form with the adjacent nitrogen atom is one of preferable modes, such as pyrrolidine, piperazine, N-methylpiperazine, piperidine, morpholine, etc.

When $Q^1$ or $Q^2$ is an optional substitution group selected from the above substituent groups, it is preferably —$COOR^{10}$, —$COSR^{10}$, —$OCOOR^{10}$, or —$CONR^{11}R^{12}$, more preferably —$COOR^{10}$. In addition m is preferably 1.

The 9 to 14 membered bi or tricyclic fused ring which $R^{10}$ or $R^{11}$ are taken to form with the adjacent Ring A in $Q^2$ is preferably the group selected from the following formulas:

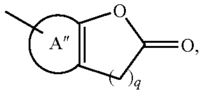

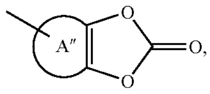

wherein Ring A" is the same as Ring A, and q is an integer selected from 1 to 3, more preferably the group of the following formulas:

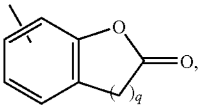

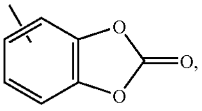

wherein q is the same as defined above.

The adenine compound of the present invention, according to the kinds of substituents, may include a tautomer, a geometrical isomer, a stereoisomer or a mixture thereof.

Namely when at least one asymmetrical carbon atom presents in a compound of the general formula (1), a diastereomer or an enantiomer exists and these isolated isomers or a mixture thereof are included in the present invention.

In addition, the adenine compound of the general formula (1) and its tautomer are chemically equivalent and the adenine compound of the present invention includes the tautomer. Said tautomer is illustratively an oxo compound of the general formula (1'):

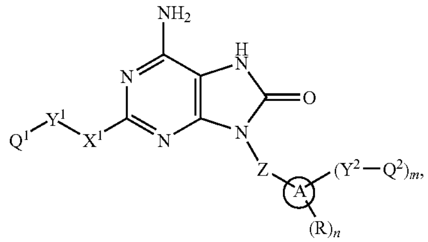

wherein Ring A, m, n, R, $X^1$, $Y^1$, $Y^2$, Z, $Q^1$, and $Q^2$ are the same as defined above.

The pharmaceutically acceptable salt includes acid addition salts or base addition salts. The acid addition salt includes for example, inorganic salts such as hydrochloride, hydrobromide, hydrosulfate, hydroiodide, nitrate, phosphate, etc., organic salts, such as citrate, oxalate, acetate, formate, propionate, benzoate, trifluoroacetate, maleate, tartarate, methanesulfonate, benzenesulfonate, para-toluenesulfonate, etc. The base addition salt includes inorganic base salts such as sodium salt, potassium salt, calcium salt, magnesium salt, ammonium salt, etc., organic base salts, such as triethylammonium salt, triethanolammonium salt, pyridinium salt, diisopropylammonium salt, and amino acid salts formed with basic or acidic amino acids such as arginine, aspartic acid, glutamic acid, etc. The compound of the general formula (1) may form a hydrate(s) or a solvate(s) with ethanol, etc.

The compound of the general formula (1) can be prepared by the following methods. The starting materials which are not described below are prepared in accordance with the method described below or the known methods described, for example, in WO 98/01448 or WO 99/28321 or in accordance with the known methods.

Process 1:

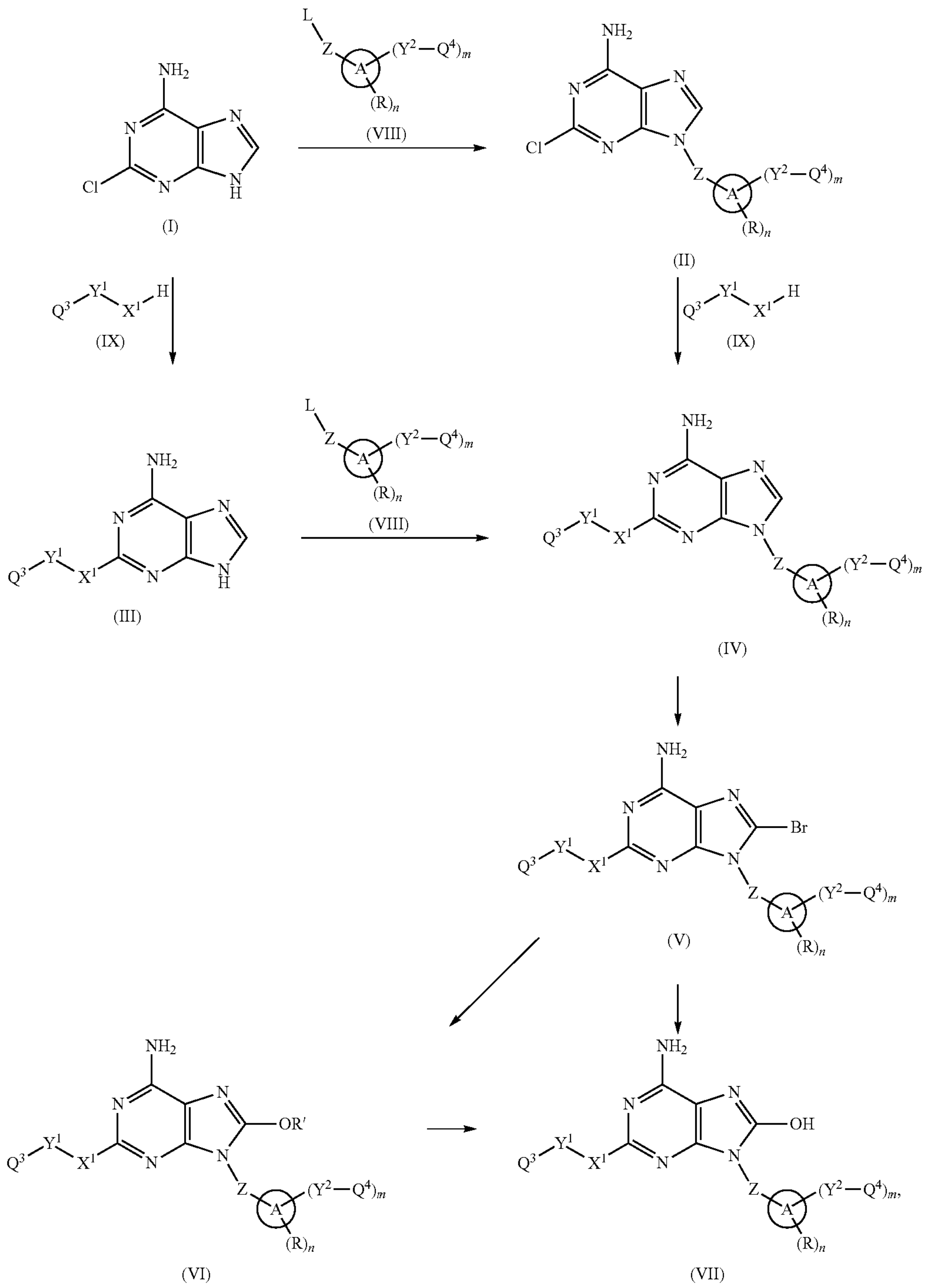

wherein in the above formulas, $Q^3$ is $Q^1$, or carboxy group, $Q^4$ is $Q^2$, carboxy group, or hydroxy group, L is a leaving group, and Ring A, m, n, R, $X^1$, $Y^1$, $Y^2$, Z, $Q^1$ and $Q^2$ are the same as defined above.

A compound (II) is obtained by reacting a compound (I) and a compound (VIII) in the presence of a base.

The base used in this reaction is an alkali metal carbonate such as sodium carbonate, potassium carbonate, etc., an alkaline earth metal carbonate such as calcium carbonate, etc., a metal hydroxide such as sodium hydroxide, potassium hydroxide, etc., a metal hydride such as sodium hydride, etc., or a metal alkoxide such as potassium t-butoxide, etc. The solvent used in this reaction is a halogenated hydrocarbon-solvent such as carbon tetrachloride, chloroform, methylene chloride, etc., an ether-solvent such as diethyl ether, tetrahydrofuran, 1,4-dioxane, etc., an aprotic solvent such as dimethylformamide, dimethyl sulfoxide, acetonitrile, etc. The reaction is carried out, for example at the range from about 0° C. to around boiling point of the solvent.

The compound (IV) is obtained by reaction a compound (II) and a compound (IX).

When $X^1$ is $NR^1$, the reaction is carried out in the presence or absence of a base. The base includes for example, an alkali metal carbonate such as sodium carbonate, potassium carbonate, etc., an alkaline earth metal carbonate such as calcium carbonate, etc., a metal hydroxide such as sodium hydroxide, potassium hydroxide, etc., an organic base such as triethylamine, diisopropylethylamine, 4-dimethylaminopyridine, etc. The solvent used in this reaction is an ether-solvent such as tetrahydrofuran, 1,4-dioxane, diglyme, etc., an alcohol-solvent such as propanol, butanol, etc., an aprotic solvent such as dimethylformamide, etc. The reaction may be carried out in the absence of a solvent. The reaction is carried out, for example at the range from about 50° C. to 200° C.

When $X^1$ is oxygen atom or sulfur atom, the reaction is carried out in the presence of a base. The base includes for example, an alkali metal such as sodium, potassium, etc., an alkali metal hydride such as sodium hydride, etc. The solvent used in this reaction is an ether-solvent such as tetrahydrofuran, 1,4-dioxane, diglyme, etc., an aprotic solvent such as dimethylformamide, dimethyl sulfoxide, etc. The reaction may be carried out in the absence of a solvent. The reaction is carried out, for example at the range from about 50° C. to 200° C.

Furthermore, in the step from a compound (I) to a compound (IV), first a compound (III) can be synthesized in the same manner as the above method and then the product (III) can be reacted with a compound (VIII) to give a compound (IV).

disulfide, etc. The reaction is carried out, for example at the range from about 0° C. to around boiling point of the solvent.

A compound (VI) is obtained by reacting a compound (V) with a metal alkoxide such as sodium methoxide, etc.

The solvent is an ether-solvent such as diethyl ether, tetrahydrofuran, 1,4-dioxane, etc., an aprotic solvent such as dimethylformamide, etc., an alcohol solvent such as methanol corresponding to the metal alkoxide used in this reaction and so on. The reaction is carried out, for example at the range of from room temperature to around boiling point of the solvent.

A compound (VII) is obtained by treating a compound (VI) or a compound (V) in an acidic condition.

The acid is for example, an inorganic acid such as hydrochloric acid, hydrobromic acid, sulfuric acid, etc., an organic acid such as trifluoroacetic acid, etc. The solvent is for example, water, a mixture of water and an organic solvent. Said organic solvent includes an ether-solvent such as diethyl ether, tetrahydrofuran, etc., an aprotic solvent such as dimethylformamide, acetonitrile, etc., an alcohol-solvent such as methanol, ethanol, etc. The reaction is carried out, for example at the range from room temperature to around boiling point of the solvent.

The compound wherein $X^1$ is a single bond in a compound of the general formula (1) can be prepared by the method described in the examples of the present specification. The intermediates corresponding to a compound (III) can be prepared in accordance with the method described in the above WO 98/01448.

Process 2

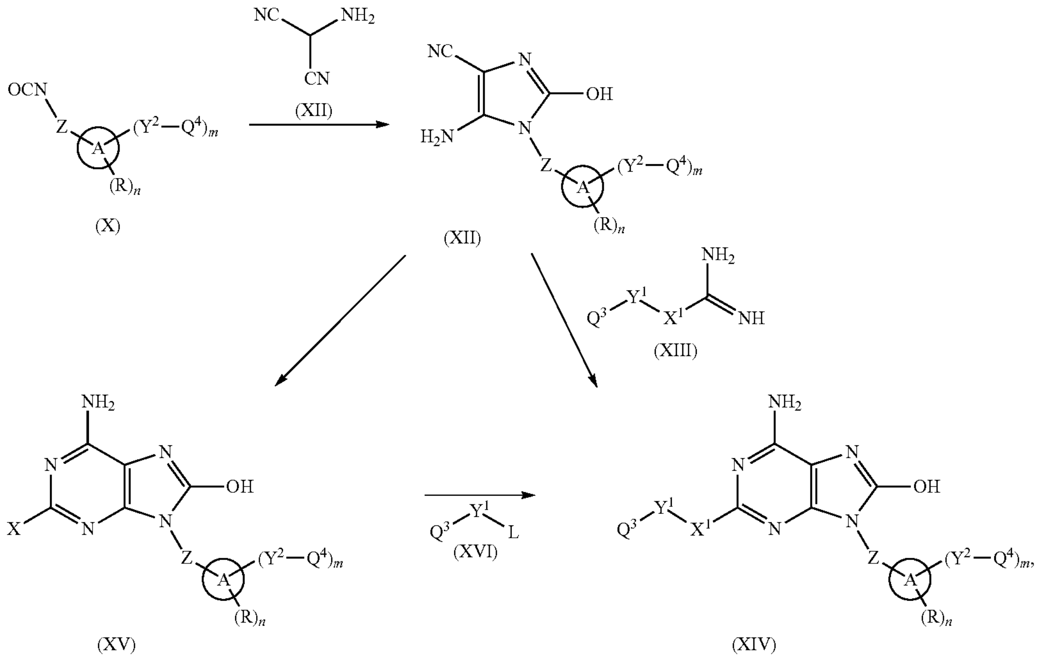

A compound (V) can be prepared by brominating a compound (IV). The brominating agent is bromine, hydrobromic acid perbromide, N-bromo succinimide, etc. Sodium acetate may be added as a reaction promoter in this reaction. The solvent is a halogenated hydrocarbon-solvent such as carbon tetrachloride, methylene chloride, dichloroethane, etc., an ether-solvent such as diethyl ether, etc., acetic acid, carbon wherein Ring A, m, n, R, $X^1$, $Y^1$, $Y^2$, Z, $Q^3$ and $Q^4$ are the same as defined above, X is amino group, hydroxy group, or mercapto group and L is a leaving group.

A compound (XII) is obtained by reacting a compound (X) and a compound (XI) in the presence of a base.

The base is for example, an alkali metal carbonate such as sodium carbonate, potassium carbonate, etc., an alkaline earth metal carbonate such as calcium carbonate, etc., a metal hydroxide, such as sodium hydroxide, potassium hydroxide, etc., an organic base such as triethylamine, diisopropylethylamine, pyridine, 4-dimethylaminopyridine, etc., a metal alkoxide such as sodium methoxide, etc. The solvent is for example, a halogenated hydrocarbon-solvent such as methylene chloride, etc., an ether-solvent such as diethyl ether, tetrahydrofuran, 1,4-dioxane, etc., an alcohol-solvent such as methanol, ethanol, etc., an aprotic solvent such as dimethylformamide, dimethyl sulfoxide, acetonitrile, etc. The reaction is carried out, for example at the range from about 0° C. to around boiling point of the solvent.

A compound (XIV) is obtained by reacting a compound (XII) and a compound (XIII) in the presence or absence of a base.

The base is for example, an inorganic base such as an alkali metal carbonate such as sodium carbonate, potassium carbonate, etc., an alkaline earth metal carbonate such as calcium carbonate, etc., a metal hydroxide such as sodium hydroxide, potassium hydroxide, etc., an organic base such as triethylamine, diisopropylethylamine, pyridine, 4-dimethylaminopyridine, etc., a metal alkoxide such as sodium methoxide, etc. The solvent used in this reaction are an ether-solvent such as tetrahydrofuran, 1,4-dioxane, diglyme, etc., an alcohol-solvent such as methanol, ethanol, etc., an aprotic solvent such as toluene, dimethylformamide, dimethyl sulfoxide, etc. The reaction may be carried out in the absence of a solvent. The reaction is carried out, for example at the range from room temperature to around boiling point of the solvent.

In the step from a compound (XII) to a compound (XIV), compound (XV) can be synthesized and the product (XV) can be reacted to give a compound (XIV).

A compound (XV) wherein X is amino group is obtained by reacting a compound (XII) and guanidine in the presence or absence of a base. The base is, for example, an alkali metal carbonate such as sodium carbonate, potassium carbonate, etc., an alkaline earth metal carbonate such as calcium carbonate, etc., a metal hydroxide, such as sodium hydroxide, potassium hydroxide, etc., an organic base such as triethylamine, diisopropylethylamine, pyridine, 4-dimethylaminopyridine, etc., a metal alkoxide such as sodium methoxide, etc. The solvent used in this reaction are an ether-solvent such as tetrahydrofuran, 1,4-dioxane, diglyme, etc., an alcohol-solvent such as methanol, ethanol, etc., an aprotic solvent such as toluene, dimethylformamide, dimethyl sulfoxide, etc. The reaction may be carried out in the absence of a solvent. The reaction is carried out, for example at the range from room temperature to around boiling point of the solvent.

A compound (XV) wherein X is hydroxy group is obtained by reacting a compound (XII) and urea in the presence or absence of a base. The base is, for example, an alkali metal carbonate such as sodium carbonate, potassium carbonate, etc., an alkaline earth metal carbonate such as calcium carbonate, etc., a metal hydroxide, such as sodium hydroxide, potassium hydroxide, etc., an organic base such as triethylamine, diisopropylethylamine, pyridine, 4-dimethylaminopyridine, etc., a metal alkoxide such as sodium methoxide, etc. The solvent used in this reaction is an ether-solvent such as tetrahydrofuran, 1,4-dioxane, diglyme, etc., an alcohol solvent such as methanol, ethanol, etc., an aprotic solvent such as toluene, dimethylformamide, dimethyl sulfoxide, etc. The reaction may be carried out in the absence of a solvent. The reaction is carried out, for example at the range from about room temperature to around boiling point of the solvent.

A compound (XV) wherein X is mercapto group is obtained by reacting a compound (XII) and benzoylisocyanate in the presence or absence of a base and then, subjecting the product to cyclization reaction. The base used in the reaction with benzoisocyanate is for example, an alkali metal carbonate such as sodium carbonate, potassium carbonate, etc., an alkaline earth metal carbonate such as calcium carbonate, etc., an organic base such as triethylamine, diisopropylethylamine, pyridine, 4-dimethylaminopyridine, etc. The solvent used in this reaction is a halogenated hydrocarbon such as methylene chloride, etc., an ether-solvent such as tetrahydrofuran, 1,4-dioxane, etc., an aprotic solvent such as dimethylformamide, dimethyl sulfoxide, etc. The reaction is carried out, for example at the range from about 0° C. to around boiling point of the solvent.

The base used in the cyclization reaction is an alkali metal hydroxide, such as sodium hydroxide, potassium hydroxide, etc., a metal alkoxide, such as sodium methoxide, potassium t-butoxide, etc. The solvent is an ether-solvent such as tetrahydrofuran, etc., an alcohol-solvent such as ethanol, 2-propanol, etc., an aprotic solvent such as, dimethylformamide, dimethyl sulfoxide, etc. The reaction is carried out, for example at the range from about room temperature to around boiling point of the solvent.

A compound (XIV) is obtained by reacting a compound (XV) and a compound (XVI) in the presence of a base.

The base is for example, an alkali metal hydrogencarbonate such as sodium hydrogencarbonate, etc., an alkali metal carbonate such as sodium carbonate, potassium carbonate, etc., an alkaline earth metal carbonate such as calcium carbonate, etc., a metal hydroxide, such as sodium hydroxide, potassium hydroxide, etc., a metal hydride such as sodium hydride, etc., an organic base such as triethylamine, diisopropylethylamine, pyridine, 4-dimethylaminopyridine, etc., a metal alkoxide such as potassium t-butoxide, etc. The solvent used in this reaction is a halogenated hydrocarbon such as carbon tetrachloride, chloroform, methylene chloride, etc., an ether-solvent such as diethyl ether, tetrahydrofuran, 1,4-dioxane, etc., an aprotic solvent such as, dimethylformamide, dimethyl sulfoxide, acetonitrile, etc. The reaction is carried out, for example from the range from about 0° C. to around boiling point of the solvent.

Process 3

When $Q^3$ or $Q^4$ is carboxy group or hydroxy group in the above general formulas (II)~(XVI), it can be converted to $Q^1$ or $Q^2$, respectively in the known method to the skilled person in the art or the similar method, for example, the method described in R. C. Larock "Comprehensive Organic Transformation (VCH Publishers, Inc, 1989)".

The reaction is concretely explained below.

(1) When $Q^1$ or $Q^2$ is —COOR$^{10}$:

After an intermediate of the compound of the present invention, namely a carboxylic acid is converted to an acid halide, the acid halide is reacted with $R^{10}$OH to give an ester. The halogenating agent is for example, thionyl chloride, phosphoryl chloride, phosphorus pentachloride, phosphorus trichloride, etc. The solvent is for example, a halogenated hydrocarbon such as carbon tetrachloride, chloroform, methylene chloride, etc., an ether-solvent such as diethyl ether, tetrahydrofuran, 1,4-dioxane, etc., an aprotic solvent such as, toluene, xylene, etc. The reaction is carried out, for example from the range from about 0° C. to around boiling point of the solvent. The base used in the esterification reaction is for example, an organic base such as triethylamine, diisopropylethylamine, pyridine, 4-dimethylaminopyridine, etc. The solvent is for example, a halogenated hydrocarbon such as methylene chloride, etc., an ether-solvent such as diethyl ether, tetrahydrofuran, etc., an aprotic solvent such as, dimethylformamide, dimethyl sulfoxide, etc. The reaction is carried out, for example from the range from about 0° C. to around boiling point of the solvent.

(2) When $Q^1$ or $Q^2$ is —$CONR^{11}R^{12}$:

After an intermediate of the compound of the present invention, namely a carboxylic acid is converted to an acid halide, the acid halide is reacted with $R^{11}R^{12}NH$ to give an amide. The caboxylic acid and $R^{11}R^{12}NH$ can be condensed to give the amide, too. The base used in the reaction with the acid halide is for example, an alkali metal carbonate such as sodium carbonate, potassium carbonate, etc., an alkaline earth metal carbonate such as calcium carbonate, etc., a metal hydroxide, such as sodium hydroxide, potassium hydroxide, etc., a metal hydride such as sodium hydride, etc., an organic lithium compound such as butyllithium, an organic base such as triethylamine, diisopropyl ethylamine, pyridine, 4-dimethylaminopyridine, etc. The solvent used in this reaction is a halogenated hydrocarbon such as methylene chloride, etc., an ether-solvent such as diethyl ether, tetrahydrofuran, etc., an aprotic solvent such as, dimethylformamide, dimethyl sulfoxide, etc. The reaction is carried out, for example at the range from about 0° C. to around boiling point of the solvent.

The condensation reaction may be carried out in the presence of an active esterification agent. The condensing agent is, for example, a carbodiimide compound such as 1-ethyl-3-(3-dimethylaminopropylcarbodiimide hydrochloride, dicyclohexylcarbodiimide, etc. The esterification agent is, for example, N-hydroxybenztriazole, N-hydroxysuccinimide, etc. The solvent is a halogenated hydrocarbon such as chloroform, methylene chloride, etc., an ether-solvent such as diethyl ether, tetrahydrofuran, etc., an aprotic solvent such as, dimethylformamide, dimethyl sulfoxide, etc. The reaction is carried out, for example at the range from about 0° C. to around boiling point of the solvent.

(3) When $Q^1$ or $Q^2$ is —$OCOOR^{10}$, —$OCOR^{10}$ or —$OCONR^{11}R^{12}$:

The intermediate of the compound of the present invention, namely a hydroxy group and $L^1COOR^{10}$, $L^1COR^{10}$, or $L^1CONR^{11}R^{12}$ (wherein $L^1$ is a leaving group, preferably halogen atom, $R^{10}$, $R^{11}$ and $R^{12}$ are the same as defined above) are reacted in the presence of a base to give a carbonate derivative, an acyl compound and a urethane derivative, respectively. The base is, for example, an organic base such as triethylamine, diisopropylethylamine, pyridine, 4-dimethylaminopyridine. The solvent is a halogenated hydrocarbon such as methylene chloride, etc., an ether-solvent such as diethyl ether, tetrahydrofuran, etc., an aprotic solvent such as dimethylformamide, dimethyl sulfoxide, etc. The reaction is carried out, for example, at the range from about 0° C. to around boiling point of the solvent.

(4) When $Q^1$ or $Q^2$ is any one of the formulas (3)~(6):

In case of the formula (3) or (4) being a lactone ring, said compound is prepared by treating a hydroxycarboxylic acid with an acid. The acid is an inorganic acid such as, hydrochloric acid, hydrobromic acid, sulfuric acid, etc., or an organic acid such as methanesulfonic acid, p-toluenesulfonic acid, etc. An acid anhydride such as acetic acid anhydride can be also used. The solvent is water, an organic solvent or a mixture of water and the organic solvent. The organic solvent is an ether-solvent such as diethyl ether, tetrahydrofuran, etc., an aprotic solvent such as benzene, acetonitrile, etc. The reaction is carried out, for example at the range from about room temperature to around boiling point of the solvent.

In case of the formula (5) or (6) being a cyclic carbonate, said compound is prepared by reacting a dihydroxy compound with tri phosgene in the presence of a base. The base is an organic base, such as triethylamine, diisopropylethylamine, pyridine, 4-dimethylaminopyridine, etc. The solvent is a halogenated hydrocarbon such as chloroform, methylene chloride, etc., an ether-solvent such as diethyl ether, tetrahydrofuran, etc., an aprotic solvent such as, benzene, toluene, etc. The reaction is carried out, for example at the range from about 0° C. to around boiling point of the solvent.

Any compound used in process 1 or 2 can use as a starting material in each step described in process 3 and each step described in process 3 may use any steps described in process 1 or 2, as long as it does not influence the reaction in the post process.

When the adenine compound of the present invention, its intermediate or its starting material has a functional group, the introduction of the substituent group or the conversion reaction into the functional group can be carried out in accordance of the conventional method known in the art, if necessary, in an appropriate step, namely a step in the middle of process 1 or 2. These methods are described in Jikken Kagaku Koza edited by Nippon Kagakukai, Maruzen, or Comprehensive Organic Transformations, by R. C. Lalock (VCH Publishers, Inc, 1989), etc. As the conversion reaction into the functional group, acylation or sulfonylation by using an acid halide, an sulfonyl halide, etc., alkylation by using an alkyl halide, etc., hydrolysis, Friedel-Crafts Reaction or C to C bond-formation reaction such as Wittig reaction, etc., oxidization or reduction reaction, etc. are illustrated.

Furthermore, when the compound of the present invention or the intermediate thereof has a functional group such as amino group, carboxy group, hydroxy group, oxo group, etc., the compound may be subjected to protection or deprotection reaction, if necessary. The preferable protecting groups, the protecting methods and the deprotecting methods are in detail explained in Protective Groups in Organic Synthesis 2nd Edition (John Wiley & Sons, Inc.; 1990) and so on.

The compound of the general formula (1) of the present invention and the intermediate for preparing it can be purified by the method known in the art such as column chromatography (e.g., silica gel chromatography, ion exchange chromatography), recrystallization, etc. The solvent for recrystallization includes an alcohol-solvent such as methanol, ethanol, 2-propanol, etc., an ether-solvent such as ethyl ether, etc., an ester-solvent such as ethyl acetate, etc., an aromatic hydrocarbon solvent such as benzene, toluene, etc., a ketone-solvent such as acetone, etc., a hydrocarbon-solvent such as hexane etc., an aprotic solvent such as dimethylformamide, acetonitrile, water or a mixture thereof. Other purification methods are explained in Jikken Kagaku Koza Vol. 1 (edited by Nippon Kagaku Kai, Maruzen).

The compound of the general formula (1) of the present invention which has one or more asymmetric centers can be prepared by the conventional method by using a starting material having an asymmetric carbon atom(s), or otherwise in a way of the process for the preparation by introducing the asymmetric center(s). For example, the enantiomer compound can be prepared by using an optically active compound as a starting compound or by optical resolution in an appropriate way of the process for the preparation. The optical resolution is carried out by the diastereomar method, namely by salt-forming the compound of the general formula (1) of the present invention or an intermediate thereof with an optically active acid such as a monocarboxylic acid (e.g., mandelic acid, N-benzyloxyalanine, lactic acid, etc.), a dicarboxylic acid (e.g., tartaric acid, o-diisopropylidene tartaric acid, malic acid, etc.), a sulfonic acid (e.g., camphorsulfonic acid, bromocamphorsulfonic acid, etc.) in an inert solvent such as an alcohol-solvent (e.g., methanol, ethanol, 2-propanol, etc.), an ether-solvent (e.g., diethyl ether, etc.), an ester solvent (e.g., ethyl acetate, etc.), a hydrocarbon-solvent (e.g., toluene, etc.), an aprotic solvent (e.g., acetonitrile, etc.), or a mixture thereof.

The compound of the general formula (1) of the present invention or an intermediate thereof which has an acidic functional group such as carboxy group, can be prepared by salt-forming with an optically active amine (an organic amine such as a-phenethylamine, kinin, quinidine, cinchonidine, cinchonine, strychnine, etc.).

The salt formation is carried out at the range from room temperature to the boiling temperature of the solvent. In order to promote the optical purity of the object compound, it is preferable to raise once the temperature to around the boiling point of the solvent. The yield can be raised by cooling the reaction mixture, if necessary, before filtrating a crystallized precipitate. The amount of the optically active acid or amine is preferably about 0.5 to about 2.0 moles per a substrate, more preferably around 1 mole. The precipitate is, if necessary, recrystallized from an inert solvent such as an alcohol-solvent (e.g., methanol, ethanol, 2-propanol, etc.), an ether-solvent (e.g., ethyl ether, etc.), an ester-solvent (e.g., ethyl acetate, etc.), a hydrocarbon-solvent (e.g., toluene, etc.), an aprotic solvent (e.g., acetonitrile, etc.), a mixture thereof to give an optically purified compound. Furthermore, if necessary, an optically resolved salt is treated with an acid or a base by the conventional method to give a free form.

The adenine compound of the present invention, and a tautomer thereof, or a pharmaceutically acceptable salt thereof shows interferon inducing activity, and/or IL-4 and IL-5 production suppressing activity, and therefore, is effective as a prophylactic or therapeutic agent for viral diseases, allergic diseases, or dermatosis. Furthermore, the adenine compound of the present invention, a tautomer thereof, or a pharmaceutically acceptable salt thereof is characterized in, when topically administered, showing an medical effect at the applied lesion, but in systematically showing none of the pharmacological activity because the compound is converted by an enzyme in vivo to other compound (degraded compound) having substantially reduced medical effect and therefore, is useful as a topically administered agent. The medical effect used herein means a pharmacological activity of the compound, such as interferon inducing activity, IL-4 production suppressing activity and/or IL-5 production suppressing activity, etc.

The medical effect of the degraded compound is preferably 10 times, more preferably 100 times, further more preferably 1000 times reduced comparing with that of the parent compound.

Said pharmacological activities can be evaluated by the conventional measuring method known in the art, preferably by the measuring method in vitro. For example, there are illustrated methods described in Method in ENZYMOLOGY (Academic press), etc. or the method by using the commercialized ELISA Kit (e.g., AN' ALYSA (Immunoassay System), etc.), or the method described in Example of the present specification, etc.

For example, by measuring interferon inducing activity with bioassay using cells of mouse spleen, the amount of each interferon induction (IU)/ml at the same concentration of the parent compound (the compound of the present invention) and the degraded compound can be compared. In addition, each concentration showing the definite amount of interferon production can be compared with the parent compound and its degraded compound, too.

As a pharmacological activity, the activity in vivo caused by interferon inducing activity, etc. is illustrated. Said activity in vivo includes immune activating activity, influenza-like symptom, etc. The immune activating activity includes the induction of cytotoxic activity such as NK cells, etc. The influenza-like symptom includes fever, etc. The fever means the rise of the body temperature of a mammalian, for example, in case of human, the fever means that the body temperature rises more than normal temperature. The topical administration method is not limited, and the administration is done in case of administration via nasal cavity, alveolus or air way, by aeration or inhalation, in case of administration to skin, by spreading on the skin, and in case of administration to eye, by eye dropping, etc. Preferable administration is done by aeration or inhalation.

It can be also confirmed that the compound of the present specification, when it is topically administered, is converted to a degraded compound in the blood, etc. in human or animal for example, by its half life in the serum or in liver S9 in vitro. The test method to determine the half life of the compound of the present invention in vitro is known.

The above "degraded compound" means a compound having carboxy group or hydroxy group which is prepared by hydrolyzing the amide bond or ester bond contained in the subsistent(s), $Q^1$ and/or $Q^2$ in the general formula (1).

The measuring method of the half life in liver S9 of the compound of the present invention is as follows:

The compound of the present invention is added to liver S9 solution, and the mixture is incubated at 37±0.5° C. for 5 minutes to 2 hours. By quantitatively analyzing at the definite interval the amount of the compound of the present invention remaining in the liver S9 solution with HPLC (high performance liquid chromatography), etc., the constant of quenching velocity is calculated and the half life is calculated. The liver S9 means the supernatant prepared by the liver of mammalian being homogenated in an aqueous solution, such as physiological saline, sucrose solution, KCl solution, etc., the homogenate being centrifuged at 9000×g and its supernatant fraction being collected. The aqueous solution is usually used 2 to 4 times as much as the amount of liver. The liver of human, dog, rabbit, guinea pig, rat, mouse, etc. are used. The liver S9 diluted with buffer, etc., if necessary can be used.

The measuring method of the half life in the serum of the compound of the present invention is as follows:

The compound of the present invention is added to the serum solution, and the mixture is incubated at 37±0.5° C. for 5 minutes to 2 hours. By quantitatively analyzing at the definite interval the amount of the compound of the present invention remaining in the serum solution with HPLC (high performance liquid chromatography), etc., the constant of quenching velocity calculated and the half life is calculated. The method described in Example is illustrated.

The serum herein means the supernatant fraction obtained by excluding hemocytes and blood coagulation factor from blood by centrifugation, etc. The serum diluted with buffer, etc. can be used.

The compound of the present invention is not limited as long as the compound is formed into the preparation for topical administration. The preparation is prepared by the conventional known method and the preparation may contain ordinal carriers, excipients, binders, stabilizers, buffer, solubilizing agents, isotonic agents, etc.

Examples of the preparation for topical administration are ointments, lotion, creams, gels, tapes, dermal patches, poultices, sprays, aerosols, or aqueous solutions/suspensions for spray used for inhalator or cartridge for insufflator, eye drops, nose drops, powders for topical administration, etc.

The ointments, creams and gels usually contain 0.01 to 10 w/w % of the compound of the present invention. An aqueous or oil base used in them may contain suitable viscosity-increasing agents and/or gelling agents and/or solvents. Said base includes for example, water and/or liquid paraffin or an oil such as squalane, various fatty acid esters, vegetable oils such as arachis oil, castor oil, animal oils such as squalene or polyethylene glycol. The viscosity-increasing agent and gelling agent include soft paraffin, aluminium stearate, cetostearyl alcohol, polyethylene glycol, sheep wool fat, beeswax, carboxy methylene and cellulose derivative and/or nonionic emulsifying agent such as glycerin monostearate.

The lotion usually contains 0.01 to 10 w/w % of the compound of the present invention and the lotion preparation may be formulated by an aqueous or oil base and may usually contain an emulsifying agent, a stabilizer, a dispersion agent, a suspension agent, or a viscosity-increasing agent.

The powder for external administration usually contains 0.01 to 10 w/w % of the compound of the present invention and may be made of suitable bases such as talc, lactose or starch.

The eye drop preparation may be formed by an aqueous or nonaqueous base and may contain a dispersing agent, a solubilizing agent, a suspending agent or a preservative.

The splay may be formed into an aqueous solution or suspension by for example, using a suitable liquid jet, or into aerosols distributed from a pressured bag such as a measuring inhalator.

The aerosol suitable for inhalation is either a suspension or a solution and may usually contain the compound of the present invention and a suitable jet such as fluorocarbon, hydrogen-containing chlorofluorocarbon or a mixture thereof, especially hydrofluoroalkane, more especially 1,1,1,2-tetrafluoroethane, 1,1,1,2,3,3,3-heptafluoro n-propane or a mixture thereof. The aerosol may further contain, if necessary, excipients well known in the art, such as a surfactant such as oleic acid or lecithin and a co-solvent such as ethanol.

A gelatin capsule or cartridge used for inhalator or for insufflator may be formed by using a powdered mixture and a suitable powdered base such as lactose or starch, etc., for inhalating the compound of the present invention. Each capsule or cartridge may usually contain 20 μg~10 mg of the compound of the present invention. As another method, the compound of the present invention may be administered without any excipients such as lactose.

The amount of the compound of the present invention contained in the preparation for external administration depends on the kind of preparations, but is generally 0.001 to 10% by weight, preferably 0.005 to 1% by weight. In case of the powder for inhalation, the amount of the compound of the present invention is a range of 0.1 to 5% by weight.

In regard to the aerosol each a measured amount or one blown (splayed) amount of the compound of the present invention is preferably 20 μg to 2000 μg, preferably about 20 μg to 500 μg. The dosage is once or several times (for example, 2 to 4 or 8 times) a day. One to three dose units are administered per each time.

The composition of the present invention may be administered in combination with other therapeutically effective medicament. When administered as an antiasthma, the composition of the present invention can be used in a combination with a β2-adrenaline receptor agonist, an antihistamine or an antiallergic agent, especially a β2-adrenaline receptor agonist. The each medicament used in a combination may be administered at the same time or different time separately or in the form of a mixture thereof.

EXAMPLE

The present invention is explained in detail by illustrating Examples and Reference examples below, but should not be limited by them.

Reference Example 1

2-Butoxyadenine

After sodium (13.56 g, 590 mmol) was dissolved in n-butanol (480 ml), 2-chloroadenine (4.0 g, 23.59 mmol) was added thereto and the mixture was stirred at 140° C. for 19 hours. After the mixture was allowed to cool, water (400 ml) was added thereto and the mixture was stirred for 30 minutes. And then the organic layer was separated and concentrated. Water (400 ml) was added to the residue and the solution was neutralized with concentrated hydrochloric acid. The resulting precipitate was filtered and washed with ethanol to give the captioned compound (3.72 g, 17.97 mmol, yield 76%) as a white solid.

Reference Example 2

Methyl 3-bromomethylbenzoate

3-Bromomethylbenzoyl chloride (1.96 g, 10.37 mmol) was dissolved in methanol (20 ml), and triethylamine (1.5 ml) was added thereto. The mixture was stirred at room temperature for 1 hour. The mixture was poured into a saturated sodium hydrogencarbonate solution and was extracted with dichloromethane. The organic layer was dried over anhydrous magnesium sulfate and concentrated to give the captioned compound (1.90 g, 10.29 mmol, yield: 97%) as a colorless oil.

Reference Example 3

2-Butoxy-9-(3-methoxycarbonylbenzyl)adenine

After 2-butoxyadenine (0.66 g, 3.19 mmol) obtained by Reference example 1 and potassium carbonate (0.80 g, 5.79 mmol) were added to DMF (40 ml), the compound (1.99 g, 10.78 mmol) obtained by Reference example 2 was added thereto and the mixture was stirred at room temperature for 18 hours. After removing the solvent the residue was poured into water and extracted with dichloromethane. The organic layer was dried over anhydrous magnesium sulfate and concentrated. The residue was purified by column chromatography ($SiO_2$ 20 g, eluting solvent: $CHCl_3$/MeOH=300/1~50/1) to give the captioned compound (0.50 g, 1.41 mmol, yield: 44%) as a white solid.

Reference Example 4

8-Bromo-2-butoxy-9-(3-methoxycarbonylbenzyl) adenine

After 2-butoxy-9-(3-methoxycarbonylbenzyl)adenine (0.41 g, 1.54 mmol) obtained by Reference example 3, and sodium acetate (1.14 g, 13.90 mmol) were dissolved in acetic acid (50 ml), bromine (0.1 ml, 7.7 mmol) was added thereto. The mixture was stirred at room temperature for 5 hours. After removing the solvent the residue was poured into water and extracted with dichloromethane. After the organic layer was washed with a saturated sodium hydrogencarbonate solution, a saturated sodium hydrogensulfite solution and saturated brine in that order, the organic layer was dried over anhydrous magnesium sulfate and concentrated to give the captioned compound (0.45 g, 1.04 mmol, yield: 90%) as a yellow tar.

Reference Example 5

2-Butoxy-9-(3-carboxybenzyl)-8-methoxyadenine

After sodium (0.49 g, 21.30 mmol) was dissolved in methanol (50 ml), 8-bromo-2-butoxy-9-(3-methoxycarbonylbenzyl)adenine (0.22 g, 0.51 mmol) obtained by Reference example 4 was added thereto and the mixture was refluxed for 30 hours. After being allowed to cool, the solution was neutralized with concentrated hydrochloric acid and concentrated. The residue was poured into water. The resulting precipitate was filtered and washed with methanol to give the captioned compound (0.13 g, 0.35 mmol, yield: 69%) as a white solid.

Reference Example 6

2-n-Butylaminoadenine

2-Chloroadenine (6.0 g, 35.4 mmol) and n-butylamine (30 ml) were reacted in an autoclave (200 ml) at 130° C. for 150 hours. After the reaction mixture was concentrated under reduced pressure, the residue was poured into water to precipitate the solid. The precipitated solid was successively washed with methylene chloride and methanol to give the captioned compound (2.08 g, yield 30%) as a yellowish orange powdered solid.

Reference Example 7

9-Benzyl-2-(2-hydroxyethylamino)adenine

9-Benzyl-2-chloroadenine (1.0 g, 3.8 mmol) was stirred in 2-aminoethanol (8 ml) at 110° C. for 4 hours. Water (100 ml) was added to the reaction mixture and the resulting precipitate was filtered to give the captioned compound (1.1 g, 3.8 mmol, yield: 100%) as a white solid.

Reference Example 8

9-Benzyl-8-bromo-2-(2-hydroxyethylamino)adenine

9-Benzyl-2-(2-hydroxyethylamino)adenine (100 mg, 0.35 mmol) obtained by Reference example 7 was dissolved in acetic acid and thereto was added 2.0 M bromine/acetic acid (0.18 ml, 0.36 mmol). The mixture was stirred at room temperature for 3 hours. After adding water (3 ml) to the reaction mixture, the solution was neutralized with 40% sodium hydroxide solution under ice cooling and the resulting precipitate was filtered to give the captioned compound (130 mg, 0.36 mmol, yield: 100%) as a white solid.

Reference Example 9

2-(2-Hydroxyethylamino)-9-{(6-methyl-3-pyridyl)methyl}adenine

The captioned compound was prepared in accordance with the method of Reference example 7.

Reference Example 10

8-Bromo-2-(2-hydroxyethylamino)-9-{(6-methyl-3-pyridyl)methyl}adenine

The captioned compound was prepared in accordance with the method of Reference example 8.

Reference Example 11

2-(2-Hydroxyethoxy)-9-{(6-methyl-3-pyridyl)methyl}adenine)

After sodium (2.1 g, 91 mmol) was dissolved in ethylene glycol (30 ml), 2-chloro-9-{(6-methyl3-pyridyl)methyl}adenine (3.0 g, 11 mmol) was added thereto and the mixture was stirred at 100° C. for 3 hours. After the mixture was allowed to cool, water (80 ml) was added thereto and the resulting precipitate was filtered to give the captioned compound (3.1 g, 10 mmol, yield: 94%) as a white solid.

Reference Example 12

8-Bromo-2-(2-hydroxyethoxy)-9-{(6-methyl-3-pyridyl)methyl}adenine

The captioned compound was prepared in accordance with the method of Reference example 8.

Reference Example 13

2-(2-Hydroxyethoxy)-8-methoxy-9-{(6-methyl-3-pyridyl)methyl}adenine

After 8-bromo-2-(2-hydroxyethoxy)-9-{(6-methyl-3-pyridyl)methyl}adenine (2.3 g, 7.7 mmol) obtained by Reference example 12 was suspended in a mixture of 1N sodium hydroxide solution (30 ml) and methanol (30 ml), the mixture was stirred at 100° C. for 10 hours. Water was added to the reaction mixture and the mixture was extracted with chloroform. The organic layer was dried over anhydrous magnesium sulfate and concentrated to give the captioned compound (670 mg, 2.0 mmol, yield: 26%) as a pale yellow solid.

Reference Example 14

2-{2-(N,N-Dimethylaminocarbonyloxy)ethoxy}-8-methoxy-9-{(6-methyl-3-pyridyl)methyl}adenine 2-(2-Hydroxyethoxy)-8-methoxy-9-{(6-methyl-3-pyridyl)methyl}adenine (200 mg, 0.61 mmol) obtained by Reference example 13, dimethylaminopyridine (5 mg, 0.4 mmol) and N,N-diisopropylethylamine (0.32 mmol, 1.8 mmol) were dissolved in a mixed solvent of pyridine (2 ml) and dimethylformamide (2 ml), and thereto was added under ice cooling N,N-dimethylcarbamoyl chloride (1.1 ml, 12 mmol). The mixture was stirred for 21 hours. Water was added to the reaction mixture and the mixture was extracted with chloroform. The organic layer was dried over anhydrous magnesium sulfate and concentrated. The residue was purified by silica gel column chromatography to give the captioned compound (66 mg, 0.16 mmol, yield: 27%) as a white solid.

Reference Example 15

9-Benzyl-8-hydroxy-2-thioadenine

After aminomalononitrile p-toluenesulfonate (45 g, 178 mmol) was added to tetrahydrofuran, thereto were added benzylisocyanate (25 g, 188 mmol) and N,N-diisopropylethylamine (23.5 ml, 130 mmol). The mixture was stirred at room temperature for 14 hours. After removing the solvent, the residue was poured into water and extracted with ethyl acetate. The organic layer was dried over anhydrous sodium sulfate and concentrated. To the residue were added tetrahydrofuran and 1N sodium hydroxide solution. The mixture was stirred at 50° C. for 20 minutes and neutralized with 15% potassium hydrogensulphate. The resulting precipitate was filtered, added to tetrahydrofuran and thereto was dropped benzoylisothiocyanate (41 ml, 305 mmol). The mixture was stirred at room temperature over a night and the solvent was removed. The precipitate was collected by adding ether to the residue, refluxed in a mixed solvent of tetrahydrofuran and 2N sodium hydroxide solution for 50 hours and neutralized with 10% potassium hydrogensulfate solution. The resulting precipitate was collected and recrystallized from ethyl acetate to give the captioned compound as a white powdered solid.

Reference Example 16

2-(2,3-Dihydroxypropylamino)-9-{(6-methyl-3-pyridyl)methyl}adenine

The captioned compound was prepared in accordance with the method of Reference example 7.

Reference Example 17

8-Bromo-2-(2,3-dihydroxypropylamino)-9-{(6-methyl-3-pyridyl)methyl}adenine

The captioned compound was prepared in accordance with the method of Reference example 10.

Reference Example 18

2-(2,3-Dihydroxypropylamino)-8-methoxy-9-{(6-methyl-3-pyridyl)methyl}adenine

The captioned compound was prepared in accordance with the method of Reference example 13.

Reference Example 19

8-Methoxy-9-{(6-methyl-3-pyridyl)methyl}-2-{(2-oxo-1,3-dioxolan-4-yl)methylamino}adenine 2-(2,3-Dihydroxypropylamino)-8-methoxy-9-{(6-methyl-3-pyridyl)methyl}adenine (230 mg, 0.64 mmol) obtained by Reference example 18, 4-dimethylaminopyridine (5 mg, 0.04 mmol) and triethylamine (0.02 ml, 0.14 mmol) were dissolved in dimethylformamide (2 ml). Thereto was added di-t-butyl dicarbonate (410 mg, 1.9 mmol) in the oil bath kept at 50° C. and the mixture was stirred for 14 hours. The reaction mixture was concentrated and the residue was purified by preparative thin layer chromatography to give the captioned compound (64 mg, 0.17 mmol, yield 26%) as a white solid.

Reference Example 20

9-Benzyl-2-methoxycarbonylmethoxyadenine

9-Benzyl-8-hydroxy-2-(2-hydroxyethoxy)adenine (0.39 g, 1.37 mmol) and pyridinium dichromate (5.28 g, 14.03 mmol) were dissolved in DMF (14 ml) and the solution was stirred at room temperature for 23 hours. The reaction mixture was poured into an aqueous saturated ammonium chloride solution, and extracted with chloroform. The organic layer was concentrated and the resulting residue was added to methanol (100 ml). Thereto was added sulfuric acid (5 ml) and the mixture was refluxed under stirring for 3 hours. The mixture was neutralized with sodium hydrogencarbonate in an ice bath and extracted with chloroform. The organic layer was dried over anhydrous magnesium sulfate and concentrated. The residue was purified by column chromatography ($SiO_2$ 20 g, eluting solvent: $CHCl_3$/MeOH=300/1~100/1) to give the captioned compound (0.12 g, 0.38 mmol) as a white solid.

Reference Example 21

9-Benzyl-8-bromo-2-methoxycarbonylmethoxyadenine

9-Benzyl-2-methoxycarbonylmethoxyadenine (0.12 g, 0.38 mmol) obtained by Reference example 20 and sodium acetate (57 mg, 0.69 mmol) were dissolved in chloroform (6 ml), and thereto was added bromine (92 mg, 0.58 mmol) in an ice bath. The mixture was stirred at room temperature for 5 hours. After removing the solvent, the residue was poured into water and extracted with chloroform. The organic layer was successively washed with a saturated sodium hydrogencarbonate and 10% sodium thiosulfate, dried over anhydrous magnesium sulfate and then concentrated. The residue was purified by column chromatography ($SiO_2$ 20 g, eluting solvent: $CHCl_3$/MeOH=200/1) to give the captioned compound (0.10 g, 0.25 mmol) as a white solid.

Reference Example 22

2-(2-Methoxycarbonylethyl)adenine

9-Benzyl-2-(2-methoxycarbonylethyl)adenine (0.29 g, 0.93 mmol) obtained by Example 61 and 20% $Pd(OH)_2/C$ (0.32 g) were added to a mixed solvent of isopropanol (8 ml) and formic acid (8 ml), and the mixture was stirred at a pressure of 2 atmosphere of hydrogen at 70° C. for 40 hours. After filtration, the filtrate was concentrated to give the captioned compound (0.23 g, 0.86 mmol) as a white solid.

Reference Example 23

2-(2-Methoxycarbonylethyl)-9-{(6-methyl-3-pyridyl)methyl}adenine 2-(2-Methoxycarbonylethyl)adenine (313 mg, 1.51 mmol) obtained by Reference example 22 and potassium carbonate (0.44 g, 3.18 mmol) were added to DMF (40 ml). The mixture was at 70° C. for 1 hour and then cooled to room temperature. Thereto was added 6-methyl-3-pyridylmethyl chloride hydrochloride (0.38 g, 2.13 mmol) and the mixture was stirred at room temperature for 15 hours. After removing the solvent, the residue was poured into water and extracted with chloroform. The organic layer was dried over anhydrous magnesium sulfate and concentrated. The residue was purified by column chromatography ($SiO_2$ 20 g, eluting solvent: $CHCl_3$/MeOH=100/1~30/1) to give the captioned compound (358 mg, 1.15 mmol) as a white solid.

Reference Example 24

8-Bromo-2-(2-methoxycarbonylethyl)-9-{(6-methyl-3-pyridyl)methyl}adenine

After 2-(2-methoxycarbonylethyl)-9-{(6-methyl-3-pyridyl)methyl}adenine (70 mg, 0.21 mmol) obtained by Reference example 23 and sodium acetate (0.35 g, 4.27 mmol) were dissolved in acetic acid (8 ml), thereto was added bromine (0.34 g, 2.13 mmol) and the mixture was stirred at 70° C. for 9 hours. After removing the solvent, the residue was poured into water and extracted with dichloromethane. The organic layer was washed with saturated sodium hydrogencarbonate, saturated sodium thiosulfate, and saturated brine in that order and then dried over anhydrous magnesium sulfate. The residue was purified by column chromatography ($SiO_2$ 20 g, eluting solvent: $CHCl_3$/MeOH=100/1~40/1) to give the captioned compound (31 mg, 0.076 mmol) as a pale yellow solid.

Reference Example 25

2-Butoxy-8-hydroxy-9-(5-methoxycarbonylfurfuryl) adenine

Lithium aluminium hydride (54 mg, 1.42 mmol) was added to THF (4 ml), and thereto butoxy-8-hydroxy-9-(5-methoxycarbonylfurfuryl)adenine (62 mg, 0.17 mmol) obtained by Example 15 in THF (10 ml) was dropped in an ice bath. The mixture was stirred at room temperature for 1 hour. Thereto were added water (54 μl), 1N sodium hydroxide (162 μl) and water (162 μl) in that order in an ice bath. The reaction mixture was filtered and the filtrate was concentrated. The residue was purified by column chromatography ($SiO_2$ 20 g, eluting solvent: $CHCl_3$/MeOH=30/1~20/1) to give the captioned compound (50 mg, 0.15 mmol) as a white solid.

Reference Example 26

2-Butoxy-9-(5-cyanomethylfurfuryl)-8-hydroxyadenine

After 2-butoxy-8-hydroxy-9-(5-hydroxymethylfurfuryl) adenine (42 mg, 0.13 mmol) obtained by Reference example 25 was dissolved in chloroform (10 ml), thereto was added thionyl chloride (0.2 ml) and the mixture was refluxed for 2 hours. After removing the solvent, the residue was dissolved in DMF (5 ml). Thereto was added sodium cyanide (35 mg, 0.71 mmol) and the mixture was stirred at room temperature for 4 hours. After removing the solvent, the residue was poured into water, neutralized with 1N hydrochloric acid and extracted with chloroform. The organic layer was dried over anhydrous magnesium sulfate and concentrated. The residue was purified by column chromatography ($SiO_2$ 20 g, eluting solvent: $CHCl_3$/MeOH=50/1~30/1) to give the captioned compound (31 mg, 0.091 mmol) as a white solid.

Reference Example 27

3,4-Dimethoxycarbonylbenzyl bromide

After 3,4-dimethoxycarbonyltoluene (5.28 g, 25.36 mmol) was added to carbon tetrachloride (250 ml), thereto were added N-bromosuccinimide (6.33 g, 35.56 mmol) and benzoylperoxide (0.53 g, 2.19 mmol) and the mixture was refluxed for 10 hours under stirring. After removing the solvent, the residue was poured into water and extracted with ether. The combined organic layer was dried over anhydrous magnesium sulfate and concentrated. The residue was purified by column chromatography ($SiO_2$ 250 g, eluting solvent: Hexane/$CHCl_3$=10/1~$CHCl_3$ only) to give the captioned compound (2.05 g, 7.14 mmol) as a colorless transparent oil.

Reference Example 28

2-Butoxy-9-(3,4-dimethoxycarbonylbenzyl)adenine

2-Butoxyadenine (0.50 g, 2.41 mmol) obtained by Reference example 1 and potassium carbonate (0.25 g, 1.81 mmol) were added to DMF (12 ml) and the mixture was stirred at 70° C. for 1 hour. After the mixture was cooled to room temperature, 4-dimethoxycarbonylbenzyl bromide obtained by Reference example 27 (1.99 g, 10.78 mmol) was added thereto and the mixture was stirred at room temperature for 9 hours. After removing the solvent, the residue was poured into water and extracted with chloroform. The organic layer was dried over anhydrous magnesium sulfate and concentrated. The residue was purified by column chromatography ($SiO_2$ 20 g, eluting solvent: $CHCl_3$/MeOH=300/1~100/1) to give the captioned compound (775 mg, 1.88 mmol) as a pale yellow solid.

Reference Example 29

2-Butoxy-8-methoxy-9-{(6-methoxycarbonyl-3-pyridyl)methyl}adenine

2-Butoxy-9-{(6-carboxyl-3-pyridyl)methyl}-8-methoxyadenine (87 mg, 0.23 mmol), potassium carbonate (32 mg, 0.24 mmol) and methyl iodide (66 mg, 0.46 mmol) were added in DMF (10 ml), and the mixture was stirred at room temperature for 3 hours. After removing the solvent, the residue was poured into water and extracted with chloroform. The organic layer was washed with saturated brine, dried over anhydrous magnesium sulfate and concentrated. The residue was purified by column chromatography ($SiO_2$ 20 g, eluting solvent: $CHCl_3$/MeOH=100/1) to give the captioned compound (78 mg, 0.20 mmol) as a yellow tar.

Reference Example 30

2-Butoxy-9-{6-thio-3-pyridyl}methyl)adenine

2-Butoxy-9-{6-chloro-3-pyridyl}methyl}-8-hydroxyadenine (1.00 g, 3.00 mmol) and 70% NaSH nH2O (3.40 g) were added to DMF (35 ml) and the mixture was stirred at 120° C. for 9 hours. After removing the solvent, the residue was poured into water and neutralized with concentrated hydrochloric acid. The resulting precipitate was filtered, successively washed with water and chloroform and dried in vacuo under heating to give the captioned compound (0.98 g, 2.97 mmol) as a yellow solid.

Reference Example 31

2-Butoxy-9-{6-(γ-butyrolactonyl)thio-3-pyridyl}methyl)adenine

2-Butoxy-9-{6-thio-3-pyridyl}methyl)adenine (0.25 g, 0.76 mmol) obtained by Reference example 30, potassium carbonate (78 mg, 0.51 mmol) and α-bromo-γ-butyrolactone (190 mg, 1.15 mmol) were added to DMF (18 ml), and the mixture was stirred at room temperature for 17 hours. After removing the solvent, the residue was poured into water and extracted with chloroform. The organic layer was washed with saturated brine, dried over anhydrous magnesium sulfate and concentrated. The residue was purified by column chromatography ($SiO_2$ 10 g, eluting solvent: $CHCl_3$/MeOH=200/1~50/1) to give the captioned compound (0.31 g, 0.75 mmol) as a white solid.

Reference Example 32

8-Bromo-2-butoxy-9-{4-(γ-butyrolactonyloxy) benzyl}adenine

8-Bromo-2-butoxy-9-(4-hydroxybenzyl)adenine (0.20 g, 0.51 mmol), cesium carbonate (0.42 g, 1.29 mmol) and α-bromo-γ-butyrolactone (0.42 g, (2.55 mmol) were added to DMF (7 ml), and the mixture was stirred at room temperature for 55 hours. After removing the solvent, the residue was poured into water and extracted with chloroform. The organic layer was washed with saturated brine, dried over anhydrous magnesium sulfate and concentrated. The residue was purified by column chromatography ($SiO_2$ 10 g, eluting solvent: $CHCl_3$/MeOH=300/1~100/1) to give the captioned compound (0.19 g, 0.40 mmol) as a yellow tar.

Reference Example 33

2-(2-Methoxyethoxy)adenine

After sodium (3.00 g, 130 mmol) was dissolved in 2-methoxyethanol (150 ml), thereto was added 2-chloroadenine (3.00 g, 17.69 mmol) and the mixture was refluxed for 8 hours. After the mixture was allowed to cool, water (400 ml) was added thereto and neutralized with concentrated hydrochloric acid. The resulting precipitate was filtered and washed with methanol to give the captioned compound (3.06 g, 14.48 mmol, yield 73%) as a white solid.

Reference Example 34

(9-(3-Methoxycarbonylmethylbenzyl)-2-(2-methoxyethoxy)adenine 2-(2-Methoxyethoxy)adenine (0.19 g, 0.90 mmol) obtained by Reference example 33 and potassium carbonate (0.87 g, 6.30 mmol) were added to DMF (10 ml) and the mixture was stirred at 60° C. for 1.5 hours. After cooling to room temperature, methyl 3-bromo methylphenylacetate (0.44 g, 1.80 mmol) was added thereto and the mixture was stirred at room temperature for 1.5 hours. After removing the solvent, the residue was poured into 5% citric acid and extracted with chloroform. The organic layer was dried over anhydrous magnesium sulfate and concentrated. The residue was purified by column chromatography ($SiO_2$ 6.0 g, eluting solvent: $CHCl_3$/MeOH=200/1~50/1) to give the captioned compound (0.23 g, 0.63 mmol, yield; 70%) as a pale yellow solid.

Reference Example 35

8-Bromo-9-(3-methoxycarbonylmethylbenzyl)-2-(2-methoxyethoxy)adenine

After 9-(3-methoxycarbonylmethylbenzyl)-2-(2-methoxyethoxy)adenine (0.23 g, 0.63 mmol) obtained by Reference example 34 and sodium acetate (0.093 g, 1.13 mmol) were dissolved in chloroform (10 ml), bromine (0.15 g, 0.95 mmol) was added thereto and the mixture was stirred at room temperature for 3 hours. After removing the solvent, the residue was poured into water and extracted with chloroform. The organic layer was washed with saturated sodium hydrogencarbonate, saturated sodium hydrogen sulfite, and saturated brine in that order and dried over anhydrous magnesium sulfate. The residue was purified by column chromatography ($SiO_2$ 7.0 g, eluting solvent: $CHCl_3$/MeOH=100/0~200/1) to give the captioned compound (0.22 g, 0.50 mmol, yield: 79%) a brown solid.

Reference Example 36

2-Butylamino-9-(3-methoxycarbonylmethylbenzyl) adenine

2-Butylaminoadenine (0.21 g, 1.00 mmol) obtained by Reference example 6 and potassium carbonate (0.69 g, 5.00 mmol) were added to DMF (7 ml), and thereto was added methyl 3-bromomethylphenylacetate (0.49 g, 2.00 mmol). The mixture was stirred at room temperature for 2 hours. After removing the solvent, the residue was poured into 5% citric acid and extracted with chloroform. The organic layer was dried over anhydrous magnesium sulfate and concentrated. The residue was purified by column chromatography ($SiO_2$ 6.3 g, eluting solvent: $CHCl_3$/MeOH=100/0~50/1) to give the captioned compound (0.23 g, 0.61 mmol, yield: 61%) as a white solid.

Reference Example 37

8-Bromo-2-butylamino-9-(3-methoxycarbonylmethylbenzyl)adenine

After 2-butylamino-9-(3-methoxycarbonylmethylbenzyl) adenine obtained by Reference example 36 (0.23 g, 0.61 mmol) was dissolved in chloroform (10 ml), bromine (0.15 g, 0.92 mmol) was added thereto and the mixture was stirred at room temperature for 1 hour. After removing the solvent, the residue was poured into water and extracted with chloroform. The organic layer was washed with saturated sodium hydrogencarbonate, saturated sodium hydrogensulfite and saturated brine in that order, dried over anhydrous magnesium sulfate and concentrated to give the captioned compound (0.23 g, 0.51 mmol, yield: 83%) as a pale yellow solid.

Reference Example 38

2-Chloro-9-(3-methoxycarbonylmethylbenzyl)adenine

2-Chloroadenine (1.70 g, 10.0 mmol) and potassium carbonate (9.67 g, 70.0 mmol) were added to DMF (35 ml) and the mixture was stirred at 60° C. for 1.5 hours. After cooling to room temperature, methyl 3-bromomethylphenylacetate (3.16 g, 13.0 mmol) was added thereto and the mixture was stirred at room temperature for 1.5 hours. After removing the solvent, thereto was added chloroform (50 ml) and the resulting solid was washed with water to give the captioned compound (2.13 g, 6.41 mmol, yield: 64%) as a pale yellow solid.

Reference Example 39

8-Bromo-2-chloro-9-(3-methoxycarbonylmethylbenzyl)adenine

After 2-chloro-9-(3-methoxycarbonylmethylbenzyl)adenine obtained by Reference example 38 (2.00 g, 6.03 mmol) and sodium acetate (2.95 g, 36.0 mmol) were dissolved in chloroform (100 ml), bromine (4.79 g, 30.0 mmol) was added thereto and the mixture was stirred at room temperature for 5 hours. After removing the solvent, the residue was poured into water and extracted with chloroform. The organic layer was washed with saturated sodium hydrogencarbonate, saturated sodium hydrogensulfite and saturated brine in that order, dried over anhydrous magnesium sulfate and concentrated to give the captioned compound (1.78 g, 4.34 mmol, yield: 72%) as a brown solid.

Reference Example 40

Methyl 2-(4-bromomethyl)phenylpropionate

Thionyl chloride (5.80 ml, 80 mmol) was added to methanol (100 ml) under ice cooling and the mixture was stirred for 1 hour. Thereto was dropped 2-(4-bromomethyl)phenylpropionic acid (4.86 g, 20 mmol) in methanol (30 ml). After stirring at room temperature for 2 hours, the solvent was removed. Water was added to the residue and the mixture was extracted with ethyl acetate. The organic layer was washed with 5% sodium carbonate and 5% brine, dried over anhydrous magnesium sulfate and concentrated. The residue was purified by column chromatography (hexane-ethyl acetate) to give the captioned compound (4.71 g, 18.3 mmol, yield: 92%) as a colorless oil.

Reference Example 41

Ethyl α,α-dimethyl-m-tolylacetate

After potassium t-butoxide (11.22 g, 50 mmol) was added to ethyl m-tolylacetate (7.12 g, 40 mmol) and iodomethane (14.20 g, 100 mmol) in THF solution (300 ml) at −80° C., the mixture was stirred at room temperature for 3 hours. After saturated ammonium chloride solution (200 ml) was added thereto, the solvent was removed and the residue was extracted with chloroform. The organic layer was washed with brine, dried over anhydrous magnesium sulfate and concentrated. The residue was purified by column chromatography (hexane-ethyl acetate) to give the captioned compound (4.92 g, 23.9 mmol, yield: 84%) as a colorless oil.

Reference Example 42

Ethyl α,α-dimethyl-m-bromomethylphenylacetate

To ethyl α,α-dimethyl-m-tolylacetate (4.12 g, 20 mmol) obtained by Reference example 41 in carbon tetrachloride (140 ml) were added N-bromosuccinimide (3.56 g, 20 mmol) and benzoylperoxide (100 mg, 0.41 mmol) and the mixture was refluxed for 3 hours. To the reaction mixture was 5% sodium hydrogensulfite and the organic layer was separated. The organic layer was washed with brine, dried over anhydrous magnesium sulfate and concentrated. The residue was purified by column chromatography (hexane-ethyl acetate) to give the captioned compound (4.62 g) as a colorless oil.

Reference Example 43

Methyl 4-(2-bromoethyl)benzoate

Thionyl chloride (5.80 ml, 80 mmol) was added to methanol (100 ml) under ice cooling. The mixture was stirred for 1 hour and thereto was dropped 2-(4-bromoethyl)benzoic acid (4.58 g, 20 mmol) in methanol (30 ml). After stirring at room temperature for 2 hours, the solvent was removed. Water was added to the residue and mixture was extracted with ethyl acetate. The organic layer was washed with 5% sodium carbonate and 5% brine, dried over anhydrous magnesium sulfate and concentrated to give the captioned compound (4.79 g, 18.3 mmol, yield: 99%) as a colorless oil.

The compounds of Reference examples 44~46 below were obtained in accordance with the method of Reference example 40.

Reference Example 44

Methyl o-tolylacetate (4.36 g, 26.6 mmol, yield: 89%)

Reference Example 45

Methyl p-tolylacetate (4.42 g, 27.0 mmol, yield: 90%)

Reference Example 46

Methyl 2-fluoro-5-methylbenzoate (3.07 g, 18.3 mmol, yield: 91%)

Reference Example 47

Methyl 2-methoxy-5-methylbenzoate

To 5-methylsalicylic acid (3.04 g, 20 mmol) in DMF (100 ml) were added potassium carbonate (8.28 g, 60 mmol) and iodomethane (6.24 g, 44 mmol) under ice cooling and then the mixture was stirred at room temperature for 12 hours. The mixture were extracted by adding 5% sodium hydrogensulfite and ethyl acetate, and the extracted organic layer was washed with 5% citric acid and 5% brine. The organic layer was dried over anhydrous magnesium sulfate and concentrated. The residue was purified by column chromatography (hexane-ethyl acetate) to give the captioned compound (3.43 g, 19.1 mmol, yield: 95%) as a colorless oil.

Reference Example 48

Methyl α,α-dimethyl-p-tolylacetate

The captioned compound was obtained in accordance with the method of Example 41 (2.26 g, 11.8 mmol, yield: 75%).

Reference Example 49

Ethyl(2R,S)-3-methylphenylpropionate

To ethyl m-tolylacetate (3.56 g, 20 mmol) in THF (300 ml) was added iodomethane (3.12 g, 22 mmol). Thereto at −80° C. was added potassium t-butoxide (2.47 g, 22 mmol) and the mixture was stirred at room temperature for 3 hours. After saturated ammonium chloride (200 ml) was added thereto at −80° C., THF was removed and the residue was extracted with chloroform. The organic layer was dried over anhydrous magnesium sulfate, concentrated and purified by column chromatography (hexane-ethyl acetate) to give the captioned compound (2.97 g, 15.5 mmol, yield: 77%) as a colorless oil.

The compounds of Reference examples 50~54 below were prepared in accordance with the method of Reference example 42.

Reference Example 50

Methyl o-bromomethylphenylacetate

Reference Example 51

Methyl 3-bromomethyl-6-fluorobenzoate

Reference Example 52

Methyl 3-bromomethyl-6-methoxybenzoate

Reference Example 53

Methyl α,α-dimethyl-p-bromomethylphenylacetate

Reference Example 54

Ethyl(2R,S)-3-bromomethylphenylpropionate

Reference Example 55

Methyl dimethoxy(3-methylphenyl)acetate

To 3-methylacetophenone (5.0 g, 37 mmol) in pyridine (50 ml) was added selenium dioxide (7.44 g, 67 mmol), and the mixture was refluxed for 3.5 hours. The resulting black solid was filtered off. The filtrate was neutralized with concentrated hydrochloric acid and extracted with ether to give 3-methylphenylglyoxylic acid (6.12 g, 37 mmol, yield: 100%). Then to the obtained 3-methylphenyloxoacetic acid (4.0 g, 24 mmol) in methanol (250 ml) was added concentrated sulfuric acid (13 ml), and the mixture was refluxed for 5 hours. After being neutralized with saturated sodium hydrogencarbonate, the solution was extracted with chloroform. The organic layer was dried over anhydrous magnesium sulfate and concentrated. The residue was purified by column chromatography ($SiO_2$ 170 g, eluting solvent: Hex/AcOEt=200/1~0/1) to give the captioned compound (3.75 g, 16.7 mmol, yield: 69%) as a pale yellow oil.

Reference Example 56

Methyl dimethoxy(3-bromomethylphenyl)acetate

The captioned compound was obtained in accordance with the method of Reference example 27. Yield: 69%

Reference Example 57

2-Butoxy-9-[3-(1,1,2-trimethoxy-2-oxoethyl)benzyl] adenine

The captioned compound as a yellow solid was obtained in accordance with the method of Reference example 3, yield: 75%.

Reference Example 58

8-Bromo-2-butoxy-9-[3-(1,1,2-trimethoxy-2-oxoethyl)benzyl]adenine

The captioned compound was obtained in accordance with the method of Reference example 21, yield: 95%.

Example 1

2-Butoxy-8-hydroxy-9-(3-methoxycarbonylbenzyl) adenine

After 2-butoxy-8-methoxy-9-(3-carboxybenzyl)adenine (0.60 g, 1.61 mmol) obtained by Reference example 5 was dissolved in methanol (20 ml), thereto was added sulfuric acid (1 ml) and the solution was refluxed for 1 hour under stirring. After the reaction mixture was neutralized with saturated sodium hydrogencarbonate solution in an ice bath, the resulting precipitate was filtered and washed with methanol to give the captioned compound (0.48 g, 1.29 mmol, yield: 80%) as a white solid.

The compounds of Examples 2~4 below were obtained in accordance with the method of Example 1.

Example 2

2-Butoxy-8-hydroxy-9-(3-ethoxycarbonylbenzyl) adenine

Example 3

2-Butoxy-8-hydroxy-9-(3-isopropoxycarbonylbenzyl)adenine

Example 4

2-Butoxy-8-hydroxy-9-{3-(2,2,2-trifluorroethoxycarbonyl)benzyl}adenine

Example 5

2-Butoxy-8-hydroxy-9-{3-(2-benzyloxyethoxycarbonyl)benzyl}adenine

After 2-butoxy-9-(3-carboxybenzyl)-8-methoxyadenine (0.06 g, 0.16 mmol) obtained by Reference example 5 and triethylamine (0.03 g, 0.28 mmol) were added to acetonitrile (10 ml), benzyl 2-bromoethyl ether (0.06 g, 0.28 mmol) was added thereto, and the mixture was refluxed for 50 hours under stirring. After removing the solvent, the residue was poured into water and extracted with dichloromethane. The organic layer was dried over anhydrous magnesium sulfate and concentrated. The solid was added to methanol (10 ml) and concentrated hydrochloric acid (10 ml), and the mixture was stirred at room temperature for 18 hours. After neutralizing with saturated sodium hydrogencarbonate solution, the solution was extracted with dichloromethane. The organic layer was dried over anhydrous magnesium sulfate, concentrated and washed with methanol to give the captioned compound (0.03 g, 0.06 mmol, yield: 38%) as a white solid.

Example 6

2-Butoxy-8-hydroxy-9-{3-(2-hydroxyethoxycarbonyl)benzyl}adenine

2-Butoxy-8-hydroxy-9-{3-(2-benzyloxyethoxycarbonyl) benzyl}adenine (0.03 g, 0.06 mmol) obtained by Example 5, 5% Pd/C (60 mg) and concentrated hydrochloric acid (0.1 ml) were added to a mixed solvent of THF (30 ml) and methanol (30 ml), and the mixture was stirred under hydrogen atmosphere at room temperature for 60 hours. The reaction mixture was filtered, neutralized with saturated sodium hydrogencarbonate solution and extracted with dichloromethane.

The organic layer was dried over anhydrous magnesium sulfate and concentrated. The residue was purified by column chromatography ($SiO_2$ 20 g, eluting solvent: $CHCl_3$/MeOH=100/1~50/1) and washed with methanol to give the captioned compound (0.01 g, 0.02 mmol, yield: 42%) as a white solid.

The compounds of Examples 7~9 below were obtained in accordance with the method of Example 5.

Example 7

2-Butoxy-8-hydroxy-9-{3-(2-dimethylaminoethoxycarbonyl)benzyl}adenine

Example 8

2-Butoxy-8-hydroxy-9-{3-(2-morpholinoethoxycarbonyl)benzyl}adenine

Example 9

2-Butoxy-8-hydroxy-9-{3-(3-pyridylmethoxycarbonyl)benzyl}adenine

Example 10

2-Butoxy-8-hydroxy-9-{3-(S-methylthiocarbonyl)benzyl}adenine

After 2-butoxy-9-(3-carboxybenzyl)-8-methoxyadenine (0.06 g, 0.16 mmol) obtained by Reference example 5 and triethylamine (0.02 g, 0.19 mmol) were added to DMF (10 ml), methanesulfonyl chloride (0.02 g, 0.19 mmol) was added thereto in an ice bath, and the mixture was stirred for 1 hour. Methanethiol (0.1 ml, 1.43 mmol) was added thereto and the mixture was stirred at room temperature for 8 hours. After removing the solvent, the residue was poured into water and extracted with dichloromethane. The organic layer was dried over anhydrous magnesium sulfate and concentrated. The solid was added to methanol (10 ml) and concentrated hydrochloric acid (10 ml) and the mixture was refluxed under stirring at room temperature for 18 hours. After being neutralized with saturated sodium hydrogencarbonate solution, the solution was extracted with dichloromethane. The organic layer was dried over anhydrous magnesium sulfate and concentrated. The residue was purified by column chromatography ($SiO_2$ 20 g, eluting solvent: $CHCl_3$/MeOH=80/1~20/1) and washed with methanol to give the captioned compound (0.01 g, 0.03 mmol, yield: 16%) as a white solid.

The compounds of Examples 11~12 below were obtained in accordance with the method of Example 1.

Example 11

2-Butoxy-8-hydroxy-9-(4-methoxycarbonylbenzyl)adenine

Example 12

2-Butoxy-8-hydroxy-9-(4-isopropoxycarbonylbenzyl)adenine

Example 13

2-Butoxy-8-hydroxy-9-{4-(3-pyridylmethoxycarbonyl)benzyl}adenine

After 2-butoxy-9-(4-carboxybenzyl)-8-methoxyadenine (0.05 g, 0.13 mmol) prepared in accordance with the method of Reference example 5 and potassium carbonate (0.03 g, 0.22 mmol) were added to DMF (10 ml), 3-chloromethylpyridine hydrochloride (0.03 g, 0.18 mmol) was added thereto, and the mixture was stirred at room temperature for 18 hours. After removing the solvent, the residue was poured into water and extracted with dichloromethane. The organic layer was dried over anhydrous magnesium sulfate and concentrated. The residue was purified by column chromatography ($SiO_2$ 20 g, eluting solvent: $CHCl_3$/MeOH=300/1~30/1) and the resulting solid was added to methanol (10 ml) and concentrated hydrochloric acid (10 ml). The mixture was stirred at room temperature for 18 hours. After being neutralized with saturated sodium hydrogencarbonate, the solution was extracted with dichloromethane. The organic layer was dried over anhydrous magnesium sulfate, concentrated and washed with methanol to give the captioned compound (0.03 g, 0.07 mmol, yield: 52%) as a white solid.

Example 14

2-Butoxy-8-hydroxy-9-(4-benzyloxycarbonylbenzyl)adenine

The captioned compound was prepared in accordance with the method of Example 13.

The compounds of Examples 15~18 below were prepared in accordance with the method of Example 1.

Example 15

2-Butoxy-8-hydroxy-9-(5-methoxycarbonylfurfuryl)adenine

Example 16

2-Butoxy-8-hydroxy-9-(5-isopropoxycarbonylfurfuryl)adenine

Example 17

2-Butoxy-8-hydroxy-9-{(6-methoxycarbonyl-3-pyridyl)methyl}adenine

Example 18

2-Butoxy-8-hydroxy-9-{(6-isopropoxycarbonyl-3-pyridyl)methyl}adenine

Example 19

2-Butoxy-8-hydroxy-9-(3-methoxycarbonylmethylbenzyl)adenine

Lithium aluminium hydride (0.08 g, 2.15 mmol) was added to THF (10 ml), and thereto was dropped 2-butoxy-9-(3-methoxycarbonyl)benzyladenine (0.20 g, 0.56 mmol) obtained by Reference example 3 in THF (10 ml) in an ice bath, and the mixture was stirred at room temperature for 2 hours. Thereto were dropped water (0.1 ml), 5% sodium hydroxide solution (0.3 ml) and water (0.3 ml) in that order in an ice bath. After the reaction mixture was filtered, the filtrate was concentrated and the residue was purified by column chromatography ($SiO_2$ 20 g, eluting solvent: $CHCl_3$/MeOH=100/1~30/1) to give 2-butoxy-9-(3-hydroxymethylbenzyl)adenine (0.18 g, 0.55 mmol, yield: 98%) as a white solid.

2-Butoxy-9-(3-hydroxymethylbenzyl)adenine (0.09 g, 0.27 mmol), triethylamine (0.20 g, 1.98 mmol), tosyl chloride (0.30 g, 1.57 mmol) and pyridine (0.4 ml) were added to DMF (10 ml), and the mixture was stirred at room temperature for 24 hours. To the reaction mixture was added sodium cyanide (0.40 g, 9.16 mmol), and the mixture was stirred at 80° C. for 18 hours. After removing the solvent, the residue was poured into water and extracted with dichloromethane. The organic layer was dried over anhydrous magnesium sulfate, concentrated and the residue was purified by column chromatography ($SiO_2$ 20 g, eluting solvent: $CHCl_3$/MeOH=100/1) to give 2-butoxy-9-(3-cyanomethylbenzyl)adenine (0.04 g, 0.12 mmol, yield: 44%) as a white solid.

2-Butoxy-9-(3-cyanomethylbenzyl)adenine (0.04 g, 0.12 mmol) was added to a mixed solvent of 5% sodium hydroxide solution (10 ml) and methanol (10 ml), and the mixture was stirred at 80° C. for 19 hours. After extracting with dichloromethane, the aqueous layer was neutralized with concentrated hydrochloric acid, and concentrated. The residue and sulfuric acid (1 ml) were added to methanol (50 ml), and the mixture was refluxed under stirring for 1 hour. After being neutralized with saturated sodium hydrogencarbonate solution in an ice bath, the solution was extracted with dichloromethane. The combined organic layer was dried over anhydrous magnesium sulfate and concentrated to give 2-butoxy-8-hydroxy-9-(3-methoxycarbonylmethylbenzyl)adenine (0.04 g, 0.11 mmol, yield: 92%) as a pale yellow solid. And then the captioned compound was obtained in accordance with the method of Example 1, yield (three steps): 71%.

The compounds of Examples 20~21 below were obtained in accordance with the method of Example 1.

Example 20

2-Butoxy-8-hydroxy-9-(4-methoxycarbonylmethylbenzyl)adenine

Example 21

2-Butoxy-8-hydroxy-9-(4-isopropoxycarbonylmethylbenzyl)adenine

Example 22

2-Butoxy-8-hydroxy-9-(4-methoxycarbonylmethoxybenzyl)adenine

8-Bromo-2-butoxy-9-(4-acetoxybenzyl)adenine (0.29 g, 0.67 mmol) obtained in accordance with the method of Reference example 4 was added to methanol (10 ml) and 5% sodium hydroxide solution (10 ml), and the mixture was stirred at room temperature for 4 hours. After the mixture was neutralized with concentrated hydrochloric acid, the resulting solid was filtered and washed with methanol to give 8-bromo-2-butoxy-9-(4-hydroxybenzyl)adenine (0.19 g, 0.49 mmol, yield: 73%) as a white solid. Thus obtained 8-bromo-2-butoxy-9-(4-hydroxybenzyl)adenine (0.05 g, 0.13 mmol) and potassium carbonate (0.02 g, 0.14 mmol) were added to DMF (10 ml), and then thereto was added ethyl bromoacetate (0.04 g, 0.24 mmol). The mixture was stirred at room temperature for 18 hours. After removing the solvent, the residue was poured into water and extracted with dichloromethane. The combined organic layer was dried over anhydrous magnesium sulfate, and concentrated. The residue was purified by column chromatography ($SiO_2$ 20 g, eluting solvent: $CHCl_3$/MeOH=100/1~50/1) to give 8-bromo-2-butoxy-9-(4-ethoxycarbonylmethoxybenzyl)adenine (0.06 g, 0.12 mmol, yield: 96%) as a white solid. And then the captioned compound was obtained in accordance with the method of Example 1, Yield: 80%.

Example 23

2-Butoxy-8-hydroxy-9-{3-bromo-4-(methoxycarbonylmethoxy)benzyl}adenine

After 2-butoxyadenine (0.11 g, 0.53 mmol) obtained by Reference example 1 and potassium carbonate (0.05 g, 0.36 mmol) were added to DMF (10 ml), 4-(chloromethyl)phenol acetate (0.12 g, 6.50 mmol) was added thereto, and the mixture was stirred at room temperature for 18 hours. After removing the solvent, the residue was poured into water and extracted with dichloromethane. The organic layer was dried over anhydrous magnesium sulfate and concentrated. The residue was purified by column chromatography ($SiO_2$ 20 g, eluting solvent: $CHCl_3$/MeOH=300/1~30/1) to give 2-butoxy-9-(4-acetoxybenzyl)adenine (0.08 g, 1.41 mmol, yield: 42%) as a white solid. Thus obtained solid was added to methanol (10 ml) and 5% sodium hydroxide solution (10 ml), and the mixture was stirred at room temperature for 2 hours. After being neutralized with concentrated hydrochloric acid, the solution was extracted with dichloromethane. The combined organic layer was dried over anhydrous magnesium sulfate and concentrated to give 2-butoxy-9-(4-hydroxybenzyl)adenine (0.06 g, 0.19 mmol. yield: 86%) as a white solid. Thus obtained solid and potassium carbonate (0.02 g, 0.14 mmol) were added to DMF (10 ml), and then thereto was added ethyl bromoacetate (0.04 g, 0.24 mmol). The mixture was stirred at room temperature for 18 hours. After removing the solvent, the residue was poured into water and extracted with dichloromethane. The combined organic layer was dried over anhydrous magnesium sulfate, concentrated and the residue was purified by column chromatography ($SiO_2$ 20 g, eluting solvent: $CHCl_3$/MeOH=100/1~50/1) to give 2-butoxy-9-{4-(ethoxycarbonyl methoxy)benzyl}adenine (0.06 g, 0.15 mmol, yield: 79%) as a white solid. And then the captioned compound was obtained in accordance with the method of Example 1.

Example 24

2-Butoxy-8-hydroxy-9-{6-(4-ethoxycarbonyl-1-piperidyl)-3-pyridylmethyl}adenine 2-Butoxy-9-(6-chloro-3-pyridylmethyl)-8-methoxyadenine (0.28 mg, 0.77 mmol) was added to 4-ethoxycarbonylpiperidine (10 ml), and the mixture was refluxed under stirring for 8 hours. After the mixture was allowed to cool, ethanol was added thereto. The resulting solid was filtered and purified by column chromatography ($SiO_2$ 20 g, eluting solvent: $CHCl_3$/MeOH=80/1~20/1) to give the captioned compound (0.15 g, 1.41 mmol, yield: 44%) as a white solid.

Example 25

2-Butoxy-8-hydroxy-9-{6-(3-ethoxycarbonyl-1-piperidyl)-3-pyridylmethyl}adenine The captioned compound was obtained in accordance with the method of Example 24.

Example 26

2-Butoxy-8-hydroxy-9-{(6-ethoxycarbonylmethoxy-2-naphthyl)methyl}adenine)

The captioned compound was obtained in accordance with the method of Example 5.

The compounds of Examples 27~28 below were obtained in accordance with the method of Example 1.

Example 27

2-Butylamino-8-hydroxy-9-(4-methoxycarbonylbenzyl)adenine

Example 28

2-Butylamino-8-hydroxy-9-(5-ethoxycarbonylfurfuryl)adenine

Example 29

9-Benzyl-8-hydroxy-2-methoxycarbonylmethyladenine

After sodium cyanide (0.20 g, 4.08 mmol) and 9-benzyl-2-chloromethyl-8-hydroxyadenine (0.20 g, 0.69 mmol) were added to DMF (10 ml), the mixture was stirred at 80° C. for 7 hours. After removing the solvent, the residue was poured into water and the solution was neutralized with concentrated hydrochloric acid. The solution was extracted with dichloromethane, and the organic layer was dried over anhydrous magnesium sulfate and concentrated. The residue was purified by column chromatography ($SiO_2$ 20 g, eluting solvent: $CHCl_3$/MeOH=100/1~50/1) and washed with methanol to give 9-benzyl-2-cyanomethyl-8-hydroxyadenine (0.16 g, 0.57 mmol) as a pale yellow solid. Thus obtained 9-benzyl-2-cyanomethyl-8-hydroxyadenine (0.08 g, 0.29 mmol) was added to a mixed solvent of 5% sodium hydroxide solution (20 ml) and methanol (10 ml), and the mixture was stirred at 60° C. for 8 hours. After the mixture was neutralized with concentrated hydrochloric acid, the solvent was removed. The residue and sulfuric acid (1 ml) were added to methanol (50 ml), and the mixture was refluxed for 3 hours under stirring. After being neutralized with saturated sodium hydrogencarbonate solution in an ice bath, the solution was extracted with dichloromethane. The organic layer was dried over anhydrous magnesium sulfate and concentrated. The residue was purified with column chromatography ($SiO_2$ 20 g, eluting solvent: $CHCl_3$/MeOH=100/1~30/1) and washed with methanol to give the captioned compound (0.02 g, 0.06 mmol) as a white solid.

Example 30

9-Benzyl-2-ethoxycarbonylmethyl-8-hydroxyadenine

The captioned compound was obtained in accordance with the method of Example 29.

Example 31

9-Benzyl-8-hydroxy-2-methoxycarbonylmethylaminoadenine

9-Benzyl-2-chloroadenine (0.30 g, 1.12 mmol), glycine methyl ester hydrochloride (0.72 g, 5.73 mmol) and diisopropylethylamine (1.48 g, 11.47 mmol) were added to n-butanol (10 ml), and the mixture was stirred in an autoclave at 150° C. for 19 hours. The solvent was removed and the residue was poured into water. The solution was extracted with dichloromethane. The organic layer was dried over anhydrous magnesium sulfate, concentrated and the residue was purified by column chromatography to give 9-benzyl-2-methoxycarbonylmethylaminoadenine (0.06 g) as a brown tar. Thus obtained 9-benzyl-2-methoxycarbonylmethylaminoadenine was dissolved in dichloromethane (10 ml) and to the solution was added bromine (0.05 ml) in an ice bath. The mixture was stirred at room temperature for 1 hour. After removing the solvent, the residue was poured into water and extracted with dichloromethane. The organic layer was dried over anhydrous magnesium sulfate, concentrated and the residue was purified by column chromatography to give 9-benzyl-8-bromo-2-methoxycarbonylmethylaminoadenine (0.06 g) as a yellow solid.

Thus obtained 9-benzyl-8-bromo-2-methoxycarbonylmethylaminoadenine was added to concentrated hydrochloric acid (10 ml), and the mixture was stirred for 8 hours at 100° C. The mixture was neutralized in an ice bath with 5% sodium hydroxide solution (pH 7) and the solvent was removed. To the residue were added methanol (30 ml) and sulfuric acid (1 ml), and the mixture was refluxed for 4 hours. After being neutralized (pH 6) in an ice bath with saturated sodium hydrogencarbonate solution, the solution was extracted with dichloromethane. The organic layer was dried over anhydrous magnesium sulfate, and concentrated. The residue was purified by column chromatography and the obtained compound was washed with methanol to give the captioned compound (0.02 g) as a white solid.

Example 32

8-Hydroxy-2-methoxycarbonylmethylamino-9-{(6-methyl-3-pyridyl)methyl}adenine

The captioned compound was obtained in accordance with the method of Example 31.

Example 33

2-(2-Acetoxyethylamino)-8-hydroxy-9-{(6-methyl-3-pyridyl)methyl}adenine

To 8-hydroxy-2-(2-hydroxyethylamino)-9-{(6-methyl-3-pyridyl)methyl}adenine (100 mg, 0.32 mmol) prepared by Comparative example 10 in pyridine (1 ml) was added under ice cooling acetic anhydride (0.033 ml, 0.35 mmol), and the mixture was stirred for 3 hours. To the reaction mixture was added sodium hydrogen carbonate solution, and the mixture was extracted with chloroform. The organic layer was dried over anhydrous magnesium sulfate and concentrated. The residue was purified by preparative thin-layer chromatography to give the captioned compound (14 mg, 0.039 mmol, yield: 12%) as a white solid.

The compounds of Examples 34-35 below were obtained in accordance with the method of Example 33.

Example 34

8-Hydroxy-2-(2-methoxycarbonyloxyethylamino)-9-{(6-methyl-3-pyridyl)methyl}adenine Example 35

2-(2-Acetoxyethylamino)-9-benzyl-8-hydroxyadenine

Example 36

2-(2-Acetoxyethoxy)-8-hydroxy-9-{(6-methyl-3-pyridyl)methyl}adenine

To 8-hydroxy-2-(2-hydroxyethoxy)-9-[(6-methyl-3-pyridyl)methyl]adenine (90 mg, 0.29 mmol) obtained by Comparative example 11 and dimethylaminopyridine (5 mg, 0.4 mmol) in pyridine (2 ml) was added under ice cooling acetic anhydride (0.027 ml, 0.29 mmol), and the mixture was stirred for 15 hours. To the reaction mixture was added water, and the solution was extracted with chloroform. The combined organic layer was dried over anhydrous magnesium sulfate, concentrated and the residue was purified by silica gel column chromatography to give the captioned compound (11 mg, 0.031 mmol, yield: 11%) as a white solid.

Example 37

8-Hydroxy-9-(6-methyl-3-pyridyl)methyl-2-{2-(propionyloxy)ethoxy}adenine

The captioned compound was obtained in accordance with the method of Example 36.

Example 38

2-{2-(Methoxycarbonyloxy)ethoxy}-8-hydroxy-9-{(6-methyl-3-pyridyl)methyl}adenine To 8-hydroxy-2-(2-hydroxyethoxy)-9-{(6-methyl-3-pyridyl)methyl}adenine (90 mg, 0.29 mmol) obtained by Comparative example 11 in pyridine (2 ml) was added under ice cooling methyl chloroformate (0.022 ml, 0.29 mmol), and the mixture was stirred for 3 hours. To the reaction mixture was added water, and the solution was extracted with chloroform. The combined organic layer was dried over anhydrous magnesium sulfate and concentrated to give the captioned compound (68 mg, 0.18 mmol, yield: 63%) as a white solid.

Example 39

2-{2-(N,N-Dimethylaminocarbonyloxy)ethoxy}-8-hydroxy-9-{(6-methyl-3-pyridyl)methyl}adenine The captioned compound was obtained in accordance with the method of Comparative example 11.

Example 40

9-Benzyl-8-hydroxy-2-(methoxycarbonylmethyl)thioadenine

After 9-benzyl-8-hydroxy-2-thioadenine (200 mg, 0.73 mmol) obtained by Reference example 7 was dissolved in dimethylformamide (8 ml), thereto were added potassium carbonate (150 mg, 1.1 mmol) and methyl bromoacetate (0.1 ml, 1.1 mmol) in that order, and the mixture was stirred at room temperature for 2 hours. After removing the solvent, the residue was poured into water and the solution was extracted with chloroform. The combined organic layer was dried over anhydrous magnesium sulfate, concentrated and the residue was purified by silica gel column chromatography to give the captioned compound (173 mg, yield: 69%) as a white solid.

The compounds of Examples 41-59 below are obtained in accordance with the method of Example 40.

Example 41

9-Benzyl-2-(ethoxycarbonylmethyl)thio-8-hydroxyadenine

Example 42

9-Benzyl-8-hydroxy-2-(octyloxycarbonylmethyl)thioadenine

Example 43

9-Benzyl-2-(t-butoxycarbonylmethyl)thio-8-hydroxyadenine

Example 44

2-(Allyloxycarbonylmethyl)thio-9-benzyl-8-hydroxyadenine

Example 45

2-(Benzyloxycarbonylmethyl)thio-9-benzyl-8-hydroxyadenine

Example 46

9-Benzyl-2-(2-fluoroethoxycarbonylmetyl)thio-8-hydroxyadenine

Example 47

9-Benzyl-2-(2,2-difluoroethoxycarbonylmetyl)thio-8-hydroxyadenine

Example 48

9-Benzyl-2-(2,2,2-trifluoroethoxycarbonylmetyl)thio-8-hydroxyadenine

Example 49

9-Benzyl-8-hydroxy-2-(2-methoxyethoxycarbonylmethyl)thioadenine

Example 50

9-Benzyl-2-(ethylcarbamoylmethyl)thio-8-hydroxyadenine

Example 51

9-Benzyl-8-hydroxy-2-(1-piperidinocarbonylmethyl)thioadenine

Example 52

9-Benzyl-8-hydroxy-2-(morphorinocarbonylmethyl)thioadenine

Example 53

9-Benzyl-8-hydroxy-2-(1-ethoxycarbonylethyl)thioadenine

Example 54

9-Benzyl-8-hydroxy-2-(2-methoxycarbonylethyl)thioadenine

Example 55

9-Benzyl-2-(2-ethoxycarbonylethyl)thio-8-hydroxyadenine

Example 56

9-Benzyl-2-(3-ethoxycarbonylpropyl)thio-8-hydroxyadenine

Example 57

9-Benzyl-2-(4-ethoxycarbonylbutyl)thio-8-hydroxyadenine

Example 58

9-Benzyl-2-(ethoxycarbonylmethylcarbonylmethyl)thio-8-hydroxyadenine

Example 59

9-Benzyl-2-(2-butyrolactino)thio-8-hydroxyadenine

Example 60

8-Hydroxy-9-{(6-methyl-3-pyridyl)methyl}-2-{(2-oxo-1,3-dioxolan-4-yl)methylamino}adenine 8-Methoxy-9-{(6-methyl-3-pyridyl)methyl}-2-{(2-oxo-1,3-dioxolan-4-yl)methylamino}adenine (65 mg, 0.17 mmol) obtained by Reference example 19 was added to concentrated hydrochloric acid, and the solution was stirred under ice cooling for 15 hours. The solution was neutralized under ice cooling with 40% sodium hydroxide solution, and the resulting white crystals were purified by preparative thin-layer chromatography to give the captioned compound (18 mg, 0.049 mmol, yield: 29%) as a white solid.

Example 61

9-Benzyl-8-hydroxy-2-(2-methoxycarbonylethyl)adenine

After 9-benzyl-2-(2-carboxyethyl)-8-hydroxyadenine (100 mg, 0.32 mmol) obtained by Comparative example 15 was added to methanol (20 ml), sulfuric acid (2 ml) was added thereto, and the mixture was refluxed for 4 hours under stirring. After being neutralized in an ice bath with saturated sodium hydrogencarbonate solution, the solution was extracted with chloroform. The organic layer was dried over anhydrous magnesium sulfate and concentrated. The residue was purified by column chromatography ($SiO_2$ 20 g, eluting solvent: $CHCl_3$/MeOH=100/1~30/1) and the obtained compound was washed with methanol to give the captioned compound (74 mg, 0.23 mmol) as a white solid.

Example 62

9-Benzyl-2-ethoxycarbonylethyl-8-hydroxy adenine

The captioned compound was obtained in accordance with the method of Example 61.

Example 63

9-Benzyl-8-hydroxy-2-(S-methylthiocarbonyl ethyladenine

To DMF (3 ml) were added 9-benzyl-2-(2-carboxyethyl)-8-hydroxyadenine (49 mg, 0.16 mmol) obtained by Comparative example 15, N-hydroxybenzotriazole (47 mg, 0.35 mmol), methanethiol, aqueous 15% sodium salt solution (161 mg, 0.34 mmol) and 1-ethyl-3-(3-dimethylaminopropyl)carbodiimide hydrochloride (66 mg, 0.34 mmol), and the mixture was stirred at room temperature for 30 hours. After removing the solvent, the residue was poured into water and the solution was extracted with chloroform. The organic layer was dried over anhydrous magnesium sulfate and concentrated. The residue was purified by column chromatography ($SiO_2$ 20 g, eluting solvent: $CHCl_3$/MeOH=100/1~30/1) and the obtained compound was washed with methanol to give the captioned compound (17 mg, 0.050 mmol) as a white solid.

Example 64

9-Benzyl-8-hydroxy-2-methoxycarbonylmethoxyadenine

After sodium (0.30 g, 13.04 mmol) was dissolved in methanol (30 ml), thereto was added 9-benzyl-8-bromo-2-methoxycarbonylmethoxyadenine (0.10 g, 0.25 mmol) obtained by Reference example 21, and the mixture was refluxed for 7 hours under stirring. After being allowed to cool, the solution was neutralized with concentrated hydrochloric acid and concentrated. After the residue was dissolved in methanol (30 ml), thereto was added sulfuric acid (2 ml) and the solution was stirred for 7 hours. After being neutralized in an ice bath with saturated sodium hydrogencarbonate solution, the solution was extracted with chloroform. The organic layer was dried over anhydrous magnesium sulfate and concentrated. The residue was purified by column chromatography ($SiO_2$ 20 g, eluting solvent: $CHCl_3$/MeOH=100/1~30/1) and the obtained compound was washed with methanol to give the captioned compound (62 mg, 0.19 mmol) as a white solid.

Example 65

9-Benzyl-2-ethoxycarbonylmethoxy-8-hydroxyadenine

The captioned compound was obtained in accordance with the method of Example 61.

Example 66

8-Hydroxy-2-methoxycarbonylethyl-9-{(6-methyl-3-pyridyl)methyl}adenine

8-Bromo-2-(2-methoxycarbonylethyl)-9-{(6-methyl-3-pyridyl)methyl}adenine (31 mg, 0.076 mmol) obtained by Reference example 24 was added to concentrated hydrochloric acid (5 ml), and the mixture was stirred at 100° C. for 4 hours. The solution was neutralized in an ice bath with 1N sodium hydroxide solution, concentrated and the residue was dissolved in methanol (70 ml). Thereto was added sulfuric acid (7 ml) and the mixture was refluxed for 2 hours under stirring. After being neutralized in an ice bath with saturated sodium hydrogencarbonate solution, the solution was extracted with chloroform. The organic layer was dried over anhydrous magnesium sulfate and concentrated. The residue was purified by column chromatography ($SiO_2$ 20 g, eluting solvent: $CHCl_3$/MeOH=50/1~20/1), the obtained compound was washed with chloroform and dried in vacuo under heating to give the captioned compound (12 mg, 0.035 mmol) as a white solid.

Example 67

8-Hydroxy-2-(2-methoxycarbonylethyl)-9-(4-methoxycarbonylmethylbenzyl)adenine

The captioned compound was obtained in accordance with the method of Example 66.

Example 68

2-Butoxy-8-hydroxy-9-(4-ethoxycarbonylmethylbenzyl)adenine

The captioned compound was obtained in accordance with the method of Example 61.

Example 69

2-Butoxy-8-hydroxy-9-{3-(2,2,2-trifluoroethoxycarbonyl)methylbenzyl}adenine

To DMF (3 ml) were added 2-butoxy-9-(4-carboxylmethylbenzyl)-8-methoxyadenine (40 mg, 0.10 mmol) obtained in accordance with the method of Reference example 5, N-hydroxybenzotriazole (31 mg, 0.23 mmol), 2,2,2-trifluoroethanol (23 mg, 0.23 mmol), diisopropylethylamine (59 mg, 0.46 mmol), and 1-ethyl-3-(3-dimethylaminopropyl)carbodiimide hydrochloride (44 mg, 0.23 mmol), and the mixture was stirred at room temperature for 17 hours. After removing the solvent, the residue was poured into water and the solution was extracted with chloroform. The organic layer was dried over anhydrous magnesium sulfate, concentrated and the residue was purified by column chromatography ($SiO_2$ 20 g, eluting solvent: $CHCl_3$/MeOH=200/1~100/1). The resulting residue was added to THF (5.5 ml) and thereto was added concentrated hydrochloric acid (0.5 ml). The mixture was stirred at room temperature for 1 hour and neutralized with saturated sodium hydrogencarbonate solution. The mixture was extracted with chloroform. The organic layer was dried over anhydrous magnesium sulfate and concentrated. The residue was purified by column chromatography ($SiO_2$ 20 g, eluting solvent: $CHCl_3$/MeOH=200/1~40/1) and the obtained compound was washed with methanol to give the captioned compound (10 mg, 0.022 mmol) as a white solid.

The compounds of Examples 70~71 below were obtained in accordance with the method of Example 69.

Example 70

2-Butoxy-8-hydroxy-9-{3-(2-fluoroethoxycarbonyl)methylbenzyl}adenine

Example 71

2-Butoxy-8-hydroxy-9-{4-(2-hydroxyethoxycarbonyl)methylbenzyl}adenine

Example 72

2-Butoxy-8-hydroxy-9-{4-(2-dimethylaminoethoxycarbonyl)methylbenzyl}adenine hydrochloride 2-Butoxy-9-(4-carboxylmethylbenzyl)-8-methoxyadenine (84 mg, 0.22 mmol) and potassium carbonate (133 mg, 0.96 mmol) were added to DMF (4 ml), and thereto was added 2-(dimethylamino)ethyl chloride hydrochloride (94 mg, 0.65 mmol). The mixture was stirred at room temperature for 16 hours. After removing the solvent, the residue was poured into water and extracted with chloroform. The organic layer was washed with saturated brine, dried over anhydrous magnesium sulfate, concentrated and purified by column chromatography ($SiO_2$ 20 g, eluting solvent: $CHCl_3$/MeOH=100/1~30/1). The resulting residue was added to THF (5.5 ml), and thereto was added concentrated hydrochloric acid (0.5 ml). The mixture was stirred at room temperature for 1 hour. The solution was neutralized with sodium hydrogencarbonate solution, extracted with chloroform. The organic layer was dried over anhydrous magnesium sulfate, concentrated and the residue was purified by column chromatography ($SiO_2$ 20 g, eluting solvent: $CHCl_3$/MeOH=200/1~40/1). The resulting residue was dissolved into THF (3 ml) and thereto was added concentrated hydrochloric acid (5.5 μl). The mixture was stirred at room temperature for 30 minutes. The precipitated solid was filtered and dried in vacuo under heating to give the captioned compound (16 mg, 0.033 mmol) as a white solid.

Example 73

2-Butoxy-8-hydroxy-9-{4-(2-morpholinoethoxycarbonyl)methylbenzyl}adenine

The captioned compound was obtained in accordance with the method of Example 72.

Example 74

2-Butoxy-8-hydroxy-9-{4-(S-methylthiocarbonyl)methylbenzyl}adenine

The captioned compound was obtained in accordance with the method of Example 63.

The compounds of Examples 75~79 below were obtained in accordance with the method of Example 69.

Example 75

2-Butoxy-9-{4-(S-ethylthiocarbonyl)methylbenzyl}-8-hydroxyadenine

Example 76

2-Butoxy-8-hydroxy-9-(4-carbamoylmethylbenzyl)adenine

Example 77

2-Butoxy-8-hydroxy-9-(4-methylcarbamoylmethylbenzyl)adenine

Example 78

2-Butoxy-8-hydroxy-9-(4-dimethylcarbamoylmethylbenzyl)adenine

Example 79

2-Butoxy-8-hydroxy-9-(4-morpholinomethylbenzyl)adenine

Example 80

2-Butoxy-9-(3-ethoxycarbonylmethylbenzyl)-8-hydroxyadenine

The captioned compound was obtained in accordance with the method of Example 61.

Example 81

2-Butoxy-8-hydroxy-9-(5-methoxycarbonylmethylfurfuryl)adenine

2-Butoxy-9-(5-cyanomethylfurfuryl)-8-hydroxyadenine (29 mg, 0.085 mmol) obtained by Reference example 26 was added to a mixed solvent of 4N sodium hydroxide solution (3 ml) and methanol (3 ml), and the mixture was refluxed for 4 hours. The solution was neutralized in an ice bath with concentrated hydrochloric acid. After removing the solvent in vacuo, the residue and sulfuric acid (3 ml) were added to methanol (30 ml). The mixture was refluxed for 2 hours under stirring. The solution was neutralized in an ice bath with saturated sodium hydrogencarbonate solution, and extracted with chloroform. The combined organic layer was dried over anhydrous magnesium sulfate and concentrated. The residue was purified by column chromatography ($SiO_2$ 20 g, eluting solvent: $CHCl_3$/MeOH=70/1~40/1), and the obtained compound was washed with methanol and dried in vacuo under heating to give the captioned compound (16 mg, 0.091 mmol) as a white solid.

Example 82

2-Butoxy-8-hydroxy-9-{(6-S-methylthiocarbonyl-3-pyridyl)methyl}adenine

The captioned compound was obtained in accordance with the method of Example 63.

Example 83

2-Butoxy-9-{(6-carbamoyl-3-pyridyl)methyl}-8-hydroxyadenine

The captioned compound was obtained in accordance with the method of Example 69.

Example 84

2-Butoxy-8-hydroxy-9-(3-methoxycarbonylethylbenzyl)adenine

2-Butoxy-9-(3-methoxycarbonylethylbenzyl)adenine was obtained in accordance with the method of Example 81. And then the captioned compound was obtained in accordance with the method of Example 1.

Example 85

2-Butoxy-8-hydroxy-9-(4-methoxycarbonylethylbenzyl)adenine

The captioned compound was obtained in accordance with the method of Example 84.

Example 86

2-Butoxy-9-(4-ethoxycarbonylethylbenzyl)-8-hydroxyadenine

The captioned compound was obtained in accordance with the method of Example 61.

The compounds of Examples 87~89 below were obtained in accordance with the method of Example 1.

Example 87

2-Butoxy-8-hydroxy-9-{6-(4-methoxycarbonyl-1-piperidyl)-3-pyridylmethyl}adenine

Example 88

2-Butoxy-8-hydroxy-9-{6-(3-methoxycarbonyl-1-piperidyl)-3-pyridylmethyl}adenine

Example 89

2-Butoxy-8-hydroxy-9-{(6-methoxycarbonylmethoxy-2-naphthyl)methyl}adenine

Example 90

2-Butoxy-9-(3,4-dimethoxycarbonylbenzyl)-8-hydroxyadenine

Staring from 2-butoxy-9-(3,4-dimethoxycarbonylbenzyl)adenine obtained by Reference example 28, the captioned compound was obtained in accordance with the method of Example 1.

Example 91

2-Butoxy-9-(3,5-dimethoxycarbonylbenzyl)-8-hydroxyadenine

The captioned compound was obtained in accordance with the method of Example 90.

Example 92

2-Butoxy-8-hydroxy-9-{(6-methoxycarbonylmethyl-3-pyridyl)methyl}adenine

The captioned compound was obtained in accordance with the method of Example 81.

Example 93

2-Butoxy-9-{6-(γ-butyrolactonyl)thio-3-pyridyl}methyl}-8-hydroxyadenine

Starting from 2-butoxy-9-{6-(γ-butyrolactonyl)thio-3-pyridyl}methyl)adenine obtained by Reference example 31, the captioned compound was obtained in accordance with the method of Example 1.

Example 94

2-Butoxy-9-{4-(γ-butyrolactonyloxy)benzyl}-8-hydroxyadenine

Starting from 8-bromo-2-butoxy-9-{4-(γ-butyrolactonyloxy)benzyl}adenine obtained by Reference example 32, the captioned compound was obtained in accordance with the method of Example 1.

Example 95

2-Butoxy-9-{4-(1-hydroxy-3-methoxycarbonylpropoxy)benzyl}-8-hydroxyadenine

The captioned compound was obtained in accordance with the method of Example 1.

Example 96

8-Hydroxy-9-(3-methoxycarbonylmethylbenzyl)-2-(2-methoxyethoxy)adenine 9-(3-Carboxymethylbenzyl)-8-hydroxy-2-(2-methoxyethoxy)adenine (81 mg, 0.22 mmol) obtained by Comparative example 27 was dissolved in methanol (3 ml), and thereto was added concentrated sulfuric acid (0.11 g, 1.10 mmol). The mixture was refluxed for 20 minutes. The solution was neutralized with saturated sodium hydrogencarbonate solution, extracted with chloroform, dried over anhydrous magnesium sulfate and concentrated. The residue was washed with diethyl ether to give the captioned compound (33 mg, yield 39%) as a white solid.

Example 97

2-Butylamino-8-hydroxy-9-(3-methoxycarbonyl methylbenzyl)adenine

The captioned compound was obtained in accordance with the method of Example 96.

Example 98

2-Chloro-8-hydroxy-9-(3-methoxycarbonylmethylbenzyl)adenine

8-Bromo-2-chloro-9-(3-methoxycarbonylmethylbenzyl) adenine (1.78 g, 4.34 mmol) obtained by Reference example 39 was suspended in the mixed solvent of 1N sodium hydroxide solution (150 ml) and methanol (150 ml), and the mixture was stirred at 100° C. for 30 minutes. The residue was neutralized with 12N hydrochloric acid. After removing the solvent, to the residue were added methanol (50 ml) and concentrated sulfuric acid (2.45 g, 25.0 mmol) and the mixture was refluxed for 1 hour under heating. The solution was neutralized with saturated sodium hydrogencarbonate solution and extracted with chloroform. The organic layer was dried over anhydrous magnesium sulfate, concentrated and the residue was purified by column chromatography ($SiO_2$ 90.0 g, eluting solvent: $CHCl_3$/MeOH=100/0~50/1) to give the captioned compound (0.84 g, 2.41 mmol, yield: 56%) as a white solid.

Example 99

8-Hydroxy-2-(2-hydroxyethylthio)-9-(3-methoxycarbonylmethylbenzyl)adenine

Sodium (67 mg, 2.90 mmol) was dissolved in 2-mercapt ethanol (2.5 ml) and thereto was added 2-chloro-8-hydroxy-9-(3-methoxycarbonylmethylbenzyl)adenine (100 mg, 0.29 mmol) obtained by Example 98. The mixture was stirred at 120° C. for 4 hours and then neutralized with 12N hydrochloric acid. After removing the solvent, to the residue were added methanol (3.0 ml) and concentrated sulfuric acid (0.14 g, 1.43 mmol), and the mixture was refluxed for 30 minutes. The solution was neutralized with saturated sodium hydrogencarbonate solution and extracted with chloroform. The organic layer was dried over anhydrous magnesium sulfate and concentrated. To the residue was added water, the mixture was filtered and washed with water to give the captioned compound (55 mg, 0.14 mmol, yield: 49%) as a white solid.

The compounds of Examples 100~102 below were obtained in accordance with the method of Example 1.

Example 100

2-Butoxy-8-hydroxy-9-[4-(1-methoxycarbonylethyl) benzyl]adenine

Example 101

2-Butoxy-8-hydroxy-9-[3-(2-methoxycarbonyl-2-propyl)benzyl]adenine

Example 102

2-Butoxy-8-hydroxy-9-(4-methoxycarbonylphenethyl)adenine

The compounds of Examples 103~106 were obtained in accordance with the method of Example 40.

Example 103

9-Benzyl-8-hydroxy-2-[(3-methoxycarbonylbenzyl)thio]adenine

Example 104

9-Benzyl-8-hydroxy-2-[(4-methoxycarbonylbenzyl)thio]adenine

Example 105

9-Benzyl-8-hydroxy-2-[(3-methoxycarbonylmethyl-benzyl)thio]adenine

Example 106

9-Benzyl-8-hydroxy-2-[(4-methoxycarbonylmethyl-benzyl)thio]adenine

The compounds of Examples 107~109 below were obtained in accordance with the method of Example 29.

Example 107

9-Benzyl-2-butoxycarbonylmethyl-8-hydroxyadenine

Example 108

9-Benzyl-8-hydroxy-2-(isopropoxycarbonylmethyl)adenine

Example 109

9-Benzyl-2-(2-fluoroethoxycarbonyl)methyl-8-hydroxyadenine

Example 110

9-Benzyl-8-hydroxy-2-(morpholinocarbonylmethyl)adenine

9-Benzyl-2-carboxymethyl-8-hydroxyadenine (15 mg, 0.050 mmol) obtained by Comparative example 8, N-hydroxybenzotriazole (12 mg, 0.075 mmol), morpholine (7 mg, 0.075 mmol) and 1-ethyl-3-(3-dimethylaminopropyl)carbodiimide hydrochloride (15 mg, 0.075 mmol) were added to dichloromethane (10 ml), and the mixture was stirred at room temperature for 5 hours. After removing the solvent, the residue was poured into water and extracted with chloroform. The organic layer was dried over anhydrous magnesium sulfate, concentrated and the residue was purified by column chromatography ($SiO_2$ 20 g, eluting solvent: $CHCl_3$/MeOH=100/3~20/1) to give the captioned compound (8 mg, yield: 43%) as a white solid.

The compounds of Examples 111~115 below were obtained in accordance with the method of Example 1.

Example 111

2-Butoxy-8-hydroxy-9-[(2-methoxycarbonylmethyl)benzyl]adenine (108 mg, 0.28 mmol)

Example 112

2-Butoxy-8-hydroxy-9-[(4-fluoro-3-methoxycarbonyl)benzyl]adenine)

(170 mg, 0.44 mmol)

Example 113

2-Butoxy-8-hydroxy-9-[(4-methoxy-3-methoxycarbonyl)benzyl]adenine (369 mg, 0.92 mmol)

Example 114

2-Butoxy-8-hydroxy-9-[4-(2-methoxycarbonyl-2-methylethyl)benzyl]adenine (305 mg, 0.74 mmol)

Example 115

2-Butoxy-8-hydroxy-9-[3-((2R,S)-methoxycarbonyl-ethyl)benzyl]adenine (287 mg, 0.72 mmol)

Example 116

2-Butoxy-8-hydroxy-9-{3-[methoxy(oxo)acetyl]benzyl}adenine

2-Butoxy-8-hydroxy-9-[3-(oxocarboxymethyl)benzyl]adenine (0.13 g, 0.34 mmol) obtained by Comparative example 43 was dissolved in methanol (3.5 ml), and thereto was added at 0° C. concentrated sulfuric acid (0.2 ml). The solution was stirred at room temperature for 2 hours and neutralized with saturated sodium hydrogencarbonate solution. After adding water, the precipitated solid was filtered, purified by column chromatography ($SiO_2$ 5.0 g, eluting solvent: $CHCl_3$/MeOH=10/1) and the obtained compound was washed with water to give the captioned compound (0.086 g, 0.22 mmol, yield: 64%) as a white solid.

Example 117

2-Butoxy-8-hydroxy-9-{3-[(1-hydroxy-2-methoxy)acetyl]benzyl}adenine

The captioned compound was obtained in accordance with the method of Example 116, Yield: 82%.

The compounds of Examples 118~119 below were obtained in accordance with the method of Example 1.

Example 118

2-Butoxy-8-hydroxy-9-{(2-methoxycarbonyl-4-pyridyl)methyl}adenine

Example 119

2-Butoxy-8-hydroxy-9-{(5-methoxycarbonyl-2-thienyl)methyl}adenine

The compounds of Examples 120~121 below were obtained in accordance with the method of Example 81.

Example 120

9-{3,5-Bis(methoxycarbonylmethyl)benzyl}-2-butoxy-8-hydroxyadenine

Example 121

2-Butoxy-8-hydroxy-9-{(5-methoxycarbonylmethyl-3-pyridyl)methyl}adenine

Example 122

Interferon Inducing Activity on Cells of Mouse Spleen (In Vitro)

By using a spleen extracted from a C3H/HeJ mouse (male; 8-10 weeks old), a suspension of spleen cells ($2\times10^6$ cells/ml) was prepared in MEM broth containing 5% FBS. To each well of a 24-well microplate was poured the suspension (0.5 ml). To each well was added 0.5 ml of the test compound (containing 0.2% DMSO) diluted with the same broth, and the microplate was incubated at 37° C. for 24 hours in a 5% $CO_2$ incubator. The culture broth was aseptically filtered by a filter (0.2 micrometer) to give a supernatant. The interferon activity in the supernatant was quantitatively measured by the bioassay method described in J. A. Armstrong, Methods in Enzymology 78, 381-7. Namely, after mouse fibroblast L929 ($1\times10^4$ cells/50 μl) were cultured in a 96-well culture plate for 24 hours, thereto was added 50 μl of the diluted culture supernatant and the mixture was further cultivated for 24 hours. And then 100 μl of vesicular stomatitis virus were added to each well. Forty four hours after the virus infection, the effect of the cell denaturation was confirmed by the crystal violet stain. The quantitative analysis was carried out by dissolving the pigment in 2% sodium deoxycholate solution and measuring absorbance at 595 nm. In Table 1, interferon inducting activity on each compound (Minimum effective concentration) was shown.

TABLE 1

| Compound | Minimum effective concentration (μM) |
|---|---|
| Example 1 | <0.001 |
| Example 6 | <0.001 |
| Example 7 | <0.001 |
| Example 15 | 0.003 |
| Example 16 | 0.003 |
| Example 19 | <0.001 |
| Example 20 | 0.003 |
| Example 21 | 0.003 |
| Example 24 | <0.001 |
| Example 25 | 0.003 |
| Example 29 | 0.01 |
| Example 30 | 0.01 |
| Example 32 | 0.01 |
| Example 33 | 0.1 |
| Example 34 | 0.1 |
| Example 38 | 0.01 |
| Example 40 | 0.01 |
| Example 48 | 0.3 |
| Example 50 | 0.1 |
| Example 51 | 0.1 |
| Example 53 | 0.1 |
| Example 54 | 0.1 |
| Example 58 | 0.1 |
| Example 59 | 0.1 |
| Comparative example 1 | 0.003 |
| Comparative example 3 | 0.1 |
| Comparative example 5 | 0.1 |
| Comparative example 6 | 0.03 |
| Comparative example 8 | 10 |
| Comparative example 10 | 1 |
| Comparative example 11 | 0.1 |
| Comparative example 12 | 10 |
| Comparative example 13 | 10 |

Example 123

Interferon Inducing Activity on Cells of Rat Spleen (In Vitro)

By using a spleen extracted from a SD rat (male; 8-10 weeks old), a suspension of spleen cells ($2\times10^6$ cells/ml) was prepared in MEM broth not containing any blood. To each well of a 24-well microplate was poured the suspension (0.5 ml). To each well was added 0.5 ml of the test compound (containing 0.2% DMSO) diluted with the same broth, and the microplate was incubated at 37° C. for 24 hours in a 5% $CO_2$ incubator. The culture broth was aseptically filtered by a filter (0.2 micrometer) to give a supernatant. The interferon activity in the supernatant was quantitatively measured by the bioassay method described in J. A. Armstrong, Methods in Enzymology 78, 381-7. Namely, after mouse fibroblast L929 ($1\times10^4$ cells/50 μl) were cultured in 96-wells culture plate for 24 hours, thereto was added 50 μl of diluted culture supernatant and the mixture was further cultivated for 24 hours. And then 100 μl of vesicular stomatitis virus were added. Forty four hours after the virus infection, the effect of the cell denaturation was confirmed by crystal violet stain. The quantitative analysis was carried out by extracting the pigment with 50% ethanol and PBS solution and measuring absorbance at 540 nm. In Table 2, interferon inducting activity on each compound (Minimum effective concentration) was shown.

TABLE 2

| Compound | Minimum effective concentration (nM) |
|---|---|
| Example 1 | 0.3 |
| Example 2 | 1 |
| Example 15 | 1 |
| Example 17 | 1 |
| Example 19 | 0.3 |
| Example 20 | 0.1 |
| Example 21 | 1 |
| Example 23 | 100 |
| Example 24 | 0.3 |
| Example 29 | 10 |
| Example 30 | 10 |
| Example 40 | 10 |
| Example 54 | 10 |
| Example 61 | 3 |
| Example 62 | 30 |
| Example 63 | 100 |
| Example 64 | 3 |
| Example 65 | 30 |
| Example 66 | 1 |
| Example 67 | 1 |
| Example 68 | 0.3 |
| Example 70 | 1 |
| Example 71 | 0.3 |
| Example 73 | 0.3 |
| Example 74 | 1 |
| Example 75 | 3 |
| Example 76 | 0.1 |

TABLE 2-continued

| Compound | Minimum effective concentration (nM) |
|---|---|
| Example 77 | 0.3 |
| Example 78 | 0.03 |
| Example 79 | 0.3 |
| Example 80 | 1 |
| Example 81 | 1 |
| Example 82 | 100 |
| Example 83 | 0.3 |
| Example 84 | 10 |
| Example 87 | 1 |
| Example 90 | 0.3 |
| Example 93 | 3 |
| Example 95 | 1 |
| Example 96 | 3 |
| Example 100 | 0.3 |
| Example 103 | 10 |
| Example 104 | 100 |
| Example 105 | 300 |
| Example 106 | 100 |
| Example 107 | 100 |
| Example 108 | 30 |
| Example 109 | 30 |
| Example 110 | 100 |
| Comparative ex. 1 | 10 |
| Comparative ex. 3 | 10 |
| Comparative ex. 5 | 10 |
| Comparative ex. 6 | 10 |
| Comparative ex. 8 | 3000 |
| Comparative ex. 12 | 300 |
| Comparative ex. 13 | 300 |
| Comparative ex. 15 | 1000 |
| Comparative ex. 16 | 1000 |
| Comparative ex. 17 | 300 |
| Comparative ex. 18 | 3000 |
| Comparative ex. 19 | 30 |
| Comparative ex. 20 | 30 |
| Comparative ex. 21 | 3 |
| Comparative ex. 23 | 100 |
| Comparative ex. 26 | 3 |
| Comparative ex. 27 | 300 |
| Comparative ex. 31 | 30 |
| Comparative ex. 34 | 300 |
| Comparative ex. 35 | 1000 |
| Comparative ex. 36 | 3000 |
| Comparative ex. 37 | 1000 |

Example 124

Metabolic Stability Test on Serum

Plasma was prepared from fresh blood of a SD rat (male; 8-10 weeks old) and thereto was added the test compound to give the final concentration 10 μM (containing 1% DMSO) After the mixture was metabolized with a plasma esterase at 37° C. for 15 minutes, the test-compound was extracted with ethyl acetate, and was quantitatively analyzed by reverse phase HPLC. The metabolic stability of the test compound was presented by the residual amount (%) per the concentration of pre-metabolization. The result was shown in Table 3.

TABLE 3

| Compound | Residual rate (%) |
|---|---|
| Example 1 | 32 |
| Example 2 | 5 |
| Example 3 | 20 |
| Example 4 | 23 |
| Example 5 | 18 |
| Example 6 | 14 |
| Example 7 | 1 |
| Example 8 | 16 |

TABLE 3-continued

| Compound | Residual rate (%) |
|---|---|
| Example 9 | 1 |
| Example 11 | 13 |
| Example 12 | 29 |
| Example 13 | 10 |
| Example 15 | 0 |
| Example 16 | 0 |
| Example 17 | 0 |
| Example 18 | 0 |
| Example 19 | 1 |
| Example 20 | 0 |
| Example 21 | 0* |
| Example 22 | 0 |
| Example 24 | 7 |
| Example 25 | 16 |
| Example 27 | 0 |
| Example 29 | 0 |
| Example 30 | 0 |
| Example 31 | 0 |
| Example 32 | 0 |
| Example 34 | 11 |
| Example 37 | 0 |
| Example 38 | 2 |
| Example 40 | 0 |
| Example 41 | 0 |
| Example 42 | 0 |
| Example 43 | 0 |
| Example 44 | 0 |
| Example 45 | 0 |
| Example 46 | 0 |
| Example 47 | 0 |
| Example 48 | 0 |
| Example 49 | 0 |
| Example 53 | 0 |
| Example 54 | 0 |
| Example 55 | 0 |
| Example 56 | 0 |
| Example 58 | 0 |
| Example 59 | 0 |
| Example 61 | 0* |
| Example 62 | 0* |
| Example 64 | 0* |
| Example 65 | 0* |
| Example 68 | 0* |
| Example 70 | 0* |
| Example 71 | 0* |
| Example 73 | 4* |
| Example 74 | 0* |
| Example 75 | 0* |
| Example 80 | 0* |
| Example 103 | 6* |

*The concentration of the test compound: 1 μM

Example 125

Metabolic Stability on River S9 of Rat

The reaction on river S9 of a rat was carried out on a 96-well plate by using a robot for screening by Tecan Company. S9 solution was prepared by adding to 10 ml of liver S9 of a rat, 20 ml of 250 mM Kpi (pH 7.4) and 20 ml of deionized water. Cofactor solution was prepared by dissolving NADPH (220 mg) in deionized water (40.5 ml) to give finally a 6 mM solution. IS (Internal Standard) solution was prepared by adding 300 μL of IS solution (1 mM DMSO solution) to 30 ml of acetonitrile solution (100 times dilution). The test compound (1 μM DMSO solution) was dissolved in an incubator at 37° C., 35 μL of it was poured into each well of a 96-well plate (24 samples/plate and then, plates (a sample plate, a 96 well-plate for dilution, deep well plates for reaction and recovering, a plate for extraction of the solid phase) and the test samples (S9 solution, Cofactor solution, IS (Internal Standard) solution, Stop solution, acetonitrile for elution)

were set to the specified position in the booth of the robot. The reaction started (the concentration of the test compound was 1 μM) and the mixture was incubated at 37° C. under stirring. The solid phase was extracted and at the same time the internal standard for analysis was added. To the recovered sample (200 μL/well) was added 50 μL of acetonitrile per each well and to 2 plates of FALCON Deep well were poured 100 μL of the solution per well. By subjecting to the LC/MS analysis, the chromatogram of the test sample and the internal standard were described and the peak area was calculated. And then, the stability (residual rate after reaction) was calculated by the internal standard method. The result was shown in Table 4.

TABLE 4

| Compound | Residual rate (%) |
|---|---|
| Example 1 | 7 |
| Example 2 | 11 |
| Example 3 | 19 |
| Example 4 | 25 |
| Example 8 | 1 |
| Example 14 | 22 |
| Example 15 | 11 |
| Example 16 | 0 |
| Example 17 | 28 |
| Example 19 | 0 |
| Example 20 | 0 |
| Example 21 | 26 |
| Example 22 | 31 |
| Example 30 | 4 |
| Example 31 | 3 |
| Example 33 | 2* |
| Example 34 | 1* |
| Example 41 | 2* |
| Example 42 | 3 |
| Example 43 | 2 |
| Example 44 | 0 |
| Example 45 | 8* |
| Example 46 | 0 |
| Example 47 | 0 |
| Example 48 | 0 |
| Example 49 | 0 |
| Example 50 | 7 |
| Example 51 | 0 |
| Example 52 | 24 |
| Example 53 | 2 |
| Example 55 | 4* |
| Example 56 | 1 |
| Example 57 | 3 |
| Example 59 | 7 |
| Example 61 | 0 |
| Example 62 | 0 |
| Example 63 | 0 |
| Example 64 | 2 |
| Example 66 | 0 |
| Example 67 | 0 |
| Example 68 | 13 |
| Example 70 | 16 |
| Example 71 | 0 |
| Example 72 | 4 |
| Example 73 | 0 |
| Example 74 | 7 |
| Example 79 | 17 |
| Example 80 | 0 |
| Example 81 | 2 |
| Example 82 | 2 |
| Example 84 | 1 |
| Example 86 | 18 |
| Example 90 | 3 |
| Example 94 | 2 |
| Example 95 | 4 |
| Example 96 | 0 |
| Example 100 | 1 |
| Example 103 | 7 |
| Example 105 | 1 |
| Example 106 | 3 |
| Example 107 | 3 |

TABLE 4-continued

| Compound | Residual rate (%) |
|---|---|
| Example 108 | 3 |
| Example 109 | 0 |

*The concentration of the test compound: 10 μM

Example 126

The Measurement of the Amount of Leucocytes and Cytokines in Bronchoalveolar Lavege Fluid (BALF) on an Asthma Modeled Mouse C57BL/6 mouse was immunized by dermally administering denatured ovalbumin by heating (40 mg). Fourteen days later after the first immunization, ovalbumin (100 μg) was nasally busted. Twenty one days later after the first immunization, the solution (1 ml/kg) prepared by suspending the test compound (10 mg/kg) in physiological saline was nasally administered (10 μl/10 g/body weight). After 2 hours ovalbumin (100 μg) was nasally challenged. After 18 hours, bronchoalveolar lavege fluid (BALF) was collected, and the total number of leucocytes in BALF and fractioned leukocyte in the cytospin sample were measured. By ELISA method, IL-4 and IL-5 in the supernatant were measured. The number of leucocytes (inhibition %) was shown in Table 5 and the production inhibition activity of IL-4 and IL-5 (inhibition % to control) was shown in Table 6.

TABLE 5

| Compound | Number of total leukocyte | Acidophile | Netrophile |
|---|---|---|---|
| Example 15 | 84 | 101 | −92 |
| Beclometasone dipropionate | 92 | 89 | 90 |

TABLE 6

| Compound | IL-4 | IL-5 |
|---|---|---|
| Example 15 | 80 | 75 |
| Beclometasone dipropionate | 97 | 100 |

Example 127

Anti HSV Activity of Antedrug for Herpes Virus (HSV) Infected Vagina of Modeled Rat On the back of a BALB/c female mouse (6 weeks old: Nippon SLC) 3 mg of Depo-Provera/mouse (Registered Trade Mark) was dermally administered and the mice were fed for 6 days. By doing this the sexual cycle was tuned and the sensitivity between mice to herpes virus was balanced. The slime of mouse vagina was removed by a cotton swab for baby, and the ointment (20 mg) containing 0.5% of compound of Example 20 or the ointment (10 mg) containing 5% of compound of Example 20 was spread to the vagina (corresponding 0.1 mg and 0.5 mg per mouse of the compound of Example). As a control, the placebo ointment not containing the compound was spread as well. As the ointment, the base consisting of 80% Vaseline and 20% liquid paraffin were used. On the next day, the slime of mouse vagina was removed by a cotton swab for baby and then, $2\times10^4$ pfu type 2 herpes virus (HSV-2)(10 μl/mouse) was administered to the vagina by pipette. After infection the death or survival of the mice was observed.

The survived rate of mice 9 days later after virus-infection was shown in FIG. 1. The groups spread by the ointments containing 0.5% and 5% of the compound of Example 20, respectively showed clearly higher survived rate comparing with a control group, and the dosage dependency was observed. Furthermore, though the survived rate of the control group was 0%, in the group of 5% ointment its survived rate was 100% and the latter showed clearly anti-viral effect.

Example 128

The aerosol preparation (1 g) containing the following ingredients are prepared.

Compound of Example 15: 0.641 mg (0.06%)

Ethanol: 26.816 mg (2.68%)

1,1,1,2-Tetrafuruoroethane: 972.543 mg (97.25%)

Example 129

The aerosol preparation (1 g) containing the following ingredients are prepared.

Compound of Example 22: 0.641 mg (0.06%)

Ethanol: 26.816 mg (2.68%)

1,1,1,2-Tetrafuruoroethane: 972.543 mg (97.25%)

Example 130

The aerosol preparation (1 g) containing the following ingredients are prepared.

Compound of Example 41: 0.641 mg (0.06%)

Ethanol: 26.816 mg (2.68%)

1,1,1,2-Tetrafuruoroethane: 972.543 mg (97.25%)

Example 131

The aerosol preparation (1 g) containing the following ingredients are prepared.

Compound of Example 19: 0.641 mg (0.06%)

Ethanol: 26.816 mg (2.68%)

1,1,1,2-Tetrafuruoroethane: 972.543 mg (97.25%)

Example 132

The aerosol preparation (1 g) containing the following ingredients are prepared.

Compound of Example 67: 0.641 mg (0.06%)

Ethanol: 26.816 mg (2.68%)

1,1,1,2-Tetrafuruoroethane: 972.543 mg (97.25%)

Comparative Example 1

2-Butoxy-8-hydroxy-9-(3-carboxy benzyl)adenine

2-Butoxy-8-hydroxy-9-(3-methoxycarbonylbenzyl)adenine (0.10 g, 0.27 mmol) obtained by Example 1 was added to 5% sodium hydroxide solution (10 ml) and the solution was stirred at room temperature for 2 hours. After the reaction mixture was neutralized with concentrated hydrochloric acid, the resulting solid was filtered and washed with methanol to give the captioned compound (0.06 g, 0.17 mmol, yield: 61%) as a white solid.

The compounds of Comparative examples 3-8 below were obtained in accordance with the method of Comparative example 1.

Comparative Example 3

2-Butoxy-8-hydroxy-9-(5-carboxyfurfuryl)adenine

Comparative Example 5

2-Butoxy-8-hydroxy-9-(3-carboxymethylbenzyl)adenine

Comparative Example 6

2-Butoxy-8-hydroxy-9-(4-carboxymethylbenzyl)adenine

Comparative Example 8

9-Benzyl-2-carboxymethyl-8-hydroxyadenine

Comparative Example 9

9-Benzyl-8-hydroxy-2-(2-hydroxyethylamino)adenine

9-Benzyl-8-bromo-2-(2-hydroxyethylamino)adenine 600 mg (1.7 mmol) obtained by Reference example 8 in 6N hydrochloric acid (3 ml) was stirred at 100° C. for 8 hours. After the reaction mixture was neutralized under ice cooling with 40% sodium hydroxide solution, the resulting solid was filtered and washed with water to give the captioned compound (190 mg, 0.63 mmol, yield: 38%) as a white solid.

Comparative Example 10

8-Hydroxy-2-(2-hydroxyethylamino)-9-{(6-methyl-3-pyridyl)methyl}adenine

The captioned compound was obtained in accordance with the method of Comparative example 9.

Comparative Example 11

8-Hydroxy-2-(2-hydroxyethoxy)-9-{(6-methyl-3-pyridyl)methyl}adenine

2-Hydroxyethoxy-8-methoxy-9-[(6-methyl-3-pyridyl)methyl]adenine (640 mg, 1.9 mmol) obtained by Reference example 13 in concentrated hydrochloric acid (5 ml) was stirred at room temperature for 6 hours. After the reaction mixture was neutralized under ice cooling with 24% sodium hydroxide solution, the resulting solid was filtered and washed with water to give the captioned compound (440 mg, 1.4 mmol, yield: 73%) as a white solid.

Comparative Example 12

9-Benzyl-8-hydroxy-2-(calboxylmethyl)thioadenine

To sodium hydroxide (500 mg) in methanol (5 ml) was added 9-benzyl-8-hydroxy-2-(methoxycarbonylmethyl)thioprine (64 mg, 0.19 mmol), and the mixture was refluxed for 2 hours. After the reaction mixture was neutralized with 2N hydrochloric acid, the resulting solid was filtered and washed with water to give the captioned compound (32 mg, yield: 52%) as a white solid.

Comparative Example 13

9-Benzyl-8-hydroxy-2-(2-calboxylethyl)thioadenine

The captioned compound was obtained in accordance with the method of Example 40.

Comparative Example 14

2-(2,3-dihydroxypropylamino)-8-hydroxy-9-{(6-methyl-3-pyridyl)methyl}adenine

The captioned compound was obtained in accordance with the method of Comparative example 10.

Comparative Example 15

9-Benzyl-2-(2-carboxyethyl)-8-hydroxyadenine

To dimethyl malonate (493 mg, 3.73 mmol) in DMF (8 ml) was added in an ice bath sodium hydride (75 mg, 3.13 mmol). Then the mixture was stirred at room temperature for 30 minutes. Thereto was added 9-benzyl-2-chloromethyl-8-hydroxyadenine (0.10 g, 0.37 mmol), and the mixture was stirred at room temperature for 21 hours. After removing the solvent, the residue was poured into water, concentrated, and neutralized with hydrochloric acid. The resulting solid was filtered, washed with water and dried in vacuo under heating to give 9-benzyl-2-(2,2-dimethoxycarbonylethyl)-8-hydroxyadenine (92 mg, 0.24 mmol) as a white solid. Thus obtained 9-benzyl-2-(2,2-dimethoxycarbonylethyl)-8-hydroxyadenine (79 mg, 0.20 mmol) was added to a mixed solvent of concentrated hydrochloric acid (2 ml) and 1,4-dioxane (6 ml), and the mixture was refluxed for 6 hours. After the reaction mixture was neutralized in an ice bath with saturated sodium hydrogencarbonate solution, the resulting solid was filtered, washed with water and dried in vacuo under heating to give the captioned compound (55 mg, 0.18 mmol) as a white solid.

Comparative Example 16

9-Benzyl-8-hydroxy-2-calboxylmethoxyadenine

The captioned compound was obtained in accordance with the method of Comparative example 1.

Comparative Example 17

2-(2-Carbonxylethyl)-8-hydroxy-9-{(6-methyl-3-pyridyl)methyl}adenine)hydrochloride 8-Hydroxy-2-(2-methoxycarbonylethyl)-9-{(6-methyl-3-pyridyl)methyl}adenine (9 mg, 0.026 mmol) obtained by Example 66 was added to concentrated hydrochloric acid (1 ml), and the solution was stirred at 100° C. for 1 hour. After removing the solvent, the residue was dissolved in methanol and the solution was added to diisopropyl ether. The resulting solid was filtered and dried in vacuo under heating to give the captioned compound (7 mg, 0.019 mmol) as a white solid.

The compounds of Comparative examples 18~26 below were obtained in accordance with the method of Comparative example 1.

Comparative Example 18

2-(2-Carboxylethyl)-9-(4-carboxylmethylbenzyl)-8-hydroxyadenine

Comparative Example 19

2-Butoxy-9-(5-carboxylmethylfurfuryl)-8-hydroxyadenine

Comparative Example 20

2-Butoxy-9-(3-carboxylethylbenzyl-8-hydroxyadenine

Comparative Example 21

2-Butoxy-9-{6-(4-carboxyl-1-piperidyl)-3-pyridylmethyl-8-hydroxyadenine

Comparative Example 22

2-Butoxy-9-{6-(3-carboxyl-1-piperidyl)-3-pyridylmethyl-8-hydroxyadenine

Comparative Example 23

2-Butoxy-9-(3,4-dicarboxylbenzyl)-8-hydroxyadenine

Comparative Example 24

2-Butoxy-9-(3,5-dicarboxylbenzyl)-8-hydroxyadenine

Comparative Example 25

2-Butoxy-9-{(6-carboxylmethyl-3-pyridyl)methyl}-8-hydroxyadenine

Comparative Example 26

2-Butoxy-9-{6-(1-hydroxy-3-carboxylpropyl)thio-3-pyridyl}methyl}-8-hydroxyadenine Comparative Example 27

9-(3-Carboxymethylbenzyl)-8-hydroxy-2-(2-methoxyethoxy)adenine

8-Bromo-9-(3-methoxycarbonylmethylbenzyl)-2-(2-methoxyethoxy)adenine (0.22 g, 0.50 mmol) obtained by Reference example 35 was suspended in a mixed solvent of 1N sodium hydroxide solution (15 ml) and methanol (15 ml), and the suspension was stirred at 100° C. for 2.5 hours. After removing the solvent, 12N hydrochloric acid (10 ml) was added to the reaction mixture and the mixture was stirred at room temperature for 3.5 hours. After the reaction mixture was neutralized with saturated sodium hydrogencarbonate solution, the resulting solid was successively washed by water and methanol to give the captioned compound (0.14 g, 0.37 mmol, yield: 73%) as a pale red solid.

Comparative Example 28

2-Butylamino-9-(3-carboxymethylbenzyl)-8-hydroxyadenine

The captioned compound was obtained in accordance with the method of Comparative example 27.

Comparative Example 29

9-(3-Carboxymethylbenzyl)-2-chloro-8-hydroxyadenine

2-Chloro-8-hydroxy-9-(3-methoxycarbonylmethylbenzyl)adenine (50 mg, 0.14 mmol) obtained by Example 98 was dissolved in a mixed solvent of 1N sodium hydroxide solution (5 ml) and methanol (5 ml), and the solution was stirred at 100° C. for 5 minutes. The solution was neutralized with 12N hydrochloric acid and the solvent was removed. The residue was added to water, the resulting solid was filtered and washed with water to give the captioned compound (24 mg, 0.072 mmol, yield: 50%) as a pale red solid.

Comparative Example 30

9-(3-Carboxymethylbenzyl)-8-hydroxy-2-(2-hydroxyethylthio)adenine

The captioned compound was obtained in accordance with the method of Comparative example 29.

The compounds of Comparative examples 31~37 below were obtained in accordance with the method of Comparative example 1.

Comparative Example 31

2-Butoxy-8-hydroxy-9-[4-(1-carboxyethyl)benzyl]adenine

Comparative Example 32

2-Butoxy-8-hydroxy-9-[3-(2-carboxy-2-propyl)benzyl]adenine

Comparative Example 33

2-Butoxy-8-hydroxy-9-(4-carboxyphenethyl)adenine

Comparative Example 34

9-Benzyl-8-hydroxy-2-[(3-carboxybenzyl)thio]adenine

Comparative Example 35

9-Benzyl-8-hydroxy-2-[(4-carboxybenzyl)thio]adenine

Comparative Example 36

9-Benzyl-8-hydroxy-2-[(3-carboxymethylbenzyl)thio]adenine

Comparative Example 37

9-Benzyl-8-hydroxy-2-[(4-carboxymethylbenzyl)thio]adenine

The structures and physical properties of the compounds of Reference examples, Examples and Comparative examples are shown below.

TABLE 7

| Reference ex. | Structure | Yield |
| --- | --- | --- |
| 1 | 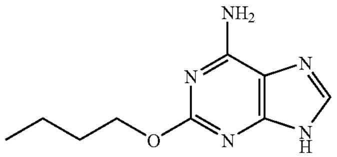 | 3.72 g |
| 2 | 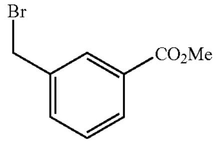 | 1.90 g |
| 3 | 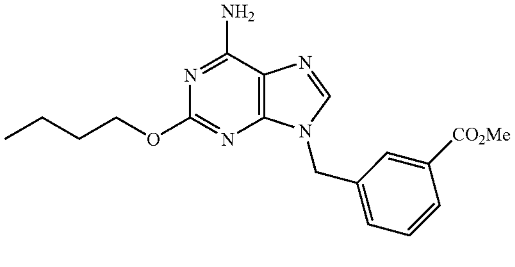 | 0.50 g |

TABLE 7-continued
| Reference ex. | Structure | Yield |
|---|---|---|
| 4 | 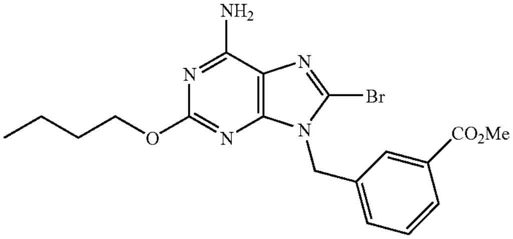 | 0.45 g |
| 5 | 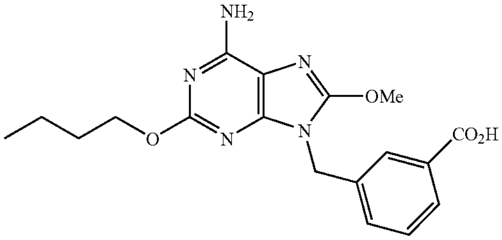 | 0.13 g |
| 6 | 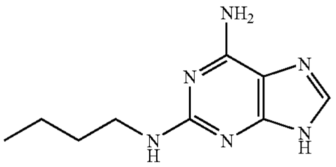 | 2.08 g |
TABLE 8
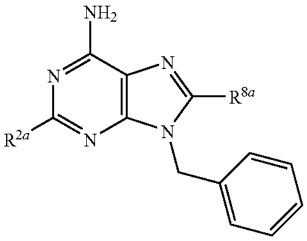
| Reference ex. | —$R^{2a}$ | —$R^{8a}$ | $^1$H-NMR |
|---|---|---|---|
| 7 | —$NH(CH_2)_2OH$ | —H | ($DMSO-d_6$) δ 87.76 (1H, s), 7.27 (5H, m), 6.66 (2H, brs), 6.08 (1H, t, J = 5.0 Hz), 5.13 (2H, s), 4.62 (1H, t, J = 5.0 Hz), 3.46 (2H, q, J = 5.0 Hz), 2.46 (2H, q, J = 5.0 Hz). |
| 8 | —$NH(CH_2)_2OH$ | —Br | ($DMSO-d_6$) δ 7.28 (5H, m), 6.92 (2H, brs), 6.30 (1H, t, J = 6.0 Hz), 5.17 (2H, s), 3.49 (2H, q, J = 6.0 Hz), 3.31 (2H, q, J = 6.0 Hz). |
TABLE 8-continued
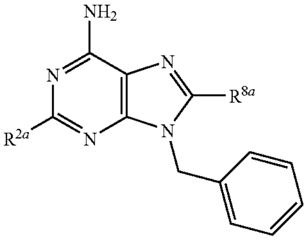
| Reference ex. | —$R^{2a}$ | —$R^{8a}$ | $^1$H-NMR |
|---|---|---|---|
| 15 | —SH | —H | ($DMSO-d_6$) δ 12.10 (1H, brs), 10.06 (1H, brs), 7.30 (5H, m), 6.74 (2H, brs), 4.85 (2H, s). |

TABLE 9

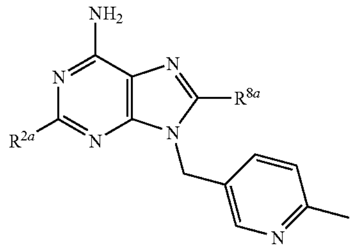

| Reference ex. | —$R^{2a}$ | —$R^{8a}$ | $^1$H-NMR |
|---|---|---|---|
| 9 | —$NH(CH_2)_2OH$ | —H | ($DMSO-d_6$) δ 8.48 (1H, s), 7.82 (1H, s), 7.63 (1H, d, J = 6.8 Hz), 7.21 (1H, d, J = 6.8 Hz), 6.71 (2H, brs), 6.13 (1H, t, J = 5.6 Hz), 5.12 (2H, s), 4.67 (1H, t, J = 5.6 Hz), 3.50 (2H, q, J = 5.6 Hz), 3.30 (2H, q, J = 5.6 Hz), 2.42 (3H, s). |
| 10 | —$NH(CH_2)_2OH$ | —Br | ($DMSO-d_6$) δ 8.44 (1H, s), 7.54 (1H, d, J = 6.8 Hz), 7.22 (1H, d, J = 6.8 Hz), 6.92 (2H, brs), 6.32 (1H, t, J = 5.6 Hz), 5.16 (2H, s), 3.50 (2H, t, J = 5.6 Hz), 3.32 (2H, q, J = 5.6 Hz), 2.43 (3H, s). |
| 11 | —$(CH_2)_2OH$ | —H | ($DMSO-d_6$) δ 8.50 (1H, d, J = 1.6 Hz), 8.06 (1H, s), 7.63 (1H, dd, J = 7.6, 1.6 Hz), 7.23 (2H, brs), 7.21 (1H, d, J = 7.6 Hz), 5.24 (2H, s), 4.82 (1H, t, J = 5.2 Hz), 4.22 (2H, t, J = 5.2 Hz), 3.67 (2H, q, J = 5.2 Hz), 2.40 (3H, s). |
| 12 | —$O(CH_2)_2OH$ | —Br | ($DMSO-d_6$) δ 12.02 (1H, brs), 8.53 (1H, d, J = 2.0 Hz), 7.69 (1H, dd, J = 4.0, 2.0 Hz), 7.47 (2H, brs), 7.33 (1H, d, J = 4.0 Hz), 5.28 (2H, s), 4.23 (2H, t, J = 5.6 Hz), 3.67 (2H, t, J = 5.6 Hz), 2.48 (3H, s). |
| 13 | —$O(CH_2)_2OH$ | —OMe | ($DMSO-d_6$) δ 8.41 (1H, d, J = 2.0 Hz), 7.53 (1H, dd, J = 8.0, 2.0 Hz), 7.21 (1H, d, J = 8.0 Hz), 6.87 (2H, brs), 5.02 (2H, s), 4.80 (1H, t, J = 5.6 Hz), 4.19 (2H, t, J = 5.6 Hz), 4.05 (3H, s), 3.67 (2H, q, J = 5.6 Hz), 2.41 (3H, s). |
| 14 | —$O(CH_2)_2OCONMe_2$ | —OMe | ($DMSO-d_6$) δ 8.54 (1H, d, J = 2.0 Hz), 7.58 (1H, dd, J = 8.0, 2.0 Hz), 7.09 (1H, d, J = 8.0 Hz), 5.20 (2H, brs), 5.06 (2H, s), 4.54 (2H, m), 4.43 (2H, m), 4.11 (3H, s), 2.90 (6H, d, J = 8.0 Hz), 2.52 (3H, s). |
| 16 | —$NHCH_2CH(OH)CH_2OH$ | —H | ($DMSO-d_6$) δ 8.49 (1H, s), 7.83 (1H, s), 7.64 (1H, d, J = 8.0 Hz), 7.21 (1H, d, J = 8.0 Hz), 6.76 (2H, brs), 6.08 (1H, t, J = 5.6 Hz), 5.16 (2H, s), 4.90 (1H, d, J = 4.8 Hz), 4.62 (1H, t, J = 6.0 Hz), 3.60 (1H, m), 3.40 (3H, m), 3.20 (1H, m), 2.42 (3H, s). |
| 17 | —$NHCH_2CH(OH)CH_2OH$ | —Br | ($DMSO-d_6$) δ 8.45(1H, s), 7.56 (1H, d, J = 7.2 Hz), 7.64 (1H, d, J = 7.2 Hz), |

TABLE 9-continued
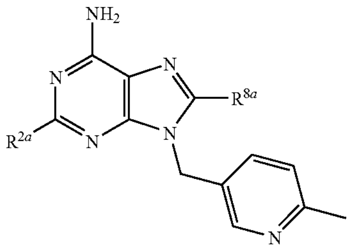
| Reference ex. | —$R^{2a}$ | —$R^{8a}$ | $^1$H-NMR |
|---|---|---|---|
| | | | 7.02 (2H, brs), 6.27 (1H, t, J = 6.7 Hz), 5.16 (2H, s), 4.83 (1H, brs), 4.60 (1H, brs), 3.63 (1H, m), 3.40 (3H, m), 3.20 (1H, m), 2.42 (3H, s). |
| 18 | —$NHCH_2CH(OH)CH_2OH$ | —OMe | (DMSO-$d_6$) δ 8.40 (1H, d, J = 2.0 Hz), 7.54 (1H, dd, J = 8.0, 2.0 Hz), 7.20 (1H, d, J = 8.0 Hz), 6.44 (2H, brs), 5.94 (1H, t, J = 5.6 Hz), 4.95 (2H, s), 4.90 (1H, d, J = 4.4 Hz), 4.60 (1H, t, J = 5.6 Hz), 4.00 (3H, s), 3.60 (1H, m), 3.39 (3H, m), 3.19 (1H, m), 2.42 (3H, s). |
| 19 | 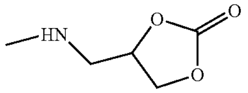 | —OMe | $^1$H NMR (DMSO-$d_6$) δ 8.39 (1H, d, J = 1.4 Hz), 7.53 (1H, dd, J = 8.0, 1.4 Hz), 7.20 (1H, d, J = 8.0 Hz), 6.52 (1H, t, J = 5.6 Hz), 6.47 (2H, brs), 4.97 (2H, s), 4.93 (1H, m), 4.52 (1H, t, J = 8.4 Hz), 4.37 (1H, m), 4.01 (3H, s), 3.60 (1H, m), 3.50 (1H, m), 2.42 (3H, s). |
TABLE 10
| Reference ex. | Structure | Yield |
|---|---|---|
| 20 | 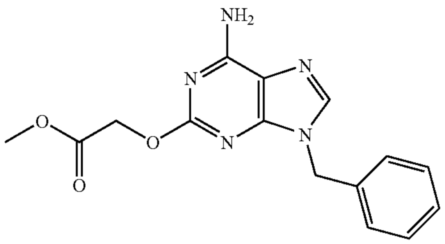 | 0.12 g |
| 21 | 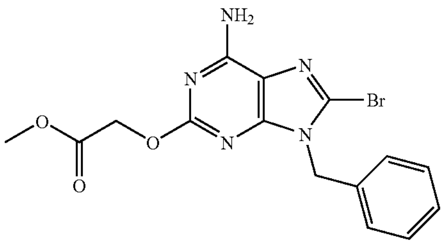 | 0.10 g |

TABLE 10-continued
| Reference ex. | Structure | Yield |
|---|---|---|
| 22 | 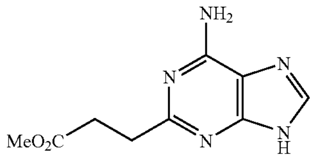 | 0.23 g |
| 23 | 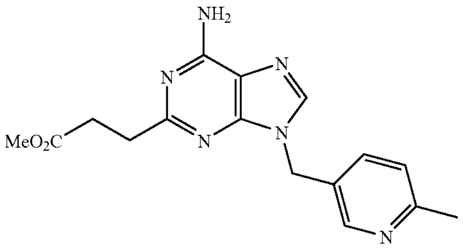 | 358 m g |
| 24 | 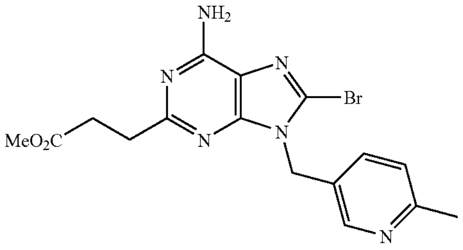 | 31 mg |
| 25 | 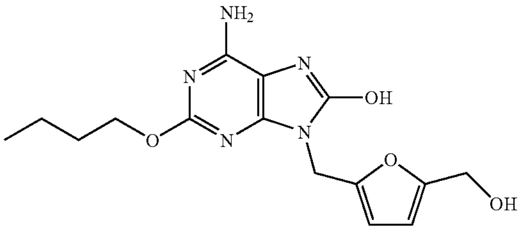 | 50 mg |
| 26 | 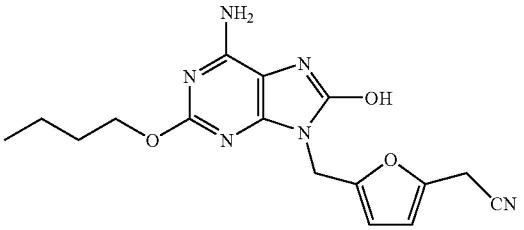 | 31 mg |
| 27 | 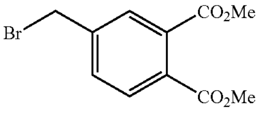 | 2.05 g |
| 28 | 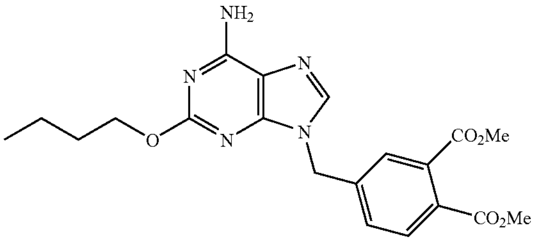 | 775 mg |

TABLE 10-continued
| Reference ex. | Structure | Yield |
|---|---|---|
| 29 | 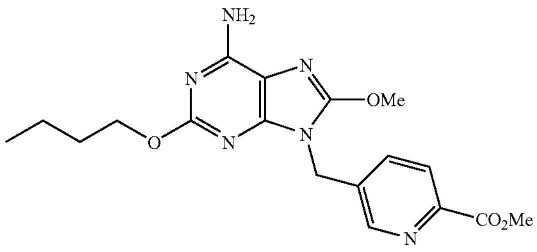 | 78 mg |
| 30 | 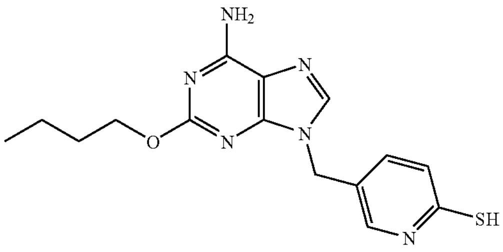 | 0.98 g |
| 31 | 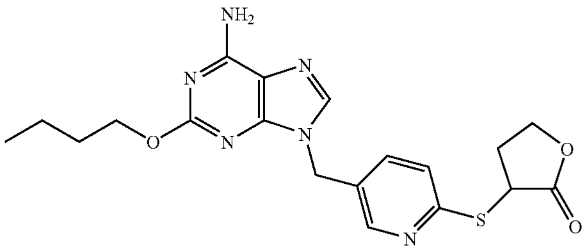 | 0.31 g |
| 32 | 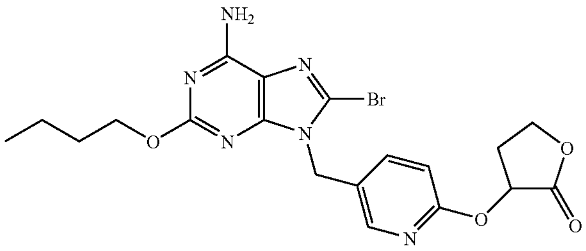 | 0.19 g |
| 33 | 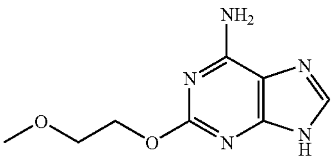 | 3.06 g |

TABLE 11

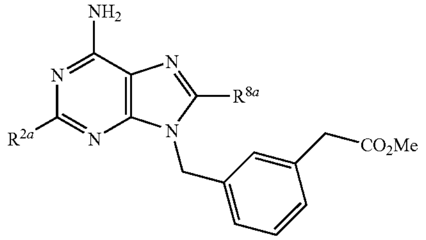

| Reference ex. | —$R^{2a}$ | —$R^{8a}$ | $^{1}$H-NMR |
|---|---|---|---|
| 34 | —$O(CH_2)_2OMe$ | —H | ($DMSO-d_6$) δ 8.04 (1H, s), 7.29 (1H, dd, J = 7.6 Hz, 7.6 Hz), 7.24-7.17 (5H, m), 5.24 (2H, s), 4.32 (2H, t, J = 4.8 Hz), 3.65 (2H, s), 3.61 (2H, t, J = 4.8 Hz), 3.58 (3H, s), 3.28 (3H, s). |
| 35 | —$O(CH_2)_2OMe$ | —Br | ($CDCl_3$) δ 7.29-7.20 (4H, m), 6.44 (2H, brs), 5.28 (2H, s), 4.49 (2H, t, J = 4.4 Hz), 3.75 (2H, t, J = 4.4 Hz), 3.67 (3H, s), 3.60 (2H, s), 3.43 (3H, s). |
| 36 | —NH-Butyl | —H | ($DMSO-d_6$) δ 7.44 (1H, s), 7.31-7.18 (4H, m), 5.66 (2H, brs), 5.19 (2H, s), 4.97 (1H, brs), 3.66 (3H, s), 3.60 (2H, s), 3.40 (2H, dt, J = 6.0 Hz, 7.2 Hz), 1.56 (2H, tt, J = 7.6 Hz, 7.2 Hz), 1.39 (2H, tq, J = 7.6 Hz, 7.2 Hz), 0.93 (3H, t, J = 7.2 Hz). |
| 37 | —NH-Butyl | —Br | ($CDCl_3$) δ 7.29-7.19 (4H, m), 5.75 (2H, brs), 5.20 (2H, s), 5.07 (1H, brs), 3.67 (3H, s), 3.60 (2H, s), 3.39 (2H, dt, J = 6.8 Hz, 6.8 Hz), 1.56 (2H, tt, J = 6.8 Hz, 7.6 Hz), 1.38 (2H, tq, J = 7.6 Hz, 7.2 Hz), 0.92 (3H, t, J = 7.2 Hz). |
| 38 | —Cl | —H | ($DMSO-d_6$) δ 8.24 (1H, s), 7.80 (2H, brs), 7.31 (1H, dd, J = 7.6 Hz, 7.6 Hz), 7.19 (1H, d, 7.6 Hz), 7.18 (1H, s), 7.14 (1H, d, 7.6 Hz), 5.32 (2H, s), 3.66 (2H, s), 3.59 (3H, s). |
| 39 | —Cl | —Br | ($CDCl_3$) δ 7.32 (1H, dd, J = 8.0 Hz, 7.6 Hz), 7.26-7.19 (3H, m), 5.72 (2H, brs), 5.34 (2H, s), 3.70 (3H, s), 3.61 (2H, s). |

TABLE 12

| Reference ex. | Structure | Yield |
|---|---|---|
| 40 | 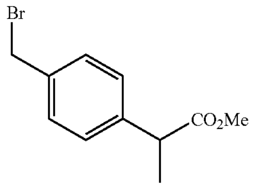 | 4.71 g |
| 41 | 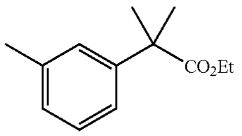 | 4.92 g |
| 42 | 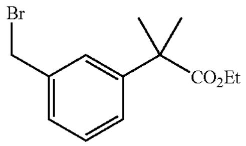 | 4.62 g |

TABLE 12-continued

| Reference ex. | Structure | Yield |
|---|---|---|
| 43 | 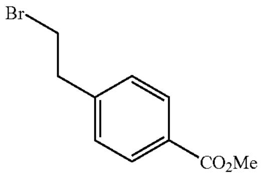 | 4.79 g |
| 44 | 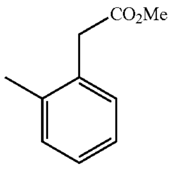 | 4.36 g |
| 45 | 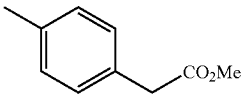 | 4.42 g |
| 46 | 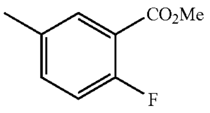 | 3.07 g |
| 47 | 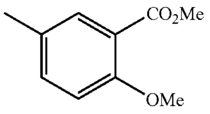 | 3.43 g |
| 48 | 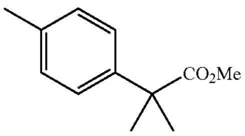 | 2.26 g |
| 49 | 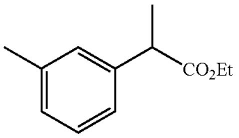 | 2.97 g |
| 50 | 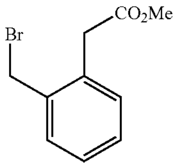 | 2.90 g |
| 51 | 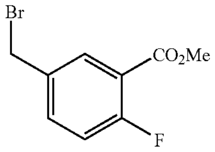 | 2.80 g |

TABLE 12-continued
| Reference ex. | Structure | Yield |
|---|---|---|
| 52 | 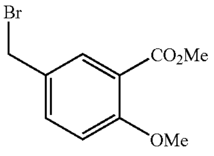 | 2.84 g |
| 53 | 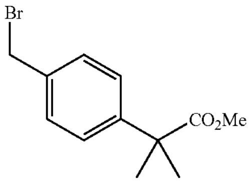 | 2.48 g |
| 54 | 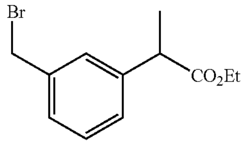 | 2.16 g |
| 55 | 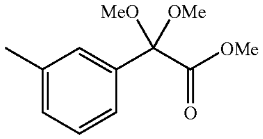 | 3.75 g |
TABLE 13
| Reference ex. | Structure | $^1$H-NMR (ppm) |
|---|---|---|
| 56 | 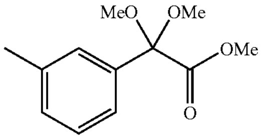 | ($CDCl_3$) δ 7.64 (1H, s), 7.60-7.51 (1H, m), 7.42-7.34 (2H, m), 4.50 (2H, s), 3.74 (3H, s), 3.27 (6H, s). |
| 57 | 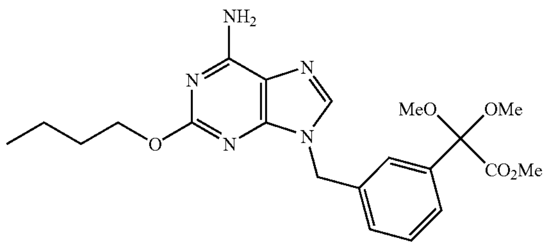 | $^1$H NMR ($CDCl_3$) δ 7.65 (1H, s), 7.61 (1H, s), 7.53 (1H, d, J = 7.7 Hz), 7.35 (1H, dd, J = 7.7 Hz, 7.7 Hz), 7.26 (1H, d, J = 7.7 Hz), 6.41 (2H, brs), 5.29 (2H, s), 4.34 (2H, t, J = 6.6 Hz), 3.71 (3H, s), 3.25 (6H, s), 1.78 (2H, tt, J = 6.6 Hz, 5.8 Hz), 1.52 (2H, tq, J = 5.8 Hz, 7.4 Hz), 0.97 (3H, t, J = 7.4 Hz). |
| 58 | 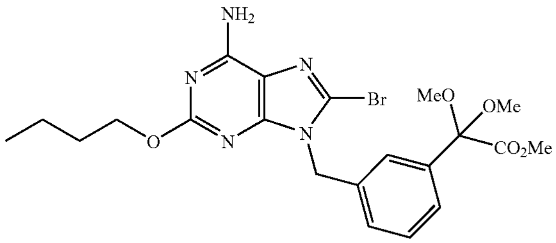 | $^1$H NMR ($CDCl_3$) δ 7.70 (1H, s), 7.53 (1H, d, J = 7.5 Hz), 7.33 (1H, dd, J = 7.6 Hz, 7.5 Hz), 7.29 (1H, d, J = 7.6 Hz), 5.95 (2H, brs), 5.31 (2H, s), 4.35 (2H, t, J = 6.6 Hz), 3.71 (3H, s), 3.25 (6H, s), 1.77 (2H, tt, J = 6.6 Hz, 5.8 Hz), 1.50 (2H, tq, J = 5.8 Hz, 7.4 Hz), 0.97 (3H, t, J = 7.4 Hz). |

TABLE 14

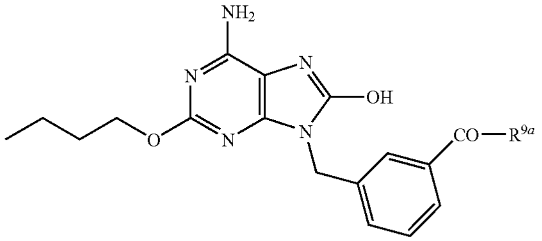

| Ex. | —$R^{9a}$ | $^1$H-NMR |
|---|---|---|
| 1 | —OMe | ($DMSO-d_6$) δ 10.02 (1H, brs), 7.93 (1H, s), 7.87 (1H, d, J = 7.3 Hz), 7.59 (1H, d, J = 7.6 Hz), 7.49 (1H, t, J = 7.6 Hz), 6.48 (2H, brs), 4.93 (2H, s), 4.14 (2H, t, J = 6.5 Hz), 3.84 (3H, s), 1.63 (2H, 5, J = 7.0 Hz), 1.36 (2H, 6, J = 7.0 Hz), 0.90 (3H, t, J = 7.3 Hz). |
| 2 | —OEt | ($DMSO-d_6$) δ 10.16 (1H, brs), 7.93 (1H, s), 7.86 (1H, d, J = 7.3 Hz), 7.58 (1H, d, J = 7.8 Hz), 7.48 (1H, t, J = 7.6 Hz), 6.52 (2H, brs), 4.92 (2H, s), 4.27 (2H, q, J = 7.0 Hz), 4.14 (2H, t, J = 6.5 Hz), 1.63 (2H, 5, J = 7.0 Hz), 1.36 (5H, m), 0.59 (3H, t, J = 7.3 Hz). |
| 3 | —OiPr | ($DMSO-d_6$) δ 10.03 (1H, brs), 7.92 (1H, s), 7.84 (1H, d, J = 7.3 Hz), 7.55 (1H, d, J = 7.8 Hz), 7.47 (1H, t, J = 7.6 Hz), 6.48 (2H, brs), 5.11 (1H, 7, J = 6.5 Hz), 4.92 (2H, s), 4.14 (2H, t, J = 6.8 Hz), 1.60 (2H, 5, J = 6.2 Hz), 1.34 (2H, 6, J = 7.0 Hz), 1.30 (6H, d, J = 6.2 Hz), 0.89 (3H, t, J = 7.3 Hz). |
| 4 | —$OCH_2CF_3$ | ($DMSO-d_6$) δ 10.03 (1H, brs), 7.96 (1H, s), 7.90 (1H, d, J = 7.8 Hz), 7.65 (1H, d, J = 7.8 Hz), 7.55 (1H, t, J = 7.8 Hz), 6.49 (2H, brs), 4.97 (4H, m), 4.13 (2H, t, J = 6.5 Hz), 1.61 (2H, 5, J = 7.6 Hz), 1.37 (2H, 6, J = 7.6 Hz), 0.89 (3H, t, J = 7.3 Hz). |
| 5 | —$O(CH_2)_2OBzl$ | ($DMSO-d_6$) δ 10.32 (1H, brs), 7.94 (1H, s), 7.86 (1H, d, J = 7.6 Hz), 7.58 (1H, d, J = 7.6 Hz), 7.50 (1H, t, J = 7.6 Hz), 7.28 (5H, m), 6.56 (2H, brs), 4.93 (2H, s), 4.54 (2H, s), 4.42 (2H, t, J = 4.6 Hz), 4.13 (2H, t, J = 6.5 Hz), 3.74 (2H, t, J = 4.6 Hz), 1.60 (2H, 5, J = 7.6 Hz), 1.34 (2H, 6, J = 7.6 Hz), 0.87 (3H, t, J = 7.6 Hz). |
| 6 | —$O(CH_2)_2OH$ | ($DMSO-d_6$) δ 9.99 (1H, brs), 7.96 (1H, s), 7.89 (1H, d, J = 7.6 Hz), 7.57 (1H, d, J = 7.6 Hz), 7.49 (1H, t, J = 7.6 Hz), 6.48 (2H, brs), 4.93 (2H, s), 4.89 (1H, m), 4.27 (2H, t, J = 5.1 Hz), 4.14 (2H, t, J = 6.8 Hz), 3.67 (2H, q, J = 5.4 Hz), 1.62 (2H, 5, J = 7.6 Hz), 1.36 (2H, 6, J = 7.6 Hz), 0.89 (3H, t, J = 7.6 Hz). |
| 7 | —$O(CH_2)_2NMe_2$ | ($DMSO-d_6$) δ 10.01 (1H, brs), 7.87 (1H, s), 7.85 (1H, d, J = 7.8 Hz), 7.59 (1H, d, J = 7.8 Hz), 7.50 (1H, t, J = 7.6 Hz), 6.49 (2H, brs), 4.93 (2H, s), 4.33 (2H, t, J = 5.4 Hz), 4.14 (2H, t, J = 6.5 Hz), 2.58 (2H, m), 2.18 (6H, s), 1.62 (2H, 5, J = 7.6 Hz), 1.36 (2H, 6, J = 7.6 Hz), 0.89 (3H, t, J = 7.6 Hz). |
| 8 | 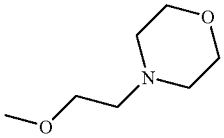 | ($DMSO-d_6$) δ 10.10 (1H, brs), 7.89 (1H, s), 7.86 (1H, d, J = 7.8 Hz), 7.60 (1H, d, J = 7.6 Hz), 7.50 (1H, t, J = 7.8 Hz), 6.51 (2H, brs), 4.93 (2H, s), 4.36 (2H, t, J = 7.6 Hz), 4.14 (2H, t, J = 6.8 Hz), 3.53 (4H, t, J = 4.6 Hz), 2.65 (2H, t, J = 5.1 Hz), 2.43 (4H, t, J = 4.6 Hz), 1.62 (2H, 5, J = 7.6 Hz), 1.36 (2H, 6, J = 7.6 Hz), 0.89 (3H, t, J = 7.6 Hz). |
| 9 | 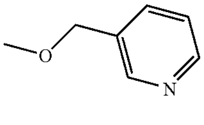 | ($DMSO-d_6$) δ 10.16 (1H, brs), 8.68 (1H, d, J = 1.6 Hz), 8.57 (1H, dd, J = 4.6, 1.6 Hz), 7.96 (1H, s), 7.86 (2H, m), 7.50 (3H, m), 6.52 (2H, s), 5.38 (2H, s), 4.93 (2H, s), 4.11 (2H, t, J = 6.5 Hz), 1.57 (2H, 5, J = 6.5 Hz), 1.34 (2H, 6, J = 7.0 Hz), 0.87 (3H, t, J = 7.3 Hz). |
| 10 | —SMe | ($DMSO-d_6$) δ 10.21 (1H, brs), 7.87 (1H, s), 7.83 (1H, d, J = 7.8 Hz), 7.60 (1H, d, J = 7.6 Hz), 7.52 (1H, t, J = 7.6 Hz), 6.54 (2H, brs), 4.94 |

TABLE 14-continued

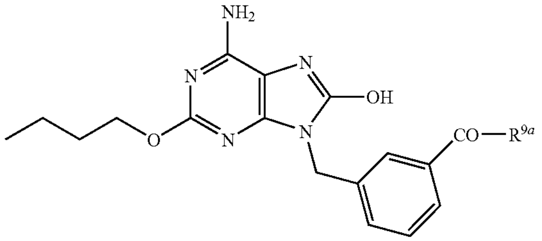

| Ex. | —$R^{9a}$ | $^1$H-NMR |
|---|---|---|
| | | (2H, s), 4.15 (2H, t, J = 6.5 Hz), 2.43 (3H, s), 1.63 (2H, 5, J = 7.0 Hz), 1.36 (2H, 6, J = 7.0 Hz), 0.90 (3H, t, J = 7.3 Hz). |

TABLE 15

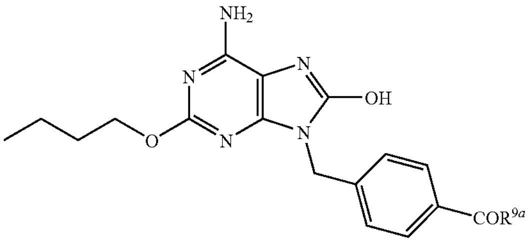

| Ex. | —$R^{9a}$ | $^1$H-NMR |
|---|---|---|
| 11 | —OMe | (DMSO-$d_6$) δ 10.21 (1H, brs), 7.92 (2H, d, J = 8.4 Hz), 7.39 (2H, d, J = 11.1 Hz), 6.54 (2H, brs), 4.93 (2H, s), 4.11 (2H, t, J = 6.8 Hz), 3.83 (3H, s), 1.62 (2H, 5, J = 6.8 Hz), 1.36 (2H, 6, J = 7.0 Hz), 0.90 (3H, t, J = 7.3 Hz). |
| 12 | —OiPr | (DMSO-$d_6$) δ 10.02 (1H, brs), 7.90 (2H, d, J = 7.8 Hz), 7.40 (2H, d, J = 8.4 Hz), 6.48 (2H, brs), 5.11 (1H, 7, J = 6.2 Hz), 4.93 (2H, s), 4.12 (2H, t, J = 6.8 Hz), 1.59 (2H, 5, J = 6.2 Hz), 1.36 (8H, m), 0.88 (3H, t, J = 7.3 Hz). |

TABLE 15-continued

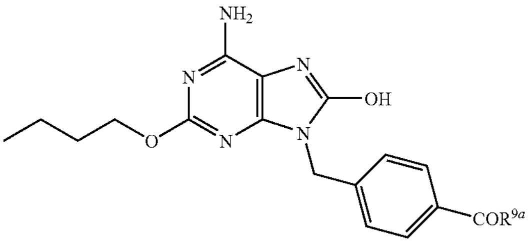

| Ex. | —$R^{9a}$ | $^1$H-NMR |
|---|---|---|
| 13 | 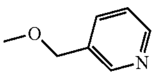 | (DMSO-$d_6$) δ 10.04 (1H, brs), 8.68 (1H, d, J = 1.4 Hz), 8.55 (1H, dd, J = 2.1, 1.6 Hz), 7.96 (2H, d, J = 8.4 Hz), 7.88 (1H, d, J = 8.4 Hz), 7.43 (3H, m), 6.49 (2H, s), 5.38 (2H, s), 4.94 (2H, s), 4.11 (2H, t, J = 6.8 Hz), 1.62 (2H, 5, J = 6.8 Hz), 1.34 (2H, 6, J = 7.0 Hz), 0.87 (3H, t, J = 7.3 Hz). |
| 14 | —OBzl | (DMSO-$d_6$) δ 10.09 (1H, brs), 7.96 (2H, d, J = 8.4 Hz), 7.39 (7H, m), 6.50 (2H, s), 5.34 (2H, s), 4.94 (2H, s), 4.11 (2H, t, J = 6.8 Hz), 1.62 (2H, 5, J = 6.8 Hz), 1.34 (2H, 6, J = 7.0 Hz), 0.87 (3H, t, J = 7.3 Hz). |

TABLE 16

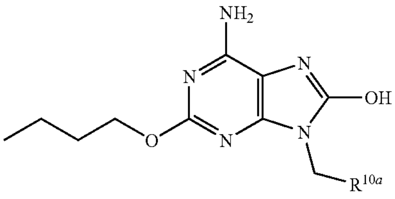

| Ex. | —$R^{10a}$ | $^1$H-NMR |
|---|---|---|
| 15 | 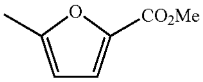 | (DMSO-$d_6$) δ 10.05 (1H, brs), 7.24 (1H, d, J = 3.8 Hz), 6.51 (3H, m), 4.93 (2H, s), 4.13 (2H, t, J = 6.5 Hz), 3.78 (3H, s), 1.64 (2H, 5, J = 6.8 Hz), 1.36 (2H, 6, J = 7.0 Hz), 0.90 (3H, t, J = 7.3 Hz). |
| 16 | 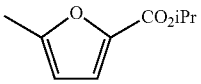 | (DMSO-$d_6$) δ 10.05 (1H, brs), 7.18 (1H, d, J = 3.5 Hz), 6.47 (3H, m), 5.08 (1H, 7, J = 6.2 Hz), 4.93 (2H, s), 4.13 (2H, t, J = 6.8 Hz), 1.60 (2H, 5, J = 6.2 Hz), 1.34 (2H, 6, J = 7.0 Hz), 1.18 (6H, d, J = 7.6 Hz), 0.90 (3H, t, J = 7.3 Hz). |

TABLE 16-continued

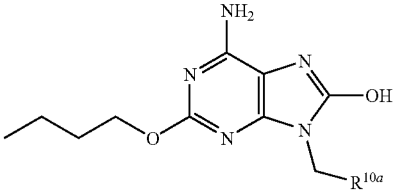

| Ex. | —$R^{10a}$ | $^1$H-NMR |
|---|---|---|
| 17 | 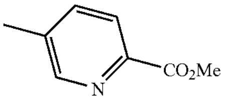 | (DMSO-$d_6$) δ 10.10 (1H, brs), 8.69 (1H, d, J = 1.9 Hz), 8.02 (1H, d, J = 8.4 Hz), 8.83 (1H, dd, J = 1.9, 8.4 Hz), 6.50 (2H, brs), 4.99 (2H, s), 4.12 (2H, t, J = 6.8 Hz), 3.86 (3H, s), 1.62 (2H, 5, J = 6.8 Hz), 1.36 (2H, 6, J = 7.0 Hz), 0.90 (3H, t, J = 7.3 Hz). |
| 18 | 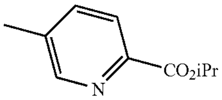 | (DMSO-$d_6$) δ 10.14 (1H, brs), 8.69 (1H, d, J = 2.2 Hz), 8.00 (1H, d, J = 7.8 Hz), 7.83 (1H, dd, J = 2.2, 8.4 Hz), 6.52 (2H, brs), 5.15 (1H, 7, J = 6.2 Hz), 4.98 (2H, s), 4.12 (2H, t, J = 6.8 Hz), 1.62 (2H, 5, J = 6.8 Hz), 1.36 (8H, m), 0.90 (3H, t, J = 7.3 Hz). |
| 19 | 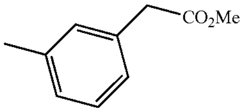 | (DMSO-$d_6$) δ 10.01 (1H, brs), 7.19 (4H, m), 6.47 (2H, brs), 4.83 (2H, s), 4.14 (2H, t, J = 6.8 Hz), 3.64 (2H, s), 3.59 (3H, s), 1.62 (2H, 5, J = 6.8 Hz), 1.36 (2H, 6, J = 7.0 Hz), 0.90 (3H, t, J = 7.3 Hz). |
| 20 | 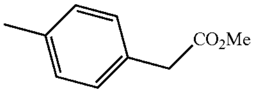 | (DMSO-$d_6$) δ 10.11 (1H, brs), 7.22 (4H, m), 6.49 (2H, brs), 4.83 (2H, s), 4.14 (2H, t, J = 6.5 Hz), 3.63 (2H, s), 3.58 (3H, s), 1.62 (2H, 5, J = 6.8 Hz), 1.36 (2H, 6, J = 7.0 Hz), 0.90 (3H, t, J = 7.3 Hz). |
| 21 | 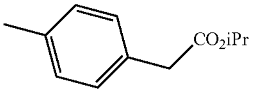 | (DMSO-$d_6$) δ 9.98 (1H, brs), 7.20 (4H, m), 6.45 (2H, brs), 4.87 (1H, 7, J = 6.2 Hz), 4.83 (2H, s), 4.14 (2H, t, J = 6.8 Hz), 3.57 (2H, s), 1.64 (2H, 5, J = 6.2 Hz), 1.34 (2H, 6, J = 7.0 Hz), 1.18 (6H, d, J = 6.5 Hz), 0.87 (3H, t, J = 7.3 Hz). |
| 22 | 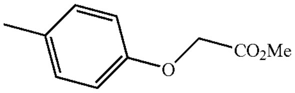 | (DMSO-$d_6$) δ 9.98 (1H, brs), 7.24 (2H, J = 8.4 Hz), 6.87 (2H, d, J = 8.6 Hz), 6.45 (2H, brs), 4.78 (2H, s), 4.76 (2H, s), 4.15 (2H, t, J = 6.2 Hz), 3.68 (3H, s), 1.63 (2H, 5, J = 6.8 Hz), 1.38 (2H, 6, J = 7.0 Hz), 0.91 (3H, t, J = 7.3 Hz). |
| 23 | 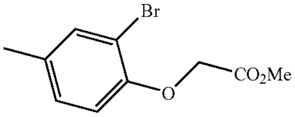 | (DMSO-$d_6$) δ 9.96 (1H, brs), 7.58 (1H, d, J = 1.9 Hz), 7.24 (1H, dd, J = 1.9, 8.4 Hz), 6.97 (1H, d, J = 8.4 Hz), 6.45 (2H, brs), 4.89 (2H, s), 4.78 (2H, s), 4.16 (2H, t, J = 6.2 Hz), 3.68 (3H, s), 1.64 (2H, 5, J = 6.8 Hz), 1.38 (2H, 6, J = 7.0 Hz), 0.91 (3H, t, J = 7.3 Hz). |
| 24 | 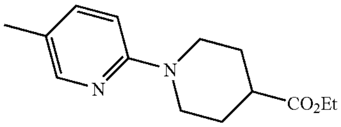 | (DMSO-$d_6$) δ 9.92 (1H, brs), 8.11 (1H, d, J = 1.9 Hz), 7.24 (1H, dd, J = 1.9, 8.4 Hz), 6.97 (1H, d, J = 8.4 Hz), 6.45 (2H, brs), 4.89 (2H, s), 4.78 (2H, s), 4.16 (2H, t, J = 6.2 Hz), 3.68 (3H, s), 1.64 (2H, 5, J = 6.8 Hz), 1.38 (2H, 6, J = 7.0 Hz), 0.91 (3H, t, J = 7.3 Hz). |
| 25 | 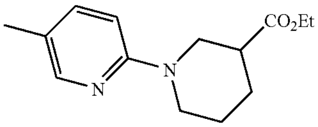 | (DMSO-$d_6$) δ 9.99 (1H, brs), 8.11 (1H, d, J = 1.9 Hz), 7.49 (1H, dd, J = 2.4, 8.4 Hz), 6.79 (1H, d, J = 8.9 Hz), 6.44 (2H, s), 4.71 (2H, s), 4.01 (6H, brm), 3.04 (2H, m), 1.91 (1H, m), 1.66 (4H, m), 1.40 (3H, m), 1.16 (3H, t, J = 6.8 Hz), 0.92 (3H, t, J = 7.3 Hz). |

TABLE 16-continued

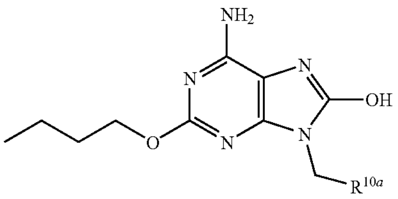

| Ex. | —$R^{10a}$ | $^1$H-NMR |
|---|---|---|
| 26 | 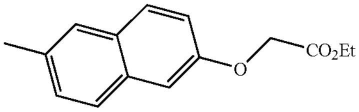 | (DMSO-$d_6$) δ 9.97 (1H, brs), 7.75 (3H, m), 7.44 (1H, dd, J = 1.6 Hz, J = 8.4 Hz), 7.22 (2H, m), 6.47 (2H, s), 4.98 (2H, s), 4.88 (2H, s), 4.15 (4H, m), 1.62 (2H, 5, J = 6.8 Hz), 1.39 (2H, 6, J = 7.3 Hz), 1.21 (3H, t, J = 7.0 Hz), 0.88 (3H, t, J = 7.3 Hz). |

TABLE 17

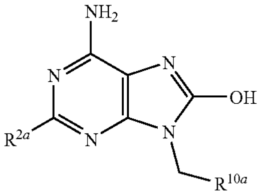

| Ex. | —$R^{2a}$ | —$R^{10a}$ | $^1$H-NMR |
|---|---|---|---|
| 27 | —NHBu | 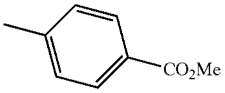 | (DMSO-$d_6$) δ 9.94 (1H, brs), 7.90 (2H, d, J = 8.4 Hz), 7.38 (2H, d, J = 8.4 Hz), 6.20 (1H, t, J = 5.6 Hz), 6.10 (2H, brs), 4.88 (2H, s), 3.83 (3H, s), 3.13 (2H, t, J = 6.8 Hz), 1.43 (2H, 5, J = 7.0 Hz), 1.25 (2H, 6, J = 7.0 Hz), 0.84 (3H, t, J = 7.0 Hz). |
| 28 | —NHBu | 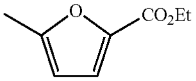 | (DMSO-$d_6$) δ 9.70 (1H, brs), 7.21 (1H, d, J = 3.2 Hz), 6.45 (1H, d, J = 3.5 Hz), 6.26 (1H, t, J = 5.6 Hz), 6.08 (2H, brs), 4.87 (2H, s), 4.25 (2H, q, J = 7.3 Hz), 3.14 (2H, t, = J 5.9 Hz), 1.43 (2H, 5, = 7.0 Hz), 1.26 (5H, m), 0.86 (3H, t, J = 7.3 Hz). |
| 29 | —$CH_2COOMe$ | 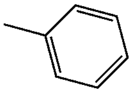 | (DMSO-$d_6$) δ 10.28 (1H, brs), 7.30 (5H, m), 6.52 (2H, s), 4.89 (2H, s), 3.65 (2H, s), 3.60 (3H, s). |
| 30 | —$CH_2COOEt$ | 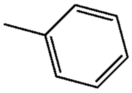 | (DMSO-$d_6$) δ 10.26 (1H, brs), 7.29 (5H, m), 6.51 (2H, s), 4.89 (2H, s), 4.06 (2H, q, J = 7.0 Hz), 3.63 (2H, s), 1.15 (3H, t, J = 7.0 Hz). (DMSO-$d_6$) δ 9.76 (1H, s), 7.29 (5H, m), 6.64 (1H, t, J = 6.2 Hz), 6.12 (2H, brs), 4.78 (2H, s), 3.90 (1H, d, J = 4.3 Hz), 3.57 (3H, s). |
| 31 | —$NHCH_2COOMe$ | 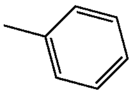 | (DMSO-$d_6$) δ 9.76 (1H, s), 7.29 (5H, m), 6.64 (1H, t, J = 6.2 Hz), 6.12 (2H, brs), 4.78 (2H, s), 3.90 (1H, d, J = 4.3 Hz), 3.57 (3H, s). |

TABLE 17-continued

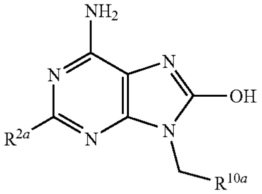

| Ex. | —$R^{2a}$ | —$R^{10a}$ | $^1$H-NMR |
|---|---|---|---|
| 32 | —$NHCH_2COOMe$ | 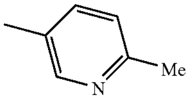 | (DMSO-$d_6$) δ 9.70 (1H, brs), 8.40 (1H, d, J = 2.0 Hz), 7.53 (1H, dd, J = 8.0, 2.0 Hz), 7.20 (1H, d, J = 8.0 Hz), 6.65 (1H, t, J = 7.1 Hz), 6.11 (2H, brs), 4.79 (2H, s), 3.92 (2H, d, J = 7.1 Hz), 3.60 (3H, s), 2.42 (3H, s). |
| 33 | —$NH(CH_2)_2OCOMe$ | 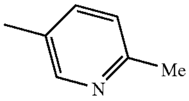 | (DMSO-$d_6$) δ 9.68 (1H, s), 8.42 (1H, d, J = 2.0 Hz), 7.59 (1H, dd, J = 8.0, 2.0 Hz), 7.20 (1H, d, J = 8.0 Hz), 6.38 (1H, t, J = 5.2 Hz), 6.08 (2H, brs), 4.79 (2H, s), 4.07 (2H, t, J = 5.2 Hz), 3.40 (2H, q, J = 5.2 Hz), 2.41 (3H, s), 1.99 (3H, s). |
| 34 | —$NH(CH_2)_2OCOOMe$ | 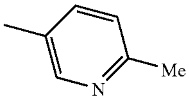 | (DMSO-$d_6$) δ 9.68 (1H, s), 8.42 (1H, d, J = 2.0 Hz), 7.58 (1H, dd, J = 8.0, 2.0 Hz), 7.20 (1H, d, J = 8.0 Hz), 6.42 (1H, t, J = 5.6 Hz), 6.08 (2H, brs), 4.79 (2H, s), 4.15 (2H, t, J = 5.6 Hz), 3.68 (3H, s), 3.40 (2H, q, J = 5.6 Hz), 2.42 (3H, s). |
| 35 | —$NH(CH_2)_2OCOMe$ | 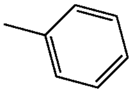 | (DMSO-$d_6$) δ 9.73 (1H, s), 7.26 (5H, m), 6.36 (1H, t, J = 6.0 Hz), 6.09 (2H, brs), 4.80 (2H, s), 4.07 (2H, t, J = 6.0 Hz), 3.40 (2H, q, J = 6.0 Hz), 1.98 (3H, s). |
| 36 | —$O(CH_2)_2OCOMe$ | 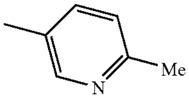 | (DMSO-$d_6$) δ 9.95 (1H, brs), 8.43 (1H, d, J = 1.6 Hz), 7.59 (1H, dd, J = 8.0, 1.6 Hz), 7.20 (1H, d, J = 8.0 Hz), 6.51 (1H, brs), 4.85 (2H, s), 4.35 (2H, m), 4.29 (2H, m), 2.42 (3H, s), 2.03 (3H, s). |
| 37 | —$O(CH_2)_2OCOEt$ | 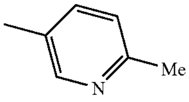 | (DMSO-$d_6$) δ 9.86 (1H, brs), 8.43 (1H, d, J = 2.0 Hz), 7.58 (1H, dd, J = 8.0, 2.0 Hz), 7.21 (1H, d, J = 8.0 Hz), 6.51 (1H, brs), 4.84 (2H, s), 4.35 (2H, m), 4.29 (2H, m), 2.42 (3H, s), 2.33 (2H, q, J = 7.6 Hz), 1.01 (3H, t, J = 7.6 Hz). |
| 38 | —$O(CH_2)_2OCOOMe$ | 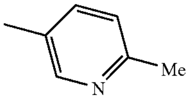 | (DMSO-$d_6$) δ 10.00 (1H, s), 8.43 (1H, d, J = 2.0 Hz), 7.60 (1H, dd, J = 8.0, 2.0 Hz), 7.21 (1H, d, J = 8.0 Hz), 6.52 (1H, brs), 4.85 (2H, s), 4.36 (4H, s), 3.70 (3H, s), 2.42 (3H, s). |

TABLE 17-continued

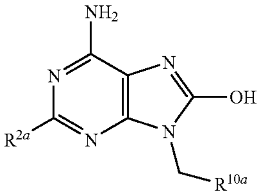

| Ex. | —$R^{2a}$ | —$R^{10a}$ | $^1$H-NMR |
|---|---|---|---|
| 39 | —$O(CH_2)_2OCONMe_2$ | 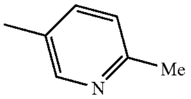 | ($DMSO-d_6$) δ 8.42 (1H, d, J = 1.6 Hz), 7.56 (1H, dd, J = 8.0, 1.6 Hz), 7.58 (1H, d, J = 8.0 Hz), 7.11 (1H, brs), 6.56 (2H, brs), 4.84 (2H, s), 4.34 (2H, m), 4.24 (2H, m), 2.82 (6H, s), 2.42 (3H, s). |

TABLE 18

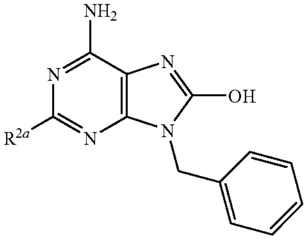

| Ex. | $R^{2a}$ | $^1$H-NMR |
|---|---|---|
| 40 | —$SCH_2COOMe$ | ($DMSO-d_6$) δ 810.12 (1H, brs), 7.30 (5H, m), 6.57 (2H, brs), 4.84 (2H, s), 3.91 (3H, s), 3.56 (2H, s). |
| 41 | —$SCH_2COOEt$ | ($DMSO-d_6$) δ 10.12 (1H, brs), 7.31 (5H, m), 6.57 (2H, brs), 4.85 (2H, s), 4.01 (2H, q, J = 7.1 Hz), 3.90 (2H, s), 1.12 (3H, t, J = 7.1 Hz). |
| 42 | —$SCH_2COO(CH_2)_7CH_3$ | ($DMSO-d_6$) δ 10.12 (1H, brs), 7.28 (5H, m), 6.56 (2H, brs), 4.84 (2H, s), 3.96 (2H, t, J = 6.5 Hz), 3.90 (2H, s), 1.45 (2H, m), 1.24 (2H, m), 1.11 (8H, m), 0.83 (3H, t, J = 7.3 Hz). |
| 43 | —$SCH_2COOtBu$ | ($DMSO-d_6$) δ 10.13 (1H, brs), 7.29 (5H, m), 6.55 (2H, brs), 4.87 (2H, s), 3.82 (2H, s), 1.37 (9H, s). |
| 44 | —$SCH_2COOCH_2CH{=}CH_2$ | ($DMSO-d_6$) δ 10.13 (1H, brs), 7.28 (5H, m), 6.58 (2H, brs), 5.86 (1H, m), 5.70 (2H, m), 4.84 (2H, s), 4.51 (2H, m), 3.96 (2H, s). |
| 45 | —$SCH_2COOBzl$ | ($DMSO-d_6$) δ 10.11 (1H, brs), 7.28 (10H, m), 6.57 (2H, brs), 5.06 (2H, s), 4.72 (2H, s), 3.97 (2H, s). |
| 46 | —$SCH_2COO(CH_2)_2F$ | ($DMSO-d_6$) δ 10.13 (1H, brs), 7.29 (5H, m), 6.56 (2H, brs), 4.84 (2H, s), 4.54 (2H, dt, J = 47.7 Hz, 7.0 Hz), 4.23 (2H, dt, J = 30.2 Hz, 7.0 Hz), 3.96 (2H, s). |
| 47 | —$CH_2COOCH_2CF_2H$ | ($DMSO-d_6$) δ 10.14 (1H, brs), 7.28 (5H, m), 6.57 (2H, brs), 6.20 (1H, m), 4.84 (2H, s), 4.27 (2H, m), 4.00 (2H, s). |
| 48 | —$SCH_2COOCH_2CF_3$ | ($DMSO-d_6$) δ 10.14 (1H, brs), 7.28 (5H, m), 6.58 (2H, brs), 4.81 (2H, s), 4.63 (2H, m), 4.04 (2H, s). |
| 49 | —$SCH_2COO(CH_2)_2OMe$ | ($DMSO-d_6$) δ 10.13 (1H, brs), 7.28 (5H, m), 6.56 (2H, brs), 4.85 (2H, s), 4.10 (2H, t, J = 4.7 Hz), 3.92 (2H, s), 3.46 (2H, t, J = 4.7 Hz), 3.19 (3H, s). |
| 50 | —$SCH_2CONHEt$ | ($DMSO-d_6$) δ 10.13 (1H, brs), 7.95 (1H, brs), 7.28 (5H, m), 6.58 (2H, s), 4.88 (2H, s), 3.71 (2H, s), 3.02 (2H, m), 0.94 (3H, t, J = 7.2 Hz). |

TABLE 18-continued

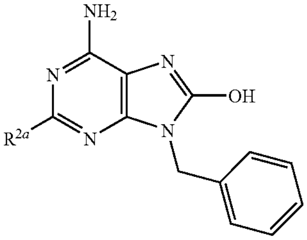

| Ex. | $R^{2a}$ | $^1$H-NMR |
|---|---|---|
| 51 | 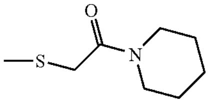 | ($DMSO-d_6$) δ 10.13 (1H, brs), 7.30 (5H, 6.57 (2H, brs), 4.88 (2H, s), 4.21 (2H, s), 3.43 (2H, m), 3.38 (2H, m), 1.54 (2H, m), 1.46 (2H, m), 1.38 (2H, m). |
| 52 | 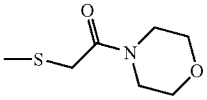 | ($DMSO-d_6$) δ 10.13 (1H, brs), 7.30 (5H, m), 6.57 (2H, brs), 4.88 (2H, s), 4.05 (2H, s), 3.44 (8H, m). |
| 53 | 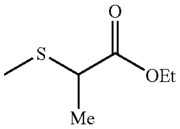 | ($DMSO-d_6$) δ 10.13 (1H, brs), 7.29 (5H, m), 6.59 (2H, brs), 4.89 (1H, d, J = 15.3 Hz), 4.82 (1H, d, J = 15.3 Hz), 4.36 (1H, d, J = 7.3 Hz), 4.03 (2H, q, J 7.1 Hz), 1.47 (3H, d, J = 7.3 Hz), 1.11 (3H, t, J = 7.1 Hz). |
| 54 | —$S(CH_2)_2COOMe$ | ($DMSO-d_6$) δ 10.12 (1H, s), 7.30 (5H, m), 6.55 (2H, brs), 4.87 (2H, s), 3.60 (3H, s), 3.19 (2H, t, J = 7.2 Hz), 2.74 (2H, t, J = 7.2 Hz). |
| 55 | —$S(CH_2)_2COOEt$ | ($DMSO-d_6$) δ 10.12 (1H, brs), 7.27 (5H, m), 6.55 (2H, brs), 4.87 (2H, s), 4.07 (2H, q, J = 7.1 Hz), 3.20 (2H, t, 7.0 Hz), 2.70 (2H, t, J = 7.0 Hz), 1.17 (3H, t, J = 7.1 Hz). |
| 56 | —$S(CH_2)_3COOEt$ | ($DMSO-d_6$) δ 10.11 (1H, brs), 7.30 (5H, m), 6.53 (2H, brs), 4.89 (2H, s), 4.04 (2H, q, J = 7.1 Hz), 3.04 (2H, t, J = 7.3 Hz), 2.38 (2H, t, J = 7.4 Hz), 1.88 (2H, m), 1.16 (3H, t, J = 7.1 Hz). |
| 57 | —$S(CH_2)_4COOEt$ | ($DMSO-d_6$) δ 10.11 (1H, brs), 7.28 (5H, m), 6.52 (2H, brs), 4.89 (2H, s), 4.03 (2H, q, J = 7.1 Hz), 3.00 (2H, t, J = 6.6 Hz), 2.28 (2H, t, J = 7.0 Hz), 1.61 (4H, m), 1.16 (3H, t, J = 7.1 Hz). |

TABLE 18-continued

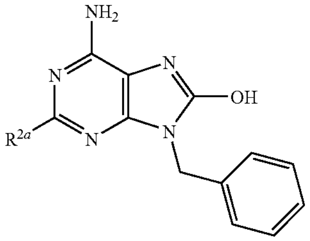

| Ex. | $R^{2a}$ | $^1$H-NMR |
|---|---|---|
| 58 | —$SCH_2COCH_2COOEt$ | ($DMSO-d_6$) δ 10.14 (1H, brs), 7.30 (5H, m), 6.58 (2H, brs), 4.87 (2H, s), 4.10 (2H, q, J = 7.1 Hz), 3.92 (2H, s), 3.71 (2H, s), 1.15 (3H, t, J = 7.1 Hz). |

TABLE 18-continued

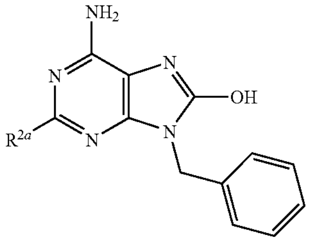

| Ex. | $R^{2a}$ | $^1$H-NMR |
|---|---|---|
| 59 | 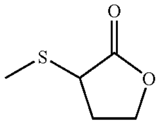 | ($DMSO-d_6$) δ 10.17 (1H, brs), 7.29 (5H, m), 6.61 (2H, brs), 4.90 (1H, d, J = 15.4 Hz), 4.84 (1H, d, J = 15.4 Hz), 4.40 (1H, t, J = 9.9 Hz), 4.22 (2H, m), 2.61 (1H, m), 2.41 (1H, m). |

TABLE 19

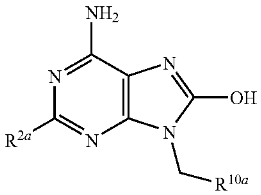

| Ex. | $R^{2a}$ | $R^{10a}$ | $^1$H-NMR |
|---|---|---|---|
| 60 | 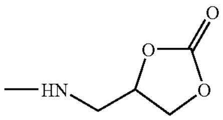 | 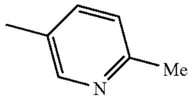 | ($DMSO-d_6$) δ 9.73 (1H, brs), 8.42 (1H, d, J = 2.0 Hz), 7.57 (1H, dd, J = 8.0, 2.0 Hz), 7.20 (1H, d, J = 8.0 Hz), 6.60 (1H, t, J = 6.0 Hz), 6.14 (2H, brs), 4.89 (1H, m), 4.80 (2H, s), 4.50 (1H, t, J = 8.0 Hz), 4.33 (1H, dd, J = 8.4, 6.0 Hz), 3.56 (1H, m), 3.45 (1H, m), 2.42 (3H, s). |
| 61 | —$(CH_2)_2COOMe$ | 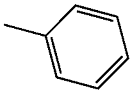 | ($DMSO-d_6$) δ 10.21 (1H, brs), 7.28 (5H, m), 6.40 (2H, s), 4.87 (2H, s), 3.53 (3H, s), 2.87 (2H, d, J = 6.9 Hz), 2.71 (2H, d, J = 6.9 Hz). |
| 62 | —$(CH_2)_2COOEt$ | 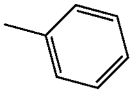 | ($DMSO-d_6$) δ 10.14 (1H, brs), 7.28 (5H, m), 6.39 (2H, s), 4.87 (2H, s), 3.98 (2H, q, J = 7.1 Hz), 2.88 (2H, d, J = 7.0 Hz), 2.69 (2H, d, J = 7.0 Hz), 1.11 (3H, d, J = 7.1 Hz). |
| 63 | —$(CH_2)_2COSMe$ | 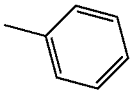 | ($DMSO-d_6$) δ 10.18 (1H, brs), 7.27 (5H, m), 6.42 (2H, s), 4.88 (2H, s), 2.87 (2H, d, J = 6.6 Hz), 2.71 (2H, d, J = 6.6 Hz), 2.20 (3H, s). |
| 64 | —$OCH_2COOMe$ | 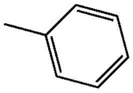 | ($DMSO-d_6$) δ 10.06 (1H, brs), 7.28 (5H, m), 6.57 (2H, brs), 4.82 (2H, s), 4.78 (2H, s), 3.61 (3H, s). |
| 65 | —$OCH_2COOEt$ | 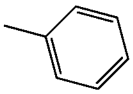 | ($DMSO-d_6$) δ 10.02 (1H, brs), 7.29 (5H, m), 6.54 (2H, brs), 4.83 (2H, s), 4.75 (2H, s), 4.07 (2H, q, J = 7.1 Hz), 1.14 (3H, d, J = 7.1 Hz). |

TABLE 19-continued

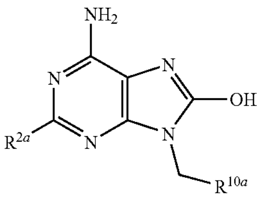

| Ex. | $R^{2a}$ | $R^{10a}$ | $^1$H-NMR |
|---|---|---|---|
| 66 | $-(CH_2)_2COOMe$ | 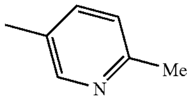 | (DMSO-$d_6$) δ 10.14 (1H, brs), 8.43 (1H, d, J = 2.0 Hz), 7.59 (1H, dd, J = 8.0, 2.3 Hz), 7.19 (1H, d, J = 8.0 Hz), 6.40 (2H, brs), 4.85 (2H, s), 3.56 (3H, s), 2.88 (2H, d, J = 6.9 Hz), 2.72 (2H, d, J = 6.9 Hz), 2.41 (3H, s). |
| 67 | $-(CH_2)_2COOMe$ | 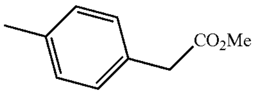 | (DMSO-$d_6$) δ 10.16 (1H, brs), 7.24 (2H, d, J = 8.2 Hz), 7.19 (2H, d, J = 8.2 Hz), 6.39 (2H, brs), 4.85 (2H, s), 3.64 (2H, s), 3.58 (3H, s), 3.53 (3H, s), 2.87 (2H, d, J = 6.9 Hz), 2.71 (2H, d, J = 6.9 Hz). |

TABLE 20

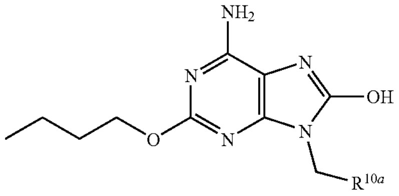

| Ex. | $R^{10a}$ | $^1$H-NMR |
|---|---|---|
| 68 | 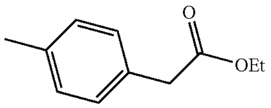 | (DMSO-$d_6$) δ 9.95 (1H, brs), 7.23 (2H, d, J = 8.3 Hz), 7.20 (2H, d, J = 8.3 Hz), 6.46 (2H, brs), 4.83 (2H, s), 4.14 (2H, t, J = 6.6 Hz), 4.04 (2H, q, J = 7.1 Hz), 3.61 (2H, s), 1.62 (2H, 5, J = 6.6 Hz), 1.36 (2H, 6, J = 6.6 Hz), 1.16 (3H, t, J = 7.1 Hz), 0.90 (3H, t, J = 7.3 Hz). |
| 69 | 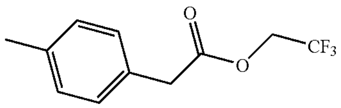 | (DMSO-$d_6$) δ 10.01 (1H, brs), 7.25 (2H, d, J = 8.6 Hz), 7.22 (2H, d, J = 8.5 Hz), 6.47 (2H, brs), 4.83 (2H, s), 4.13 (2H, q, J = 9.1 Hz), 4.13 (2H, t, J = 6.6 Hz), 3.79 (2H, s), 1.62 (2H, 5, J = 7.0 Hz), 1.37 (2H, 6, J = 7.5 Hz), 0.90 (3H, t, J = 7.4 Hz). |
| 70 | 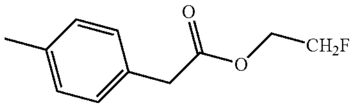 | (DMSO-$d_6$) δ 10.00 (1H, brs), 7.24 (2H, d, J = 8.6Hz), 7.21 (2H, d, J = 8.8 Hz), 6.46 (2H, brs), 4.83 (2H, s), 4.66 (1H, t, J = 4.0 Hz), 4.54 (1H, t, J = 4.0 Hz), 4.30 (1H, t, J = 4.0Hz), 4.23 (1H, t, J = 4.0 Hz), 4.13 (2H, t, J = 6.6 Hz), 3.68 (2H, s), 1.62 (2H, 5, J = 6.7 Hz), 1.36 (2H, 6, J = 7.6 Hz), 0.90 (3H, t, J = 7.3 Hz). |

TABLE 20-continued

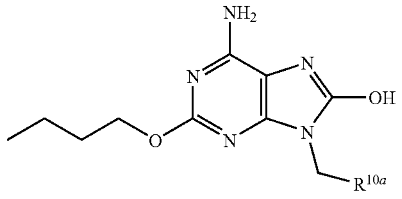

| Ex. | $R^{10a}$ | $^1$H-NMR |
|---|---|---|
| 71 | 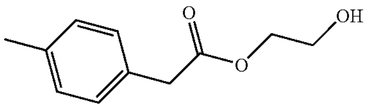 | (DMSO-$d_6$) δ 9.98 (1H, brs), 7.24 (2H, d, J = 8.5Hz), 7.21 (2H, d, J = 8.5 Hz), 6.46 (2H, brs), 4.83 (2H, s), 4.81 (1H, t, J = 5.5 Hz), 4.13 (2H, t, J = 6.6 Hz), 4.02 (2H, t, J = 5.2 Hz), 3.64 (2H, s), 3.55 (2H, q, J = 5.4 Hz), 1.62 (2H, 5, J = 6.7 Hz), 1.36 (2H, 6, J = 7.5 Hz), 0.90 (3H, t, J = 7.4 Hz). |
| 72 | 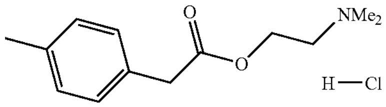 | (DMSO-$d_6$) δ 10.13 (1H, brs), 9.78 (1H, brs), 7.25 (4H, m), 6.56 (2H, brs), 4.84 (2H, s), 4.33 (2H, t, J = 5.0 Hz), 4.14 (2H, t, J = 6.6Hz), 3.70 (2H, s), 3.35 (2H, q, J = 5.0 Hz), 2.76 (3H, s), 2.75 (3H, s), 1.62 (2H, 5, J = 7.9 Hz), 1.37 (2H, 6, J = 7.6 Hz), 0.90 (3H, t, J = 7.4 Hz). |
| 73 | 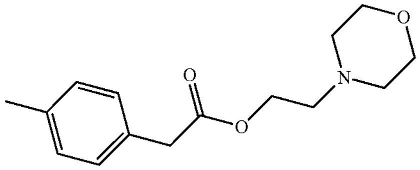 | (DMSO-$d_6$) δ 9.97 (1H, brs), 7.23 (4H, m), 6.45 (2H, brs), 4.83 (2H, s), 4.12 (4H, m), 3.62 (2H, s), 3.48 (4H, t, J = 4.7 Hz), 2.48 (2H, t, J = 5.7 Hz), 2.32 (4H, t, J = 4.8 Hz), 1.62 (2H, 5, J = 7.8 Hz), 1.36 (2H, 6, J = 7.3 Hz), 0.90 (3H, t, J = 7.3 Hz). |
| 74 | 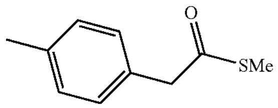 | (DMSO-$d_6$) δ 10.00 (1H, brs), 7.23 (4H, m), 6.46 (2H, brs), 4.83 (2H, s), 4.13 (2H, t, J = 6.6 Hz), 3.87 (2H, s), 2.20 (2H, s), 1.62 (2H, 5, J = 7.8 Hz), 1.37 (2H, 6, J = 7.4 Hz), 0.90 (3H, t, J = 7.4 Hz). |
| 75 | 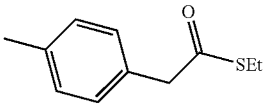 | (DMSO-$d_6$) δ 9.99 (1H, brs), 7.24 (2H, d, J = 8.4 Hz), 7.21 (2H, d, J = 8.4 Hz), 6.46 (2H, brs), 4.83 (2H, s), 4.13 (2H, t, J = 6.6 Hz), 3.85 (2H, s), 2.78 (2H, q, J = 7.4 Hz), 1.62 (2H, 5, J = 6.7 Hz), 1.36 (2H, 6, J = 7.3 Hz), 1.12 (3H, t, J = 7.4 Hz), 0.90 (3H, t, J = 7.4 Hz). |
| 76 | 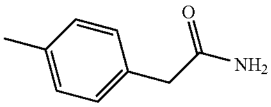 | (DMSO-$d_6$) δ 9.93 (1H, brs), 7.43 (1H, s), 7.21 (2H, d, J = 8.4Hz), 7.18 (2H, d, J = 8.3 Hz), 6.85 (1H, s), 6.44 (2H, brs), 4.81 (2H, s), 4.14 (2H, t, J = 6.7 Hz), 3.32 (2H, s), 1.62 (2H, 5, J = 6.6 Hz), 1.37 (2H, 6, J = 7. 5 Hz), 0.90 (3H, t, J = 7.3 Hz). |
| 77 | 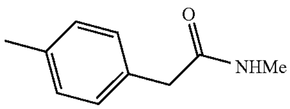 | (DMSO-$d_6$) δ 9.96 (1H, brs), 7.91 (1H, d, J = 4.3 Hz), 7.21 (2H, d, J = 8.3 Hz), 7.18 (2H, d, J = 8.3 Hz), 6.45 (2H, brs), 4.81 (2H, s), 4.14 (2H, t, J = 6.6 Hz), 2.54 (2H, s), 2.53 (3H, s), 1.62 (2H, 5, J = 6.7 Hz), 1.37 (2H, 6, J = 7.6 Hz), 0.90 (3H, t, J = 7.3 Hz). |
| 78 | 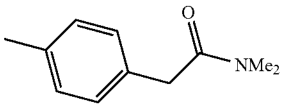 | (DMSO-$d_6$) δ 9.99 (1H, brs), 7.21 (2H, d, J = 8.1 Hz), 7.15 (2H, d, J = 8.1 Hz), 6.46 (2H, brs), 4.82 (2H, s), 4.14 (2H, t, J = 6.6 Hz), 3.63 (2H, s), 2.97 (3H, s), 2.80 (3H, s), 1.62 (2H, 5, J = 6.6 Hz), 1.37 (2H, 6, J = 7.6 Hz), 0.90 (3H, t, J = 7.3 Hz). |

TABLE 20-continued

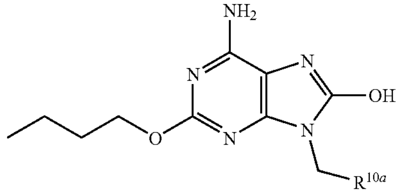

| Ex. | $R^{10a}$ | $^1$H-NMR |
|---|---|---|
| 79 | 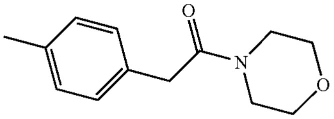 | (DMSO-$d_6$) δ 9.95 (1H, brs), 7.22 (2H, d, J = 8.0 Hz), 7.15 (2H, d, J = 8.0 Hz), 6.45 (2H, brs), 4.82 (2H, s), 4.14 (2H, t, J = 6.6 Hz), 3.67 (2H, s), 3.46 (8H, m), 1.62 (2H, 5, J = 7.7 Hz), 1.37 (2H, 6, J = 7.4 Hz), 0.90 (3H, t, J = 7.3 Hz). |
| 80 | 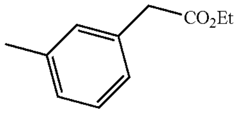 | (DMSO-$d_6$) δ 9.98 (1H, brs), 7.27 (1H, t, J = 8.0 Hz), 7.16 (3H, m), 6.46 (2H, brs), 4.83 (2H, s), 4.13 (2H, t, J = 6.6 Hz), 4.03 (2H, q, J = 7.1 Hz), 3.58 (2H, s), 1.62 (2H, 5, J = 6.6 Hz), 1.36 (2H, 6, J = 7.5 Hz), 1.14 (3H, t, J = 7.1 Hz), 0.90 (3H, t, J = 7.3 Hz). |
| 81 | 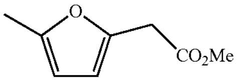 | (DMSO-$d_6$) δ 9.99 (1H, brs), 6.46 (2H, brs), 6.19 (2H, m), 4.79 (2H, s), 4.14 (2H, t, J = 6.6 Hz), 3.72 (2H, s), 3.60 (3H, s), 1.62 (2H, 5, J = 6.8 Hz), 1.36 (2H, 6, J = 7.4 Hz), 0.90 (3H, t, J = 7.3 Hz). |
| 82 | 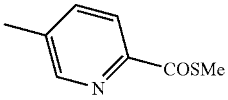 | (DMSO-$d_6$) δ 10.08 (1H, brs), 8.69 (1H, d, J = 0.9 Hz), 7.89 (2H, m), 6.51 (2H, brs), 5.00 (2H, s), 4.12 (2H, t, J = 6.6 Hz), 2.35 (3H, s), 1.62 (2H, 5, J = 6.8 Hz), 1.36 (2H, 6, J = 7.3 Hz), 0.88 (3H, t, J = 7.4 Hz). |
| 83 | 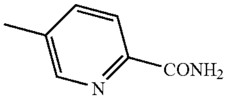 | (DMSO-$d_6$) δ 10.01 (1H, brs), 8.61 (1H, d, J = 1.7 Hz), 8.09 (1H, brs), 7.98 (1H, d, J = 8.0 Hz), 7.83 (1H, dd, J = 2.1, 8.0 Hz), 7.63 (1H, brs), 6.49 (2H, brs), 4.98 (2H, s), 4.13 (2H, t, J = 6.6 Hz), 1.61 (2H, 5, J = 6.6 Hz), 1.35 (2H, 6, J = 7.5 Hz), 0.89 (3H, t, J = 7.4 Hz). |
| 84 | 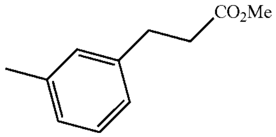 | (DMSO-$d_6$) δ 9.99 (1H, brs), 7.15 (4H, m), 6.46 (2H, brs), 4.81 (2H, s), 4.14 (2H, t, J = 6.6 Hz), 3.54 (3H, s), 2.80 (2H, t, J = 7.6Hz), 2.58 (2H, t, J = 7.6 Hz), 1.62 (2H, 5, J = 6.6 Hz), 1.36 (2H, 6, J = 7.6 Hz), 0.90 (3H, t, J = 7.3 Hz). |
| 85 | 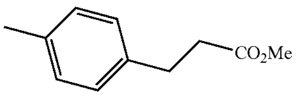 | (DMSO-$d_6$) δ 9.93 (1H, brs), 7.21 (2H, d, J = 8.3 Hz), 7.15 (2H, d, J = 8.3 Hz), 6.44 (2H, brs), 4.80 (2H, s), 4.13 (2H, t, J = 6.6 Hz), 3.56 (3H, s), 2.80 (2H, t, J = 7.7 Hz), 2.59 (2H, t, J = 7.5 Hz), 1.62 (2H, 5, J = 6.6 Hz), 1.36 (2H, 6, J = 7.3 Hz), 0.90 (3H, t, J = 7.3 Hz). |
| 86 | 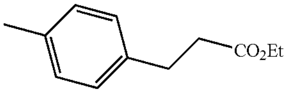 | (DMSO-$d_6$) δ 9.97 (1H, brs), 7.20 (2H, d, J = 8.3 Hz), 7.15 (2H, d, J = 8.3 Hz), 6.45 (2H, brs), 4.80 (2H, s), 4.13 (2H, t, J = 6.6Hz), 4.01 (2H, q, J = 7.1 Hz), 2.79 (2H, t, J = 7.4 Hz), 2.56 (2H, t, J = 7.7 Hz), 1.62 (2H, 5, J = 7.0 Hz), 1.36 (2H, 6, J = 7.6 Hz), 1.12 (3H, t, J = 7.1 Hz), 0.90 (3H, t, J = 7.3 Hz). |

TABLE 20-continued

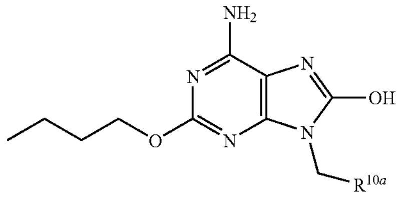

| Ex. | $R^{10a}$ | $^1$H-NMR |
|---|---|---|
| 87 | 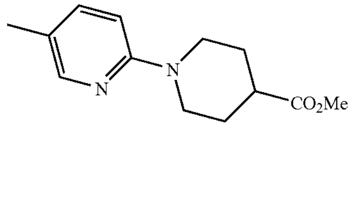 | (DMSO-$d_6$) δ 9.90 (1H, brs), 8.10 (1H, d, J = 2.1 Hz), 7.49 (1H, dd, J = 2.3, 8.9 Hz), 6.79 (1H, d, J = 8.8 Hz), 6.42 (2H, brs), 4.71 (2H, s), 4.15 (4H, m), 3.59 (3H, s), 2.86 (2H, t, J = 11.0 Hz), 2.58 (2H, m), 1.84 (1H, m), 1.63 (2H, 5, J = 7.8 Hz), 1.48 (2H, m), 1.38 (2H, 6, J = 7.3 Hz), 0.92 (3H, t, J = 7.3 Hz). |
| 88 | 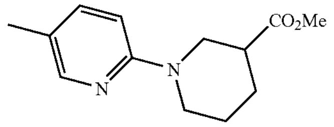 | (DMSO-$d_6$) δ 9.93 (1H, brs), 8.11 (1H, d, J = 2.3 Hz), 7.49 (1H, dd, J = 2.4, 8.8 Hz), 6.79 (1H, d, J = 8.8 Hz), 6.43 (2H, s), 4.71 (2H, s), 4.31 (1H, m), 4.16 (2H, t, J = 6.6 Hz), 3.94 (1H, m), 2.99 (2H, m), 2.45 (1H, m), 1.93 (1H, m), 1.62 (4H, m), 1.39 (3H, m), 0.92 (3H, t, J = 7.3 Hz). |
| 89 | 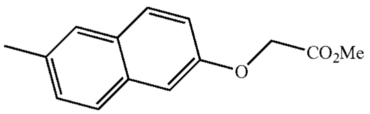 | (DMSO-$d_6$) δ 9.97 (1H, brs), 7.81 (1H, d, J = 9.0 Hz), 7.75 (1H, d, J = 8.6 Hz), 7.71 (1H, s), 7.43 (1H, d, J = 7.2 Hz), 7.26 (1H, d, J = 2.2Hz), 7.19 (1H, dd, J = 2.5, 9.0 Hz), 6.46 (2H, s), 4.98 (2H, s), 4.90 (2H, s), 4.14 (2H, t, J = 6.6 Hz), 3.71 (3H, s), 1.61 (2H, 5, J = 7.1 Hz), 1.35 (2H, 6, J = 7.6 Hz), 0.88 (3H, t, J = 7.4 Hz). |
| 90 | 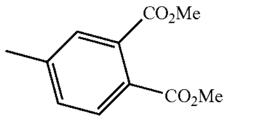 | (DMSO-$d_6$) δ 10.03 (1H, brs), 7.72 (1H, d, J = 8.0 Hz), 7.64 (1H, d, J = 1.5 Hz), 7.59 (1H, dd, J = 1,7, 8.0 Hz), 6.49 (2H, brs), 4.95 (2H, s), 4.12 (2H, t, J = 6.6 Hz), 3.80 (6H, s), 1.60 (2H, 5, J = 6.6 Hz), 1.35 (2H, 6, J = 7.5 Hz), 0.89 (3H, t, J = 7.4 Hz). |
| 91 | 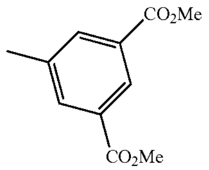 | (DMSO-$d_6$) δ 10.10 (1H, brs), 8.38 (1H, m), 8.18 (2H, d, J = 1.6 Hz), 6.52 (2H, brs), 5.00 (2H, s), 4.15 (2H, t, J = 6.6 Hz), 3.88 (6H, s), 1.62 (2H, 5, J = 6.6 Hz), 1.36 (2H, 6, J = 7.5 Hz), 0.89 (3H, t, J = 7.4 Hz). |
| 92 | 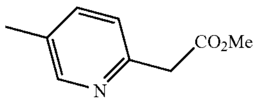 | (DMSO-$d_6$) δ 9.98 (1H, brs), 8.47 (1H, d, J = 1.8 Hz), 7.66 (1H, dd, J = 2.3, 8.0 Hz), 7.31 (1H, d, J = 7.9 Hz), 6.46 (2H, brs), 4.87 (2H, s), 4.14 (2H, t, J = 6.6 Hz), 3.59 (2H, s), 3.43 (3H, s), 1.62 (2H, 5, J = 7.0 Hz), 1.36 (2H, 6, J = 7.6 Hz), 0.90 (3H, t, J = 7.3 Hz). |
| 93 | 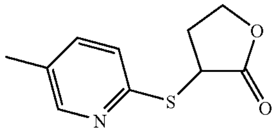 | (DMSO-$d_6$) δ 9.99 (1H, brs), 8.38 (1H, d, J = 1.6 Hz), 7.60 (1H, dd, J = 2.2, 8.3 Hz), 7.34 (1H, d, J = 8.3 Hz), 6.47 (2H, brs), 4.84 (2H, s), 4.64 (1H, t, J = 9.6 Hz), 4.39 (1H, dt, J = 3.2, 8.7 Hz), 4.31 (1H, q, J = 8.7 Hz), 4.14 (2H, t, J = 6.6 Hz), 2.69 (1H, m), 2.33 (1H, m), 1.62 (2H, 5, J = 7.0 Hz), 1.37 (2H, 6, J = 7.5 Hz), 0.91 (3H, t, J = 7.3 Hz). |

TABLE 20-continued

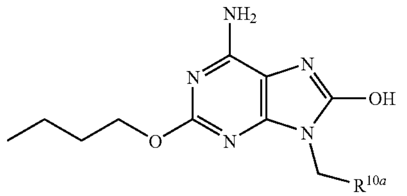

| Ex. | $R^{10a}$ | $^1$H-NMR |
|---|---|---|
| 94 | 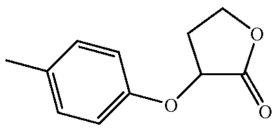 | (DMSO-$d_6$) δ 9.96 (1H, brs), 7.26 (2H, d, J = 8.3 Hz), 6.98 (2H, d, J = 8.3 Hz), 6.45 (2H, brs), 5.29 (1H, t, J = 8.7 Hz), 4.79 (2H, s), 4.39 (1H, dt, J = 2.3, 8.8 Hz), 4.31 (1H, m), 4.15 (2H, t, J = 6.6 Hz), 2.74 (1H, m), 2.22 (1H, m), 1.63 (2H, 5, J = 6.6 Hz), 1.37 (2H, 6, J = 7.6 Hz), 0.91 (3H, t, J = 7.3 Hz). |
| 95 | 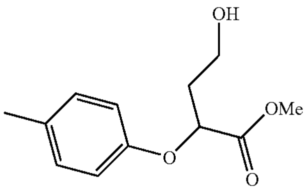 | (DMSO-$d_6$) δ 9.96 (1H, brs), 7.22 (2H, d, J = 8.7 Hz), 6.81 (2H, d, J = 8.7 Hz), 6.44 (2H, brs), 4.86 (1H, m), 4.76 (2H, s), 4.67 (1H, t, J = 5.1 Hz), 4.14 (2H, t, J = 6. 7Hz), 3.65 (3H, s), 3.53 (2H, m), 1.94 (2H, m), 1.63 (2H, 5, J = 6.6 Hz), 1.37 (2H, 6, J = 7.4 Hz), 0.91 (3H, t, J = 7.3 Hz). |

TABLE 21

| Ex. | Structure | $^1$H-NMR |
|---|---|---|
| 96 | 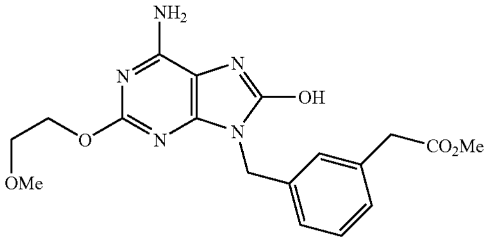 | (DMSO-$d_6$) δ 9.96 (1H, s), 7.27 (1H, dd, J = 7.6 Hz, 7.6 Hz), 7.20 (1H, s), 7.17 (1H, d, J = 7.6 Hz), 7.15 (1H, d, J = Hz), 3.65 (2H, s), 3.58 (3H, s), 7.6 Hz), 6.47 (2H, brs), 4.83 (2H, s), 4.25 (2H, t, J = 4.8 3.58 (2H, t, J = 4.8 Hz), 3.26 (3H, s). |
| 97 | 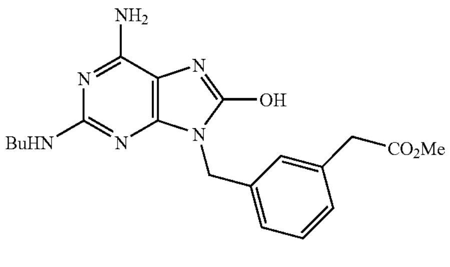 | (DMSO-$d_6$) δ 9.63 (1H, s), 7.26 (1H, dd, J = 7.6 Hz, 7.6 Hz), 7.19 (1H, s), 7.16-7.13 (2H, m), 6.20 (1H, t, J = 5.6 Hz), 6.00 (2H, s), 4.83 (2H, s), 3.77 (2H, s), 3.59 (3H, s), 3.15 (2H, dt, J = 5.6 Hz, 6.8 Hz), 1.43 (2H, tt, J = 7.6 Hz, 6.8 Hz), 1.28 (2H, tq, J = 7.6 Hz, 7.6 Hz), 0.86 (3H, t, J = 7.6 Hz). |
| 98 | 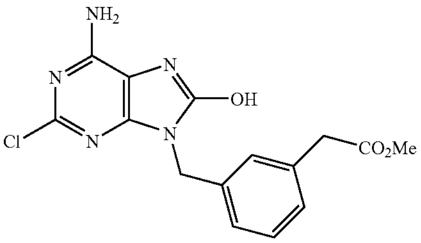 | (DMSO-$d_6$) δ 10.37 (1H, brs), 7.29 (1H, dd, J = 8.0 Hz, 4.8 Hz), 7.18-7.12 (3H, m), 6.91 (2H, brs), 4.88 (2H, s), 3.65 (2H, s), 3.58 (3H, s). |

TABLE 21-continued

| Ex. | Structure | $^{1}$H-NMR |
|---|---|---|
| 99 | 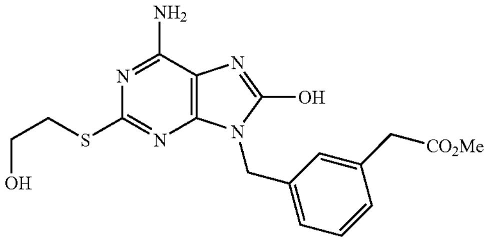 | (DMSO-$d_6$) δ 10.12 (1H, s), 7.28 (1H, dd, J = 7.6 Hz, 7.6 Hz), 7.23 (1H, s), 7.21 (1H, d, J = 7.6 Hz), 7.16 (1H, d, J = 7.6 Hz), 6.53 (2H, brs), 4.88 (1H, brs), 4.85 (2H, s), 3.65 (2H, s), 3.61-3.57 (2H, m), 3.59 (3H, s), 3.12 (2H, t, J = 6.8 Hz). |
| 100 | 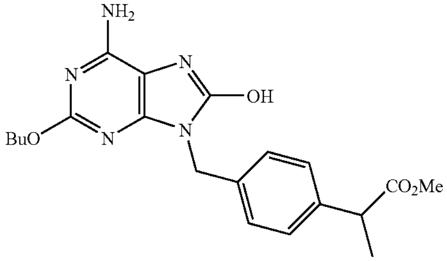 | (DMSO-$d_6$) δ 9.93 (1H, brs), 7.28 (1H, dd, J = 7.6 Hz, 7.6 Hz), 7.23 (1H, s), 7.21 (1H, d, J = 7.6 Hz), 7.16 (1H, d, J = 7.6 Hz), 6.53 (2H, brs), 4.88 (1H, brs), 4.85 (2H, s), 3.65 (2H, s), 3.61-3.57 (2H, m), 3.59 (3H, s), 3.12 (2H, t, J = 6.8 Hz). |
| 101 | 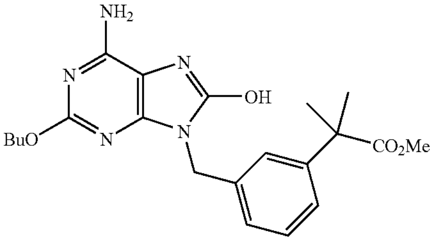 | (DMSO-$d_6$) δ 9.93 (1H, brs), 7.30-7.11 (4H, m), 6.43 (2H, brs), 4.83 (2H, s), 4.14 (2H, t, J = 6.6 Hz), 3.52 (2H, s), 3.58 (3H, s), 1.62 (2H, 5, J = 6.9 Hz), 1.45 (6H, s), 1.36 (2H, 6, J = 7.0 Hz), 0.89 (3H, t, J = 7.2 Hz). |
| 102 | 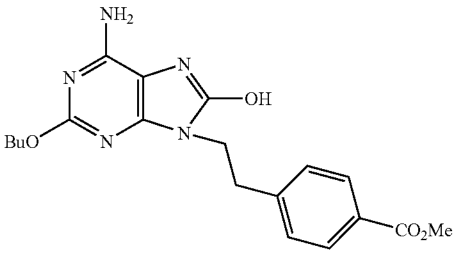 | (DMSO-$d_6$) δ 9.81 (1H, brs), 7.82 (2H, d, J = 8.3 Hz), 7.29 (2H, d, J = 8.2 Hz), 6.37 (2H, brs), 4.09 (2H, t, J = 6.6 Hz), 3.93 (2H, t, J = 7.0 Hz), 3.81 (3H, s), 3.06 (2H, t, J = 7.1 Hz), 1.61 (2H, 5, J = 7.0 Hz), 1.37 (2H, 6, J = 7.4 Hz), 0.90 (3H, t, J = 7.3 Hz). |

TABLE 22

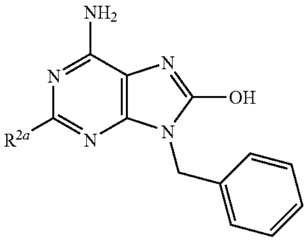

| Ex. | —$R^{2a}$ | $^{1}$H-NMR |
|---|---|---|
| 103 | 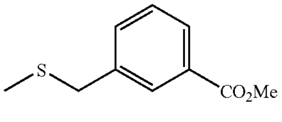 | (DMSO-$d_6$) δ 810.14 (1H, brs), 8.05 (1H, s), 7.79 (1H, d, J = 7.8 Hz), 7.64 (1H, d, J = 7.8 Hz), 7.34 (1H, t, J = 7.8 Hz), 7.28 (5H, m), 6.60 (2H, brs), 4.92 (2H, s), 4.36 (2H, s), 3.82 (3H, s). |

TABLE 22-continued

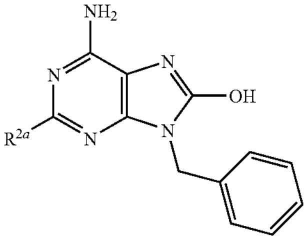

| Ex. | —$R^{2a}$ | $^1$H-NMR |
|---|---|---|
| 104 | 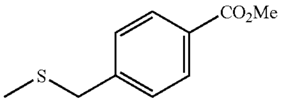 | (DMSO-$d_6$) δ 10.15 (1H, brs), 7.77 (2H, d, J = 8.2 Hz), 7.49 (2H, d, J = 8.2 Hz) 7.28 (5H, m), 6.61 (2H, brs), 4.92 (2H, s), 4.35 (2H, s), 3.83 (3H, s). |
| 105 | 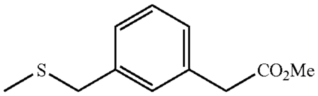 | (DMSO-$d_6$) δ 10.13 (1H, brs), 7.29 (7H, m), 7.18 (1H, t, J = 7.6 Hz), 7.09 (2H, d, J = 7.6 Hz), 6.59 (2H, brs), 4.91 (2H, s), 4.27 (2H, s), 3.60 (2H, s), 3.58 (3H, s). |
| 106 | 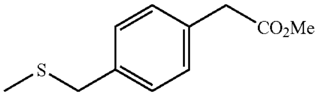 | (DMSO-$d_6$) δ 10.13 (1H, brs), 7.27 (7H, m), 7.09 (2H, d, J = 8.0 Hz), 6.58 (2H, brs), 4.91 (2H, s), 4.27 (2H, s), 3.61 (2H, s), 3.59 (3H, s). |
| 107 | 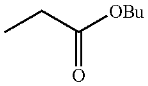 | (DMSO-$d_6$) δ 10.11 (1H, s), 7.18 (5H, m), 6.40 (2H, s), 4.80 (2H, s), 3.93 (2H, t, J = 6.6 Hz), 3.55 (2H, s), 1.42 (2H, m), 1.17 (2H, m), 0.74 (3H, t, J = 7.4 Hz). |
| 108 | 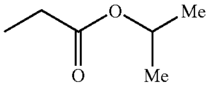 | (DMSO-$d_6$) δ 10.26 (1H, brs), 7.32 (5H, m), 6.53 (2H, s), 4.94 (3H, m), 3.64 (2H, s), 1.19 (6H, t, J = 6.3 Hz). |
| 109 | 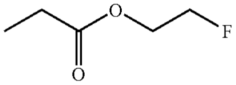 | (DMSO-$d_6$) δ 10.03 (1H, brs), 7.09 (5H, m), 6.32 (2H, s), 4.70 (2H, s), 4.39 (2H, m), 4.08 (2H, m), 3.50 (2H, s). |
| 110 | 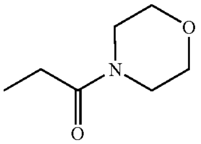 | (DMSO-$d_6$) δ 10.13 (1H, s), 7.24 (5H, m), 6.40 (2H, brs), 4.83 (2H, s), 3.63 (2H, s), 3.44-3.32 (8H, m). |

TABLE 23

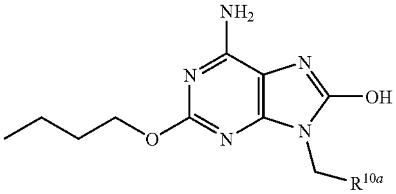

| Ex. | —$R^{10a}$ | $^1$H-NMR |
|---|---|---|
| 111 | 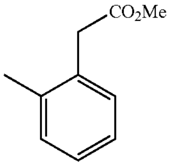 | (DMSO-$d_6$) δ 89.97 (1H, brs), 7.21 (4H, s), 6.43 (2H, brs), 4.85 (2H, s), 4.12 (2H, t, J = 6.6 Hz), 4.01 (2H, s), 3.58 (3H, s), 1.61 (2H, 5, J = 6.6 Hz), 1.36 (2H, 6, J = 7.3 Hz), 0.89 (3H, t, J = 7.3 Hz). |

TABLE 23-continued

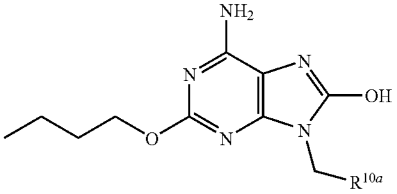

| Ex. | $—R^{10a}$ | $^{1}$H-NMR |
|---|---|---|
| 112 | 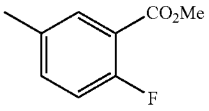 | (DMSO-$d_6$) δ 9.98 (1H, brs), 7.87-7.84 (1H, m), 7.60-7.58 (1H, m), 7.34-7.27 (1H, m), 6.45 (2H, brs), 4.88 (2H, s), 4.13 (2H, t, J = 6.6 Hz), 3.82 (3H, s), 1.61 (2H, 5, J = 6.8 Hz), 1.35 (2H, 6, J = 7.5 Hz), 0.88 (3H, t, J = 7.3 Hz). |
| 113 | 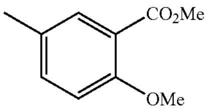 | (DMSO-$d_6$) δ 9.93 (1H, brs), 7.63 (1H, d, 2.4 Hz), 7.48 (1H, dd, J = 2.4 Hz, 8.6 Hz), 7.10 (1H, d, J = 8.8 Hz), 6.43 (2H, brs), 4.80 (2H, s), 4.14 (2H, t, J = 6.6 Hz), 3.77 (3H, s), 3,75 (3H, s), 1.62 (2H, 5, J = 6.8 Hz), 1.36 (2H, 6, J = 7.5 Hz), 0.89 (3H, t, J = 7.3 Hz). |
| 114 | 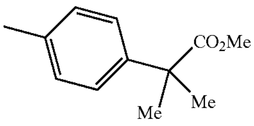 | (DMSO-$d_6$) δ 9.96 (1H, brs), 7.24 (4H, s), 6.44 (2H, brs), 4.81 (2H, s), 4.13 (2H, t, J = 6.6 Hz), 3.55 (3H, s), 1.61 (2H, 5, J = 6.8 Hz), 1.45 (6H, s), 1.36 (2H, 6, J = 7.5 Hz), 0.90 (3H, t, J = 7.3 Hz). |
| 115 | 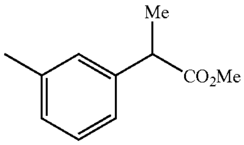 | (DMSO-$d_6$) δ 9.96 (1H, brs), 7.29-7.12 (4H, m), 6.44 (2H, brs), 4.82 (2H, s), 4.13 (2H, t, J = 6.6 Hz), 3.75 (1H, q, J = 7.1 Hz), 3.54 (3H, s), 1.61 (2H, 5, J = 6.8 Hz), 1.36 (2H, 6, J = 7.5 Hz), 1.33 (3H, d, J = 7.1), 0.89 (3H, t, J = 7.3 Hz). |
| 116 | 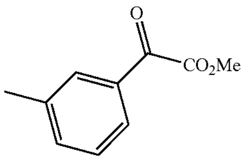 | (DMSO-$d_6$) δ 10.05 (1H, brs), 7.91 (1H, s), 7.88 (1H, d, J = 7.7 Hz), 7.69 (1H, d, J = 7.6 Hz), 7.58 (1H, dd, J = 7.7 Hz, 7.6 Hz), 6.50 (2H, brs), 4.96 (2H, s), 4.13 (2H, t, J = 6.6 Hz), 3.91 (3H, s), 1.61 (2H, tt, J = 7.4 Hz, 6.6 Hz), 1.37 (2H, tq, J = 7.4 Hz, 7.4 Hz), 0.89 (3H, t, J = 7.4 Hz). |
| 117 | 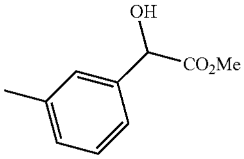 | (DMSO-$d_6$) δ 9.97 (1H, s), 7.34 (1H, s), 7.32-7.28 (2H, m), 7.24-7.20 (1H, m), 6.46 (2H, brs), 6.07 (1H, d, J = 5.1 Hz), 5.10 (1H, d, J = 5.1 Hz), 4.84 (2H, s), 4.14 (2H, t, J = 6.6 Hz), 3.57 (3H, s), 1.62 (2H, tt, J = 7.4 Hz, 6.6 Hz), 1.38 (2H, tq, J = 7.4 Hz, 7.4 Hz), 0.90 (3H, t, J = 7.4 Hz). |
| 118 | 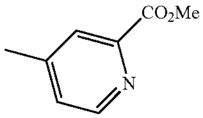 | (DMSO-$d_6$) δ 10.11 (1H, brs), 8.65 (1H, dd, J = 0.6, 5.0 Hz), 7.93 (1H, d, J = 0.9 Hz), 7.31 (1H, dd, J = 0.6, 5.0 Hz), 6.53 (2H, brs), 4.98 (2H, s), 4.11 (2H, t, J = 6.8 Hz), 3.86 (3H, s), 1.58 (2H, 5, J = 6.6 Hz), 1.33 (2H, 6, J = 7.3 Hz), 0.87 (3H, t, J = 7.3 Hz). |
| 119 | 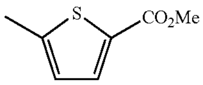 | (DMSO-$d_6$) δ 10.11 (1H, brs), 7.65 (1H, d, J = 3.8 Hz), 7.14 (1H, d, J = 3.8 Hz), 6.53 (2H, brs), 5.06 (2H, s), 4.16 (2H, t, J = 6.6 Hz), 3.78 (3H, s), 1.63 (2H, 5, J = 6.6 Hz), 1.37 (2H, 6, J = 7.3 Hz), 0.90 (3H, t, J = 7.3 Hz). |
| 120 | 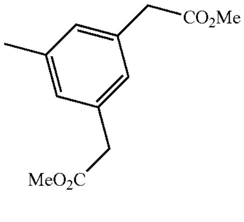 | (DMSO-$d_6$) δ 10.00 (1H, brs), 7.09 (2H, s), 7.05 (1H, s), 6.47 (2H, brs), 4.81 (2H, s), 4.14 (2H, t, J = 6.6 Hz), 3.63 (4H, s), 3.58 (6H, s), 1.62 (2H, 5, J = 6.6 Hz), 1.37 (2H, 6, J = 7.3 Hz), 0.90 (3H, t, J = 7.3 Hz). |

TABLE 23-continued

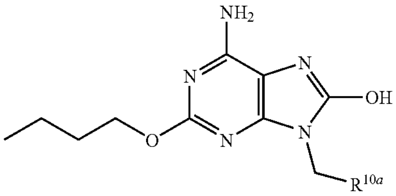

| Ex. | —$R^{10a}$ | $^1$H-NMR |
|---|---|---|
| 121 | 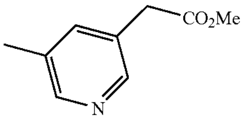 | (DMSO-$d_6$) δ 10.09 (1H, brs), 8.45 (1H, d, J = 2.0 Hz), 8.38 (1H, d, J = 2.0Hz), 7.60 (1H, m), 6.50 (2H, brs), 4.88 (2H, s), 4.14 (2H, t, J = 6.6 Hz), 3.73 (2H, s), 3.60 (3H, s), 1.62 (2H, 5, J = 6.6 Hz), 1.37 (2H, 6, J = 7.4 Hz), 0.90 (3H, t, J = 7.3 Hz). |

TABLE 24

| Comp. ex. | Structure | 1H-NMR |
|---|---|---|
| 1 | 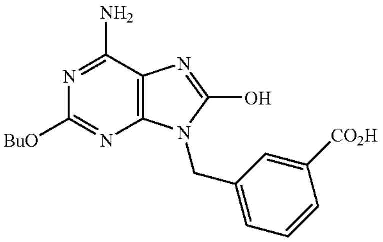 | (DMSO-$d_6$) δ 612.99 (1H, (DMSO-d6) 512.99 (1H, brs), 10.03 (1H, s), 7.88 (1H, s), 7.84 (1H, d, J = 7.8 Hz), 7.55 (1H, d, J = 7.8 Hz), 7.45 (1H, t, J = 7.8 Hz), 6.48 (2H, brs), 4.91 (2H, s), 4.14 (2H, t, J = 6.5 Hz), 1.60 (2H, 5, J = 7.0 Hz), 1.36 (2H, 6, J = 7.0 Hz), 0.89 (3H, t, J = 7.3 Hz). |
| 3 | 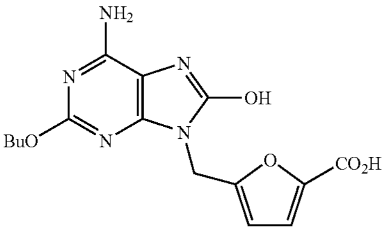 | (DMSO-$d_6$) δ 13.08 (1H, brs), 10.02 (1H, brs), 7.09 (1H, d, J = 2.4 Hz), 6.45 (3H, m), 4.91 (2H, s), 4.13 (2H, t, J = 6.5 Hz), 1.64 (2H, 5, J = 6.8 Hz), 1.36 (2H, 6, J = 7.0 Hz), 0.90 (3H, t, J = 7.3 Hz). |
| 5 | 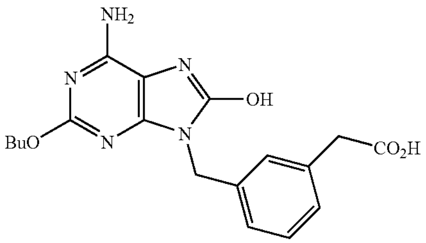 | (DMSO-$d_6$) δ 12.31 (1H, brs), 10.03 (1H, brs), 7.22 (4H, m), 6.47 (2H, brs), 4.83 (2H, s), 4.14 (2H, t, J = 6.8 Hz), 3.50 (2H, s), 1.60 (2H, 5, J = 6.8 Hz), 1.38 (2H, 6, J = 7.6 Hz), 0.90 (3H, t, J = 7.0 Hz). |
| 6 | 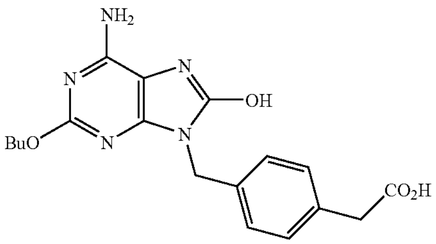 | (DMSO-$d_6$) δ 13.14 (1H, brs), 10.01 (1H, brs), 7.22 (4H, m), 6.49 (2H, brs), 4.83 (2H, s), 4.14 (2H, t, J = 6.5 Hz), 3.53 (2H, s), 1.62 (2H, 5, J = 6.8 Hz), 1.36 (2H, 6, J = 7.0 Hz), 0.90 (3H, t, J = 7.3 Hz). |

TABLE 24-continued
| Comp. ex. | Structure | 1H-NMR |
|---|---|---|
| 8 | 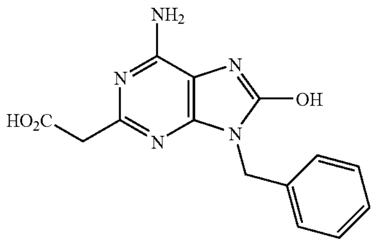 | (DMSO-$d_6$) δ 12.40 (1H, brs), 10.23 (1H, brs), 7.29 (5H, m), 6.50 (2H, s), 4.90 (2H, s), 3.53 (2H, s). |
| 9 | 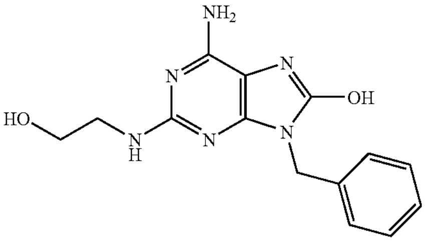 | (DMSO-$d_6$) δ 9.68 (1H, s), 7.29 (5H, m), 6.06 (3H, brs), 4.80 (2H, s), N 4.60 (1H, t, J = 4.4 Hz), 3.46 (2H, q, J = 4.4 Hz), 3.23 (2H, q, J = 4.4 Hz). |
| 10 | 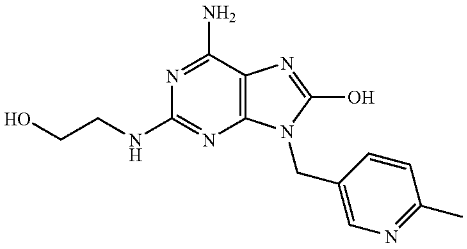 | (DMSO-$d_6$) δ 9.70 (1H, brs), 8.42 (1H, s), 7.59 (1H, d, J = 8.0 Hz), 7.20 (1H, d, J = 8.0 Hz), 6.10 (1H, t, J = 6.0 Hz), 6.06 (2H, brs), 4.78 (2H, s), 4.62 (1H, t, J = 6.0 Hz), 3.50 (1H, q, J = 6.0 Hz), 3.25 (2H, q, J = 6.0 Hz), 2.42 (3H, s). |
| 11 | 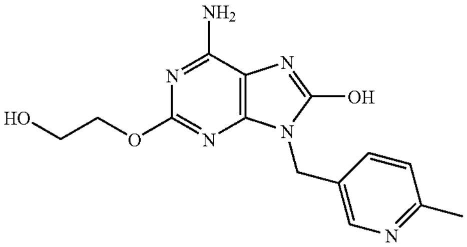 | (DMSO-$d_6$) δ 10.13 (1H, s), 8.43 (1H, d, J = 2.0 Hz), 7.60 (1H, dd, J = 8.0, 2.0 Hz), 7.22 (1H, d, J = 8.0 Hz), 6.55 (2H, brs), 4.84 (2H, s), 4.80 (1H, t, J = 4.8 Hz), 4.16 (2H, t, J = 4.8 Hz), 3.64 (2H, q, J = 4.8 Hz), 2.42 (3H, s). |
| 12 | 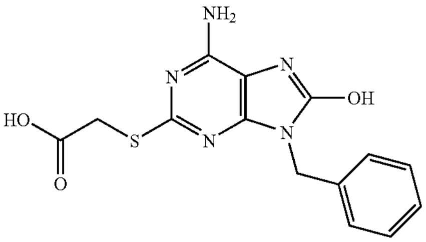 | (DMSO-$d_6$) δ 10.44 (1H, brs), 7.34 (5H, m), 6.64 (2H, brs), 4.85 (2H, s), 3.82 (2H, s). |
| 13 | 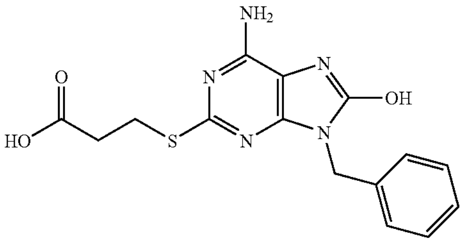 | (DMSO-$d_6$) δ 12.26 (br s, 1H), 8.16 (s, 1H), 7.39-7.17 (m, 5H), 5.29 (s, 2H), 3.22 (t, 2H, J = 7.2 Hz), 2.66 (t, 2H, J = 6.9 Hz). |

TABLE 24-continued
| Comp. ex. | Structure | 1H-NMR |
|---|---|---|
| 14 | 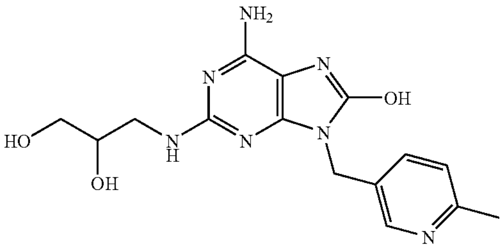 | (DMSO-$d_6$) δ 9.70 (1H, s), 8.43 (1H, d, J = 2.0 Hz), 7.60 (1H, dd, J = 8.0, 2.0 Hz), 7.20 (1H, d, J = 8.0 Hz), 6.11 (2H, brs), 6.02 (1H, t, J = 5.7 Hz), 4.81 (1H, brs), 4.78 (2H, s), 4.56 (1H, t, J = 8.3 Hz), 3.57 (1H, m), 3.33 (3H, m), 3.12 (1H, m), 2.42 (3H, s). |
| 15 | 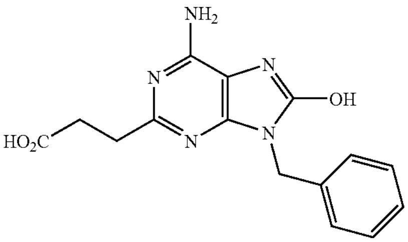 | (DMSO-$d_6$) δ 12.04 (1H, brs), 10.20 (1H, brs), 7.26 (5H, m), 6.42 (2H, s), 4.88 (2H, s), 2.83 (2H, d, J = 7.2 Hz), 2.65 (2H, d, J = 7.2 Hz). |
| 16 | 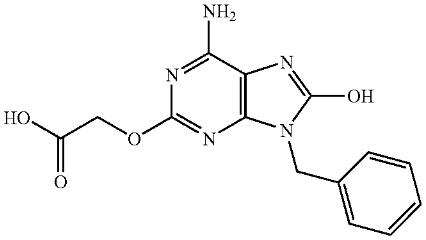 | (DMSO-$d_6$)δ 12.80 (1H, brs), 10.00 (1H, brs), 7.28 (5H, m), 6.52 (2H, s), 4.83 (2H, s), 4.70 (2H, s). |
| 17 | 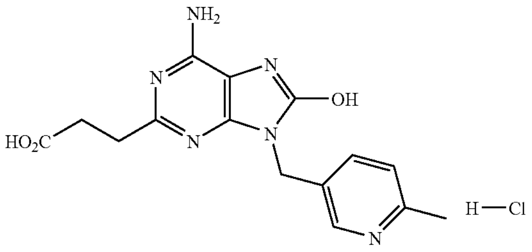 | (DMSO-$d_6$) δ 10.57 (1H, brs), 8.70 (1H, s), 8.17 (1H, s), 7.68 (1H, d, J = 7.0 Hz), 6.83 (2H, brs), 5.04 (2H, s), 2.87 (2H, d, J = 7.1 Hz), 2.66 (2H, d, J = 6.9 Hz), 2.61 (3H, s). |
| 18 | 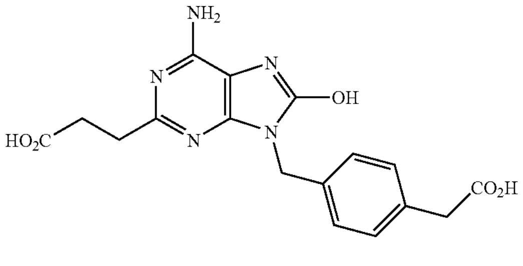 | (DMSO-$d_6$) δ 10.76 (1H, brs), 7.28 (2H, d, J = 8.1Hz), 7.19 (2H, d, J = 8.1Hz), 4.91 (2H, s), 3.52 (2H, s), 2.93 (2H, d, J = 7.1 Hz), 2.72 (2H, d, J = 6.9 Hz). |
| 19 | 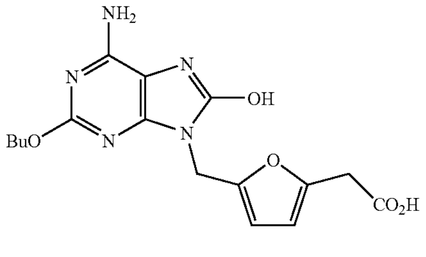 | (DMSO-$d_6$) δ 12.50 (1H, brs), 9.97 (1H, brs), 6.46 (2H, brs), 6.19 (1H, d, J = 3.1 Hz), 6.16 (1H, d, J = 3.1 Hz), 4.79 (2H, s), 4. 14 (2H, t, J = 6.6 Hz), 3.59 (2H, s), 1.63 (2H, 5, J = 6.6 Hz), 1.38 (2H, 6, J = 7.4 Hz), 0.90 (3H, t, J = 7.3 Hz). |

TABLE 24-continued

| Comp. ex. | Structure | 1H-NMR |
| --- | --- | --- |
| 20 | 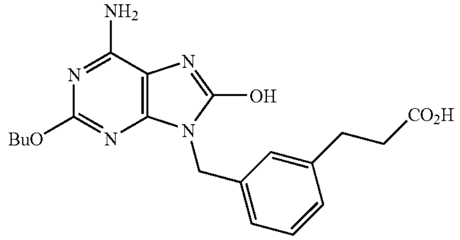 | (DMSO-$d_6$) δ 11.16 (1H, brs), 9.86 (1H, brs), 7.16 (1H, t, J = 7.6 Hz), 7.13 (1H, s), 7.08 (1H, d, J = 7.5 Hz), 7.03 (1H, d, J = 7.5 Hz), 6.76 (2H, brs), 4.79 (2H, s), 4.13 (2H, t, J = 6.6 Hz), 2.70 (2H, t, J = 7.7 Hz), 2.15 (2H, t, J = 7.7 Hz), 1.62 (2H, 5, J = 6.6 Hz), 1.36 (2H, 6, J = 7.5 Hz), 0.89 (3H, t, J = 7.4 Hz). |
| 21 | 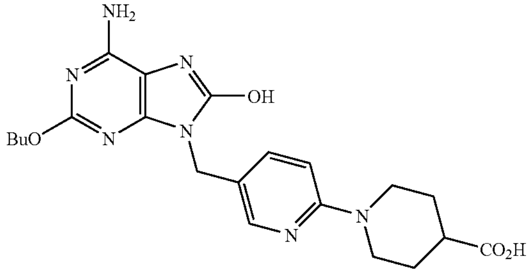 | (DMSO-$d_6$) δ 11.10 (1H, brs), 9.90 (1H, brs), 8.07 (1H, d, J = 2.2 Hz), 7.42 (1H, dd, J = 2.4, 8.8 Hz), 6.74 (3H, m), 4.68 (2H, s), 4.15 (2H, t, J = 6.6 Hz), 4.04 (2H, m), 2.85 (2H, t, J = 10.8 Hz), 2.08 (1H, m), 1.73 (2H, m), 1.64 (2H, 5, J = 6.6 Hz), 1.46 (2H, m), 1.38 (2H, 6, J = 7.3 Hz), 0.92 (3H, t, J = 7.3 Hz). |
| 22 | 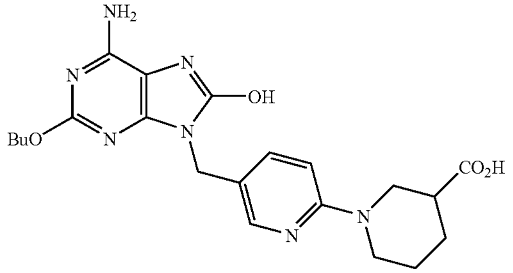 | (DMSO-$d_6$) δ 11.51 (1H, brs), 8.06 (1H, d, J = 2.3 Hz), 7.43 (1H, dd, J = 2.4, 8.8 Hz), 6.87 (2H, s), 6.79 (1H, d, J = 8.8 Hz), 4.67 (2H, s), 4.14 (4H, m), 2.75 (3H, m), 1.93 (2H, m), 1.50 (6H, m), 0.92 (3H, t, J = 7.3 Hz). |
| 23 | 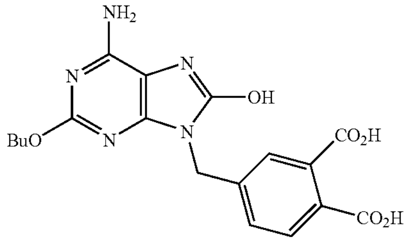 | (DMSO-$d_6$) δ 13.14 (2H, 7.64 (1H, d, J = 7.9 Hz), 7.59 (1H, d, J = 1.5 Hz), 7.45 (1H, dd, J = 1,7, 7.9 Hz), 6.48 (2H, brs), 4.93 (2H, s), 4.13 (2H, t, J = 6.6 Hz), 1.61 (2H, 5, J = 6.6 Hz), 1.35 (2H, 6, J = 7.3 Hz), 0.89 (3H, t, J = 7.4 Hz). |
| 24 | 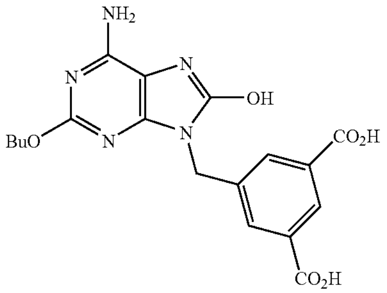 | (DMSO-$d_6$) δ 13.31 (1H, brs), 10.08 (1H, brs), 8.36 (1H, s), 8.11 (2H, s), 6.52 (2H, brs), 4.98 (2H, s), 4.15 (2H, t, J = 6.6 Hz), 1.61 (2H, 5, J = 6.7 Hz), 1.35 (2H, 6, J = 7.3 Hz), 0.89 (3H, t, J = 7.4 Hz). |

TABLE 24-continued

| Comp. ex. | Structure | 1H-NMR |
|---|---|---|
| 25 | 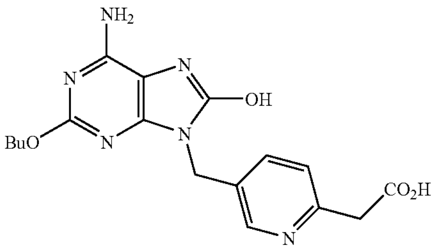 | (DMSO-$d_6$) δ 12.44 (1H, brs), 9.98 (1H, brs), 8.46 (1H, d, J = 1.9 Hz), 7.65 (1H, dd, J = 2.3, 8.0 Hz), 7.29 (1H, d, J = 7.8 Hz), 6.46 (2H, brs), 4.87 (2H, s), 4.14 (2H, t, J = 6.6 Hz), 3.43 (2H, s), 1.62 (2H, 5, J = 7.7 Hz), 1.37 (2H, 6, J = 7.6 Hz), 0.91 (3H, t, J = 7.4 Hz). |
| 26 | 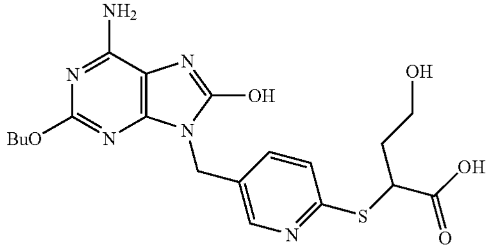 | (DMSO-$d_6$) δ 10.65 (1H, brs), 8.32 (1H, s), 7.60 (1H, d, J = 7.1 Hz), 7.34 (1H, d, J = 8.3 Hz), 6.66 (2H, brs), 5.70 (1H, brs), 4.78 (2H, s), 4.15 (4H, m), 3.51 (1H, t, J = 8.7 Hz), 3.14 (1H, m), 1.90 (2H, m), 1.63 (2H, 5, J = 7.0 Hz), 1.37 (2H, 6, J = 7.5 Hz), 0.91 (3H, t, J = 7.3 Hz). |
| 27 | 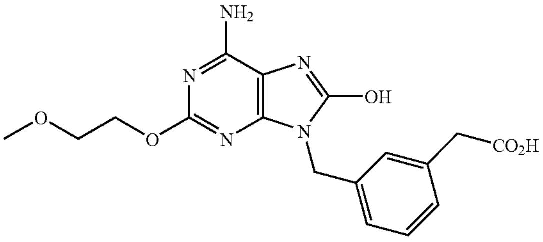 | (DMSO-$d_6$) δ 12.32 (1H, brs), 9.97 (1H, s), 7.26 (1H, dd, J = 7.6 Hz, 7.6 Hz), 7.20 (1H, s), 7.17-7.14 (2H, m), 6.47 (2H, brs), 4.83 (2H, s), 4.26 (2H, t, J = 4.8 Hz), 3.58 (2H, t, J = 4.8 Hz), 3.53 (2H, s), 3.26 (3H, s). |
| 28 | 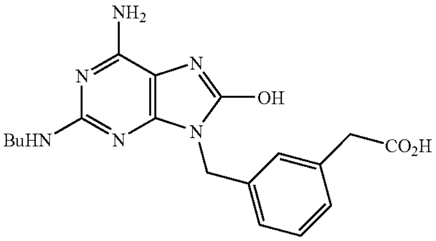 | (DMSO-$d_6$) δ 12.29 (1H, brs), 9.98 (1H, brs), 7.26 (1H, dd, J = 7.6 Hz, 7.6 Hz), 7.21 (1H, s), 7.18-7.15 (2H, m), 6.74 (2H, brs), 4.81 (2H, s), 3.69 (2H, s), 3.40-3.17 (2H, m), 1.48 (2H, tt, J = 7.2 Hz, 7.2 Hz), 1.30 (2H, tq, J = 7.2 Hz, 7.2 Hz), 0.88 (3H, t, J = 7.2 Hz). |
| 29 | 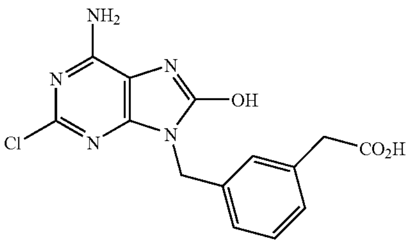 | (DMSO-$d_6$) δ 12.39 (1H, brs), 10.39 (1H, brs), 7.27-7.25 (1H, m), 7.17 (1H, s), 7.17-7.11 (2H, m), 6.91 (2H, brs), 4.92 (2H, s), 3.53 (2H, s). |
| 30 | 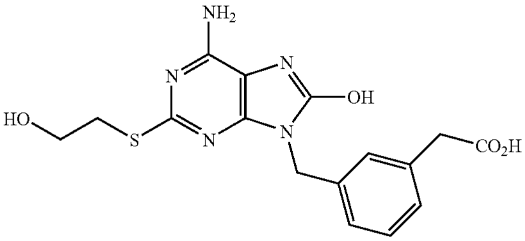 | (DMSO-$d_6$) δ 12.29 (1H, brs), 10.11 (1H, s), 7.28 (1H, dd, J = 7.6 Hz, 7.6 Hz), 7.23 (1H, s), 7.19 (1H, d, J = 7.6 Hz), 7.15 (1H, d, J = 7.6 Hz), 6.52 (2H, brs), 4.90 (1H, brs), 4.85 (2H, s), 3.60 (2H, t, J = 6.8 Hz), 3.54 (2H, s), 3.12 (2H, t, J = 6.8 Hz). |

TABLE 24-continued
| Comp. ex. | Structure | 1H-NMR |
|---|---|---|
| 31 | 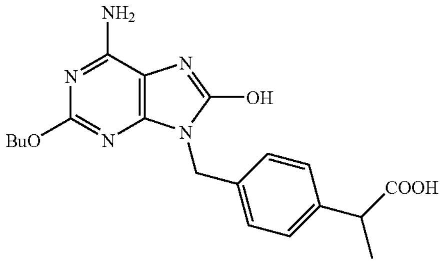 | (DMSO-$d_6$) δ 12.27 (1H, brs), 9.95 (1H, brs), 7.26-7. 19 (4H, m), 6.43 (2H, brs), 4.81 (2H, s), 4.13 (2H, t, J = 6.6 Hz), 3.62 (1H, q, J = 6.9 Hz), 1.61 (2H, 5, J = 6.9 Hz), 1.36 (2H, 6, J = 7.0 Hz), 1.30 (3H, d, J = 6.9 Hz), 0.89 (3H, t, J = 7.3 Hz). |
| 32 | 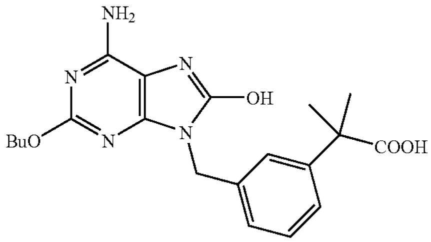 | (DMSO-$d_6$) δ 12.32 (1H, brs), 9.94 (1H, brs), 7.37-7. 10 (4H, m), 6.43 (2H, brs), 4.83 (2H, s), 4.14 (2H, t, J = 6.6 Hz), 1.62 (2H, 5, J = 6.9 Hz), 1.42 (6H, s), 1.36 (2H, 6, J = 7.0 Hz), 0.89 (3H, t, J = 7.3 Hz). |
| 33 | 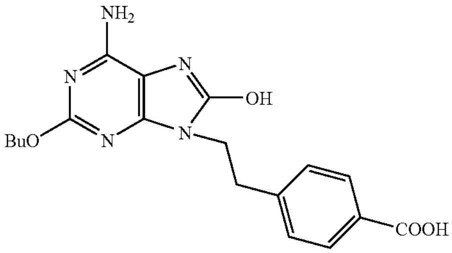 | (DMSO-$d_6$) δ 9.84 (1H, brs), 7.80 (2H, d, J = 8.1 Hz), 7.26 (2H, d, J = 8.1 Hz), 6.39 (2H, brs), 4.10 (2H, t, J = 6.6 Hz), 3.93 (2H, t, J = 6.9 Hz), 3.05 (2H, t, J = 7.3 Hz), 1.61 (2H, 5, J = 7.0 Hz), 1.37 (2H, 6, J = 7.4 Hz), 0.91 (3H, t, J = 7.3 Hz). |
| 34 | 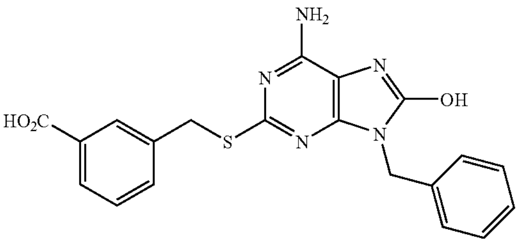 | (DMSO-$d_6$) δ 10.16 (1H, brs), 8.01 (1H, s), 7.77 (1H, d, J = 7.8 Hz), 7.59 (1H, d, J = 7.8 Hz), 7.27 (6H, m), 6.60 (2H, brs), 4.91 (2H, s), 4.35 (2H, s). |
| 35 | 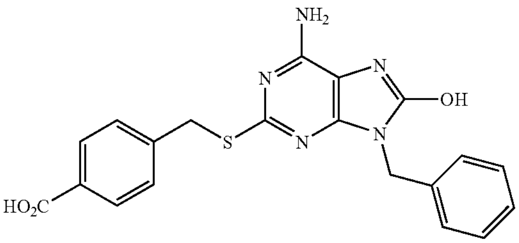 | (DMSO-$d_6$) δ 10.18 (1H, brs), 7.76 (2H, d, J = 8.2 Hz), 7.45 (2H, d, J = 8.2 Hz) 7.28 (5H, m), 6.62 (2H, brs), 4.91 (2H, s), 4.34 (2H, s). |
| 36 | 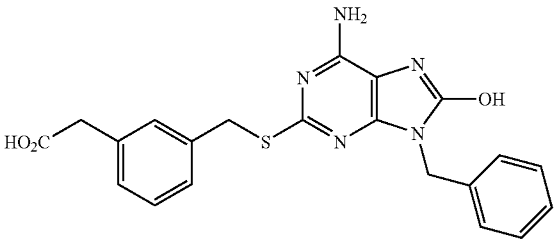 | (DMSO-$d_6$) δ 12.32 (1H, brs), 10.16 (1H, brs), 7.33-7.09 (9H, m), 6.59 (2H, brs), 4.91 (2H, s), 4.28 (2H, s), 3.49 (2H, s). |

TABLE 24-continued
| Comp. ex. | Structure | 1H-NMR |
| --- | --- | --- |
| 37 | 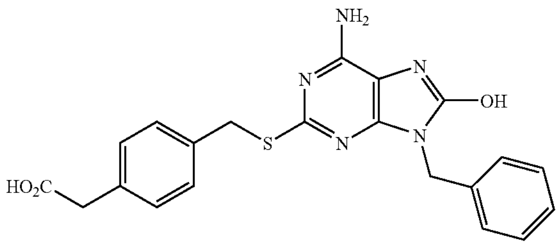 | ($DMSO-d_6$) δ12.30 (1H, brs), 10.13 (1H, brs), 7.28 (7H, m), 7.09 (2H, d, J = 8.0 Hz), 6.58 (2H, brs), 4.91 (2H, s), 4.27 (2H, s), 3.50 (2H, s). |
The preferable compounds of the present invention are illustrated below.
TABLE 25
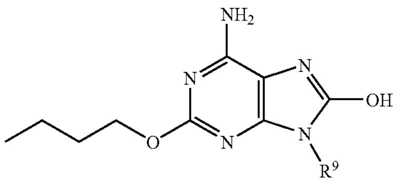
| No. | —$R^9$ |
| --- | --- |
| 201 | 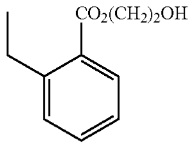 |
| 202 | 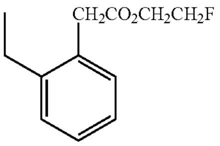 |
| 203 | 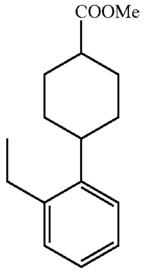 |
| 204 | 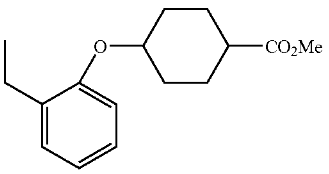 |
TABLE 25-continued
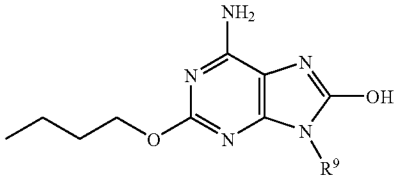
| No. | —$R^9$ |
| --- | --- |
| 205 | 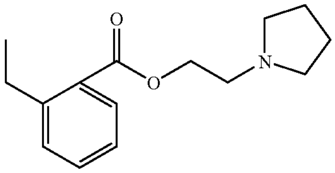 |
| 206 | 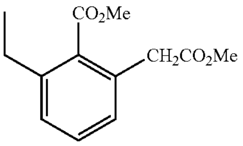 |
| 207 | 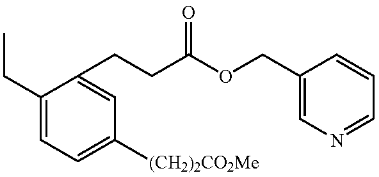 |
| 208 | 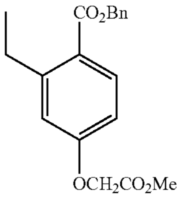 |
| 209 | 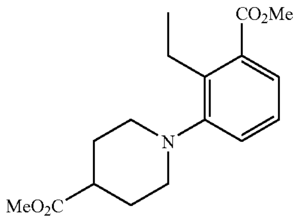 |

TABLE 25-continued
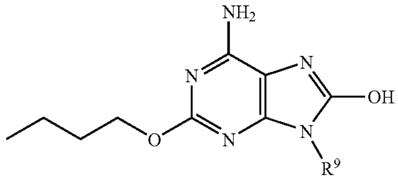
| No. | —$R^9$ |
|---|---|
| 210 | 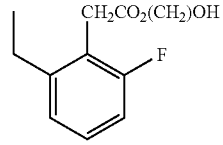 |
| 211 | 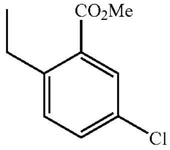 |
| 212 | 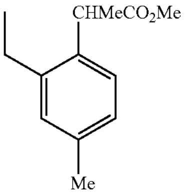 |
| 213 | 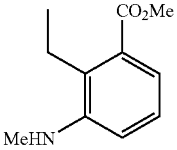 |
| 214 | 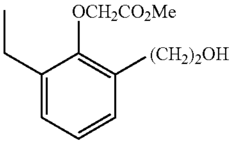 |
| 215 | 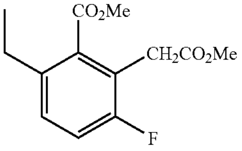 |
| 216 | 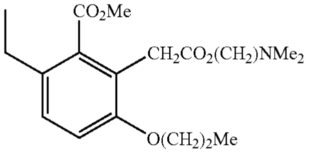 |
| 217 | 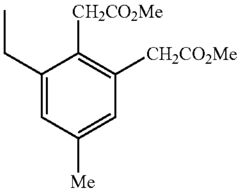 |
TABLE 25-continued
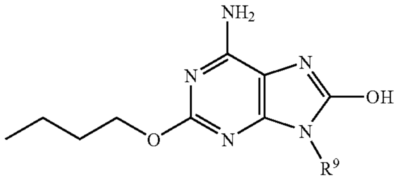
| No. | —$R^9$ |
|---|---|
| 218 | 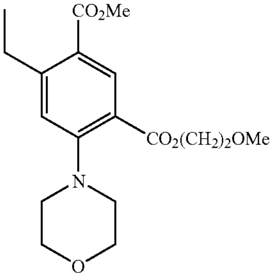 |
| 219 | 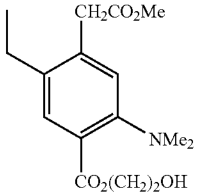 |
| 220 | 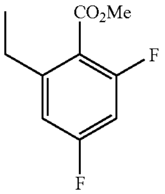 |
| 221 | 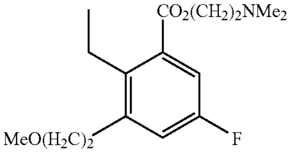 |
| 222 | 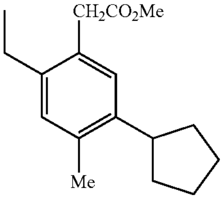 |
| 223 | 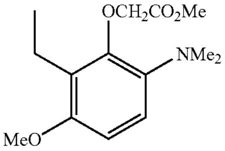 |
| 224 | 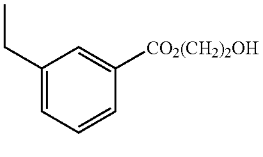 |

TABLE 25-continued
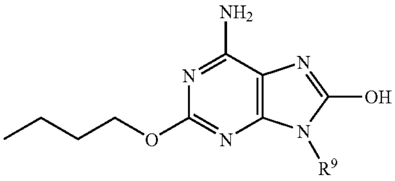
| No. | $—R^9$ |
|---|---|
| 225 | 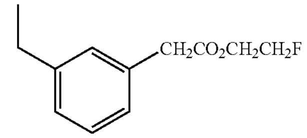 |
| 226 | 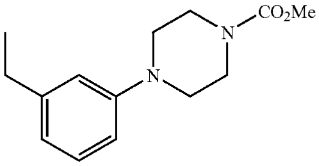 |
| 227 | 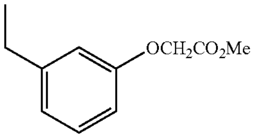 |
| 228 | 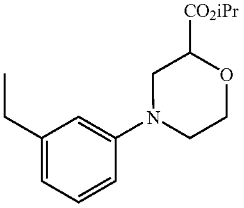 |
| 229 | 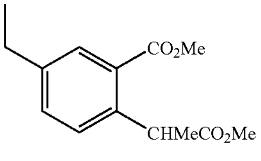 |
| 230 | 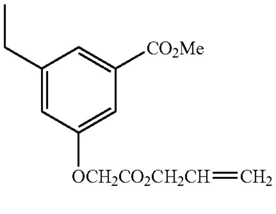 |
| 231 | 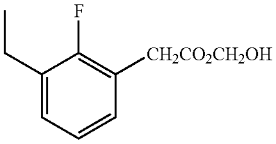 |
| 232 | 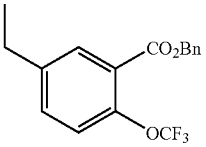 |
TABLE 25-continued
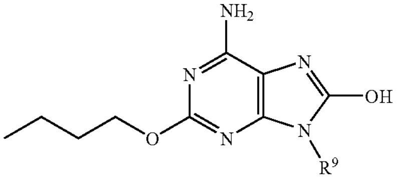
| No. | $—R^9$ |
|---|---|
| 233 | 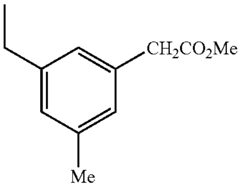 |
| 234 | 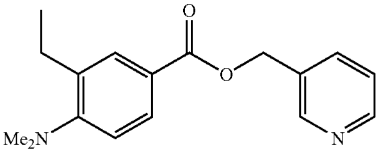 |
| 235 | 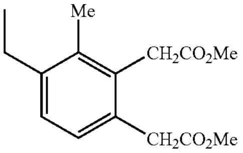 |
| 236 | 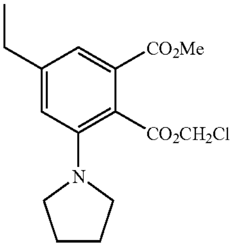 |
| 237 | 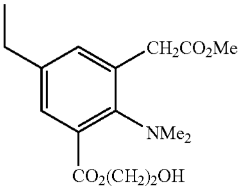 |
| 238 | 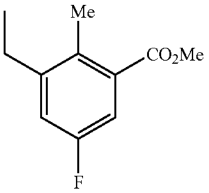 |
| 239 | 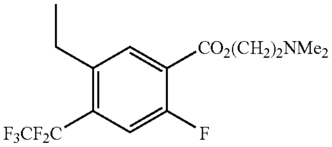 |

TABLE 25-continued
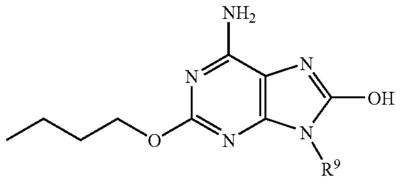
| No. | —$R^9$ |
|---|---|
| 240 | 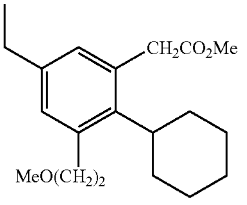 |
| 241 | 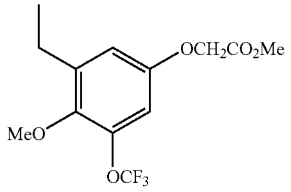 |
| 242 | 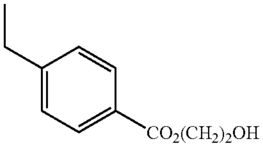 |
| 243 | 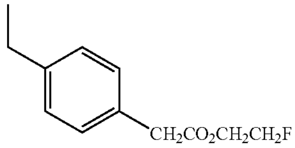 |
| 244 | 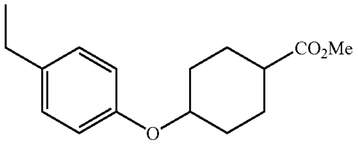 |
| 245 | 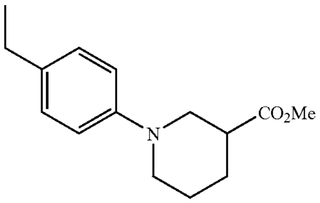 |
| 246 | 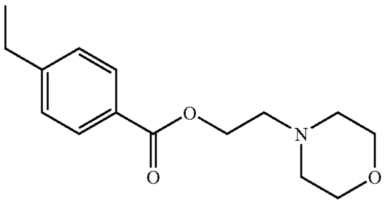 |
TABLE 25-continued
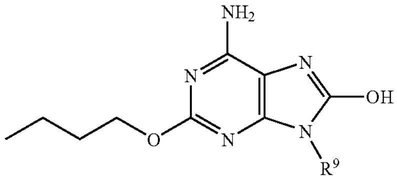
| No. | —$R^9$ |
|---|---|
| 247 | 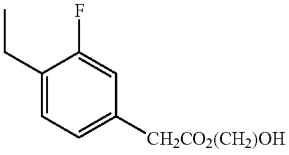 |
| 248 | 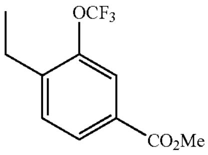 |
| 249 | 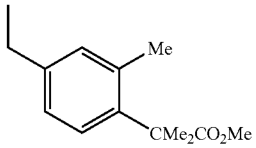 |
| 250 | 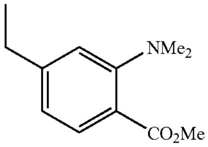 |
| 251 | 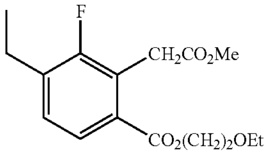 |
| 252 | 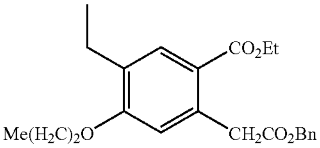 |
| 253 | 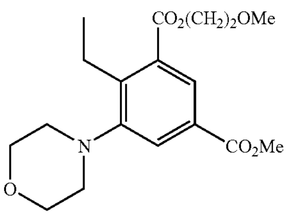 |
| 254 | 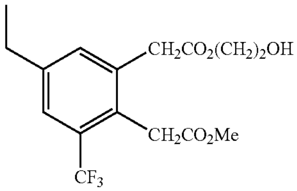 |

TABLE 25-continued
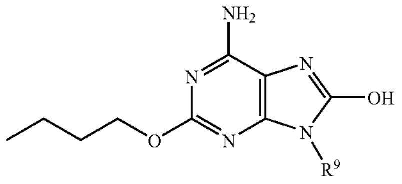
| No. | —$R^9$ |
|---|---|
| 255 | 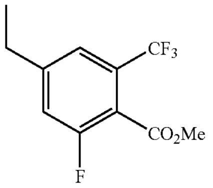 |
| 256 | 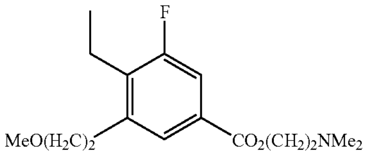 |
| 257 | 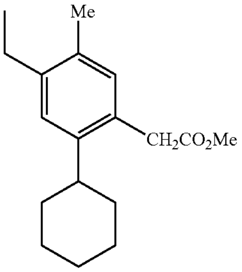 |
| 258 | 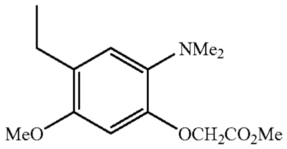 |
| 259 | 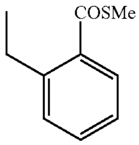 |
| 260 | 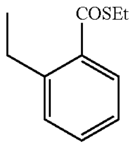 |
| 261 | 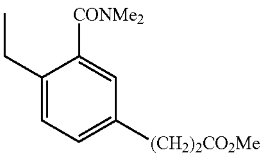 |
TABLE 25-continued
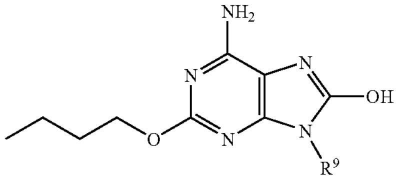
| No. | —$R^9$ |
|---|---|
| 262 | 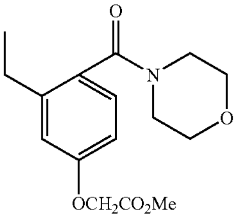 |
| 263 | 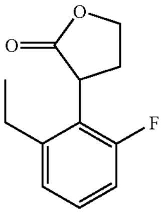 |
| 264 | 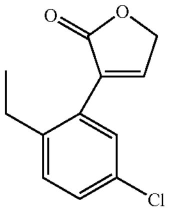 |
| 265 | 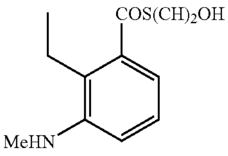 |
| 266 | 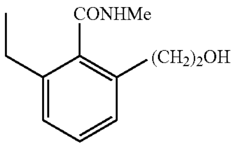 |
| 267 | 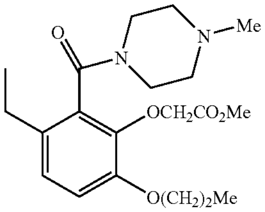 |

TABLE 25-continued
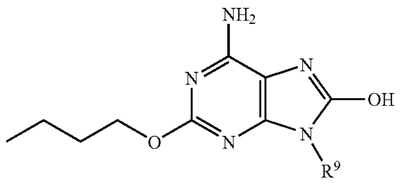
| No. | —$R^9$ |
|---|---|
| 268 | 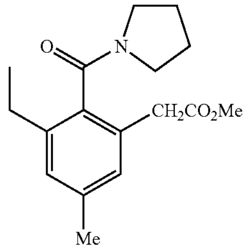 |
| 269 | 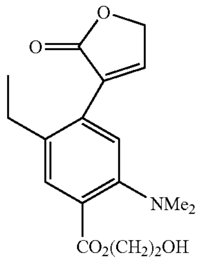 |
| 270 | 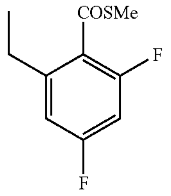 |
| 271 | 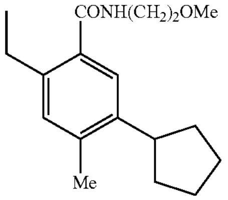 |
| 272 | 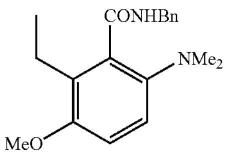 |
| 273 | 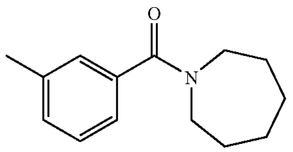 |
TABLE 25-continued
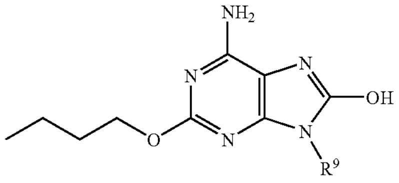
| No. | —$R^9$ |
|---|---|
| 274 | 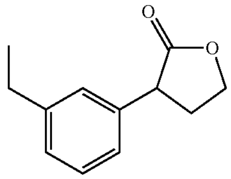 |
| 275 | 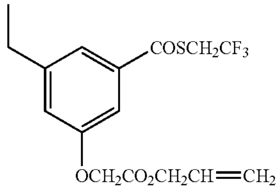 |
| 276 | 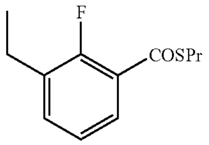 |
| 277 | 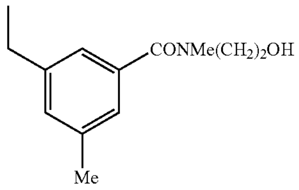 |
| 278 | 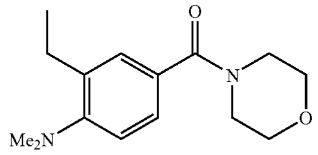 |
| 279 | 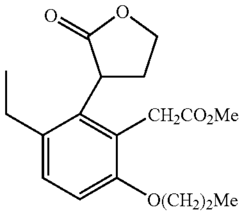 |
| 280 | 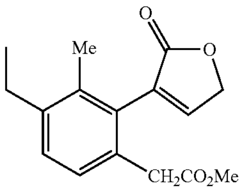 |

TABLE 25-continued
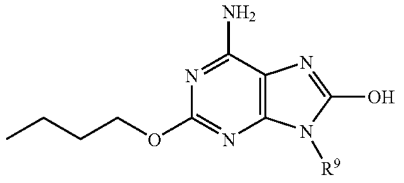
| No. | —$R^9$ |
|---|---|
| 281 | 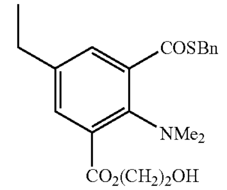 |
| 282 | 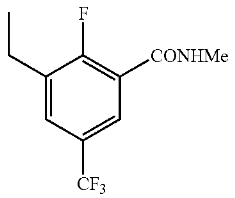 |
| 283 | 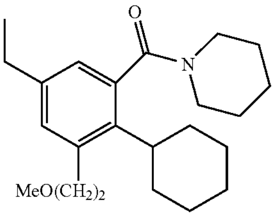 |
| 284 | 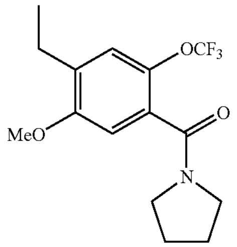 |
| 285 | 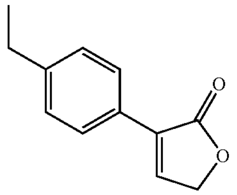 |
| 286 | 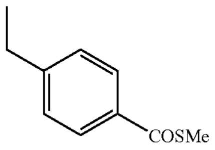 |
| 287 | 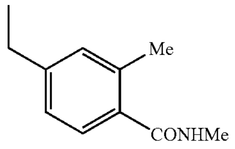 |
TABLE 25-continued
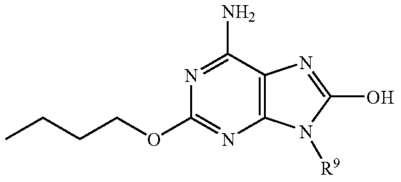
| No. | —$R^9$ |
|---|---|
| 288 | 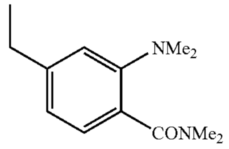 |
| 289 | 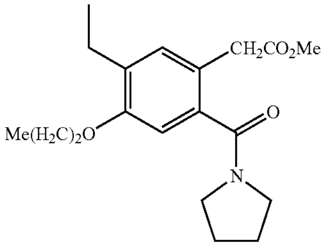 |
| 290 | 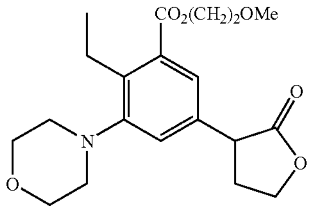 |
| 291 | 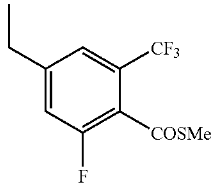 |
| 292 | 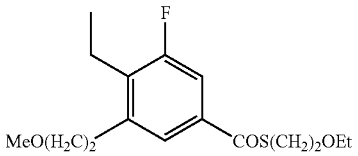 |
| 293 | 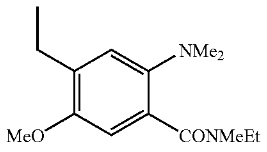 |
| 294 | 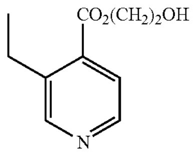 |

TABLE 25-continued
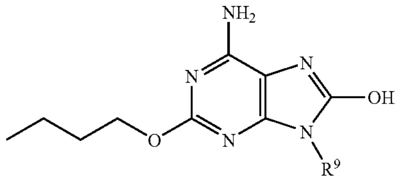
| No. | —$R^9$ |
|---|---|
| 295 | 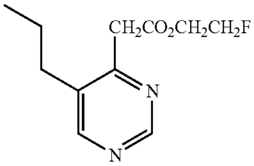 |
| 296 | 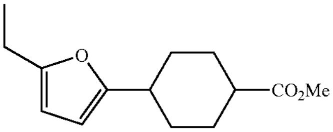 |
| 297 | 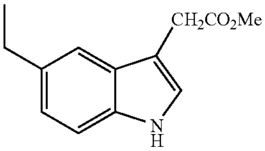 |
| 298 | 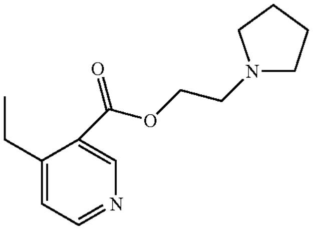 |
| 299 | 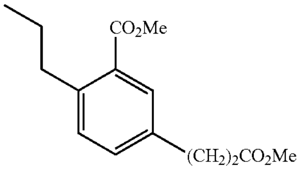 |
| 300 | 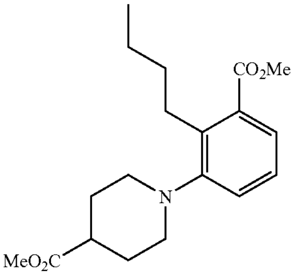 |
| 301 | 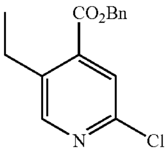 |
TABLE 25-continued
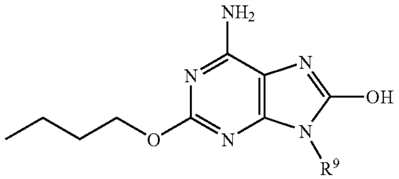
| No. | —$R^9$ |
|---|---|
| 302 | 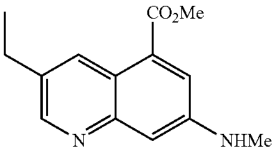 |
| 303 | 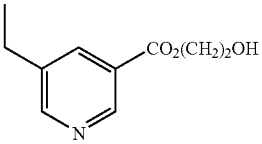 |
| 304 | 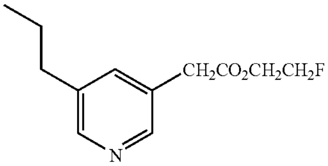 |
| 305 | 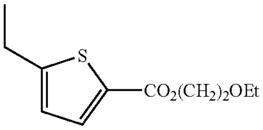 |
| 306 | 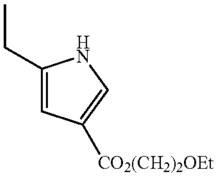 |
| 307 | 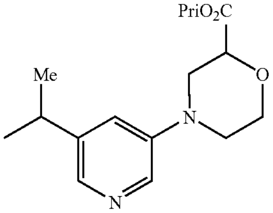 |
| 308 | 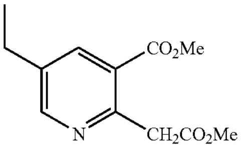 |
| 309 | 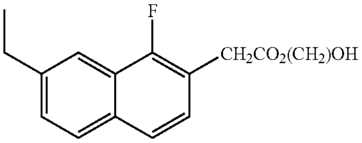 |

TABLE 25-continued
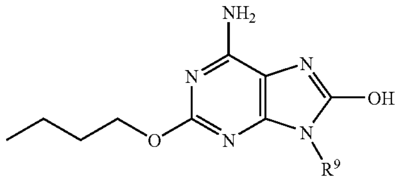
| No. | —$R^9$ |
| --- | --- |
| 310 | 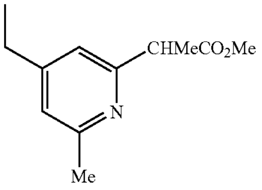 |
| 311 | 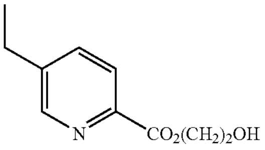 |
| 312 | 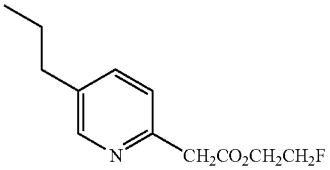 |
| 313 | 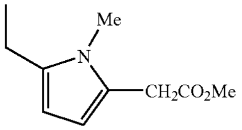 |
| 314 | 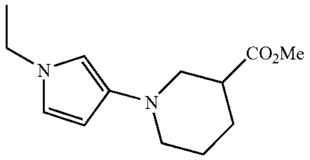 |
| 315 | 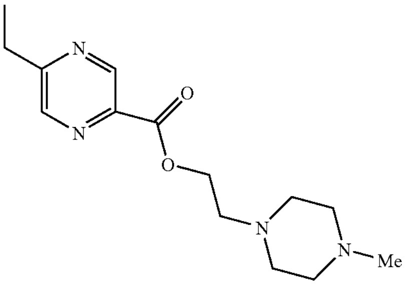 |
| 316 | 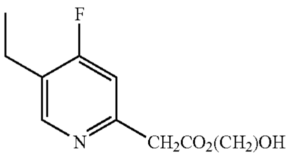 |
TABLE 25-continued
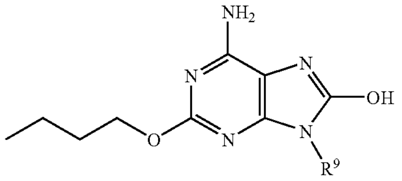
| No. | —$R^9$ |
| --- | --- |
| 317 | 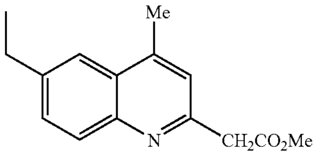 |
| 318 | 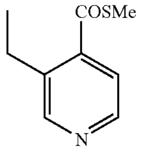 |
| 319 | 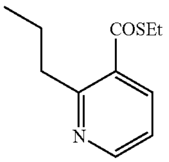 |
| 320 | 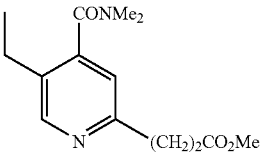 |
| 321 | 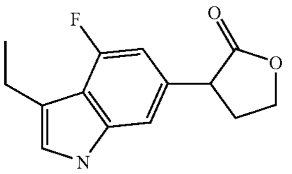 |
| 322 | 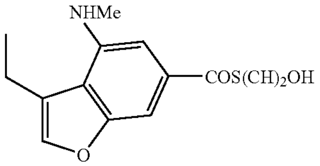 |
| 323 | 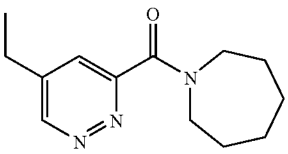 |
| 324 | 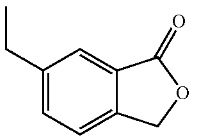 |

TABLE 25-continued
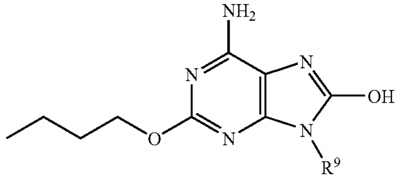
| No. | —$R^9$ |
| --- | --- |
| 325 | 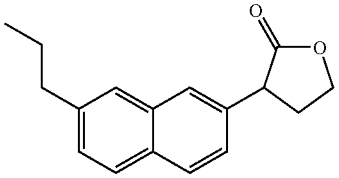 |
| 326 | 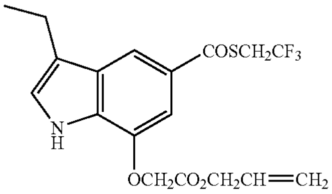 |
| 327 | 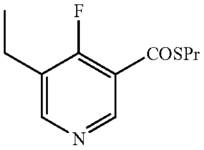 |
TABLE 25-continued
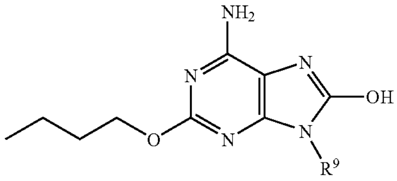
| No. | —$R^9$ |
| --- | --- |
| 328 | 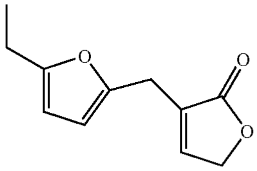 |
| 329 | 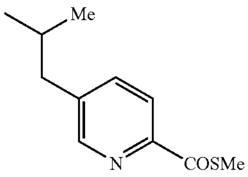 |
| 330 | 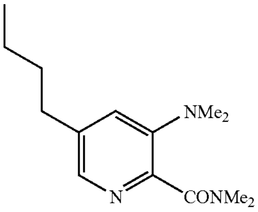 |
TABLE 26
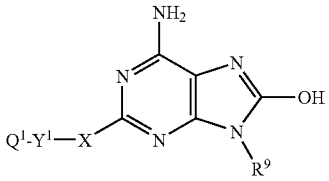
| No. | —$Y^1$—$Q^1$ | X | —$R^9$ |
| --- | --- | --- | --- |
| 331 | —Bu | — | 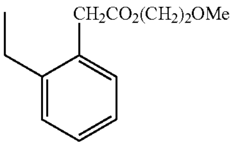 |
| 332 | —$CH_2OH$ | — | 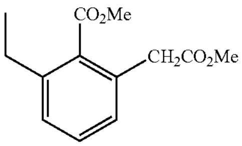 |
| 333 | —$(CH_2)_2OH$ | — | 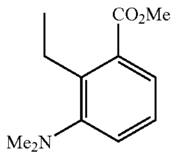 |

TABLE 26-continued
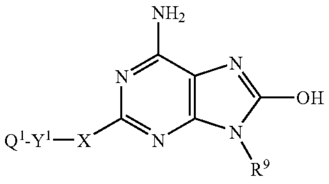
| No. | —$Y^1$—$Q^1$ | X | —$R^9$ |
|---|---|---|---|
| 334 | —$(CH)_2OMe$ | — | 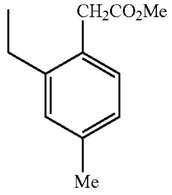 |
| 335 | —Bu | — | 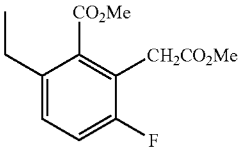 |
| 336 | —$CH_2OH$ | — | 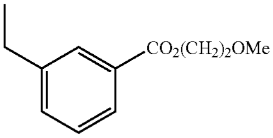 |
| 337 | —$(CH_2)_2OH$ | — | 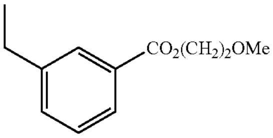 |
| 338 | —$(CH_2)_2OH$ | — | 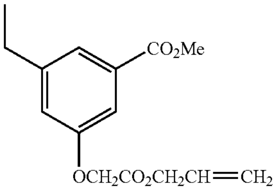 |
| 339 | —$(CH)_2OMe$ | — | 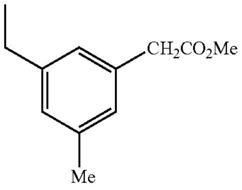 |
| 340 | —Bu | — | 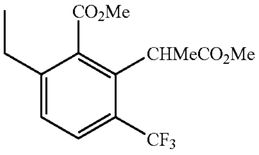 |

TABLE 26-continued
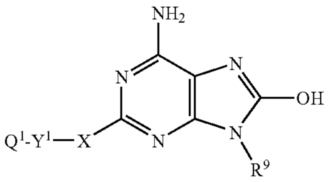
| No. | —$Y^1$—$Q^1$ | X | —$R^9$ |
|---|---|---|---|
| 341 | —$CH_2OH$ | — | 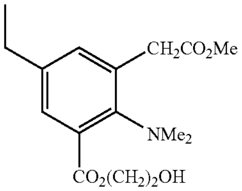 |
| 342 | —$(CH_2)_2OH$ | — | 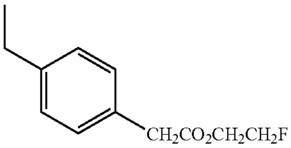 |
| 343 | —$CH_2OMe$ | — | 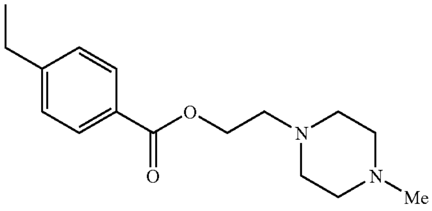 |
| 344 | —Bu | — | 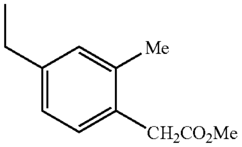 |
| 345 | —$CH_2OH$ | — | 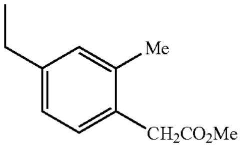 |
| 346 | —$(CH_2)_2OH$ | — | 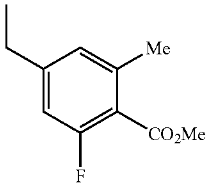 |
| 347 | —$(CH)_2OMe$ | — | 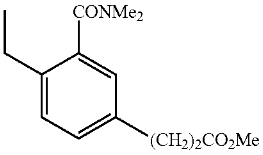 |

TABLE 26-continued
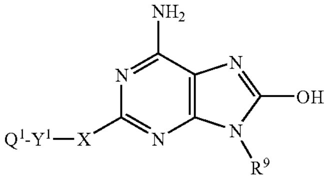
| No. | —$Y^1$—$Q^1$ | X | —$R^9$ |
|---|---|---|---|
| 348 | —Bu | — | 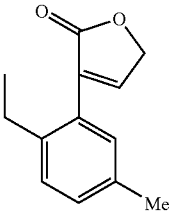 |
| 349 | —$CH_2OH$ | — | 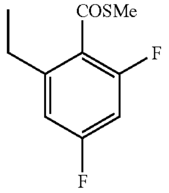 |
| 350 | —$(CH_2)_2OH$ | — | 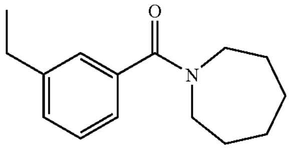 |
| 351 | —$(CH)_2OMe$ | — | 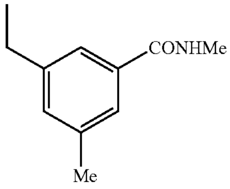 |
| 352 | —Bu | — | 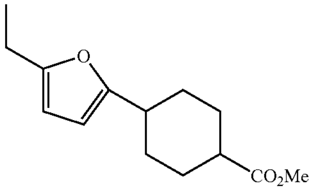 |
| 353 | —$CH_2OH$ | — | 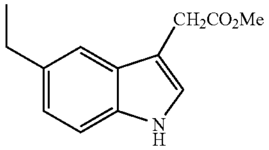 |
| 354 | —$(CH_2)_2OH$ | — | 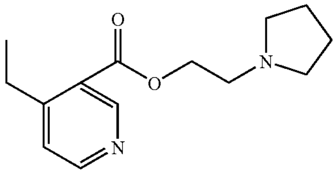 |

TABLE 26-continued
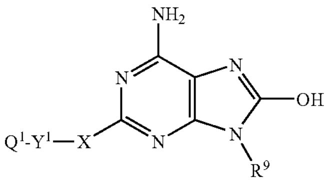
| No. | —$Y^1$—$Q^1$ | X | —$R^9$ |
|---|---|---|---|
| 355 | —$CH_2OMe$ | — | 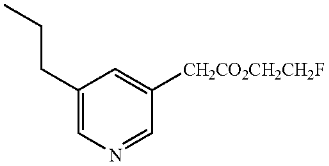 |
| 356 | —Bu | — | 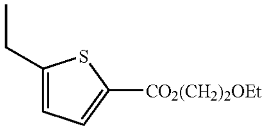 |
| 357 | —$CH_2OH$ | — | 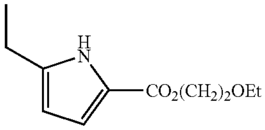 |
| 358 | —$(CH_2)_2OH$ | — | 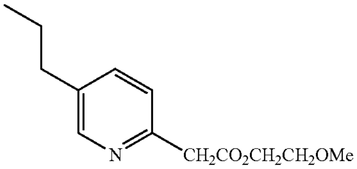 |
| 359 | —$(CH_2)OMe$ | NH | 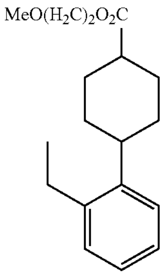 |
| 360 | —Bu | NH | 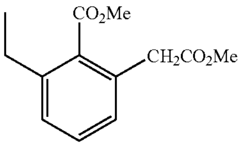 |
| 361 | —$(CH_2)_3OH$ | NMe | 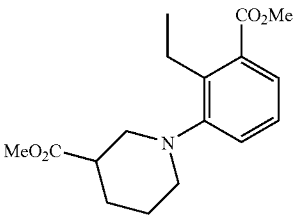 |

TABLE 26-continued
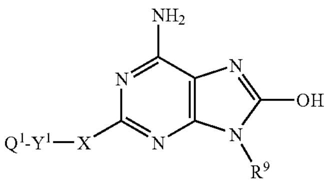
| No. | $—Y^1—Q^1$ | X | $—R^9$ |
|---|---|---|---|
| 362 | $—(CH)_2OH$ | NH | 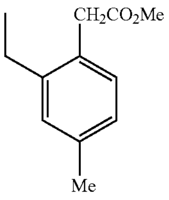 |
| 363 | $—(CH_2)_3OEt$ | NH | 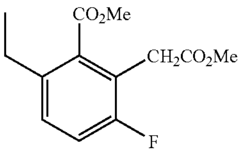 |
| 364 | $—(CH_2)OMe$ | NMe | 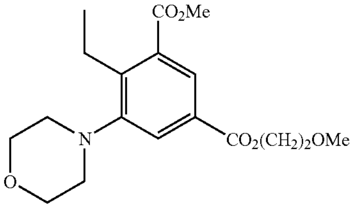 |
| 365 | —Bu | NH | 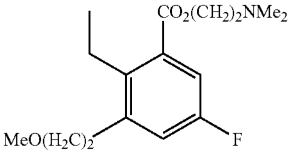 |
| 366 | $—(CH_2)_3OH$ | NH | 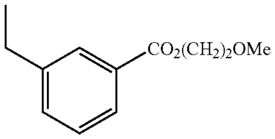 |
| 367 | $—CH_2OH$ | NH | 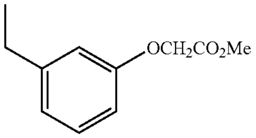 |
| 368 | $—(CH_2)_3OEt$ | NMe | 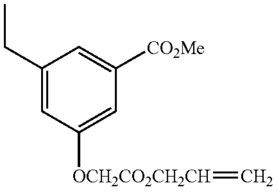 |

TABLE 26-continued
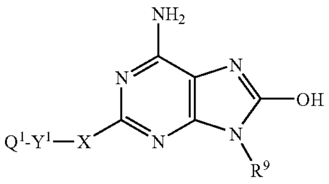
| No. | $—Y^1—Q^1$ | X | $—R^9$ |
|---|---|---|---|
| 369 | $—CH_2OMe$ | NH | 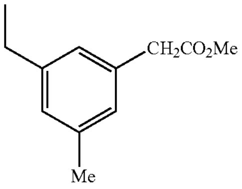 |
| 370 | —Bu | NH | 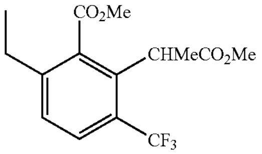 |
| 371 | $—(CH_2)_3OH$ | NMe | 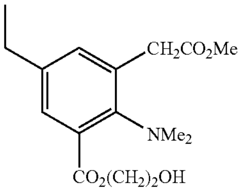 |
| 372 | $—CH_2OH$ | NH | 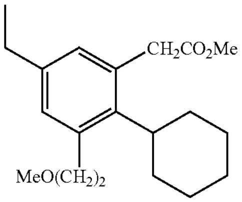 |
| 373 | $—(CH_2)_3OEt$ | NH | 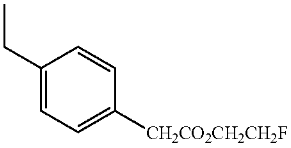 |
| 374 | $—CH_2OMe$ | NH | 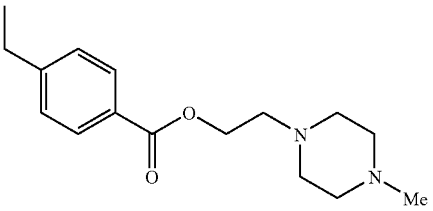 |
| 375 | —Bu | NMe | 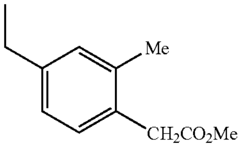 |

TABLE 26-continued
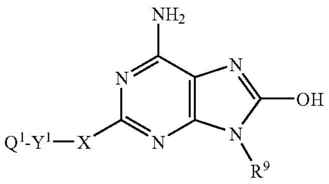
| No. | $—Y^1—Q^1$ | X | $—R^9$ |
|---|---|---|---|
| 376 | $—(CH_2)_3OH$ | NH | 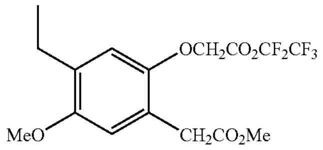 |
| 377 | $—CH_2OH$ | NH | 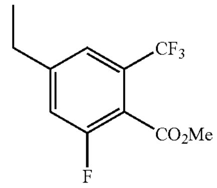 |
| 378 | $—(CH_2)_3OEt$ | NMe | 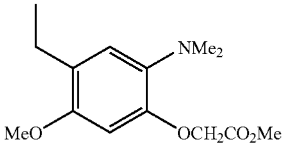 |
| 379 | $—CH_2OMe$ | NH | 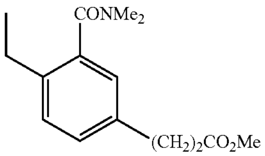 |
| 380 | —Bu | NH | 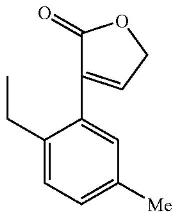 |
| 381 | $—(CH_2)_3OH$ | NH | 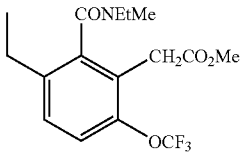 |
| 382 | $—(CH)_2H$ | NMe | 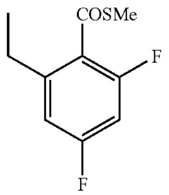 |

TABLE 26-continued
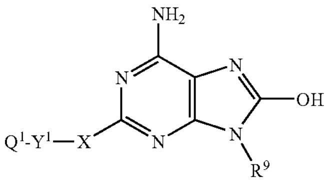
| No. | —$Y^1$—$Q^1$ | X | —$R^9$ |
|---|---|---|---|
| 383 | —$(CH_2)_3OEt$ | NH | 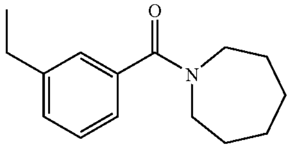 |
| 384 | —$CH_2OMe$ | NH | 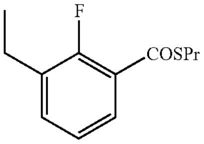 |
| 385 | —Bu | NMe | 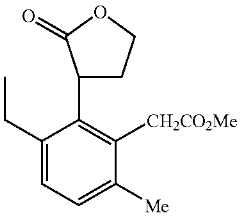 |
| 386 | —$(CH_2)_3OH$ | NH | 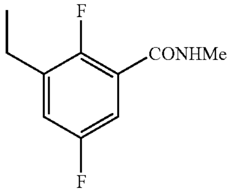 |
| 387 | —$CH_2OH$ | NH | 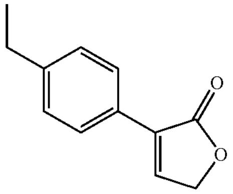 |
| 388 | —$(CH_2)_3OEt$ | NH | 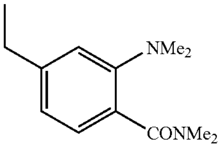 |
| 389 | —$CH_2OMe$ | NMe | 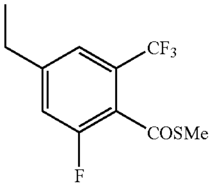 |

TABLE 26-continued
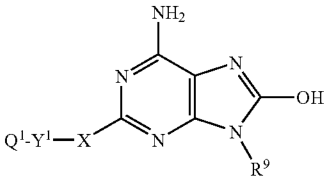
| No. | $—Y^1—Q^1$ | X | $—R^9$ |
|---|---|---|---|
| 390 | —Bu | NH | 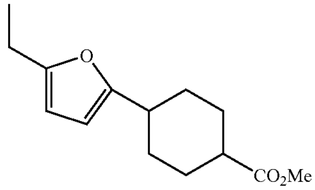 |
| 391 | $—(CH_2)_2OH$ | NH | 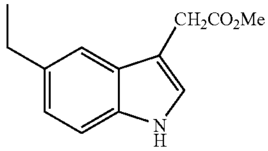 |
| 392 | $—(CH_2)_2OMe$ | NMe | 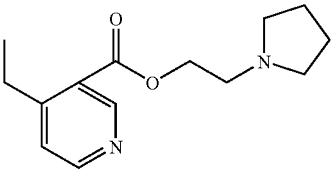 |
| 393 | —Bu | NH | 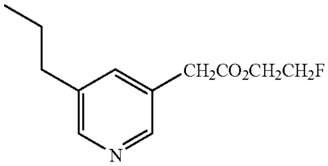 |
| 394 | $—(CH_2)_2OH$ | NH | 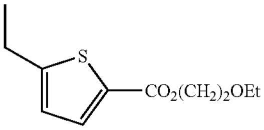 |
| 395 | $—(CH_2)2OMe$ | NH | 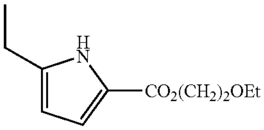 |
| 396 | —Bu | NMe | 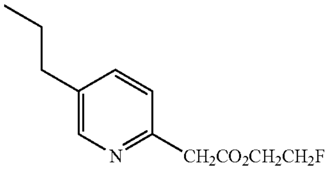 |
| 397 | $—(CH_2)_2OH$ | NH | 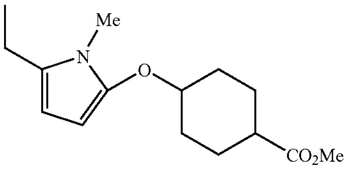 |

TABLE 26-continued
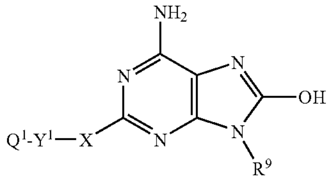
| No. | —$Y^1$—$Q^1$ | X | —$R^9$ |
|---|---|---|---|
| 398 | —$(CH_2)_2OMe$ | NH | 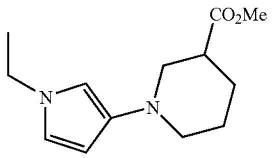 |
| 399 | —Bu | NMe | 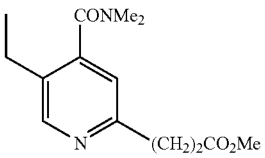 |
| 400 | —$(CH_2)_2OH$ | NH | 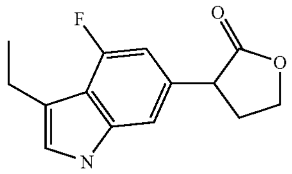 |
| 401 | —$(CH_2)_2OMe$ | NH | 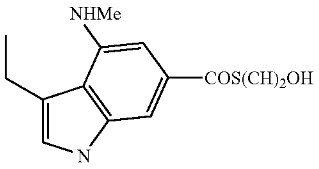 |
| 402 | —Bu | NH | 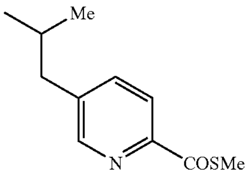 |
| 403 | —$(CH_2)_2OH$ | NMe | 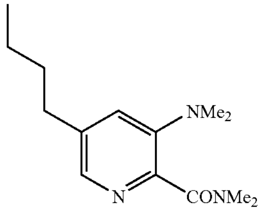 |
| 404 | —Bu | S | 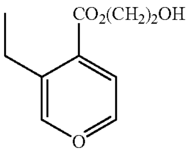 |

TABLE 26-continued
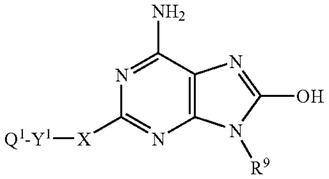
| No. | —$Y^1$—$Q^1$ | X | —$R^9$ |
|---|---|---|---|
| 405 | —$(CH_2)_3OH$ | S | 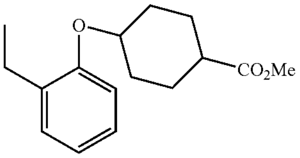 |
| 406 | —$CH_2OH$ | S | 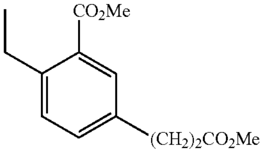 |
| 407 | —$(CH_2)_3OEt$ | S | 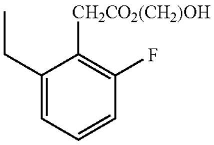 |
| 408 | —$CH_2OMe$ | S | 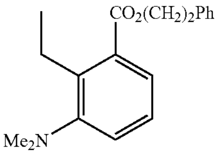 |
| 409 | —Bu | S | 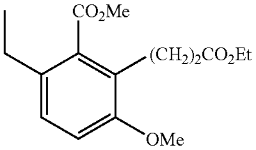 |
| 410 | —$(CH_2)_3OH$ | S | 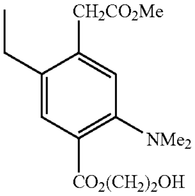 |
| 411 | —$CH_2OH$ | S | 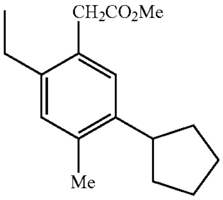 |
| 412 | —$(CH_2)_3OEt$ | S | 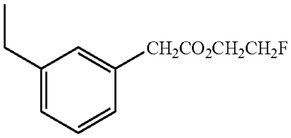 |

TABLE 26-continued
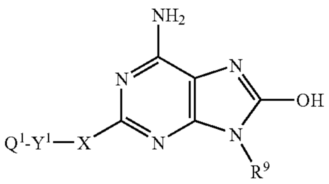
| No. | $—Y^1—Q^1$ | X | $—R^9$ |
|---|---|---|---|
| 413 | $—CH_2OMe$ | S | 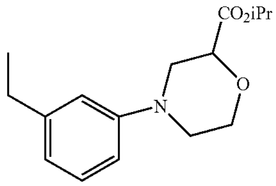 |
| 414 | —Bu | S | 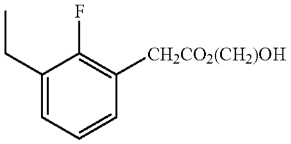 |
| 415 | $—(CH_2)_3OH$ | S | 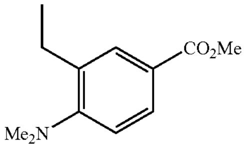 |
| 416 | $—CH_2OH$ | S | 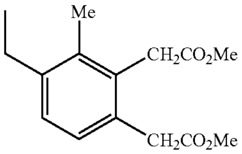 |
| 417 | $—(CH_2)_3OH$ | S | 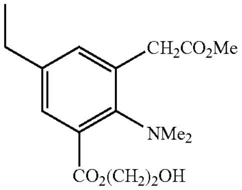 |
| 418 | $—(CH)_2OH$ | S | 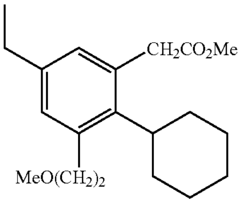 |
| 419 | $—(CH_2)_3OEt$ | S | 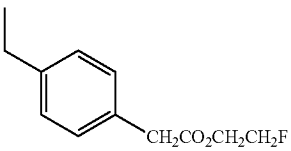 |

TABLE 26-continued
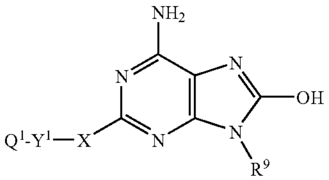
| No. | —$Y^1$—$Q^1$ | X | —$R^9$ |
|---|---|---|---|
| 420 | —$CH_2OMe$ | S | 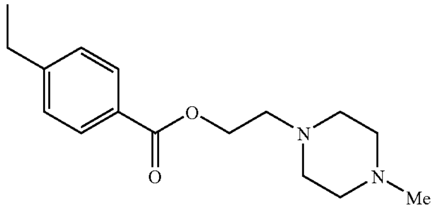 |
| 421 | —Bu | S | 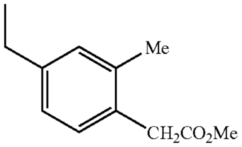 |
| 422 | —$(CH_2)_3OH$ | S | 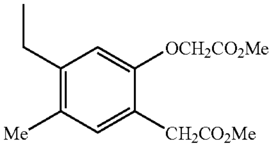 |
| 423 | —$CH_2OH$ | S | 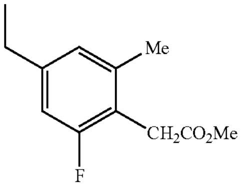 |
| 424 | —$(CH_2)_3OEt$ | S | 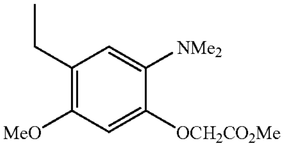 |
| 425 | —$CH_2OMe$ | S | 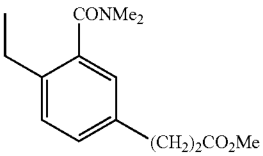 |
| 426 | —Bu | S | 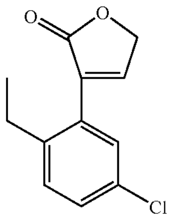 |

TABLE 26-continued
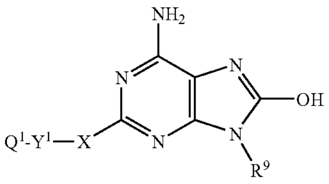
| No. | —Y¹—Q¹ | X | —R⁹ |
| --- | --- | --- | --- |
| 427 | —$(CH_2)_3OH$ | S | 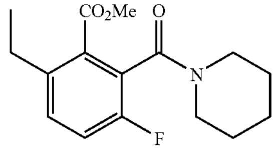 |
| 428 | —$CH_2OH$ | S | 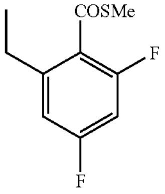 |
| 429 | —$(CH_2)_3OEt$ | S | 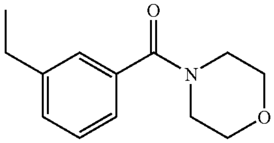 |
| 430 | —$CH_2OMe$ | S | 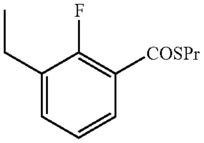 |
| 431 | —Bu | S | 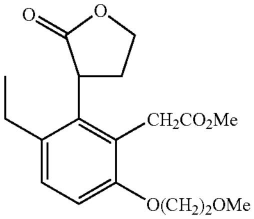 |
| 432 | —$(CH_2)_3OH$ | S | 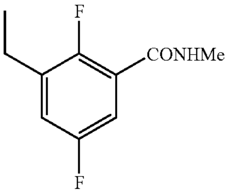 |
| 433 | —$CH_2OH$ | S | 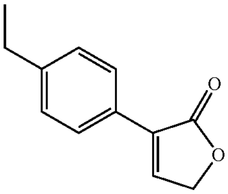 |

TABLE 26-continued
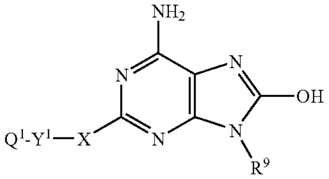
| No. | —$Y^1$—$Q^1$ | X | —$R^9$ |
|---|---|---|---|
| 434 | —$(CH_2)_3OEt$ | S | 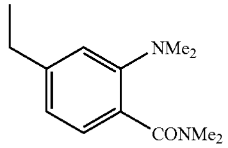 |
| 435 | —$CH_2OMe$ | S | 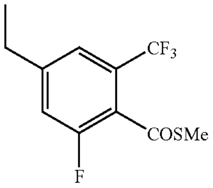 |
| 436 | —Bu | S | 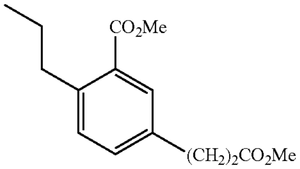 |
| 437 | —$(CH_2)_2H$ | S | 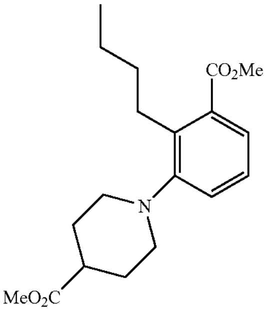 |
| 438 | —$(CH_2)_2OMe$ | S | 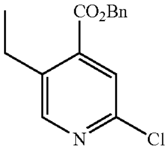 |
| 439 | —Bu | S | 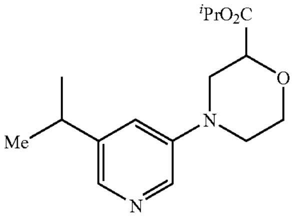 |
| 440 | —$(CH_2)_2OH$ | S | 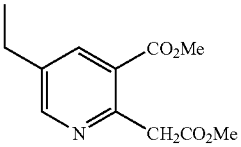 |

TABLE 26-continued
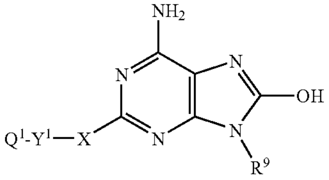
| No. | —$Y^1$—$Q^1$ | X | —$R^9$ |
|---|---|---|---|
| 441 | —$(CH_2)_2OMe$ | S | 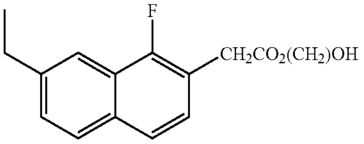 |
| 442 | —Bu | S | 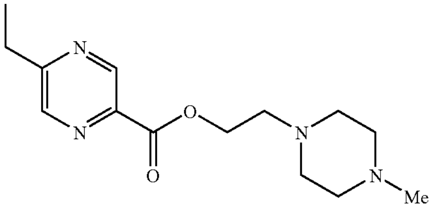 |
| 443 | —$(CH_2)_2OH$ | S | 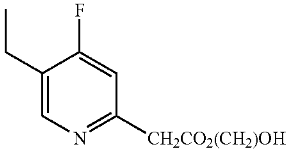 |
| 444 | —$(CH_2)_2OMe$ | S | 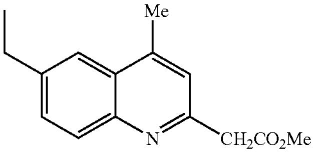 |
| 445 | —Bu | S | 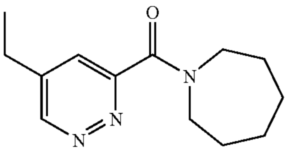 |
| 446 | —$(CH_2)_2OH$ | S | 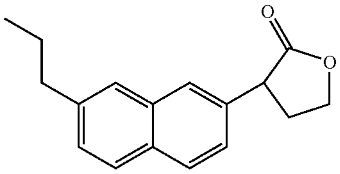 |
| 447 | —$(CH_2)_2OMe$ | S | 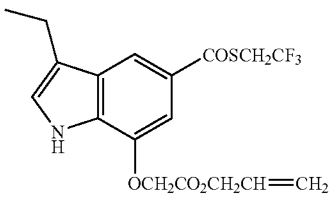 |

TABLE 26-continued
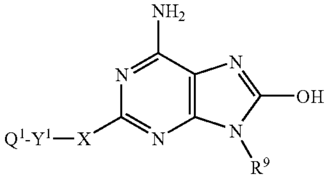
| No. | —Y¹—Q¹ | X | —R⁹ |
|---|---|---|---|
| 448 | $—CH_2OH$ | O | 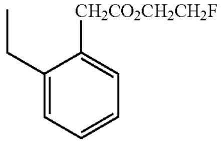 |
| 449 | $—(CH_2)_3OEt$ | O | 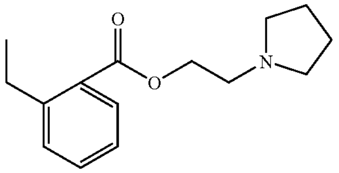 |
| 450 | $—(CH_2)_3OH$ | O | 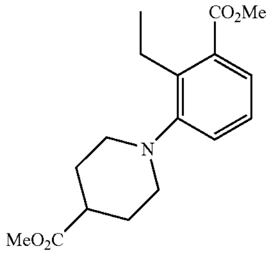 |
| 451 | $—CH_2OMe$ | O | 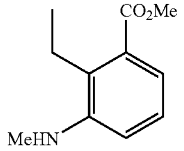 |
| 452 | $—CH_2OH$ | O | 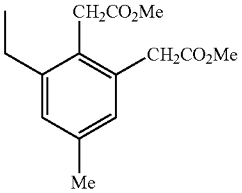 |
| 453 | $—(CH_2)_3OEt$ | O | 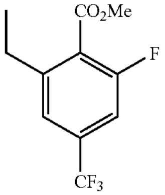 |
| 454 | $—(CH_2)_3OH$ | O | 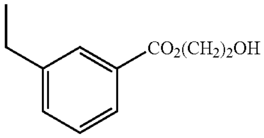 |

TABLE 26-continued
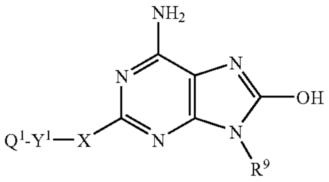
| No. | $—Y^1—Q^1$ | X | $—R^9$ |
|---|---|---|---|
| 455 | $—CH_2OMe$ | O | 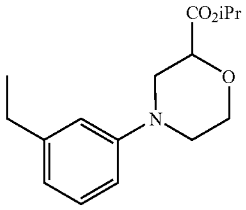 |
| 456 | $—CH_2OH$ | O | 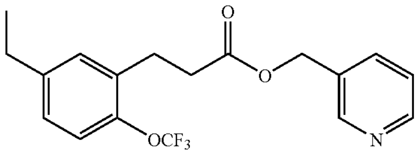 |
| 457 | $—(CH_2)_3OEt$ | O | 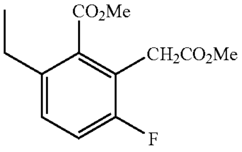 |
| 458 | $—(CH_2)_3OH$ | O | 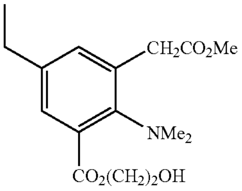 |
| 459 | $—CH_2OMe$ | O | 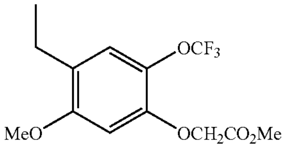 |
| 460 | $—CH_2OH$ | O | 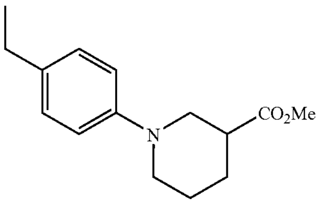 |
| 461 | $—(CH_2)_3OEt$ | O | 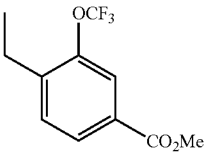 |

TABLE 26-continued
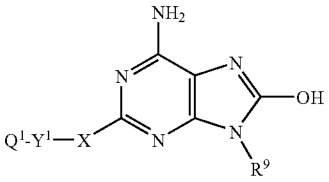
| No. | —$Y^1$—$Q^1$ | X | —$R^9$ |
|---|---|---|---|
| 462 | —$(CH_2)_3OH$ | O | 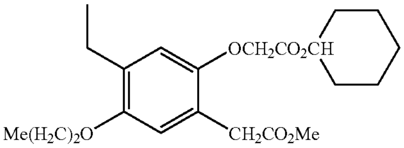 |
| 463 | —$CH_2OMe$ | O | 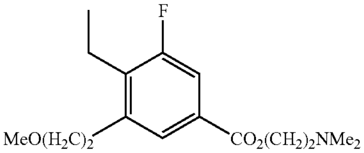 |
| 464 | —$CH_2OH$ | O | 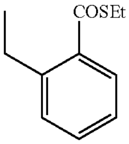 |
| 465 | —$(CH_2)_3OEt$ | O | 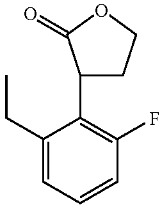 |
| 466 | —$(CH_2)_3OH$ | O | 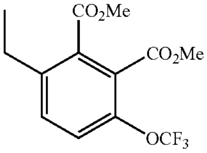 |
| 467 | —$CH_2OMe$ | O | 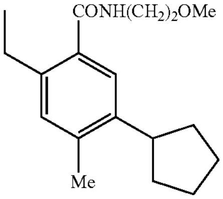 |
| 468 | —$CH_2OH$ | O | 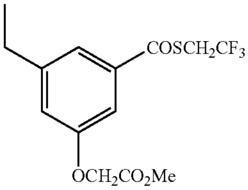 |

TABLE 26-continued
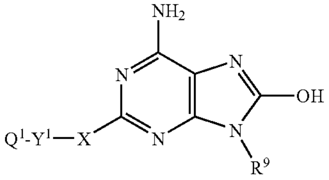
| No. | —$Y^1$—$Q^1$ | X | —$R^9$ |
|---|---|---|---|
| 469 | —$(CH_2)_3OEt$ | O | 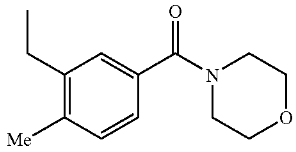 |
| 470 | —$(CH_2)_3OH$ | O | 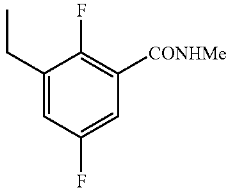 |
| 471 | —$CH_2OMe$ | O | 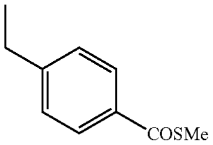 |
| 472 | —$CH_2OH$ | O | 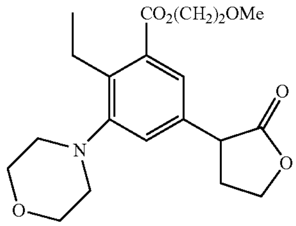 |
| 473 | —$(CH_2)_3OEt$ | O | 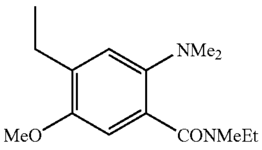 |
| 474 | —$(CH_2)_2OH$ | O | 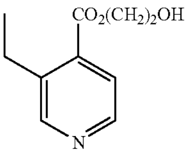 |
| 475 | —$(CH_2)_2OMe$ | O | 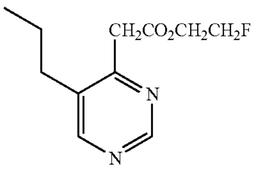 |

TABLE 26-continued
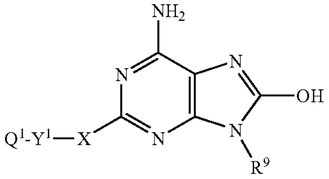
| No. | —$Y^1$—$Q^1$ | X | —$R^9$ |
|---|---|---|---|
| 476 | —$(CH_2)_2OH$ | O | 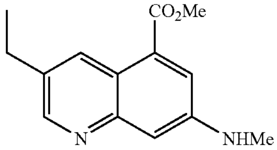 |
| 477 | —$(CH_2)_2OMe$ | O | 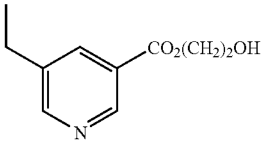 |
| 478 | —$(CH_2)_2OH$ | O | 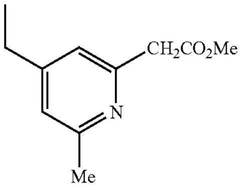 |
| 479 | —$(CH_2)_2OMe$ | O | 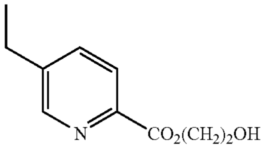 |
| 480 | —$(CH_2)_2OH$ | O | 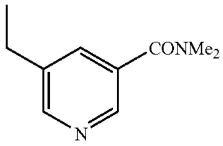 |
| 481 | —$(CH_2)_2OMe$ | O | 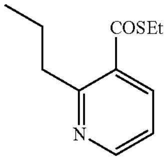 |
| 482 | —$(CH_2)_2OH$ | O | 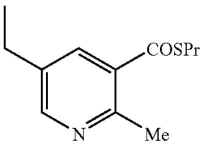 |
| 483 | —$(CH_2)_2OMe$ | O | 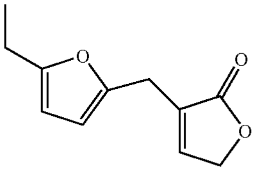 |

TABLE 27

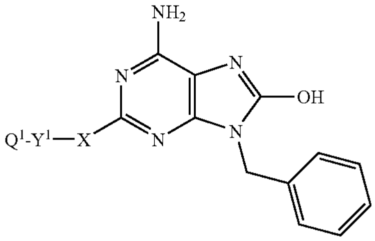

| No. | —Y1—Q1 | X |
|---|---|---|
| 484 | $-CO_2Me$ | — |
| 485 | $-CO_2CH_2CH{=}CH_2$ | — |
| 486 | $-CO_2CH_2CF_3$ | — |
| 487 | $-CO_2(CH_2)_2OMe$ | — |
| 488 | $-CO_2(CH_2)_2OH$ | — |
| 489 | $-CO_2(CH_2)NMe_2$ | — |
| 490 | $-CO_2Bn$ | — |
| 491 | 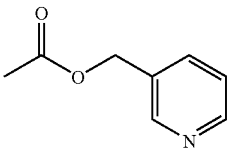 | — |
| 492 | 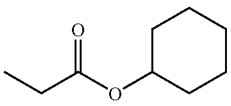 | — |
| 493 | $-CH_2CO_2CH_2Cl$ | — |
| 494 | $-CH_2CO_2(CH_2)_3OEt$ | — |
| 495 | $-CH_2CO_2(CH_2)_4OH$ | — |
| 496 | 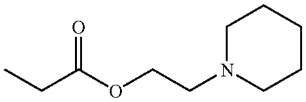 | — |
| 497 | 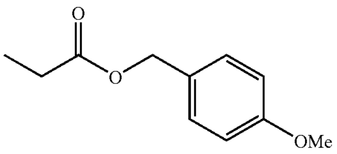 | — |
| 498 | 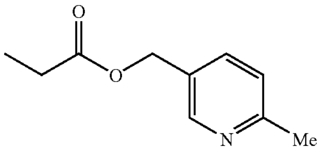 | — |
| 499 | $-(CH_2)_2CO2Bn$ | — |
| 500 | $-(CH_2)_3CO_2CH_2C1$ | — |
| 501 | $-(CH_2)_4CO_2(CH_2)_3OEt$ | — |
| 502 | $-(CH_2)_2CO_2(CH_2)_2OH$ | — |
| 503 | 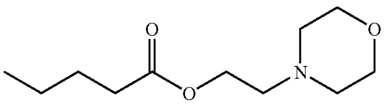 | — |
| 504 | 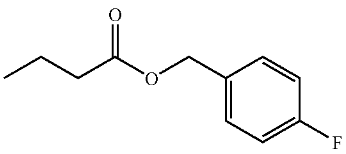 | — |

TABLE 27-continued

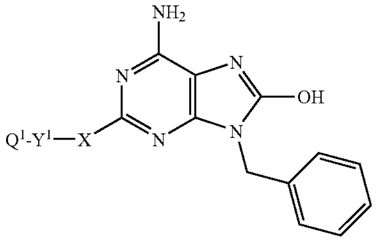

| No. | —Y1—Q1 | X |
|---|---|---|
| 505 | 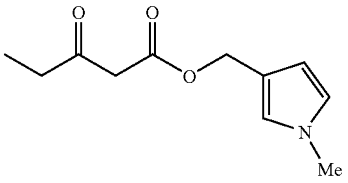 | — |
| 506 | $-COS-{}^{i}Pr$ | — |
| 507 | $-COS(CH_2)_2OH$ | — |
| 508 | $-CH_2COS(CH_2)_2OMe$ | — |
| 509 | 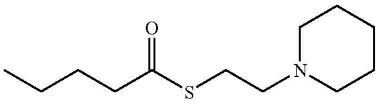 | — |
| 510 | $-CH_2OCO_2Et$ | — |
| 511 | $-(CH_2)_3OCO_2(CH_2)_2OMe$ | — |
| 512 | $-CH_2OCOEt$ | — |
| 513 | $-(CH_2)_2OCOBn$ | — |
| 514 | 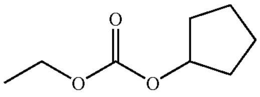 | — |
| 515 | $-CONMe_2$ | — |
| 516 | $-CH_2CONH(CH_2)NMe_2$ | — |
| 517 | 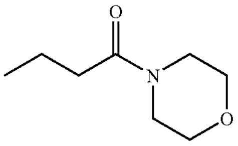 | — |
| 518 | $-(CH_2)_3CONH(CH_2)OMe$ | — |
| 519 | $-CH_2OCONMe_2$ | — |
| 520 | 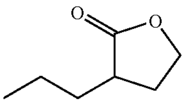 | — |
| 521 | 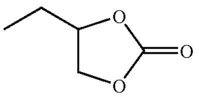 | — |
| 522 | 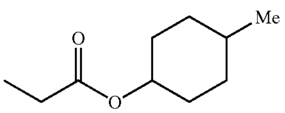 | NH |
| 523 | $-CH_2CO_2CH_2CF_3$ | NMe |
| 524 | $-CH_2CO_2(CH_2)_3OEt$ | NEt |
| 525 | $-CH_2CO_2(CH_2)_4OH$ | NH |

TABLE 27-continued

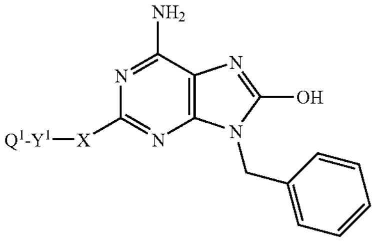

| No. | —Y1—Q1 | X |
|---|---|---|
| 526 | 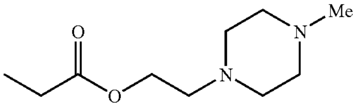 | NMe |
| 527 | 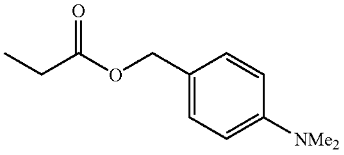 | NEt |
| 528 | 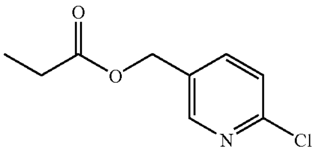 | NH |
| 529 | —$(CH_2)_2CO_2Bn$ | NMe |
| 530 | —$(CH_2)_3CO_2CH_2Cl$ | NEt |
| 531 | —$(CH_2)_4CO_2(CH_2)_3OEt$ | NH |
| 532 | —$(CH_2)_2CO_2(CH_2)_2OH$ | NMe |
| 533 | 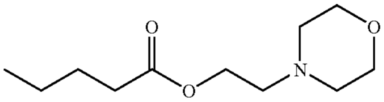 | NEt |
| 534 | 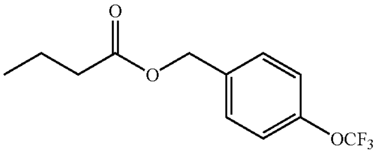 | NH |
| 535 | 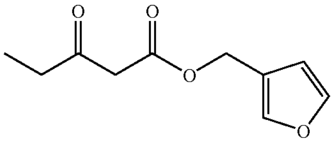 | NMe |
| 536 | —$CH_2COSBu$ | NEt |
| 537 | —$CH_2COS(CH_2)_2OH$ | NH |
| 538 | —$CH_2COS(CH_2)_2OMe$ | NMe |
| 539 | —$(CH_2)_2COS(CH_2)_2NMeEt$ | NEt |
| 540 | —$CH_2OCO_2Et$ | NH |
| 541 | —$(CH_2)_3OCO_2(CH_2)_2OMe$ | NMe |
| 542 | —$CH_2OCOEt$ | NEt |
| 543 | —$(CH_2)_2OCOBn$ | NH |
| 544 | 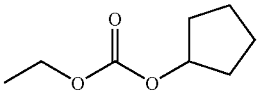 | NMe |
| 545 | —$CH_2CONMe_2$ | NEt |
| 546 | —$CH_2CONH(CH_2)NMe_2$ | NH |

TABLE 27-continued

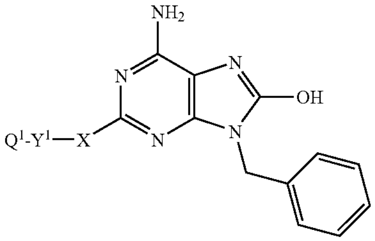

| No. | —Y1—Q1 | X |
|---|---|---|
| 547 | 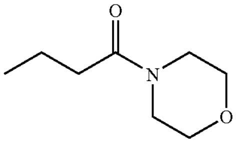 | NMe |
| 548 | —$(CH_2)_3CONH(CH_2)OMe$ | NEt |
| 549 | —$CH_2OCONMe_2$ | NH |
| 550 | 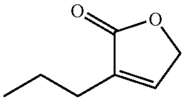 | NMe |
| 551 | 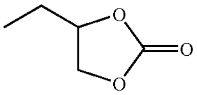 | NEt |
| 552 | 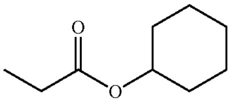 | S |
| 553 | —$CH_2CO_2CH_2CF_3$ | S |
| 554 | —$CH_2CO_2(CH_2)_4OH$ | S |
| 555 | 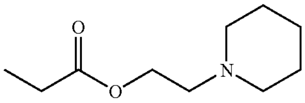 | S |
| 556 | 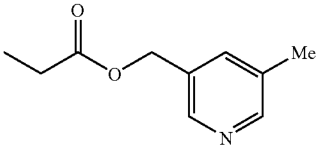 | S |
| 557 | —$(CH_2)_2CO_2Bn$ | S |
| 558 | —$(CH_2)_4CO_2(CH_2)_3OEt$ | S |
| 559 | 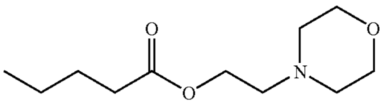 | S |
| 560 | 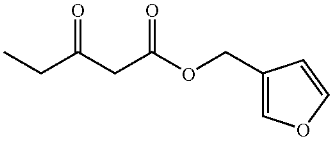 | S |
| 561 | —$CH_2COSBu$ | S |
| 562 | —$CH_2COS(CH_2)_2OMe$ | S |
| 563 | —$(CH_2)_2COS(CH_2)_2NMeEt$ | S |
| 564 | —$(CH_2)_3OCO_2(CH_2)_2OMe$ | S |

TABLE 27-continued
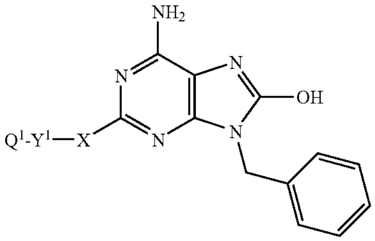
| No. | —Y1—Q1 | X |
|---|---|---|
| 565 | $—CH_2OCOEt$ | S |
| 566 | 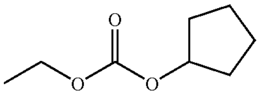 | S |
| 567 | $—CH_2CONMe_2$ | S |
| 568 | 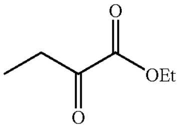 | S |
| 569 | $—(CH_2)_3CONH(CH_2)OMe$ | S |
| 570 | 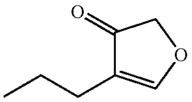 | S |
| 571 | 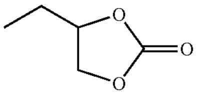 | S |
| 572 | 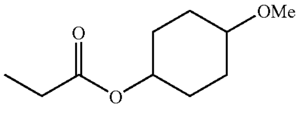 | O |
| 573 | $—CH_2CO_2(CH_2)_3OEt$ | O |
| 574 | $—CH_2CO_2(CH_2)_4OH$ | O |
| 575 | 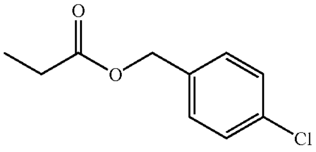 | O |
TABLE 27-continued
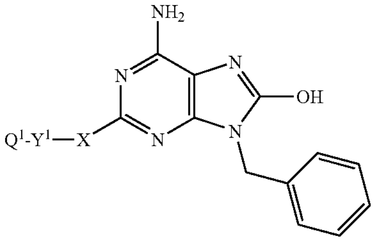
| No. | —Y1—Q1 | X |
|---|---|---|
| 576 | 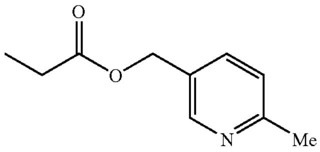 | O |
| 577 | $—(CH_2)_3CO_2CH_2Cl$ | O |
| 578 | $—(CH_2)_4CO_2(CH_2)_3OEt$ | O |
| 579 | 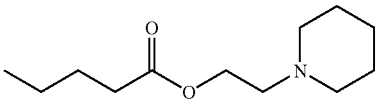 | O |
| 580 | 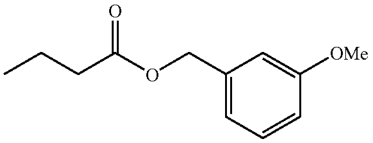 | O |
| 581 | $—CH_2COSBu$ | O |
| 582 | $—CH_2COS(CH_2)_2OH$ | O |
| 583 | $—(CH_2)_2COS(CH_2)_2NMeEt$ | O |
| 584 | $—CH_2OCO_2Et$ | O |
| 585 | $—CH_2OCOEt$ | O |
| 586 | $—(CH_2)_2OCOBn$ | O |
| 87 | $—CH_2CONMe_2$ | O |
| 588 | $—CH_2CONH(CH_2)NMe_2$ | O |
| 589 | $—(CH_2)_3CONH(CH_2)OMe$ | O |
| 590 | $—CH_2OCONMe_2$ | O |
| 591 | 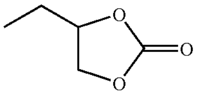 | O |

TABLE 28
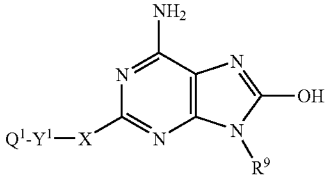
| No. | —Y¹—Q¹ | X | —R⁹ |
|---|---|---|---|
| 592 | —$CO_2$Me | — | 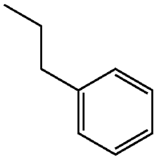 |
| 593 | —$CO_2CH_2CF_3$ | — | 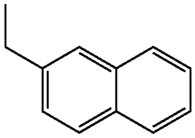 |
| 594 | —$CO_2(CH_2)_2$OH | — | 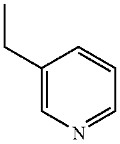 |
| 595 | —$CO_2$Bn | — | 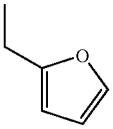 |
| 596 | 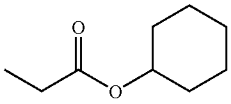 | — | 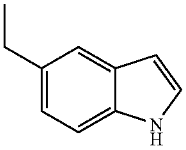 |
| 597 | —$CH_2CO_2(CH_2)_3$OEt | — | 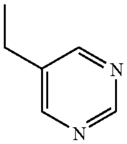 |
| 598 | 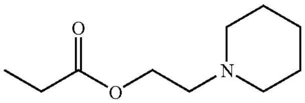 | — | 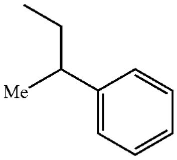 |
| 599 | 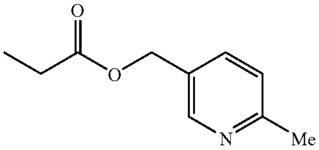 | — | 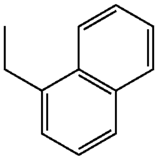 |

TABLE 28-continued
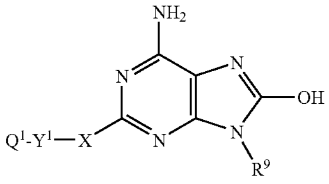
| No. | —$Y^1$—$Q^1$ | X | —$R^9$ |
|---|---|---|---|
| 600 | —$(CH_2)_3CO_2CH_2Cl$ | — | 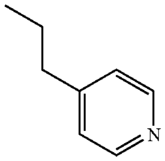 |
| 601 | —$(CH_2)_2CO_2(CH_2)_2OH$ | — | 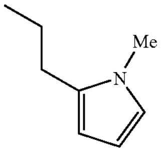 |
| 602 | 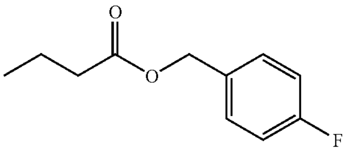 | — | 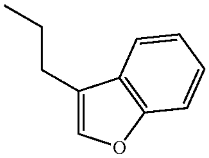 |
| 603 | —COS—$^i$Pr | — | 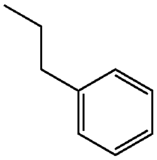 |
| 604 | —$CH_2COS(CH_2)_2OMe$ | — | 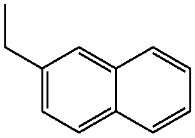 |
| 605 | —$CH_2OCO_2Et$ | — | 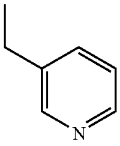 |
| 606 | —$CH_2OCOEt$ | — | 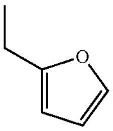 |
| 607 | 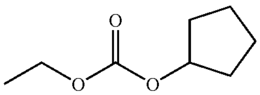 | — | 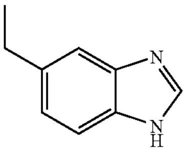 |

TABLE 28-continued
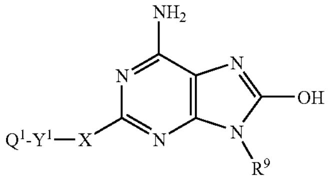
| No. | —$Y^1$—$Q^1$ | X | —$R^9$ |
|---|---|---|---|
| 608 | —$CH_2CONH(CH_2)NMe_2$ | — | 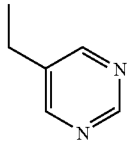 |
| 609 | —$(CH_2)_3CONH(CH_2)OMe$ | — | 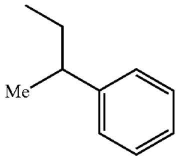 |
| 610 | 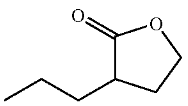 | — | 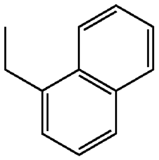 |
| 611 | —$CH_2CO_2CH_2CF_3$ | NMe | 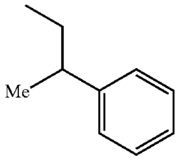 |
| 612 | —$CH_2CO_2(CH_2)_4OH$ | NH | 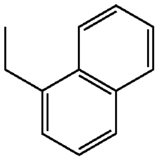 |
| 613 | 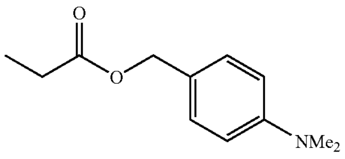 | NEt | 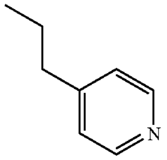 |
| 614 | —$(CH_2)_2CO_2Bn$ | NMe | 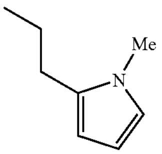 |
| 615 | —$(CH_2)_4CO_2(CH_2)_3OEt$ | NH | 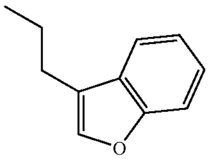 |

TABLE 28-continued
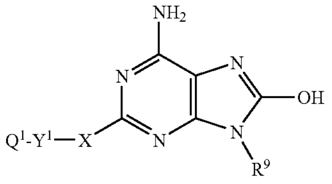
| No. | —$Y^1$—$Q^1$ | X | —$R^9$ |
|---|---|---|---|
| 616 | 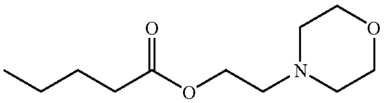 | NEt | 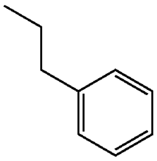 |
| 617 | 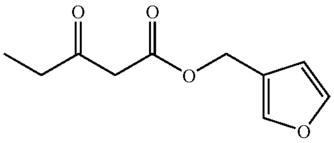 | NMe | 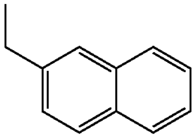 |
| 618 | —$CH_2COS(CH_2)_2OH$ | NH | 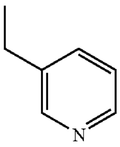 |
| 619 | —$(CH_2)_2COS(CH_2)_2NMeEt$ | NEt | 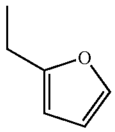 |
| 620 | —$(CH_2)_3OCO_2(CH_2)_2OMe$ | NMe | 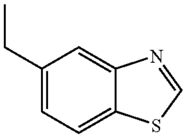 |
| 621 | —$(CH_2)_2OCOBn$ | NH | 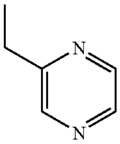 |
| 622 | —$CH_2CONMe_2$ | NEt | 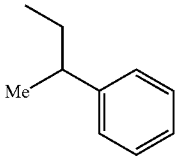 |
| 623 | 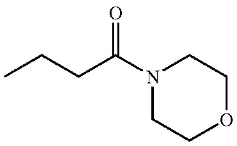 | NMe | 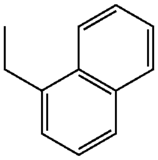 |

TABLE 28-continued
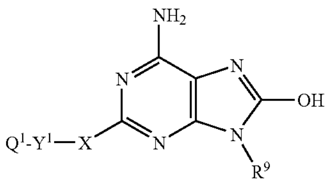
| No. | —Y¹—Q¹ | X | —R⁹ |
|---|---|---|---|
| 624 | $—CH_2OCONMe_2$ | NH | 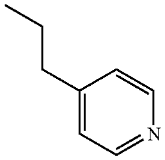 |
| 625 | 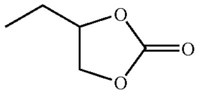 | NEt | 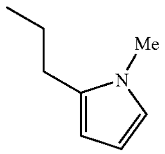 |
| 626 | 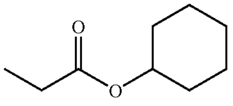 | S | 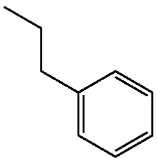 |
| 627 | $—CH_2CO_2(CH_2)_4OH$ | S | 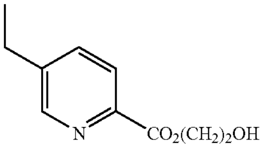 |
| 628 | 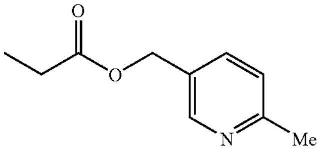 | S | 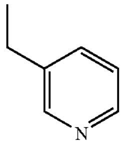 |
| 629 | $—(CH_2)_4CO_2(CH_2)_3OEt$ | S | 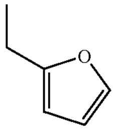 |
| 630 | 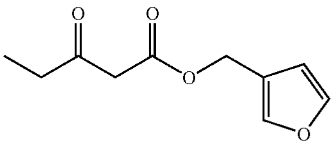 | S | 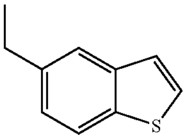 |
| 631 | $—CH_2COS(CH_2)_2OMe$ | S | 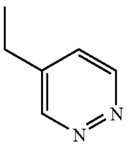 |

TABLE 28-continued
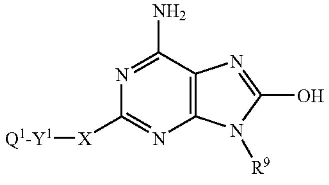
| No. | —$Y^1$—$Q^1$ | X | —$R^9$ |
|---|---|---|---|
| 632 | —$(CH_2)_3OCO_2(CH_2)_2OMe$ | S | 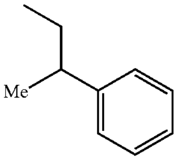 |
| 633 | 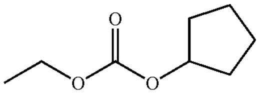 | S | 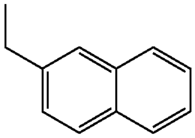 |
| 634 | 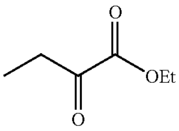 | S | 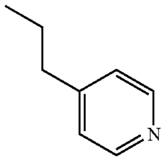 |
| 635 | 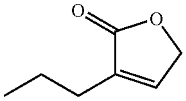 | S | 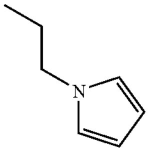 |
| 636 | —$CH_2CO_2(CH_2)_3OEt$ | O | 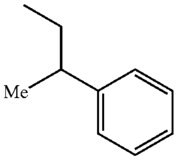 |
| 637 | 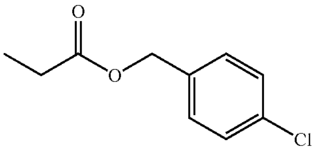 | O | 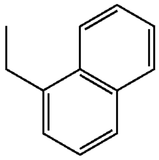 |
| 638 | —$(CH_2)_3CO_2CH_2Cl$ | O | 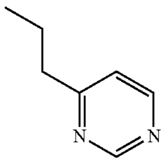 |
| 639 | 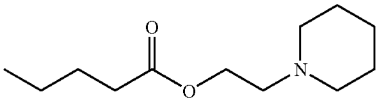 | O | 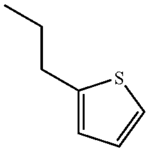 |

TABLE 28-continued
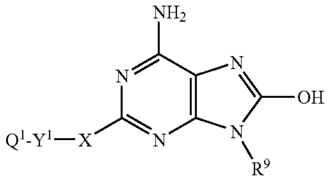
| No. | —Y¹—Q¹ | X | —R⁹ |
|---|---|---|---|
| 640 | $—CH_2COSBu$ | O | 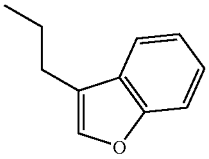 |
| 641 | $—(CH_2)_2COS(CH_2)_2NMeEt$ | O | 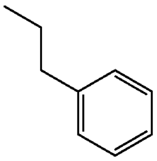 |
| 642 | $—CH_2OCOEt$ | O | 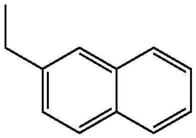 |
| 643 | $—CH_2CONMe_2$ | O | 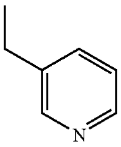 |
| 644 | $—(CH_2)_3CONH(CH_2)OMe$ | O | 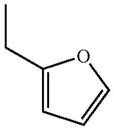 |
| 645 | 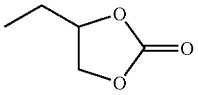 | O | 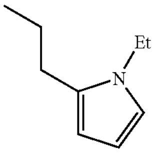 |
| 646 | $—CO_2Me$ | — | 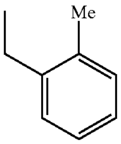 |
| 647 | $—CO_2CH_2CH{=}CH_2$ | — | 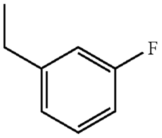 |

TABLE 28-continued
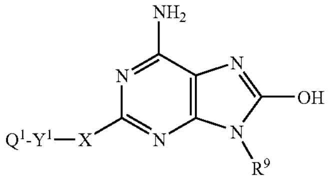
| No. | —$Y^1$—$Q^1$ | X | —$R^9$ |
| --- | --- | --- | --- |
| 648 | —$CO_2(CH_2)_2OMe$ | — | 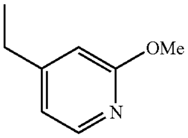 |
| 649 | —$CO_2(CH_2)_2OH$ | — | 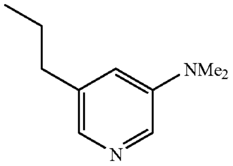 |
| 650 | —$CO_2Bn$ | — | 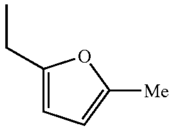 |
| 651 | 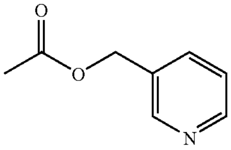 | — | 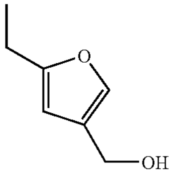 |
| 652 | —$CH_2CO_2CH_2Cl$ | — | 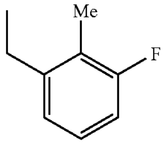 |
| 653 | —$CH_2CO_2(CH_2)_3OEt$ | — | 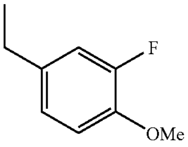 |
| 654 | 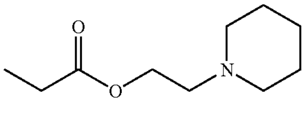 | — | 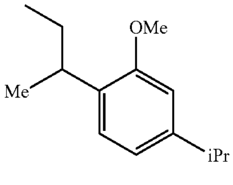 |
| 655 | 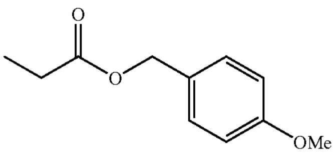 | — | 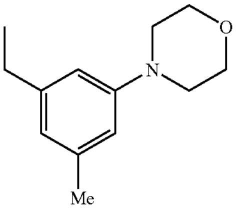 |

TABLE 28-continued
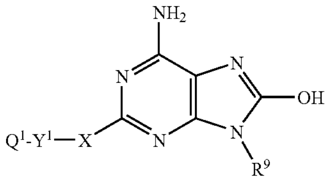
| No. | $—Y^1—Q^1$ | X | $—R^9$ |
|---|---|---|---|
| 656 | $—(CH_2)_2CO_2Bn$ | — | 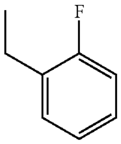 |
| 657 | $—(CH_2)_3CO_2CH_2Cl$ | — | 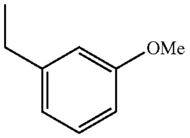 |
| 658 | $—(CH_2)_2CO_2(CH_2)_2OH$ | — | 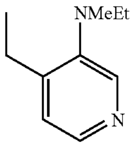 |
| 659 | 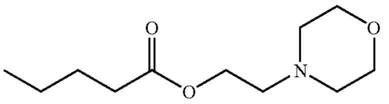 | — | 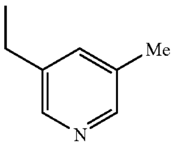 |
| 660 | 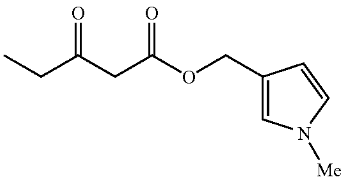 | — | 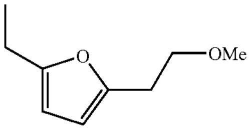 |
| 661 | $—COS—{}^iPr$ | — | 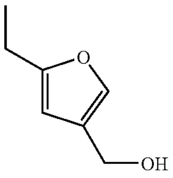 |
| 662 | $—CH_2COS(CH_2)_2OMe$ | — | 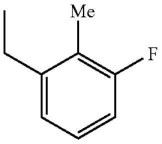 |
| 663 | $—(CH_2)_2COS(CH_2)_2NMeEt$ | — | 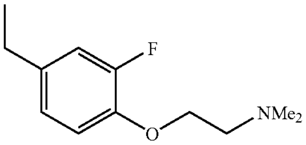 |

TABLE 28-continued
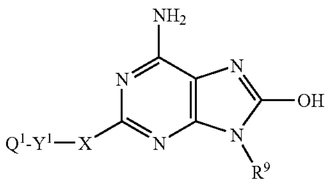
| No. | —$Y^1$—$Q^1$ | X | —$R^9$ |
|---|---|---|---|
| 664 | —$(CH_2)_3OCO_2(CH_2)_2OMe$ | — | 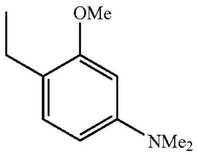 |
| 665 | —$(CH_2)_2OCOBn$ | — | 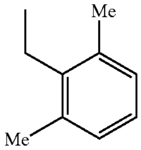 |
| 666 | 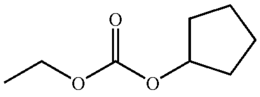 | — | 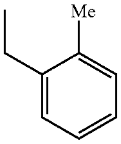 |
| 667 | —$CH_2CONH(CH_2)NMe_2$ | — | 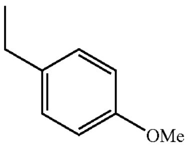 |
| 668 | 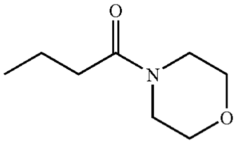 | — | 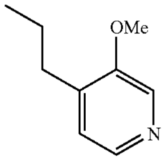 |
| 669 | —$CH_2OCONMe_2$ | — | 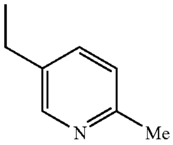 |
| 670 | 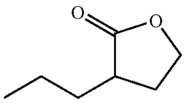 | — | 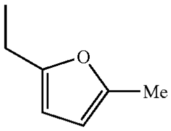 |
| 671 | —$CH_2CO_2CH_2CF_3$ | NMe | 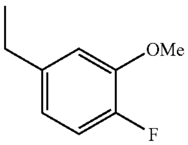 |

TABLE 28-continued
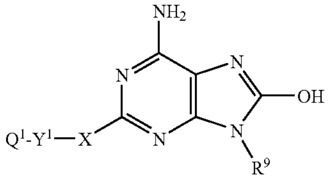
| No. | $-Y^1-Q^1$ | X | $-R^9$ |
|---|---|---|---|
| 672 | $-CH_2CO_2(CH_2)_4OH$ | NH | 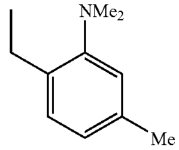 |
| 673 | 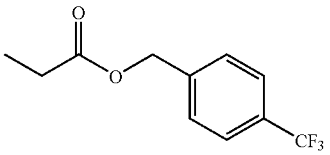 | NEt | 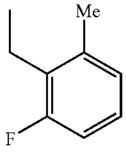 |
| 674 | $-(CH_2)_2CO_2Bn$ | NMe | 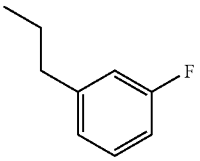 |
| 675 | $-(CH_2)_4CO_2(CH_2)_3OEt$ | NH | 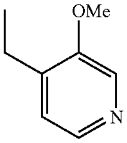 |
| 676 | 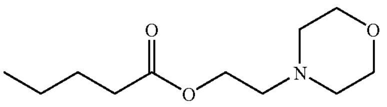 | NEt | 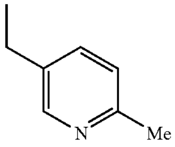 |
| 677 | 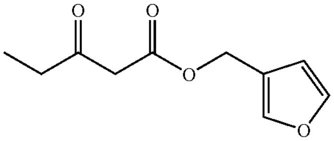 | NMe | 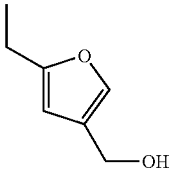 |
| 678 | $-CH_2COS(CH_2)_2OH$ | NH | 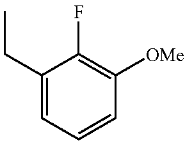 |
| 679 | $-(CH_2)_2COS(CH_2)_2NMeEt$ | NEt | 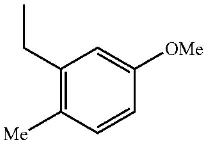 |

TABLE 28-continued
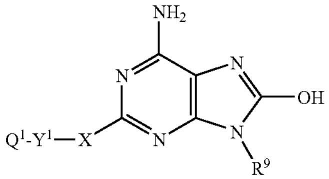
| No. | —$Y^1$—$Q^1$ | X | —$R^9$ |
|---|---|---|---|
| 680 | —$(CH_2)_3OCO_2(CH_2)_2Me$ | NMe | 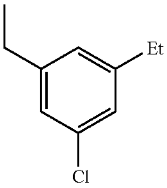 |
| 681 | —$(CH_2)_2OCOBn$ | NH | 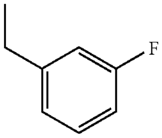 |
| 682 | —$CH_2CONMe_2$ | NEt | 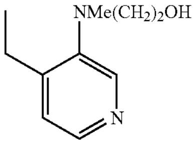 |
| 683 | 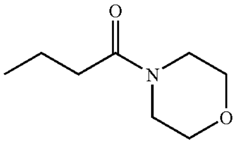 | NMe | 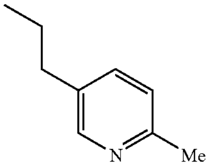 |
| 684 | —$CH_2OCONMe_2$ | NH | 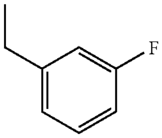 |
| 685 | 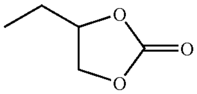 | NEt | 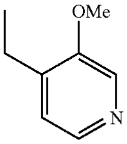 |
| 686 | 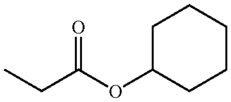 | S | 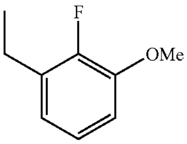 |
| 687 | —$CH_2CO_2Me$ | S | 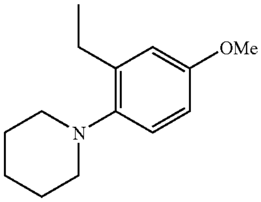 |

TABLE 28-continued
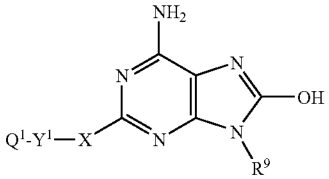
| No. | —$Y^1$—$Q^1$ | X | —$R^9$ |
|---|---|---|---|
| 688 | 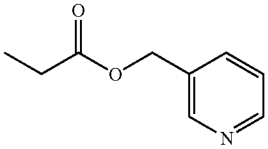 | S | 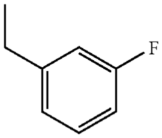 |
| 689 | —$(CH_2)_4CO_2(CH_2)_3OEt$ | S | 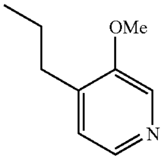 |
| 690 | 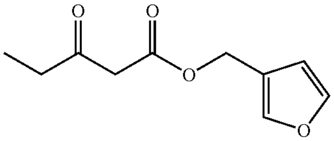 | S | 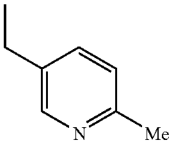 |
| 691 | —$CH_2COS(CH_2)_2OMe$ | S | 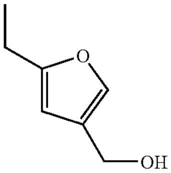 |
| 692 | —$(CH_2)_3OCO_2(CH_2)_2OMe$ | S | 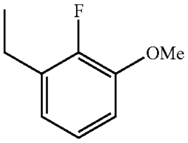 |
| 693 | 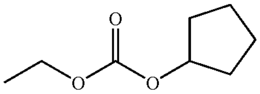 | S | 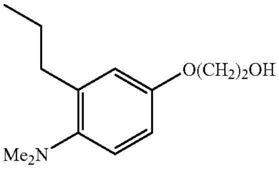 |
| 694 | 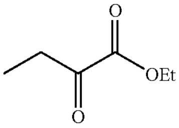 | S | 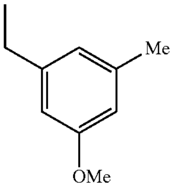 |
| 695 | 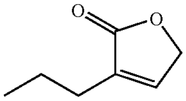 | S | 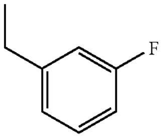 |

TABLE 28-continued
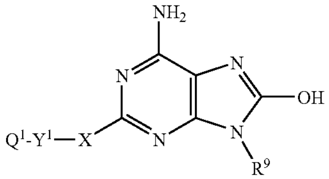
| No. | —$Y^1$—$Q^1$ | X | —$R^9$ |
| --- | --- | --- | --- |
| 696 | 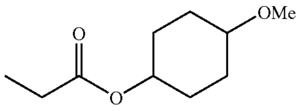 | O | 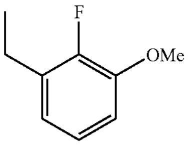 |
| 697 | —$CH_2CO_2(CH_2)_4OH$ | O | 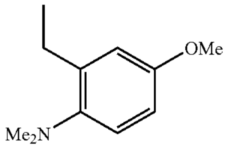 |
| 698 | 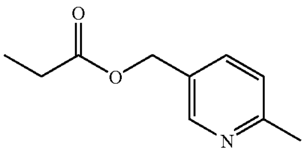 | O | 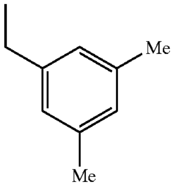 |
| 699 | —$(CH_2)_4CO_2Et$ | O | 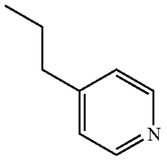 |
| 700 | 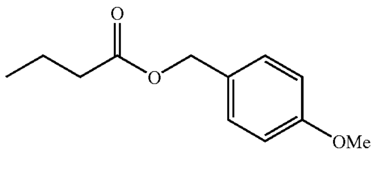 | O | 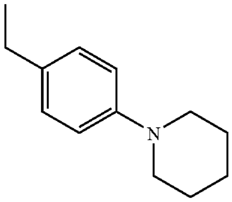 |
| 701 | —$CH_2COS(CH_2)_2OH$ | O | 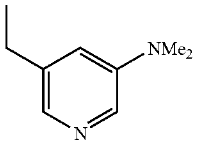 |
| 702 | —$CH_2OCO_2Et$ | O | 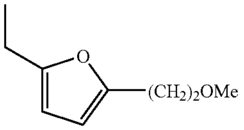 |
| 703 | —$(CH_2)_2OCOMe$ | O | 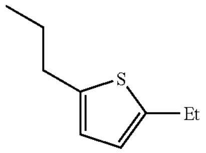 |

TABLE 28-continued
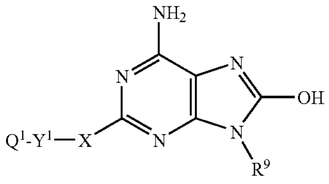
| No. | —$Y^1$—$Q^1$ | X | —$R^9$ |
|---|---|---|---|
| 704 | —$CH_2CONH(CH_2)NMe_2$ | O | 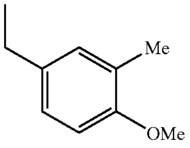 |
| 705 | —$CH_2OCONMe_2$ | O | 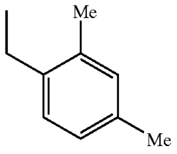 |
| 706 | —$CO_2(CH_2)_2OMe$ | — | 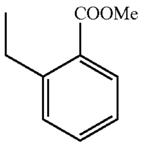 |
| 707 | —$(CH_2)_2CO_2Et$ | — | 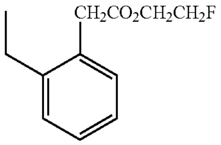 |
| 708 | 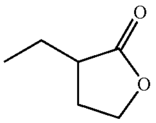 | — | 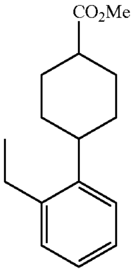 |
| 709 | —$CH_2COSMe$ | — | 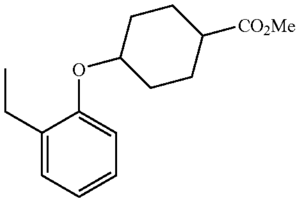 |
| 710 | —$CH_2OAc$ | — | 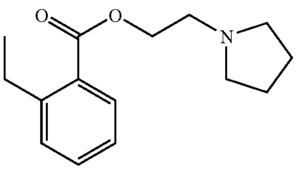 |

TABLE 28-continued
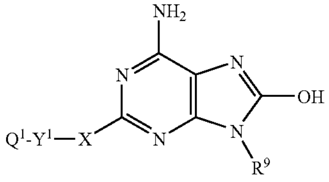
| No. | $—Y^1—Q^1$ | X | $—R^9$ |
|---|---|---|---|
| 711 | $—CH_2OCO_2Me$ | — | 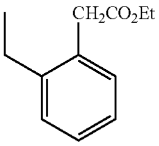 |
| 712 | $—CH_2CO_2Me$ | — | 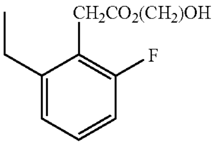 |
| 713 | $—CH_2CO_2(CH_2)_2NMe_2$ | — | 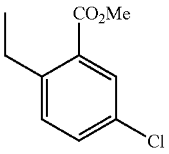 |
| 714 | $—(CH_2)_2CO_2Bn$ | — | 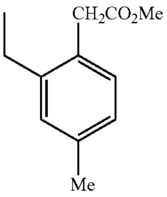 |
| 715 | 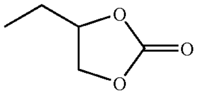 | — | 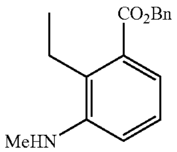 |
| 716 | 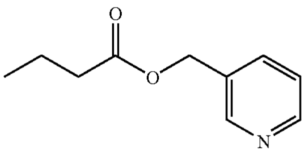 | — | 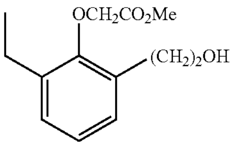 |
| 717 | 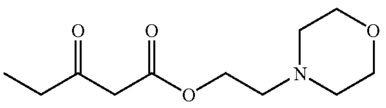 | — | 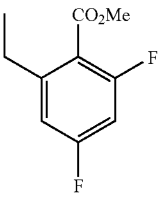 |

TABLE 28-continued
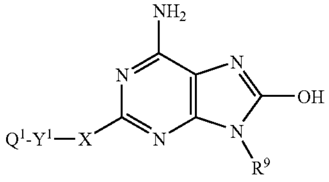
| No. | $—Y^1—Q^1$ | X | $—R^9$ |
|---|---|---|---|
| 718 | $—CH_2CHMeCO_2Me$ | — | 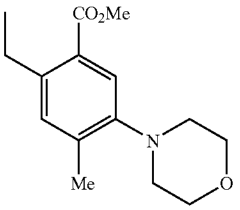 |
| 719 | 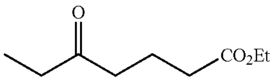 | — | 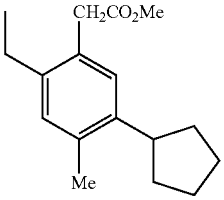 |
| 720 | 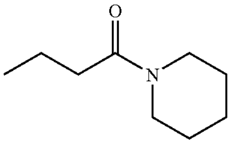 | — | 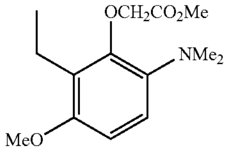 |
| 721 | $—CO_2(CH_2)_2OMe$ | — | 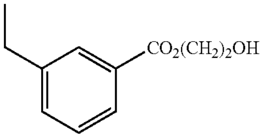 |
| 722 | $—(CH_2)_2CO_2Et$ | — | 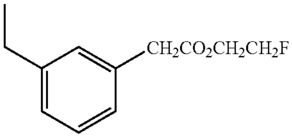 |
| 723 | 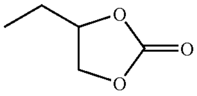 | — | 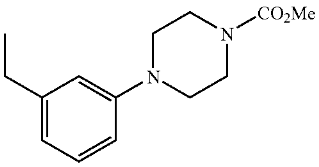 |
| 724 | $—CH_2CONMe_2$ | — | 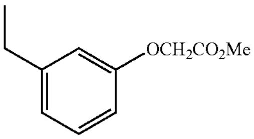 |

TABLE 28-continued
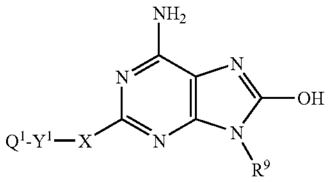
| No. | —$Y^1$—$Q^1$ | X | —$R^9$ |
|---|---|---|---|
| 725 | —$CH_2OCO(CH_2)_2OH$ | — | 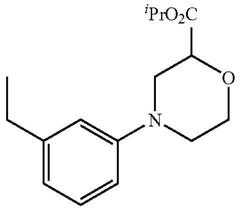 |
| 726 | —$CH_2OCONMe_2$ | — | 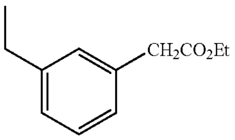 |
| 727 | —$(CH_2)_2$CO2Bn | — | 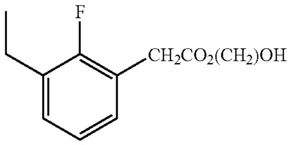 |
| 728 | 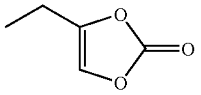 | — | 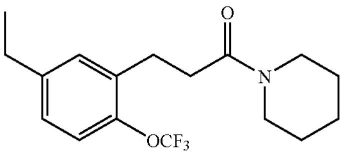 |
| 729 | 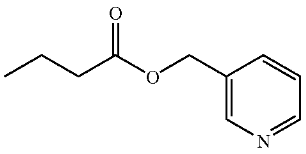 | — | 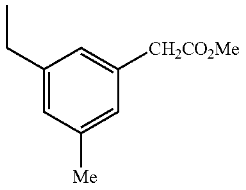 |
| 730 | 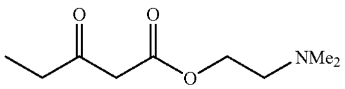 | — | 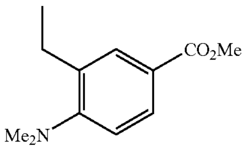 |
| 731 | —$CH_2CHMeCO_2Me$ | — | 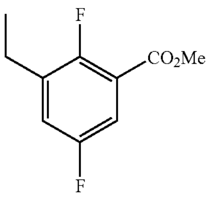 |

TABLE 28-continued
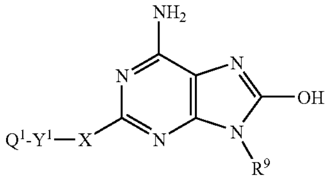
| No. | —$Y^1$—$Q^1$ | X | —$R^9$ |
| --- | --- | --- | --- |
| 732 | 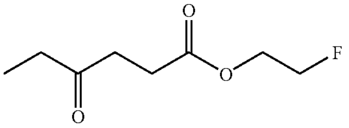 | — | 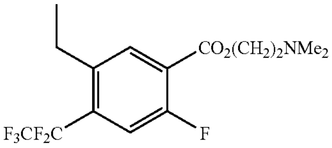 |
| 733 | 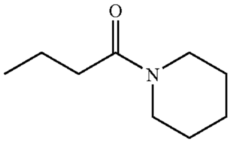 | — | 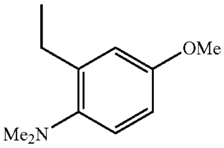 |
| 734 | —$COS(CH_2)_2OMe$ | — | 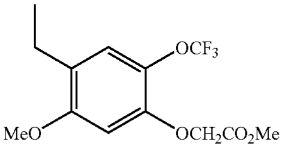 |
| 735 | —$CO_2(CH_2)_2OH$ | — | 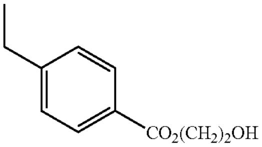 |
| 736 | —$CHMeCO_2CH_2CF_3$ | — | 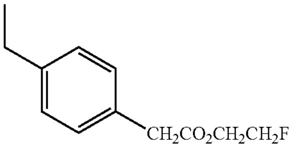 |
| 737 | 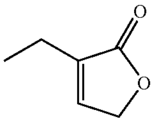 | — | 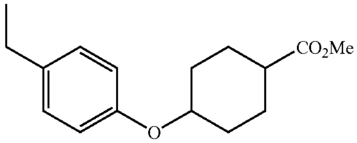 |
| 738 | —$CH_2COSMe$ | — | 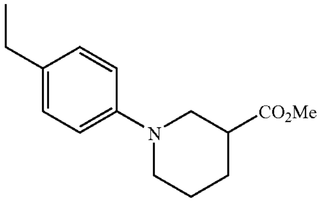 |
| 739 | —$CH_2OAc$ | — | 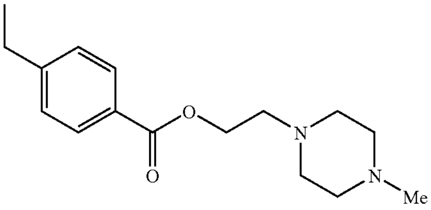 |

TABLE 28-continued
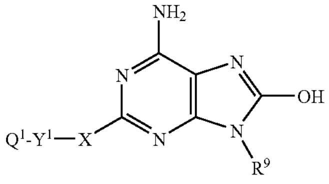
| No. | $—Y^1—Q^1$ | X | $—R^9$ |
|---|---|---|---|
| 740 | $—CH_2OCO_2Et$ | — | 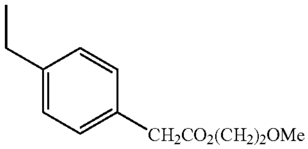 |
| 741 | $—(CH_2)_2CO_2Bn$ | — | 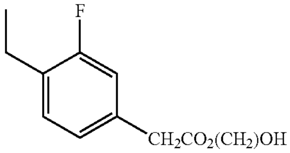 |
| 742 | 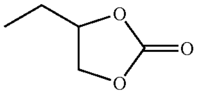 | — | 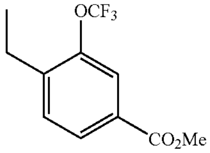 |
| 743 | 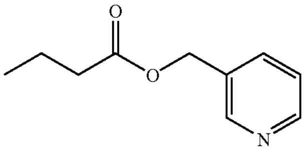 | — | 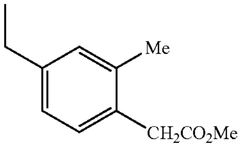 |
| 744 | 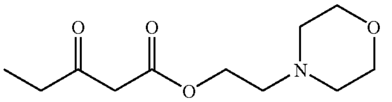 | — | 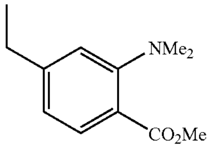 |
| 745 | $—CH_2CHMeCO_2Me$ | — | 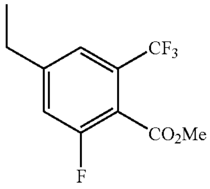 |
| 746 | 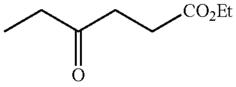 | — | 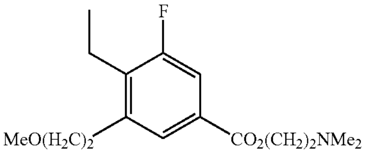 |

TABLE 28-continued
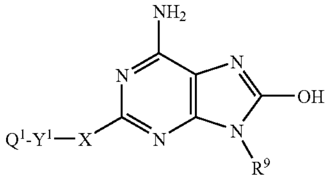
| No. | —$Y^1$—$Q^1$ | X | —$R^9$ |
|---|---|---|---|
| 747 | —$(CH_2)_2OCO_2CH_2CF_3$ | — | 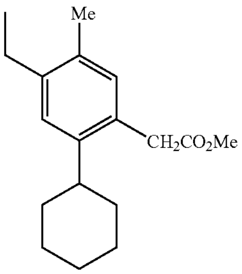 |
| 748 | —$CH_2CONMe(CH_2)_2OH$ | — | 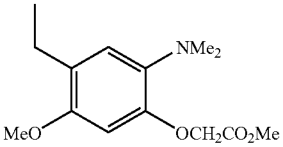 |
| 749 | —$CO_2(CH_2)_2OMe$ | — | 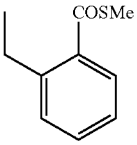 |
| 750 | —$(CH_2)_2CO_2Et$ | — | 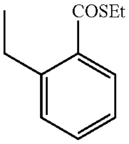 |
| 751 | 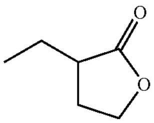 | — | 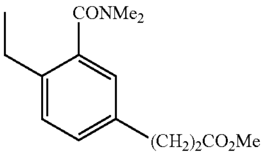 |
| 752 | —$CH_2COSMe$ | — | 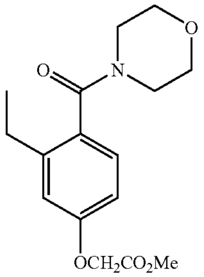 |

TABLE 28-continued
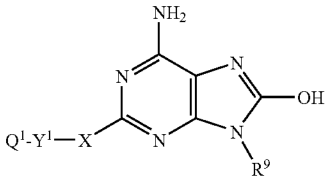
| No. | $—Y^1—Q^1$ | X | $—R^9$ |
|---|---|---|---|
| 753 | $—CH_2OAc$ | — | 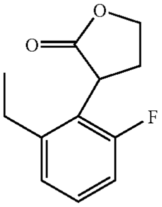 |
| 754 | $—CH_2OCO_2Me$ | — | 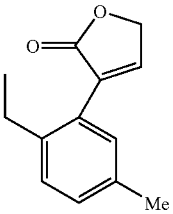 |
| 755 | 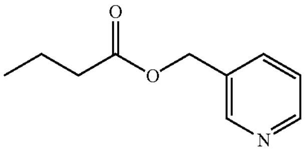 | — | 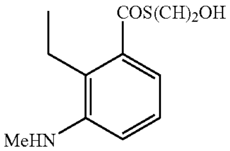 |
| 756 | 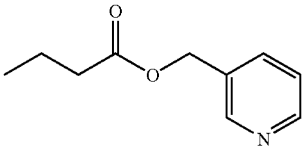 | — | 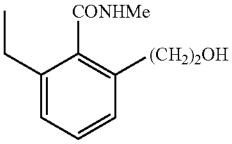 |
| 757 | $—CH_2CHMeCO_2Me$ | — | 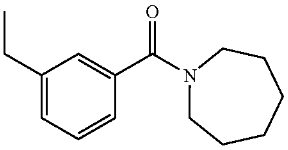 |
| 758 | 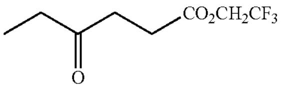 | — | 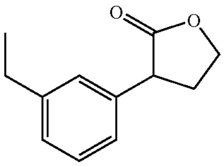 |
| 759 | $—(CH_2)_2OCO_2CH_2CF_3$ | — | 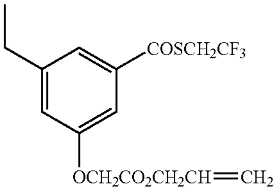 |

TABLE 28-continued
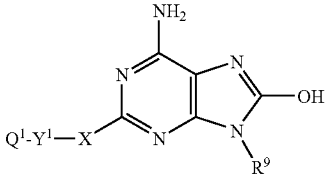
| No. | —Y$^1$—Q$^1$ | X | —R$^9$ |
|---|---|---|---|
| 760 | $—CH_2OCO(CH_2)_2OMe$ | — | 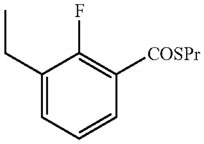 |
| 761 | $—CH_2OCONMe_2$ | — | 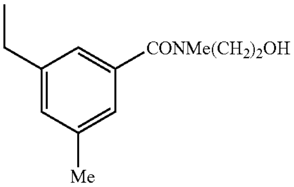 |
| 762 | $—(CH_2)_2CO_2Bn$ | — | 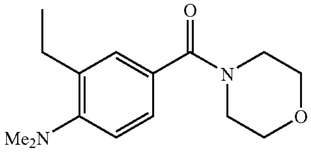 |
| 763 | 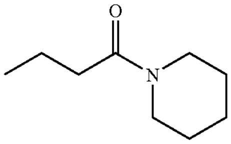 | — | 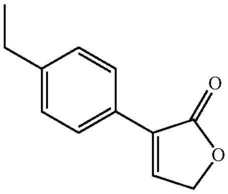 |
| 764 | $—CH_2CO_2(CH_2)_2NMe_2$ | — | 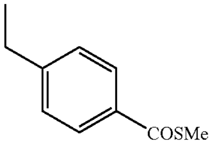 |
| 765 | $—(CH_2)_2CO_2Bn$ | — | 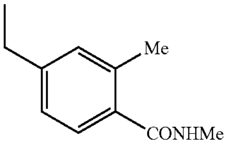 |
| 766 | 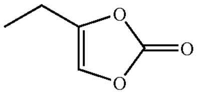 | — | 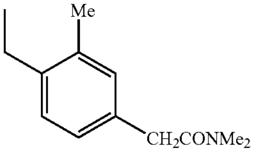 |
| 767 | $—CH_2COSMe$ | — | 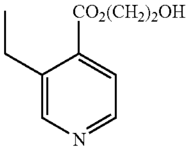 |

TABLE 28-continued
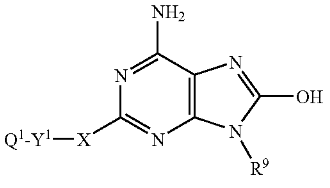
| No. | —$Y^1$—$Q^1$ | X | —$R^9$ |
|---|---|---|---|
| 768 | $-CH_2OCO_2Et$ | — | 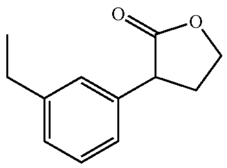 |
| 769 | $-CHMeCO_2CH_2CF_3$ | — | 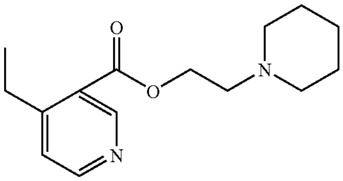 |
| 770 | $-CO_2(CH_2)_2OMe$ | — | 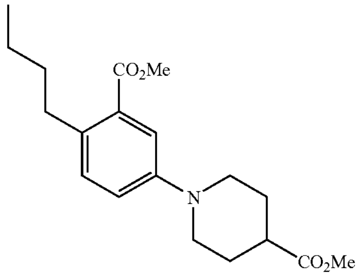 |
| 771 | 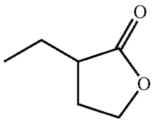 | — | 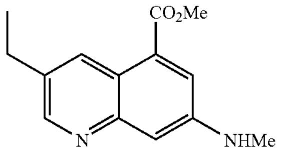 |
| 772 | $-CH_2OAc$ | — | 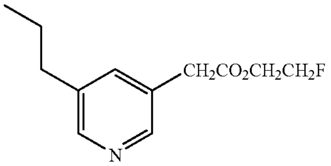 |
| 773 | 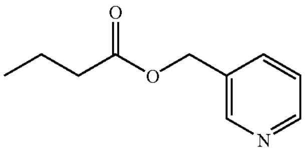 | — | 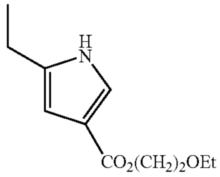 |
| 774 | $-CH_2CHMeCO_2Me$ | — | 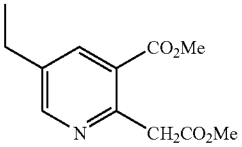 |

TABLE 28-continued
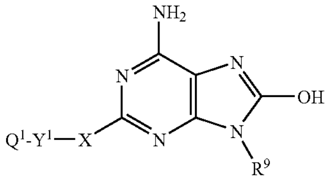
| No. | —$Y^1$—$Q^1$ | X | —$R^9$ |
|---|---|---|---|
| 775 | —$(CH_2)_2OCO_2CH_2CF_3$ | — | 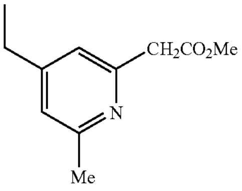 |
| 776 | —$CH_2OCONMe_2$ | — | 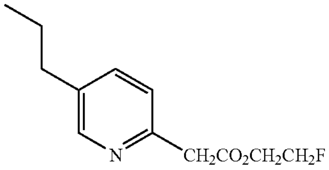 |
| 777 | 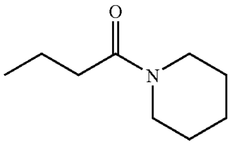 | — | 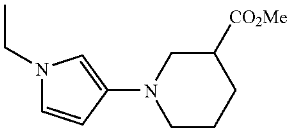 |
| 778 | —$(CH_2)_2CO_2Bn$ | — | 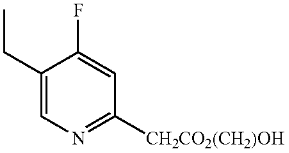 |
| 779 | —$CO_2(CH_2)_2OMe$ | — | 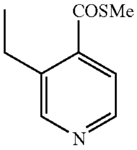 |
| 780 | 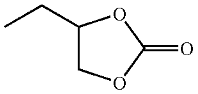 | — | 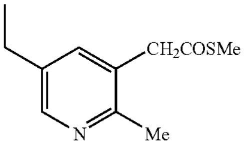 |
| 781 | —$CH_2OCO(CH_2)_2OH$ | — | 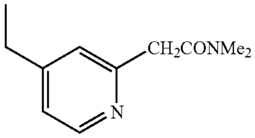 |
| 782 | —$CO_2(CH_2)_2OMe$ | — | 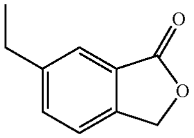 |

TABLE 28-continued
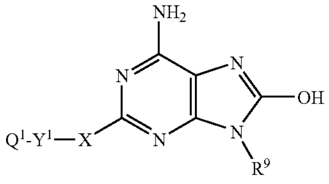
| No. | —$Y^1$—$Q^1$ | X | —$R^9$ |
|---|---|---|---|
| 783 | 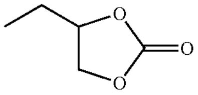 | — | 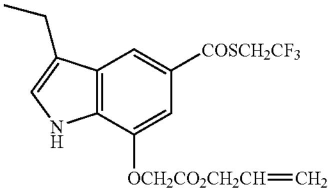 |
| 784 | —$CH_2OCO(CH_2)_2OEt$ | — | 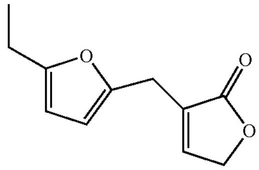 |
| 785 | —$(CH_2)_2CO_2Bn$ | — | 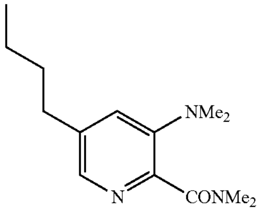 |
| 786 | —$CH_2CO_2(CH_2)_2OMe$ | NH | 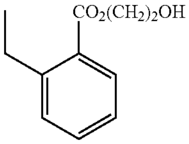 |
| 787 | 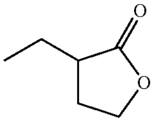 | NEt | 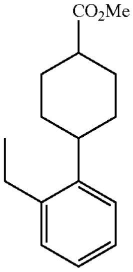 |
| 788 | —$(CH_2)_2OAc$ | NMe | 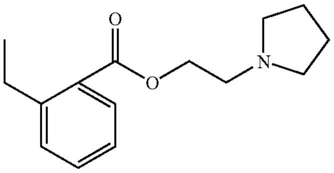 |
| 789 | —$CH_2CO_2Me$ | NH | 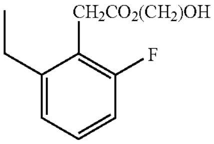 |

TABLE 28-continued
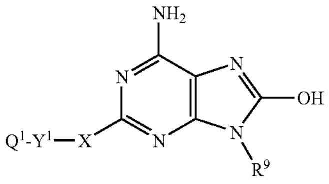
| No. | —$Y^1$—$Q^1$ | X | —$R^9$ |
|---|---|---|---|
| 790 | —$(CH_2)_2CO_2Bn$ | NEt | 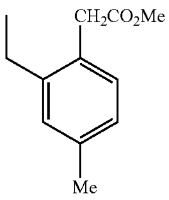 |
| 791 | 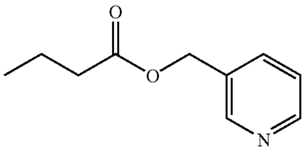 | NMe | 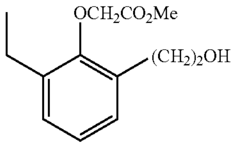 |
| 792 | —$CH_2CHMeCO_2Me$ | NH | 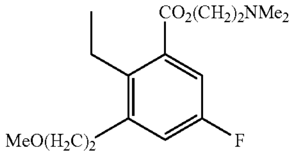 |
| 793 | 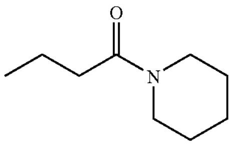 | NEt | 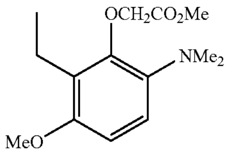 |
| 794 | —$CH_2CO_2(CH_2)_2OMe$ | NH | 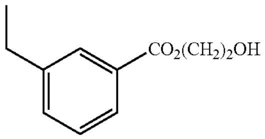 |
| 795 | 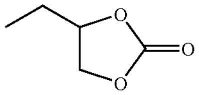 | NEt | 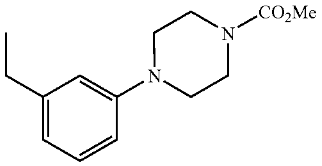 |
| 796 | —$(CH_2)_3OCO(CH_2)_2OH$ | NMe | 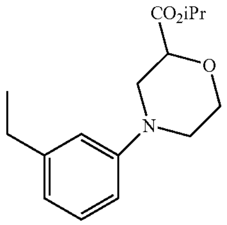 |

TABLE 28-continued
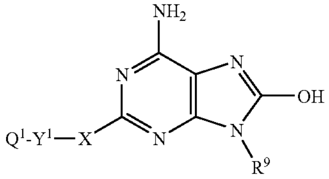
| No. | $-Y^1-Q^1$ | X | $-R^9$ |
| --- | --- | --- | --- |
| 797 | $-(CH_2)_2CO_2Bn$ | NH | 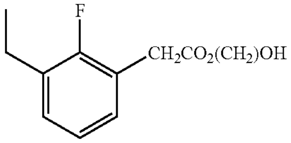 |
| 798 | 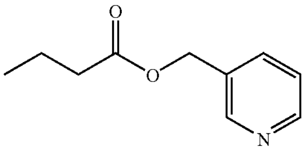 | NEt | 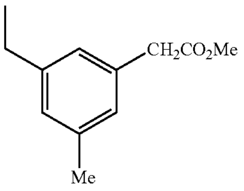 |
| 799 | $-CH_2CHMeCO_2Me$ | NMe | 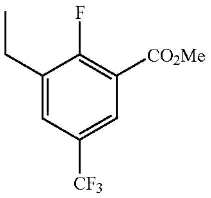 |
| 800 | 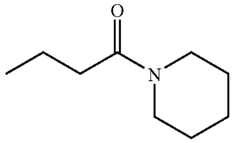 | NMe | 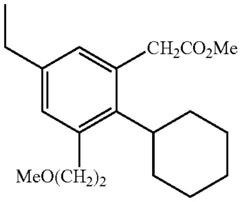 |
| 801 | $-CH_2CO_2(CH_2)_2OH$ | NH | 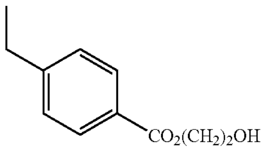 |
| 802 | 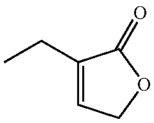 | NEt | 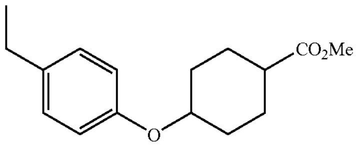 |
| 803 | $-(CH_2)2OCOPr$ | NMe | 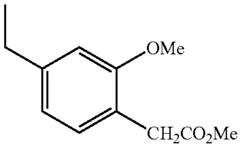 |

TABLE 28-continued
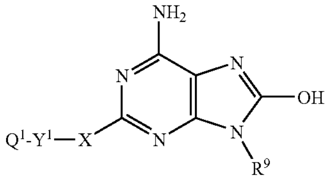
| No. | —$Y^1$—$Q^1$ | X | —$R^9$ |
|---|---|---|---|
| 804 | —$(CH_2)_2CO_2Bn$ | NH | 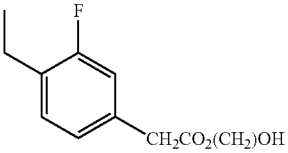 |
| 805 | 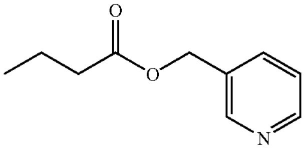 | NEt | 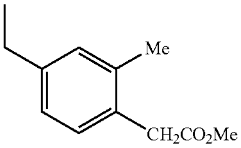 |
| 806 | —$CH_2CHMeCO_2Me$ | NMe | 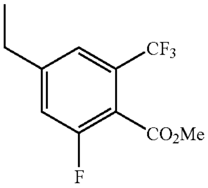 |
| 807 | —$(CH_2)_2OCO_2CH_2CF_3$ | NMe | 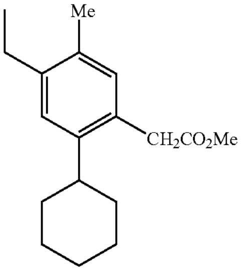 |
| 808 | —$CH_2CO_2Me$ | NH | 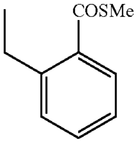 |
| 809 | 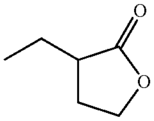 | NEt | 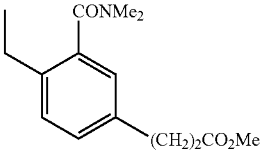 |
| 810 | —$(CH_2)_4OAc$ | NMe | 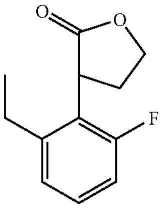 |

TABLE 28-continued
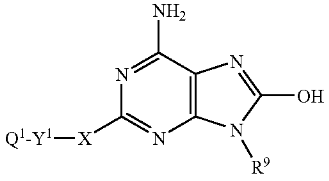
| No. | —$Y^1$—$Q^1$ | X | —$R^9$ |
|---|---|---|---|
| 811 | 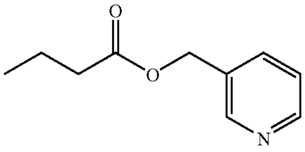 | NH | 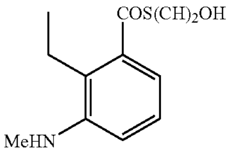 |
| 812 | —$CH_2CHMeCO_2Me$ | NEt | 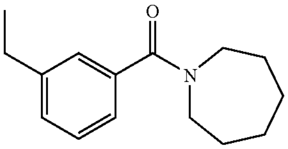 |
| 813 | —$(CH_2)_2OCO_2CH_2CF_3$ | NMe | 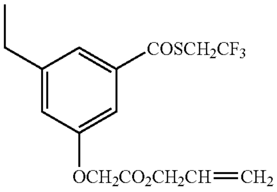 |
| 814 | —$(CH_2)_3OCONMe_2$ | NH | 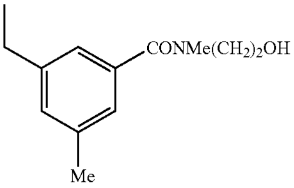 |
| 815 | 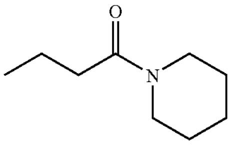 | NEt | 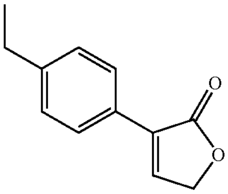 |
| 816 | —$(CH_2)_2CO_2Bn$ | NMe | 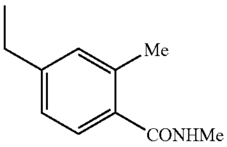 |
| 817 | —$CH_2COSMe$ | NH | 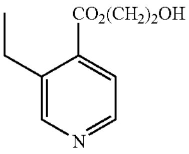 |

TABLE 28-continued
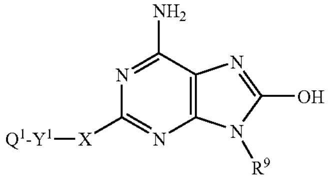
| No. | —Y¹—Q¹ | X | —R⁹ |
|---|---|---|---|
| 818 | —$CHMeCO_2CH_2CF_3$ | NEt | 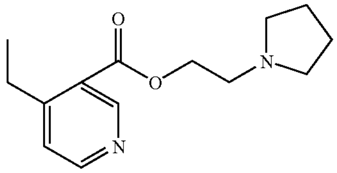 |
| 819 | 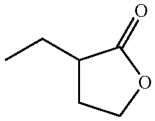 | NMe | 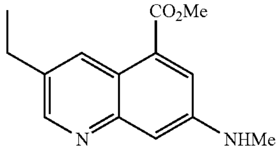 |
| 820 | 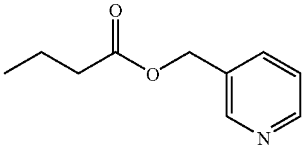 | NH | 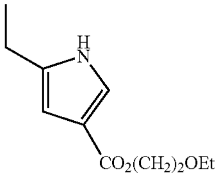 |
| 821 | —$(CH_2)_2OCO_2CH_2CF_3$ | NEt | 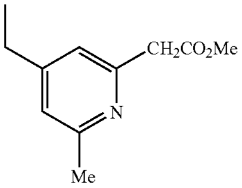 |
| 822 | 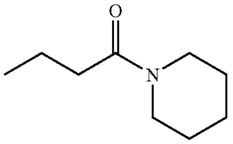 | NMe | 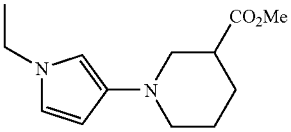 |
| 823 | —$CH_2CO_2Bu$ | NH | 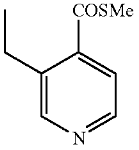 |
| 824 | —$(CH_2)_2OCO(CH_2)_2OH$ | NEt | 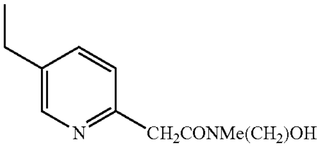 |

TABLE 28-continued
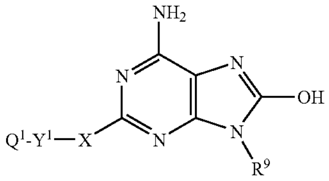
| No. | —$Y^1$—$Q^1$ | X | —$R^9$ |
|---|---|---|---|
| 825 | 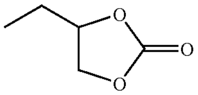 | NH | 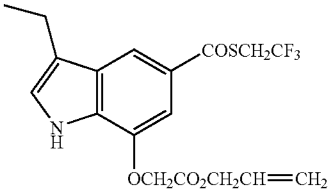 |
| 826 | —$(CH_2)_2CO_2Bn$ | NEt | 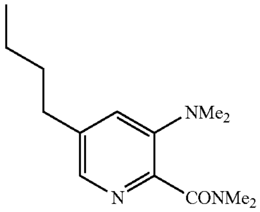 |
| 827 | —$CH_2CO_2iPr$ | S | 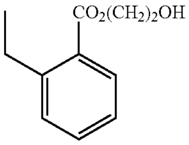 |
| 828 | —$(CH_2)_2CO_2Et$ | S | 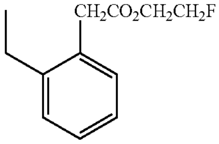 |
| 829 | —$CH_2COSMe$ | S | 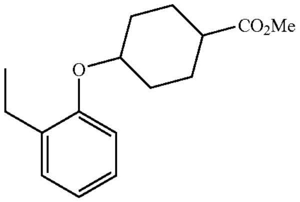 |
| 830 | —$(CH_2)_2OCOEt$ | S | 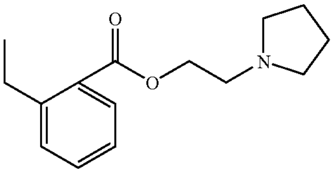 |
| 831 | -$CH_2CO_2Me$ | S | 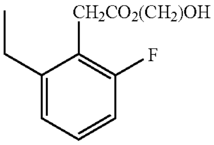 |

TABLE 28-continued
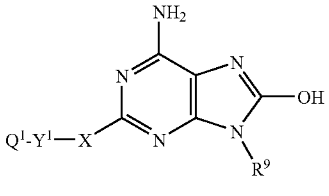
| No. | $-Y^1-Q^1$ | X | $-R^9$ |
| --- | --- | --- | --- |
| 832 | $-CH_2CO_2(CH_2)_2NMe_2$ | S | 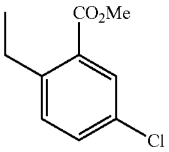 |
| 833 | 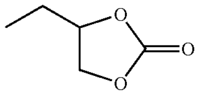 | S | 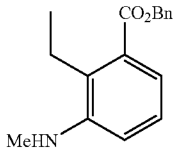 |
| 834 | 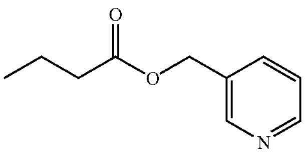 | S | 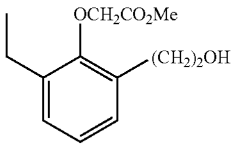 |
| 835 | $-CH_2CHMeCO_2Me$ | S | 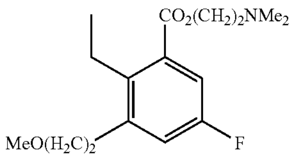 |
| 836 | 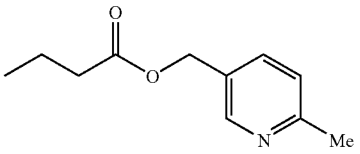 | S | 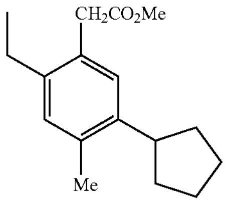 |
| 837 | $-CH_2CO_2(CH_2)_2OMe$ | S | 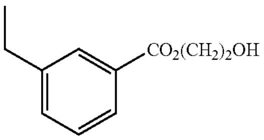 |
| 838 | $-(CH_2)_2CO_2Et$ | S | 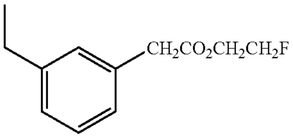 |
| 839 | $-CH_2CONMe_2$ | S | 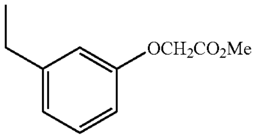 |

TABLE 28-continued
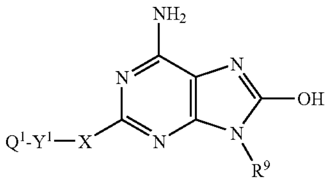
| No. | $-Y^1-Q^1$ | X | $-R^9$ |
|---|---|---|---|
| 840 | $-CH_2OCO(CH_2)_2OH$ | S | 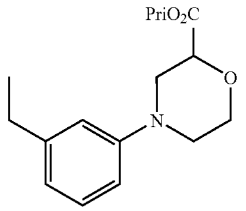 |
| 841 | $-(CH_2)_2CO_2Bn$ | S | 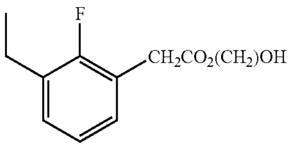 |
| 842 | 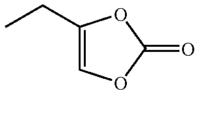 | S | 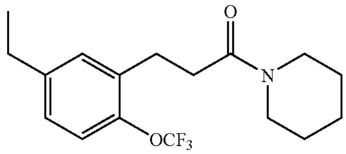 |
| 843 | 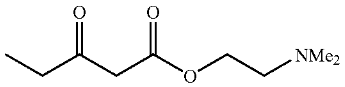 | S | 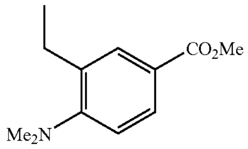 |
| 844 | $-CH_2CHMeCO_2Me$ | S | 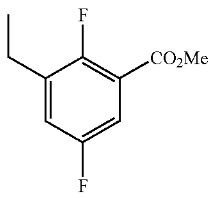 |
| 845 | 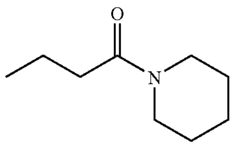 | S | 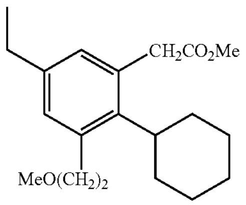 |
| 846 | $-CH_2COS(CH_2)_2NMe_2$ | S | 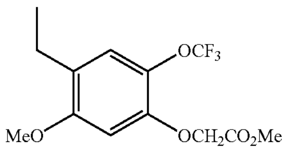 |

TABLE 28-continued
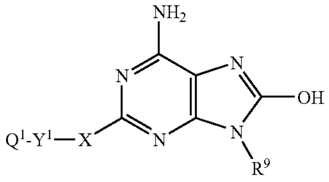
| No. | —$Y^1$—$Q^1$ | X | —$R^9$ |
|---|---|---|---|
| 847 | —$(CH_2)_4CO_2Me$ | S | 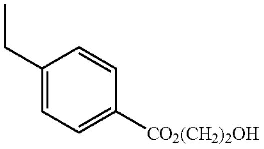 |
| 848 | —$CHMeCO_2CH_2CF_3$ | S | 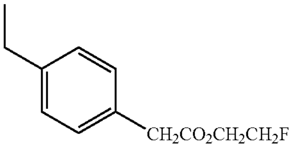 |
| 849 | —$CH_2COSMe$ | S | 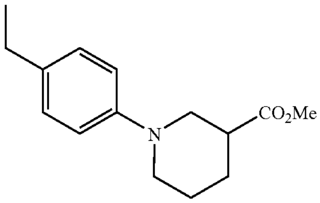 |
| 850 | —$(CH_2)_3OAc$ | S | 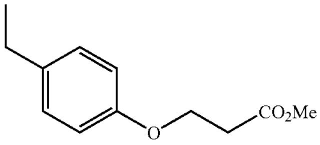 |
| 851 | —$(CH_2)_2CO_2Bn$ | S | 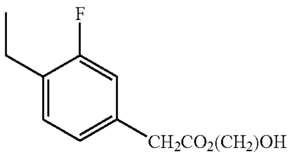 |
| 852 | 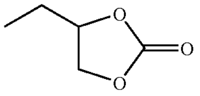 | S | 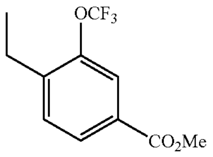 |
| 853 | 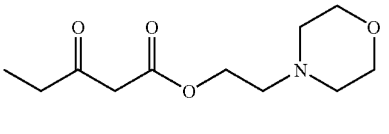 | S | 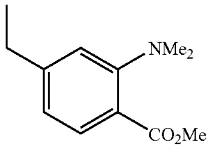 |
| 854 | —$CH_2CHMeCO_2Me$ | S | 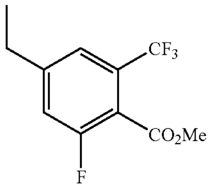 |

TABLE 28-continued
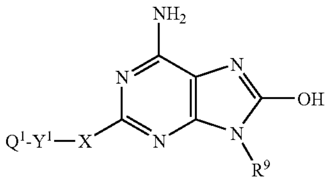
| No. | —Y¹—Q¹ | X | —R⁹ |
|---|---|---|---|
| 855 | $—(CH_2)_4OCO_2CH_2CF_3$ | S | 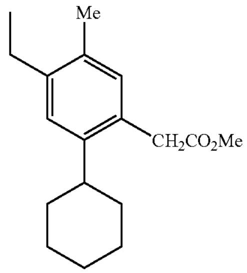 |
| 856 | $—CH_2CONMe(CH_2)_2OH$ | S | 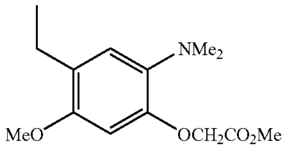 |
| 857 | $—CH_2CO_2(CH_2)_2OMe$ | S | 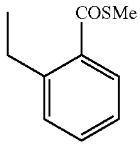 |
| 858 | $—(CH_2)_3CO_2Et$ | S | 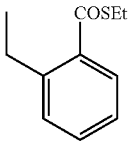 |
| 859 | $—CH_2COSMe$ | S | 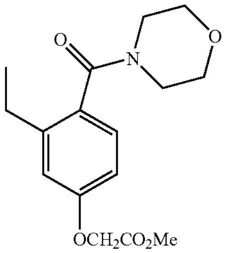 |
| 860 | $—(CH_2)_2OCO(CH_2)_2OMe$ | S | 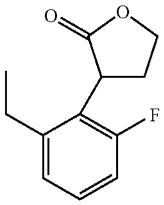 |

TABLE 28-continued
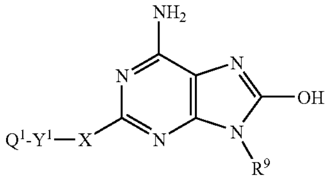
| No. | —Y¹—Q¹ | X | —R⁹ |
|---|---|---|---|
| 861 | 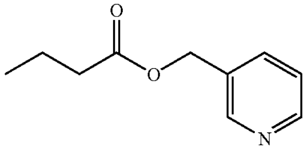 | S | 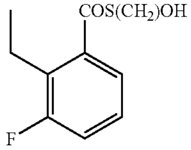 |
| 862 | 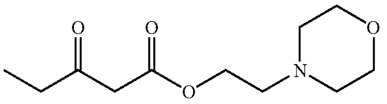 | S | 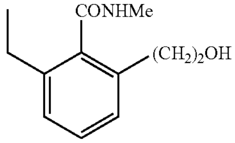 |
| 863 | 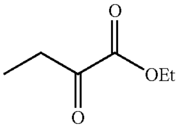 | S | 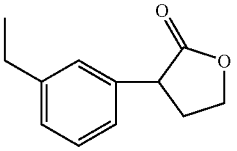 |
| 864 | $—(CH_2)_2OCO_2CH_2CF_3$ | S | 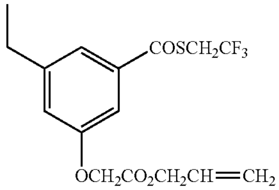 |
| 865 | $—(CH_2)_2OCONMe_2$ | S | 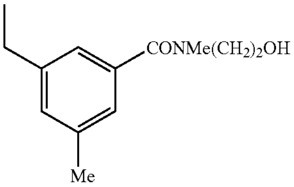 |
| 866 | $—(CH_2)_2CO_2Bn$ | S | 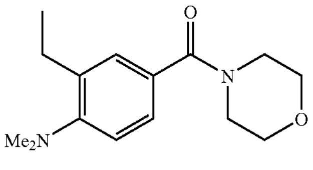 |
| 867 | $—CH_2CO_2(CH_2)_2NMeEt$ | S | 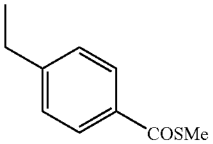 |
| 868 | $—(CH_2)_2CO_2Bn$ | S | 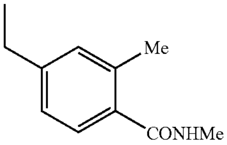 |

TABLE 28-continued
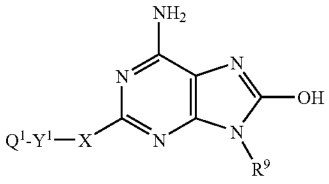
| No. | —$Y^1$—$Q^1$ | X | —$R^9$ |
|---|---|---|---|
| 869 | —$CH_2COSMe$ | S | 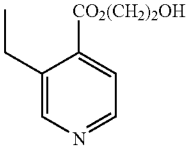 |
| 870 | —$(CH_2)_3OCO_2Et$ | S | 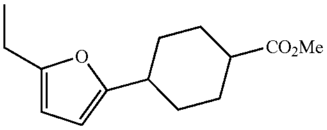 |
| 871 | —$CHMeCH_2CO_2(CH_2)_2OMe$ | S | 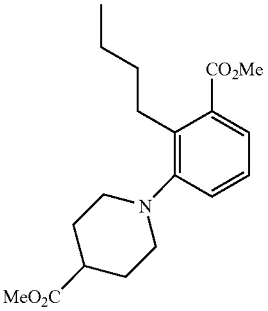 |
| 872 | 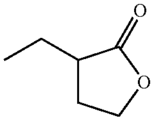 | S | 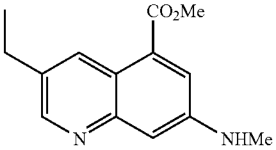 |
| 873 | 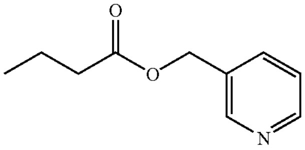 | S | 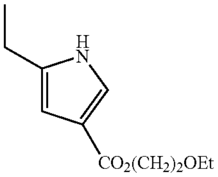 |
| 874 | —$CH_2CHMeCO_2Me$ | S | 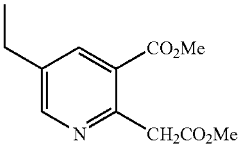 |
| 875 | —$(CH_2)_2OCONMe_2$ | S | 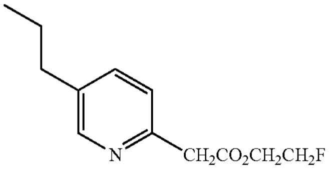 |

TABLE 28-continued
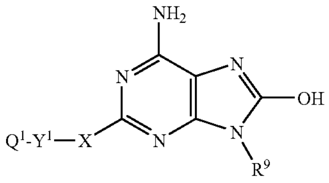
| No. | —$Y^1$—$Q^1$ | X | —$R^9$ |
|---|---|---|---|
| 876 | 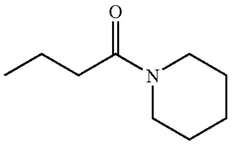 | S | 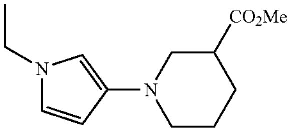 |
| 877 | —$CH_2CO_2(CH_2)_2OMe$ | S | 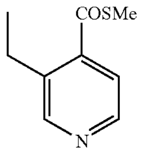 |
| 878 | 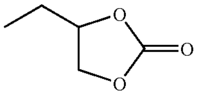 | S | 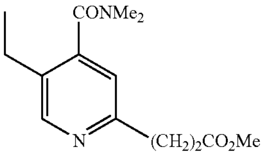 |
| 879 | —$CH_2CO_2(CH_2)_2NMe_2$ | S | 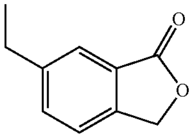 |
| 880 | 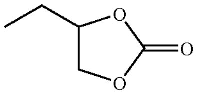 | S | 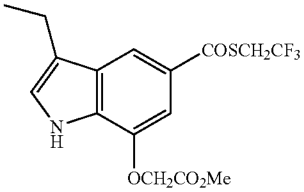 |
| 881 | —$(CH_2)_2CO_2Bn$ | S | 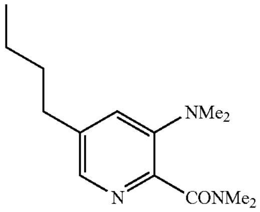 |
| 882 | —$(CH_2)_2CO_2Et$ | O | 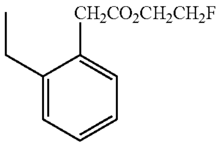 |

TABLE 28-continued
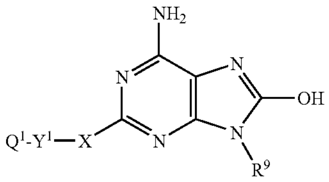
| No. | —$Y^1$—$Q^1$ | X | —$R^9$ |
| --- | --- | --- | --- |
| 883 | —$CH_2COSMe$ | O | 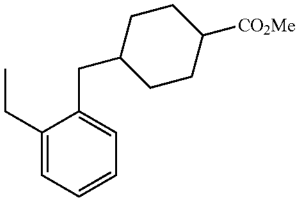 |
| 884 | —$(CH_2)_2OCO_2Me$ | O | 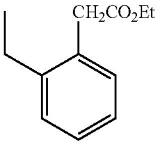 |
| 885 | —$CH_2CO_2(CH_2)_2NMe_2$ | O | 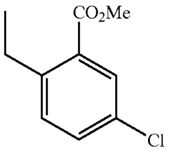 |
| 886 | 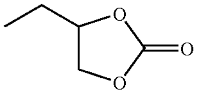 | O | 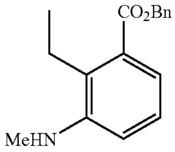 |
| 887 | 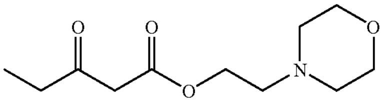 | O | 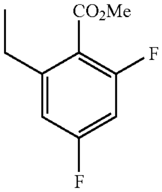 |
| 888 | 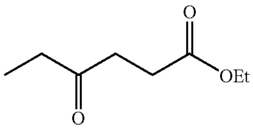 | O | 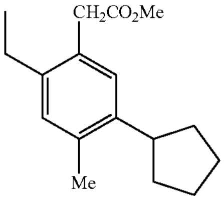 |
| 889 | —$(CH_2)_2CO_2Et$ | O | 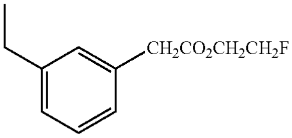 |

TABLE 28-continued
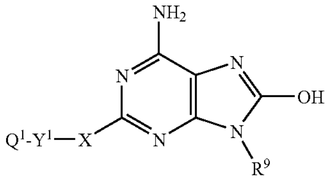
| No. | $—Y^1—Q^1$ | X | $—R^9$ |
|---|---|---|---|
| 890 | $—CH_2CONMe_2$ | O | 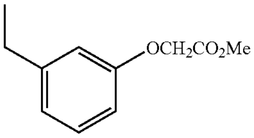 |
| 891 | $—(CH_2)_2OCONMe_2$ | O | 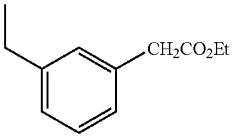 |
| 892 | 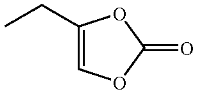 | O | 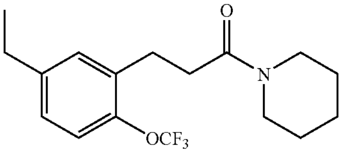 |
| 893 | 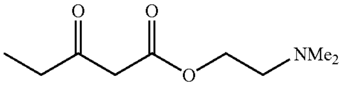 | O | 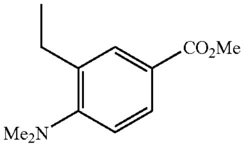 |
| 894 | 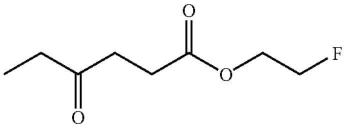 | O | 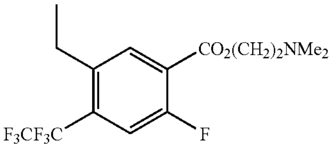 |
| 895 | $—CH_2COS(CH_2)_2OMe$ | O | 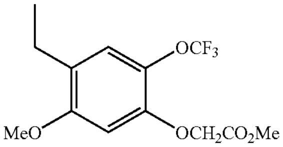 |
| 896 | $—CHMeCO_2CH_2CF_3$ | O | 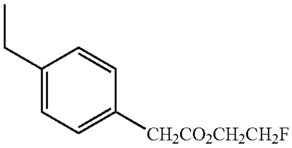 |
| 897 | $—CH_2COSMe$ | O | 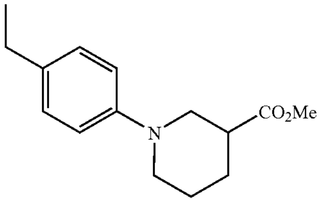 |

TABLE 28-continued
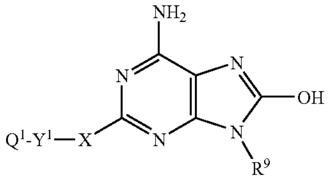
| No. | —$Y^1$—$Q^1$ | X | —$R^9$ |
| --- | --- | --- | --- |
| 898 | —$(CH_2)_5OCO_2Et$ | O | 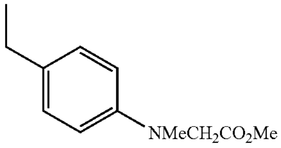 |
| 899 | 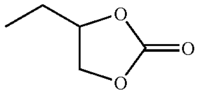 | O | 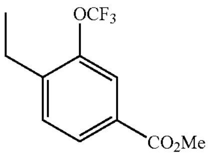 |
| 900 | 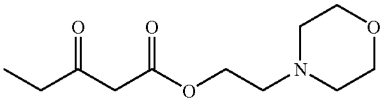 | O | 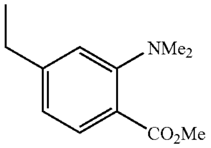 |
| 901 | 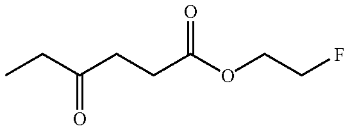 | O | 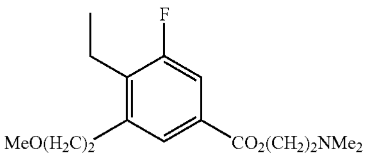 |
| 902 | —$CH_2CONMe(CH_2)_2OH$ | O | 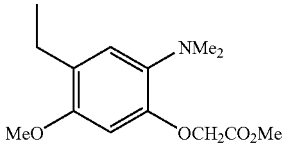 |
| 903 | —$CH_2CO_2Bu$ | O | 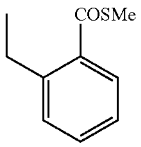 |
| 904 | 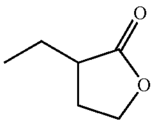 | O | 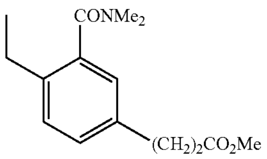 |
| 905 | —$(CH_2)_3OAc$ | O | 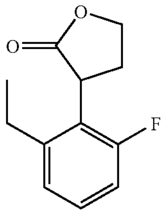 |

TABLE 28-continued
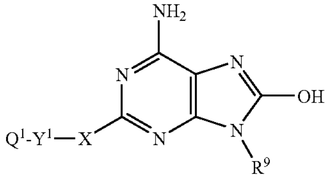
| No. | —$Y^1$—$Q^1$ | X | —$R^9$ |
|---|---|---|---|
| 906 | 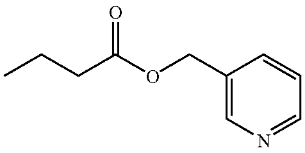 | O | 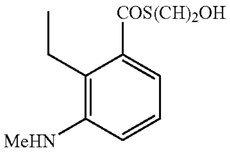 |
| 907 | —$CH_2CHMeCO_2Me$ | O | 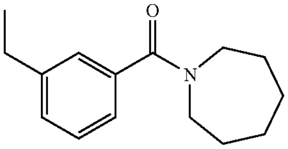 |
| 908 | —$(CH_2)_2OCO_2CH_2CF_3$ | O | 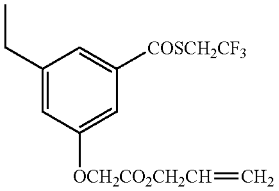 |
| 909 | —$(CH_2)_2OCONMe_2$ | O | 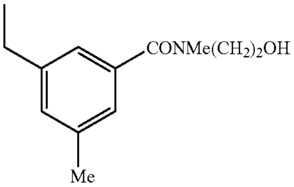 |
| 910 | 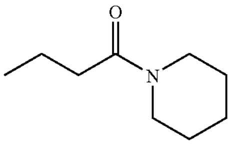 | O | 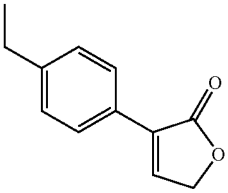 |
| 911 | —$(CH_2)_2CO_2Bn$ | O | 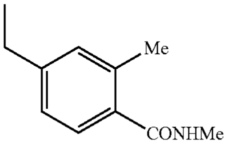 |
| 912 | —$CH_2COSMe$ | O | 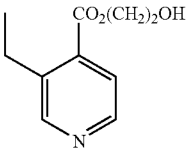 |

TABLE 28-continued
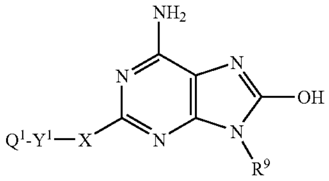
| No. | —$Y^1$—$Q^1$ | X | —$R^9$ |
|---|---|---|---|
| 913 | —$CHMeCO_2CH_2CF_3$ | O | 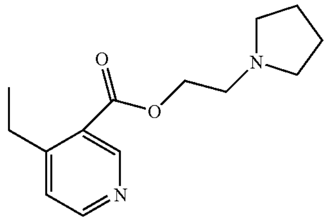 |
| 914 | 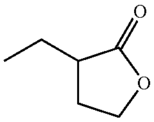 | O | 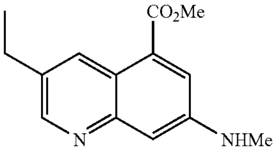 |
| 915 | 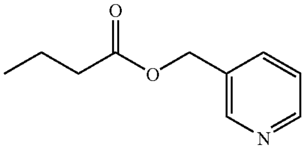 | O | 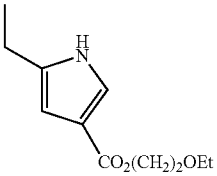 |
| 916 | —$(CH_2)_2OCO_2CH_2CF_3$ | O | 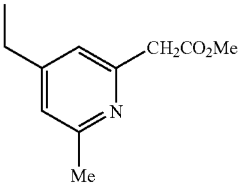 |
| 917 | 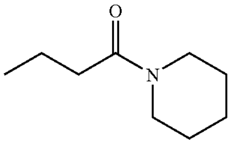 | O | 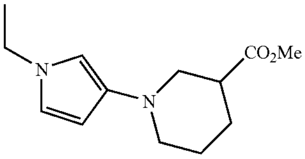 |
| 918 | —$(CH_2)_3CO_2(CH_2)_2OMe$ | O | 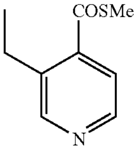 |
| 919 | —$(CH_2)_2OCO(CH_2)_2OH$ | O | 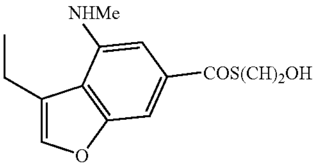 |

TABLE 28-continued

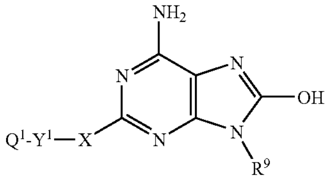

| No. | —$Y^1$—$Q^1$ | X | —$R^9$ |
|---|---|---|---|
| 920 | 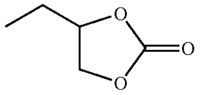 | O | 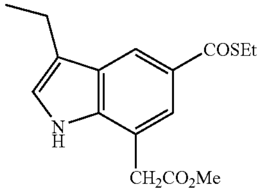 |
| 921 | —$(CH_2)_2CO_2Bn$ | O | 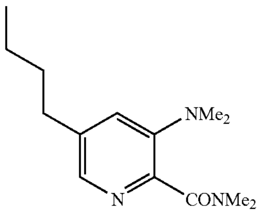 |

INDUSTRIAL APPLICABILITY

The present invention provides an adenine compound useful as a medicament for the topical administration which is characterized in showing the medical effect by the topical administration and showing none of the systemically pharmacological activity. The therapy and prevention for allergic diseases such as asthma and atopic dermatitis, viral diseases such as herpes, etc. becomes possible.

The invention claimed is:

1. An adenine compound represented by a general formula (1):

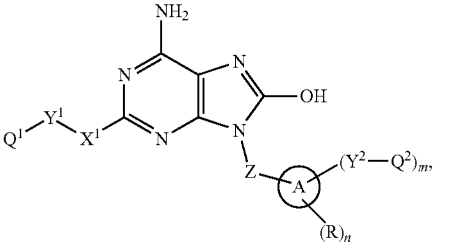

wherein

Ring A is benzene or naphthalene, n is an integer selected from 0 to 2, m is an integer selected from 1 or 2, R is halogen atom, substituted or unsubstituted alkyl group, substituted or unsubstituted cycloalkyl group, substituted or unsubstituted alkoxy group, or substituted or unsubstituted amino group, and when n is 2, R(s) may be the same or different, $X^1$ is oxygen atom, sulfur atom, $NR^1$ (wherein RI is hydrogen atom or alkyl group) or a single bond, $Y^1$ is a single bond, or alkylene which may be substituted by oxo group, $Y^2$ is alkylene or oxyalkylene, Z is alkylene, $Q^1$ is hydrogen atom, halogen atom, hydroxy group, alkoxy group, or a group selected from the group consisting of Substituents set forth below, $Q^2$ is a group selected from the group consisting of Substituents set forth below, Substituents: —$COOR^{10}$; —$COSR^{10}$ wherein $R^{10}$ is substituted or unsubstituted alkyl group, substituted or unsubstituted cycloalkyl group, substituted or unsubstituted alkenyl group, substituted or unsubstituted cycloalkenyl group, or substituted or unsubstituted alkynyl group, and when m is 2, $(Y^2\text{-}Q^2)$(s) may be the same or different, its tautomer or its pharmaceutically acceptable salt.

2. The adenine compound, its tautomer or its pharmaceutically acceptable salt according to claim 1, wherein in the general formula (1), the substituent(s), by which alkyl group, alkenyl group or alkynyl group in $R^{10}$ is substituted, are the same or different and at least one substituent selected from the group consisting of halogen atom, hydroxy group, substituted or unsubstituted alkoxy group, substituted or unsubstituted amino group, substituted or unsubstituted aryl group, and substituted or unsubstituted heterocyclic group.

3. The adenine compound, its tautomer or its pharmaceutically acceptable salt according to claim 1, wherein in the general formula (1), Z is methylene and Ring A is benzene.

4. The adenine compound, its tautomer or its pharmaceutically acceptable salt according to claim 1, wherein in the general formula (1), Z is methylene, Ring A is benzene, $R^{10}$ is alkyl group optionally substituted by hydroxy group, amino group, alkylamino group or dialkylamino group, and m is 1.

5. The adenine compound, its tautomer or its pharmaceutically acceptable salt according to claim 1; wherein in the general formula (1), $Y^1$ is $C_{1-5}$ alkylene, $Q^1$ is hydrogen atom, hydroxy group or alkoxy group, $Y^2$ is $C_{1-3}$ alkylene, $Q^2$ is —$COOR^{10}$, and m is 1.

6. The adenine compound, its tautomer or its pharmaceutically acceptable salt according to claim 1, wherein in the general formula (1), $X^1$ is oxygen atom, sulfur atom or $NR^1$ (wherein $R^1$ is hydrogen atom or alkyl group).

7. The adenine compound, its tautomer or its pharmaceutically acceptable salt according to claim 1, wherein in the general formula (1), either 1) or 2) below obtains:

1) n is 0;

2) n is 1 or 2, and R is alkyl group, alkoxy group or halogen atom.

8. An adenine compound represented by a general formula (1):

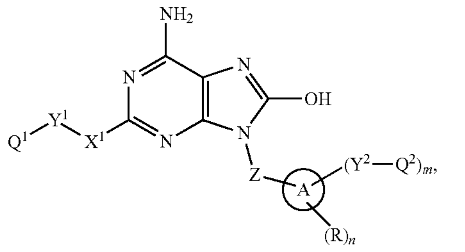

wherein

Ring A is benzene, n is an integer selected from 0 to 2, m is 1,

R is halogen atom, substituted or unsubstituted alkyl group, substituted or unsubstituted cycloalkyl group, substituted or unsubstituted alkoxy group, or substituted or unsubstituted amino group, and when n is 2, R(s) may be the same or different, $X^1$ is oxygen atom, sulfur atom, $NR^1$ (wherein $R^1$ is hydrogen atom or alkyl group) or a single bond, $Y^1$ is $C_{1-5}$ alkylene, $Y^2$ is a single bond, Z is methylene, $Q^1$ is hydrogen atom, hydroxy group or alkoxy group, $Q^2$ is —$COOR^{23}$ (wherein $R^{23}$ is alkyl group substituted by amino group, alkylamino group or dialkylamino group), and m is 1, its tautomer or its pharmaceutically acceptable.

9. The adenine compound or its pharmaceutically acceptable salt according to claim 8, wherein in the general formula (1), $X^1$ is oxygen atom, sulfur atom or $NR^1$ (wherein $R^1$ is hydrogen atom or alkyl group).

10. A compound selected from the group consisting of

2-Butoxy-8-hydroxy-9-{(6-ethoxycarbonylmethoxy-2-naphthyl)methyl}adenine),

2-Butoxy-8-hydroxy-9-{4-(S-methylthiocarbonyl)methylbenzyl}adenine,

2-Butoxy-9-{4-(S-ethylthiocarbonyl)methylbenzyl}-8-hydroxyadenine,

2-Butoxy-8-hydroxy-9-{(6-methoxycarbonylmethoxy-2-naphthyl)methyl}adenine,

2-Butoxy-8-hydroxy-9-{3-(2-hydroxyethoxycarbonyl)benzyl}adenine,

2-Butoxy-8-hydroxy-9-{3-(2-dimethylaminoethoxycarbonyl)benzyl}adenine,

2-Butoxy-8-hydroxy-9-{3-(2-morpholinoethoxycarbonyl)benzyl}adenine,

2-Butoxy-8-hydroxy-9-(3-methoxycarbonylmethylbenzyl)adenine,

2-Butoxy-8-hydroxy-9-(4-methoxycarbonylmethylbenzyl)adenine,

2-Butoxy-8-hydroxy-9-(4-isopropoxycarbonylmethylbenzyl)adenine,

2-Butoxy-8-hydroxy-9-(4-methoxycarbonylmethoxybenzyl)adenine,

2-Butoxy-8-hydroxy-9-{3-bromo-4-(methoxycarbonylmethoxy)benzyl}adenine,

8-Hydroxy-2-(2-methoxycarbonylethyl)-9-(4-methoxycarbonylmethylbenzyl)adenine,

2-Butoxy-8-hydroxy-9-(4-ethoxycarbonylmethylbenzyl)adenine,

2-Butoxy-8-hydroxy-9-{3-(2,2,2-trifluoroethoxycarbonyl)methylbenzyl}adenine,

2-Butoxy-8-hydroxy-9-{3-(2-fluoroethoxycarbonyl)methylbenzyl}adenine,

2-Butoxy-8-hydroxy-9-{4-(2-hydroxyethoxycarbonyl)methylbenzyl}adenine,

2-Butoxy-8-hydroxy-9-{4-(2-dimethylaminoethoxycarbonyl)methylbenzyl}adenine hydrochloride, 2-Butoxy-8-hydroxy-9-{4-(2-morpholinoethoxycarbonyl)methylbenzyl}adenine, 2-Butoxy-9-(3-ethoxycarbonylmethylbenzyl)-8-hydroxyadenine, 2-Butoxy-8-hydroxy-9-(3-methoxycarbonylethylbenzyl)adenine, 2-Butoxy-8-hydroxy-9-(4-methoxycarbonylethylbenzyl)adenine, 2-Butoxy-9-(4-ethoxycarbonylethylbenzyl)-8-hydroxyadenine, 2-Butoxy-9-{4-(1-hydroxy-3-methoxycarbonylpropoxy)benzyl}-8-hydroxyadenine, 8-Hydroxy-9-(3-methoxycarbonylmethylbenzyl)-2-(2-methoxyethoxy)adenine, 2-Butylamino-8-hydroxy-9-(3-methoxycarbonylmethylbenzyl)adenine, 2-Chloro-8-hydroxy-9-(3-methoxycarbonylmethylbenzyl)adenine, 8-Hydroxy-2-(2-hydroxyethylthio)-9-(3-methoxycarbonylmethylbenzyl)adenine, 2-Butoxy-8-hydroxy-9-[4-(1-methoxycarbonylethyl)benzyl]adenine, 2-Butoxy-8-hydroxy-9-[3-(2-methoxycarbonyl-2-propyl)benzyl]adenine, 2-Butoxy-8-hydroxy-9-(4-methoxycarbonylphenylethyl)adenine, 2-Butoxy-8-hydroxy-9-[(2-methoxycarbonylmethyl)benzyl]adenine, 2-Butoxy-8-hydroxy-9-[4-(2-methoxycarbonyl-2-methylethyl)benzyl]adenine, 2-Butoxy-8-hydroxy-9-[3-((2R,S)-methoxycarbonylethyl)benzyl]adenine, and 9-{3,5-Bis (methoxycarbonylmethyl)benzyl}-2-butoxy-8-hydroxyadenine.

11. A pharmaceutical composition comprising the compound of claim 1 or its pharmaceutically acceptable salt and a carrier.

12. A method for treatment of asthma or atopic dermatitis comprising administering to a patient in need thereof an effective amount of the compound of claim 1 or its pharmaceutically acceptable salt as an active ingredient.

* * * * *